(12) United States Patent
Yu et al.

(10) Patent No.: US 6,692,736 B2
(45) Date of Patent: Feb. 17, 2004

(54) CELL-SPECIFIC ADENOVIRUS VECTORS COMPRISING AN INTERNAL RIBOSOME ENTRY SITE

(75) Inventors: De-Chao Yu, Foster City, CA (US); Yuanhao Li, Palo Alto, CA (US); Andrew S. Little, Santa Ana, CA (US); Daniel R. Henderson, Palo Alto, CA (US)

(73) Assignee: Cell Genesys, Inc., South San Francisco, CA (US)

( * ) Notice: Subject to any disclaimer, the term of this patent is extended or adjusted under 35 U.S.C. 154(b) by 117 days.

(21) Appl. No.: 09/814,351

(22) Filed: Mar. 21, 2001

(65) Prior Publication Data

US 2003/0148520 A1 Aug. 7, 2003

Related U.S. Application Data

(60) Provisional application No. 60/192,156, filed on Mar. 24, 2000.

(51) Int. Cl.$^7$ ............... C12P 21/06; C12P 7/00; C12P 15/00; C12N 5/10; C12N 7/02; C12N 15/86
(52) U.S. Cl. ............... 424/93.2; 435/91.4; 435/91.41; 435/91.42; 435/320.1; 435/235.1; 435/369; 435/457; 435/375; 435/69.1; 514/44
(58) Field of Search ............... 514/44; 435/69.1, 435/91.4, 91.41, 91.42, 235.1, 320.1, 240.2, 375, 369

(56) References Cited

U.S. PATENT DOCUMENTS

| | | | |
|---|---|---|---|
| 5,698,443 A | 12/1997 | Henderson et al. | 435/320.1 |
| 5,824,543 A | 10/1998 | Sun | 435/320.1 |
| 5,998,205 A | 12/1999 | Hallenbeck et al. | 435/325 |
| 6,001,646 A | 12/1999 | Sun | 435/320.1 |
| 2002/0019051 A1 * | 2/2002 | Lusky et al. | 435/457 |
| 2002/0055172 A1 * | 5/2002 | Harrington | 435/456 |

FOREIGN PATENT DOCUMENTS

| | | |
|---|---|---|
| WO | WO 95/19434 | 7/1995 |
| WO | WO 96/17053 | 6/1996 |
| WO | WO 97/01358 | 1/1997 |
| WO | WO 99/54482 * | 4/1998 |
| WO | WO 98/37189 | 8/1998 |
| WO | WO 98/39464 | 9/1998 |
| WO | WO 98/39465 | 9/1998 |
| WO | WO 98/39466 | 9/1998 |
| WO | WO 98/39467 | 9/1998 |
| WO | WO 99/06576 | 2/1999 |
| WO | WO 99/25860 | 5/1999 |

OTHER PUBLICATIONS

E Buratti et al., Nucleic Acids Research, "Functional analysis of the interaction between HCV5'UTR and putative subunits of eukaryotic translation initiation factor eIF3,", 1998, vol. 26, No. 13, pp. 3179–3187.*

X–S He, Gene, "Construction of adenoviral and retroviral vectors coexpressing the genes encoding the hepatitis B surface antigen and B7–1 protein,"1996, 175:pp. 121–125.*

I Stein et al., Molecular and Cellular Biology, "Translatio of Vascular Endothelial Growth Factor mRNA by Internal Ribosome Entry:Implications for Translation under Hypoxia," Jun. 1998, vol. 18, No. 6, pp. 3112–3119.*

Herman, Ronald C., "Alternatives for the initiation of translation," *Trends in Biochemical Sciences*, vol. 14, No. 6, Jun. 1989.

Jackson, Richard J. et al., "Internal initiation of translation in eukaryotes: The picornavirus paradigm and beyond," *RNA* 1, pp. 985–1000, 1995.

Lin, Jun–Hsiang et al., "A tissue–specific promoter that can drive a foreign gene to express in the suprabasal urothelial cells of transgenic mice," *Proc. Natnl. Acad. Sci. USA*, vol. 92, pp. 679–683, Jan. 1995.

Rodriguez, Ron et al., "Prostate Attenuated Replication Competent Adenovirus (ARCA) CN706: A Selective Cytotoxic for Prostate–specific Antigen–positive Prostate Cancer Cells," *Cancer Research* 57, pp. 2559–2563, Jul. 1, 1997.

* cited by examiner

*Primary Examiner*—David Guzo
*Assistant Examiner*—Maria Marvich
(74) *Attorney, Agent, or Firm*—Linda R. Judge; Pamela J. Sherwood; Bozicevic, Field & Francis LLP

(57) ABSTRACT

Disclosed herein are replication-competent adenovirus vectors comprising co-transcribed first and second genes under transcriptional control of a heterologous, target cell-specific transcriptional regulatory element (TRE), wherein the second gene is under translational control of an internal ribosome entry site. Methods for the preparation and use of such vectors are also provided. The vectors provide target cell-specific virus replication in applications such as cancer therapy and gene therapy.

41 Claims, 14 Drawing Sheets

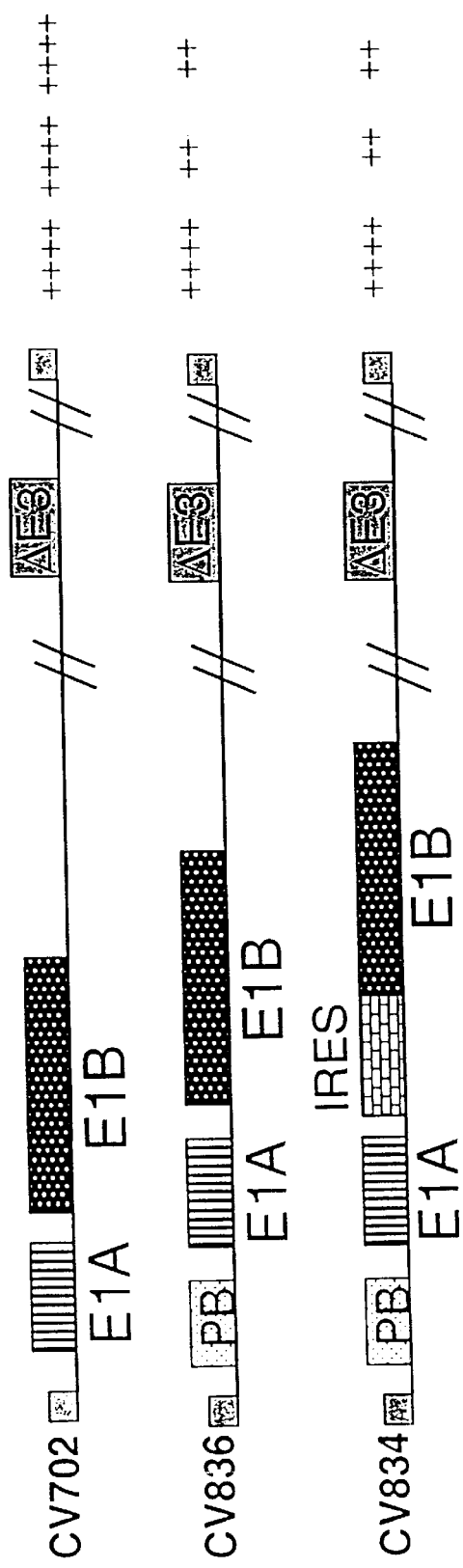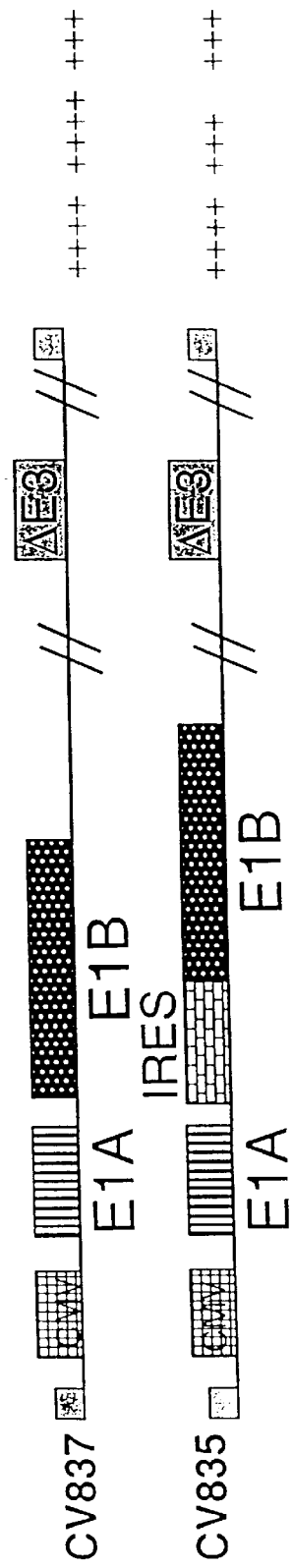
Figure 3

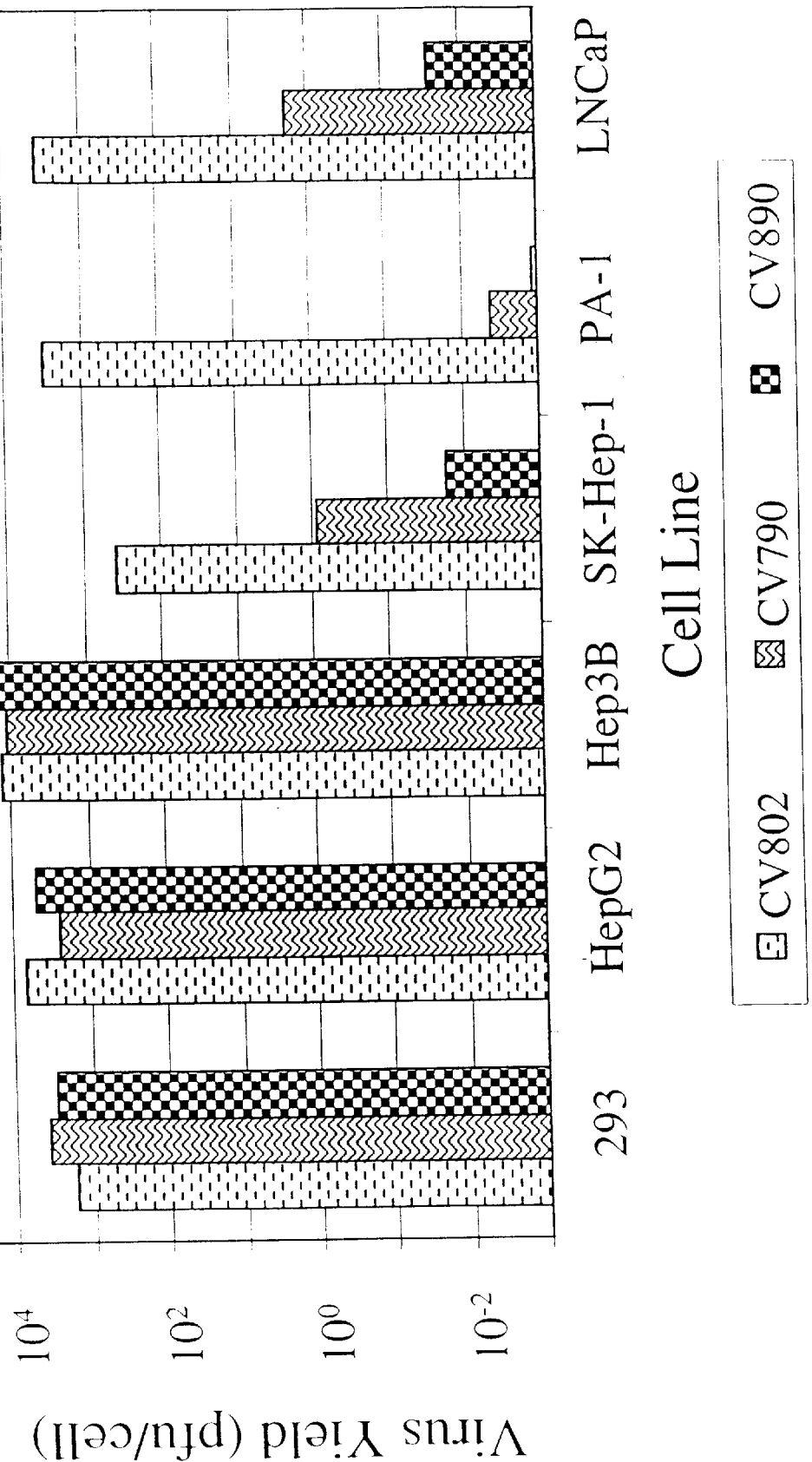

FIG. 9

```
G ATG ACC GGC TCA ACC ATC GCG CCC ACA ACG GAC TAT CGC AAC ACC
46
  Met Thr Gly Ser Thr Ile Ala Pro Thr Thr Asp Tyr Arg Asn Thr
   1           5               10                  15

ACT GCT ACC GGA CTA ACA TCT GCC CTA AAT TTA CCC CAA GTT CAT GCC
94
Thr Ala Thr Gly Leu Thr Ser Ala Leu Asn Leu Pro Gln Val His Ala
                20              25                  30

TTT GTC AAT GAC TGG GCG AGC TTG GAC ATG TGG TGG TTT TCC ATA GCG
142
Phe Val Asn Asp Trp Ala Ser Leu Asp Met Trp Trp Phe Ser Ile Ala
            35              40                  45

CTT ATG TTT GTT TGC CTT ATT ATT ATG TGG CTT ATT TGT TGC CTA AAG
190
Leu Met Phe Val Cys Leu Ile Ile Met Trp Leu Ile Cys Cys Leu Lys
            50              55                  60

CGC AGA CGC GCC AGA CCC CCC ATC TAT AGG CCT ATC ATT GTG CTC AAC
238
Arg Arg Arg Ala Arg Pro Pro Ile Tyr Arg Pro Ile Ile Val Leu Asn
        65              70              75

CCA CAC AAT GAA AAA ATT CAT AGA TTG GAC GGT CTG AAA CCA TGT TCT
286
Pro His Asn Glu Lys Ile His Arg Leu Asp Gly Leu Lys Pro Cys Ser
 80              85              90                  95

CTT CTT TTA CAG TAT GAT TAA
307
Leu Leu Leu Gln Tyr Asp
            100
```

CELL-SPECIFIC ADENOVIRUS VECTORS COMPRISING AN INTERNAL RIBOSOME ENTRY SITE

The above-identified application claims priority to U.S. Provisional application No. 60/192,156 filed on Mar. 24, 2000, which provisional application is hereby incorporated herein in its entirety.

TECHNICAL FIELD

This invention relates to new replication competent adenovirus vectors comprising an internal ribosome entry site which replicate preferentially in target cells. The present invention also relates to cell transduction using adenovirus vectors comprising an internal ribosome entry site.

BACKGROUND

Diseases involving altered cell proliferation, particularly hyperproliferation, constitute an important health problem. For example, despite numerous advances in medical research, cancer remains the second leading cause of death in the United States. In the industrialized nations, roughly one in five persons will die of cancer. Traditional modes of clinical care, such as surgical resection, radiotherapy and chemotherapy, have a significant failure rate, especially for solid tumors. Neoplasia resulting in benign tumors can usually be completely cured by surgical removal of the tumor mass. If a tumor becomes malignant, as manifested by invasion of surrounding tissue, it becomes much more difficult to eradicate. Once a malignant tumor metastasizes, it is much less likely to be eradicated.

Excluding basal cell carcinoma, there are over one million new cases of cancer per year in the United States alone, and cancer accounts for over one half million deaths per year in this country. In the world as a whole, the five most common cancers are those of lung, stomach, breast, colon/rectum, and uterine cervix, and the total number of new cases per year is over 6 million.

In the United States, transitional cell carcinoma (TCC) accounts for 90 to 95 percent of all tumors of the bladder. Squamous cell carcinoma (SCC) represents 5 to 10 percent, and adenocarcinoma approximately 1 to 2 percent. Squamous cell and adenomatous elements are often found in association with transitional cell tumors, especially with high grade tumors. Bladder cancer is generally divided into superficial and invasive disease. A critical factor is the distinction between those tumors that are confined to the mucosa and those that have penetrated the basement membrane and extended into the lamina propria. The term "superficial bladder tumor" is generally used to represent a tumor that has not invaded the muscularis. Invasive tumors are described as those that have invaded the muscularis propria, the perivesical fibroadipose tissue, or adjacent structures. Carcinoma in situ (CIS) is a high grade and aggressive manifestation of TCC of the bladder that has a highly variable course.

A number of urothelial cell-specific proteins have been described, among which are the uroplakins. Uroplakins (UP), including UPIa and UPIb (27 and 28 kDa, respectively), UPII (15 kDa), and UPIII (47 kDa), are members of a group of integral membrane proteins that are major proteins of urothelial plaques. These plaques cover a large portion of the apical surface of mammalian urothelium and may play a role as a permeability barrier and/or as a physical stabilizer of the urothelial apical surface. Wu et al. (1994) *J. Biol. Chem.* 269:13716–13724. UPs are bladder-specific proteins, and are expressed on a significant proportion of urothelial-derived tumors, including about 88% of transitional cell carcinomas. Moll et al. (1995) *Am. J. Pathol.* 147:1383–1397; and Wu et al. (1998) *Cancer Res.* 58:1291–1297. The control of the expression of the human UPII has been studied, and a 3.6-kb region upstream of the mouse UPII gene has been identified which can confer urothelial-specific transcription on heterologous genes (Lin et al. (1995) *Proc. Natl. Acad. Sci. USA* 92:679–683). See also, U.S. Pat. Nos. 5,824,543 and 6,001,646.

Melanoma, a malignant neoplasm derived from melanocytes of the skin and other sites, has been increasing in incidence worldwide. The American Joint Committee on Cancer recognizes five different forms of extraocular melanoma occurring in humans: lentigo maligna melanoma; radial spreading; nodular; acral lentiginous; and unclassified. Known melanoma-associated antigens can be classified into three main groups: tumor-associated testis-specific antigens MAGE, BAGE, GAGE, and PRAME; melanocyte differentiation antigens tyrosinase, Melan-A/MART-1 (for Melanoma Antigen Recognized by T cells), gp100, tyrosinase related protein-1(TRP-1), tyrosinase related protein-2 (TRP-2); and mutated or aberrantly expressed antigens MUM-1, cyclin-dependent kinase 4 (CDK4), beta-catenin, gp100-in4, p15, and N-acetylglucosaminyltransferase V. See, for example, Kirkin et al. (1998) *Exp. Clin. Immunogenet.* 15:19–32. Tyrosinase, TRP-1, and TRP-2 are enzymes involved in melanin biosynthesis and are specifically expressed in melanocytes. Antigenic epitopes of MART-1 have been studied extensively, with the aim of developing a melanoma vaccine. An immunodominant epitope, MART-1(27–35) has been reported to be recognized by a majority of CD8+cytotoxic T cell clones generated to MART-1. These MART-1(27–35)-specific CTLs specifically lyse autologous tumor cell lines expressing the epitope. Faure and Kourilsky (1998) *Crit. Rev. Immunol.* 18:77–86. However, others have reported that presence of such CTLs is not accompanied by a significant clinical response. Rivoltini et al. (1998) *Crit. Rev. Immunol.* 18:55–63.

A major, indeed the overwhelming, obstacle to cancer therapy is the problem of selectivity; that is, the ability to inhibit the multiplication of tumor cells without affecting the functions of normal cells. For example, in traditional chemotherapy of prostate cancer, the therapeutic ratio, (i.e., the ratio of tumor cell killing to normal cell killing) is only 1.5:1. Thus, more effective treatment methods and pharmaceutical compositions for therapy and prophylaxis of neoplasia are needed.

Accordingly, the development of more specific, targeted forms of cancer therapy, especially for cancers that are difficult to treat successfully, is of particular interest. In contrast to conventional cancer therapies, which result in relatively non-specific and often serious toxicity, more specific treatment modalities, which inhibit or kill malignant cells selectively while leaving healthy cells intact, are required.

Gene therapy, whereby a gene of interest is introduced into a malignant cell, has been attempted as an approach to treatment of many cancers. See, for example, Boulikas (1997) *Anticancer Res.* 17:1471–1505, for a description of gene therapy for prostate cancer. A gene of interest can encode a protein which is converted into a toxic substance upon treatment with another compound, or it can encode an enzyme that converts a prodrug to a drug. For example, introduction of the herpes simplex virus gene encoding thymidine kinase (HSV-tk) renders cells conditionally sensitive to ganciclovir. Zjilstra et al. (1989) *Nature* 342: 435;

Mansour et al. (1988) *Nature* 336: 348; Johnson et al. (1989) *Science* 245: 1234; Adair et al. (1989) *Proc. Natl. Acad. Sci. USA* 86: 4574; Capecchi (1989) *Science* 244: 1288. Alternatively, a gene of interest can encode a compound that is directly toxic, such as, for example, diphtheria toxin. To render these treatments specific to cancer cells, the gene of interest is placed under control of a transcriptional regulatory element (TRE) that is specifically (i.e., preferentially) active in the cancer cells. Cell- or tissue-specific expression can be achieved by using a TRE with cell-specific enhancers and/or promoters. See generally Huber et al. (1995) *Adv. Drug Delivery Reviews* 17:279–292.

A number of viral vectors and non-viral delivery systems (e.g., liposomes), have been developed for gene transfer. Of the viruses proposed for gene transfer, adenoviruses are among the most easily produced and purified. Adenovirus also has the advantage of a high efficiency of transduction (i.e., introduction of the gene of interest into the target cell) and does not require cell proliferation for efficient transduction. In addition, adenovirus can infect a wide variety of cells in vitro and in vivo. For general background references regarding adenovirus and development of adenoviral vector systems, see Graham et al. (1973) *Virology* 52:456–467; Takiff et al. (1981) *Lancet* 11:832–834; Berkner et al. (1983) *Nucleic Acid Research* 11:6003–6020; Graham (1984) *EMBO J* 3:2917–2922; Bett et al. (1993) *J. Virology* 67:5911–5921; and Bett et al. (1994) *Proc. Natl. Acad. Sci. USA* 91:8802–8806.

Adenoviruses generally undergo a lytic replication cycle following infection of a host cell. In addition to lysing the infected cell, the replicative process of adenovirus blocks the transport and translation host cell mRNA, thus inhibiting cellular protein synthesis. For a review of adenoviruses and adenovirus replication, see Shenk, T. and Horwitz, M. S., *Virology*, third edition, Fields, B. N. et al., eds., Raven Press Limited, New York (1996), Chapters 67 and 68, respectively.

When used for gene transfer, adenovirus vectors are often designed to be replication-defective and are thus deliberately engineered to fail to replicate in the target cell. In these vectors, the early adenovirus gene products E1A and/or E1B are often deleted, and the gene to be transduced is commonly inserted into the E1A and/or E1B region of the deleted virus genome. Bett et al. (1994) supra. Such vectors are propagated in packaging cell lines such as the 293 line, which provides E1A and E1B functions in trans. Graham et al. (1987) *J. Gen. Virol* 36:59–72; Graham (1977) *J. Gen. Virol.* 68:937–940. The use of replication-defective adenovirus vectors as vehicles for efficient transduction of genes has been described by, inter alia, Stratford-Perricaudet (1990) *Human Gene Therapy* 1:241–256; Rosenfeld (1991) *Science* 252:431–434; Wang et al. (1991) *Adv. Exp. Med. Biol.* 309:61–66; Jaffe et al. (1992) *Nature Gen.* 1:372–378; Quantin et al. (1992) *Proc. Natl. Acad. Sci. USA* 89:2581–2584; Rosenfeld et al. (1992) *Cell* 68:143–155; Stratford-Perricaudet et al. (1992) *J. Clin. Invest.* 90:626–630; Le Gal Le Salle et al. (1993) *Science* 259:988–990; Mastrangeli et al. (1993) *J. Clin. Invest.* 91:225–234; Ragot et al. (1993) *Nature* 361:647–650; Hayaski et al. (1994) *J. Biol. Chem.* 269:23872–23875; and Bett et al. (1994) supra.

In the treatment of cancer by replication-defective adenoviruses, the host immune response limits the duration of repeat doses at two levels. First, the capsid proteins of the adenovirus delivery vehicle itself are immunogenic. Second, viral late genes are frequently expressed in transduced cells, eliciting cellular immunity. Thus, the ability to repeatedly administer cytokines, tumor suppressor genes, ribozymes, suicide genes, or genes which convert a prodrug to an active drug has been limited by the immunogenicity of both the gene transfer vehicle and the viral gene products of the transfer vehicle, coupled with the transient nature of gene expression. Despite these limitations, development of adenoviral vectors for gene therapy has focused almost exclusively on the use of the virus as a vehicle for introducing a gene of interest, not as an effector in itself. In fact, replication of adenovirus vectors has been viewed as an undesirable result, largely due to the host immune response.

More recently, however, the use of adenovirus vectors as effectors has been described. International Patent Application Nos. PCT/US98/04080, PCT/US98/04084, PCT/US98/04133, PCT/US98/04132, PCT/US98/16312, PCT/US95/00845, PCT/US96/10838, PCT/EP98/07380 and U.S. Pat. No. 5,998,205. Adenovirus E1A and E1B genes are disclosed in Rao et al. (1992, *Proc. Natl. Acad. Sci. USA* vol. 89: 7742–7746).

Replication-competent adenovirus vectors, which take advantage of the cytotoxic effects associated with adenovirus replication, have recently been described as agents for effecting selective cell growth inhibition. In such systems, a cell-specific transcriptional regulatory element (TRE) is used to control the expression of a gene essential for viral replication, thus limiting viral replication to cells in which the TRE is functional. See, for example International Patent Application No. PCT/EP99/07380, Henderson et al., U.S. Pat. No. 5,698,443; Hallenbeck et al., PCT/US95/15455 and U.S. Pat. No. 5,998,205; Rodriguez et al. (1997) *Cancer Res.* 57:2559–2563.

PCT publication PCT/US98/04080 discloses replication-competent, target cell-specific adenovirus vectors comprising heterologous TREs, such as those regulating expression of prostate-specific antigen (PSA), probasin (PB), α-fetoprotein (AFP), kallikrien (hKLK2), mucin (MUC1) and carcinoembryonic antigen (CEA). PCT/US98/04084 discloses replication-competent adenovirus vectors comprising an α-fetoprotein (AFP) TRE that replicate specifically in cells expressing AFP, such as hepatoma cells.

Internal ribosome entry sites (IRES) are sequences which initiate translation from an internal initiation codon (usually AUG) within a bi- or multi-cistronic RNA transcript continuing multiple protein coding regions. IRES have been characterized in encephalomyocarditis virus and related picornaviruses. See, for example, Jackson et al. (1995) *RNA* 1: 985–1000 and Herman (1989) *Trends in Biochemical Sciences* 14(6): 219–222. IRES sequences are also detected in mRNAs from other viruses such as cardiovirus, rhinovirus, aphthovirus, hepatitis C virus (HCV), Friend murine leukemia virus (FrMLV) and Moloney murine leukemia virus (MoMLV). The presence of IRES in cellular RNAs has also been described. Examples of cellular mRNAs containing IRES include those encoding immunoglobulin heavy-chain binding protein (BiP), vascular endothelial growth factor (VEGF), fibroblast growth factor 2, insulin-like growth factor, translational initiation factor eIF4G, and the yeast transcription factors TFIID and HAP4. See, for example; Macejak et al. (1991) *Nature* 353:90–94; Oh et al. (1992) *Genes Dev.* 6:1643–1653; Vagner et al. (1995) *Mol. Cell. Biol.* 15:35–44; He et al. (1996) *Proc. Natl. Acad. Sci USA* 93:7274–7278; He et al. (1996) *Gene* 175:121–125; Tomanin et al. (1997) *Gene* 193:129–140; Gambotto et al. (1999) *Cancer Gene Therapy* 6:45–53; Qiao et al. (1999) *Cancer Gene Therapy* 6:373–379. Expression vectors containing IRES elements have been described. See, for example, International Patent Application No. PCT/US98/03699 and International Patent Application No. PCT/EP98/07380.

Thus, there is a continuing need for improved replication-competent adenovirus vectors in which cell-specific replication can be further enhanced, while minimizing the extent of replication in non-target (i.e., non-cancerous cells).

The disclosure of all patents and publications cited herein are incorporated by reference in their entirety.

SUMMARY OF THE INVENTION

The present invention provides improved replication competent adenovirus vectors comprising co-transcribed first and second genes under transcriptional control of a heterologous, target cell-specific transcriptional regulatory element (TRE), wherein the second gene is under translational control of an internal ribosome entry site (IRES). In one embodiment, the first and second genes are co-transcribed as a single mRNA and the second gene has a mutation in or deletion of its endogenous promoter. The present invention further provides host cells and methods using the adenovirus vectors.

In one aspect, the first and/or second genes are adenovirus genes and in another aspect, the first and/or second adenovirus genes are essential for viral replication. An essential gene can be an early viral gene, including for example, E1A; E1B; E2; and/or E4, or a late viral gene. In another aspect an early gene is E3.

In one embodiment, the first gene is an adenovirus gene and the second gene is a therapeutic gene. In another embodiment, both genes are adenovirus genes. In an additional embodiment, the first adenovirus gene is E1A, and the second adenovirus gene is E1B. Optionally, the endogenous promoter for one of the co-transcribed adenovirus gene essential for viral replication, such as for example, E1A, is deleted and/or mutated such that the gene is under sole transcriptional control of a target cell-specific TRE.

In another aspect, the present invention provides adenovirus vectors comprising an adenovirus gene essential for viral replication under control of a target cell-specific TRE, wherein said adenovirus gene has a mutation of or deletion in its endogenous promoter. In one embodiment, the adenovirus gene is essential for viral replication. In another embodiment, the adenovirus gene is E1A wherein the E1A promoter is deleted and wherein the E1A gene is under transcriptional control of a heterologous cell-specific TRE. In another embodiment, the adenovirus gene is E1B wherein the E1B promoter is deleted and wherein the E1B gene is under transcriptional control of a heterologous cell-specific TRE.

In another aspect, the present invention provides adenovirus vectors comprising E1B under control of a target cell-specific TRE, wherein said E1B has a deletion in or mutation of the 19-kDa region of E1B, that encodes a product shown to inhibit apoptosis.

In other embodiments, an enhancer element for the first and/or second adenovirus genes is inactivated. The present invention provides an adenovirus vector comprising E1A wherein an E1A enhancer is inactivated. In yet other embodiments, the present invention provides an adenovirus vector comprising E1A wherein the E1A promoter is inactivated and E1A enhancer I is inactivated. In further embodiments, the present invention provides an adenovirus vector comprising a TRE which has its endogenous silencer element inactivated.

Any TRE which directs cell-specific expression can be used in the disclosed vectors. In one embodiment, TREs include, for example, TREs specific for prostate cancer cells, breast cancer cells, hepatoma cells, melanoma cells, bladder cells and/or colon cancer cells. In another embodiment, the TREs include, probasin (PB) TRE; prostate-specific antigen (PSA) TRE; mucin (MUC1) TRE; α-fetoprotein (AFP) TRE; hKLK2 TRE; tyrosinase TRE; human uroplakin II TRE (hUPII) and carcinoembryonic antigen (CEA) TRE. In other embodiments, the target cell-specific TRE is a cell status-specific TRE. In yet other embodiments, the target cell-specific TRE is a tissue specific TRE.

In additional embodiments, the adenovirus vector comprises at least one additional co-transcribed gene under the control of the cell-specific TRE. In another embodiment, an additional co-transcribed gene is under the translational control of an IRES.

In another aspect of the present invention, adenovirus vectors further comprise a transgene such as, for example, a cytotoxic gene. In one embodiment, the transgene is under the transcriptional control of the same TRE as the first gene and second genes and optionally under the translational control of an internal ribosome entry site. In another embodiment, the transgene is under the transcriptional control of a different TRE that is functional in the same cell as the TRE regulating transcription of the first and second genes and optionally under the translational control of an IRES.

The present invention also provides compositions comprising the replication-competent adenovirus vectors described herein. In one embodiment, the compositions further comprise a pharmaceutically acceptable excipient. The present invention also provides kits comprising the replication-competent adnenovirus vectors described herein.

Host cells comprising the disclosed adenovirus vectors are also provided. Host cells include those used for propagation of a vector and those into which a vector is introduced for therapeutic purposes.

In another aspect, methods are provided for propagating replication-competent adenovirus vectors of the present invention specific for mammalian cells which permit the function of a target cell-specific TRE, said method comprising combining an adenovirus vector(s) described herein with mammalian cells that permit the function of a target cell-specific TRE, such that the adenovirus vector(s) enters the cell, whereby said adenovirus is propagated.

In another aspect, methods are provided for conferring selective cytotoxicity in target cells, comprising contacting the cells with an adenovirus vector(s) described herein, whereby the vector enters the cell.

The invention further provides methods of suppressing tumor cell growth, more particularly a target tumor cell, comprising contacting a tumor cell with an adenovirus vector(s) of the invention such that the adenovirus vector enters the tumor cell and exhibits selective cytotoxicity for the tumor cell.

In another aspect, methods are provided for detecting a cell which allows the function of a target cell-specific TRE, which comprise contacting a cell in a biological sample with an adenovirus vector(s) of the invention, and detecting replication of the adenovirus vector(s), if any.

In another aspect, methods are provided for modifying the genotype of a target cell, comprising contacting the cell with an adenovirus vector as described herein, wherein the adenovirus vector enters the cell.

The present invention provides an adenovirus vector comprising an adenovirus gene, wherein said adenovirus gene is under transcriptional control of a melanocyte-specific TRE. In another embodiment, a melanocyte-specific TRE is human. In another embodiment, a melanocyte-specific TRE comprises a melanocyte-specific promoter and a heterologous enhancer. In other embodiments, a melanocyte-specific TRE comprises a melanocyte-specific promoter. In other embodiments, a melanocyte-specific TRE comprises a melanocyte-specific enhancer and a heterologous promoter. In other embodiments, a melanocyte-specific TRE comprises a melanocyte-specific promoter and a melanocyte-specific enhancer.

In some embodiments, the adenovirus gene under transcriptional control of a melanocyte-specific TRE is an adenovirus gene essential for replication. In some embodiments, the adenoviral gene essential for replication is an early gene. In another embodiment, the early gene is E1A. In another embodiment, the early gene is E1B. In yet another embodiment, both E1A and E1B are under transcriptional control of a melanocyte-specific TRE. In further embodiments, the adenovirus gene essential for replication is E1B, and E1B has a deletion in the 19-kDa region.

In some embodiments, the melanocyte-specific TRE is derived from the 5' flanking region of a tyrosinase gene. In other embodiments, the melanocyte-specific TRE is derived from the 5' flanking region of a tyrosinase related protein-1 gene. In other embodiments, the melanocyte-specific TRE is derived from the 5'-flanking region of a tyrosinase related protein-2 gene. In other embodiments, the melanocyte-specific TRE is derived from the 5' flanking region of a MART-1 gene. In other embodiments, the melanocyte-specific TRE is derived from the 5'-flanking region of a gene which is aberrantly expressed in melanomas.

In other embodiments, the invention provides an adenovirus vector comprising (a) an adenovirus gene under transcriptional control of a melanocyte-specific TRE; and (b) an E3 region. In some of these embodiments the E3 region is under transcriptional control of a melanocyte-specific TRE.

In another aspect, the invention provides a host cell comprising the melanocyte specific adenovirus vector(s) described herein.

In another aspect, the invention provides pharmaceutical compositions comprising a melanocyte specific adenovirus vector(s) described herein.

In another aspect, the invention provides kits which contain a melanocyte adenoviral vector(s) described herein.

In another aspect, methods are provided for conferring selective cytotoxicity in target cells (i.e., cells which permit or induce a melanocyte-specific TRE to function), comprising contacting the cells with an adenovirus vector(s) described herein, whereby the vector enters the cell.

In another aspect, methods are provided for propagating an adenovirus specific for melanocytes, said method comprising combining an melanocyte specific adenovirus vector(s) described herein with melanocytes, whereby said adenovirus is propagated.

The invention further provides methods of suppressing melanoma cell growth, comprising contacting a melanoma cell with a melanocyte specific adenoviral vector of the invention such that the adenoviral vector enters the melanoma cell and exhibits selective cytotoxicity for the melanoma cell.

In another aspect, methods are provided for detecting melanocytes, including melanoma cells, in a biological sample, comprising contacting cells of a biological sample with a melanocyte adenovirus vector(s) described herein, and detecting replication of the adenovirus vector, if any.

BRIEF DESCRIPTION OF THE DRAWINGS

FIG. 3 depicts the replication efficiency of different viruses as described in Example 4.

FIGS. 4A and 4B show viral yield for different liver-specific vectors in different cell types.

FIG. 9 depicts an ADP nucleotide SEQ ID NO: 17 and amino acid sequence SEQ ID NO.: 18.

MODES FOR CARRYING OUT THE INVENTION

Figure 1:
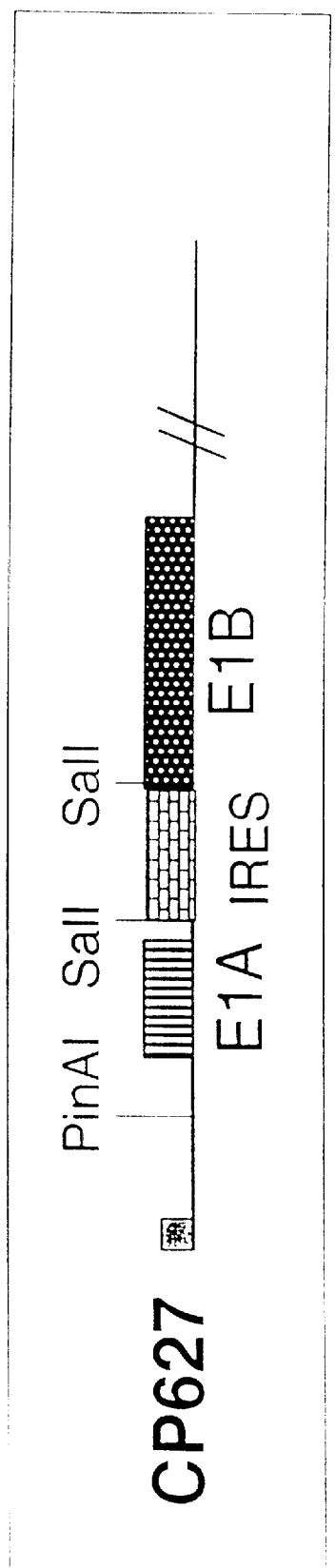
FIG. 1 is a schematic of plasmid construct CP627 as described in Example 1.
Figure 2A:
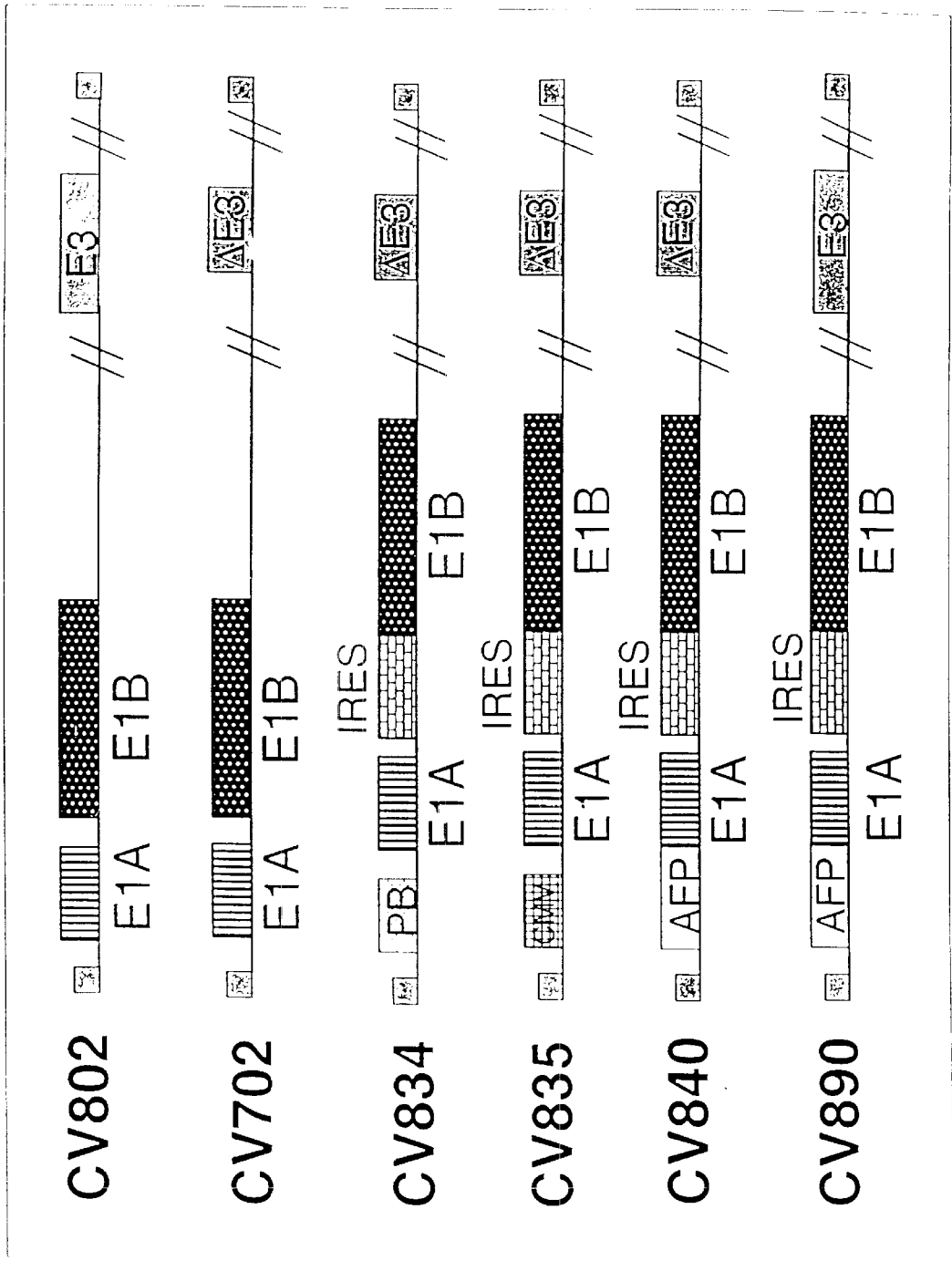
FIGS. 2A–2B is a series of schematic depictions of various adenoviruses described herein.
Figure 2B:
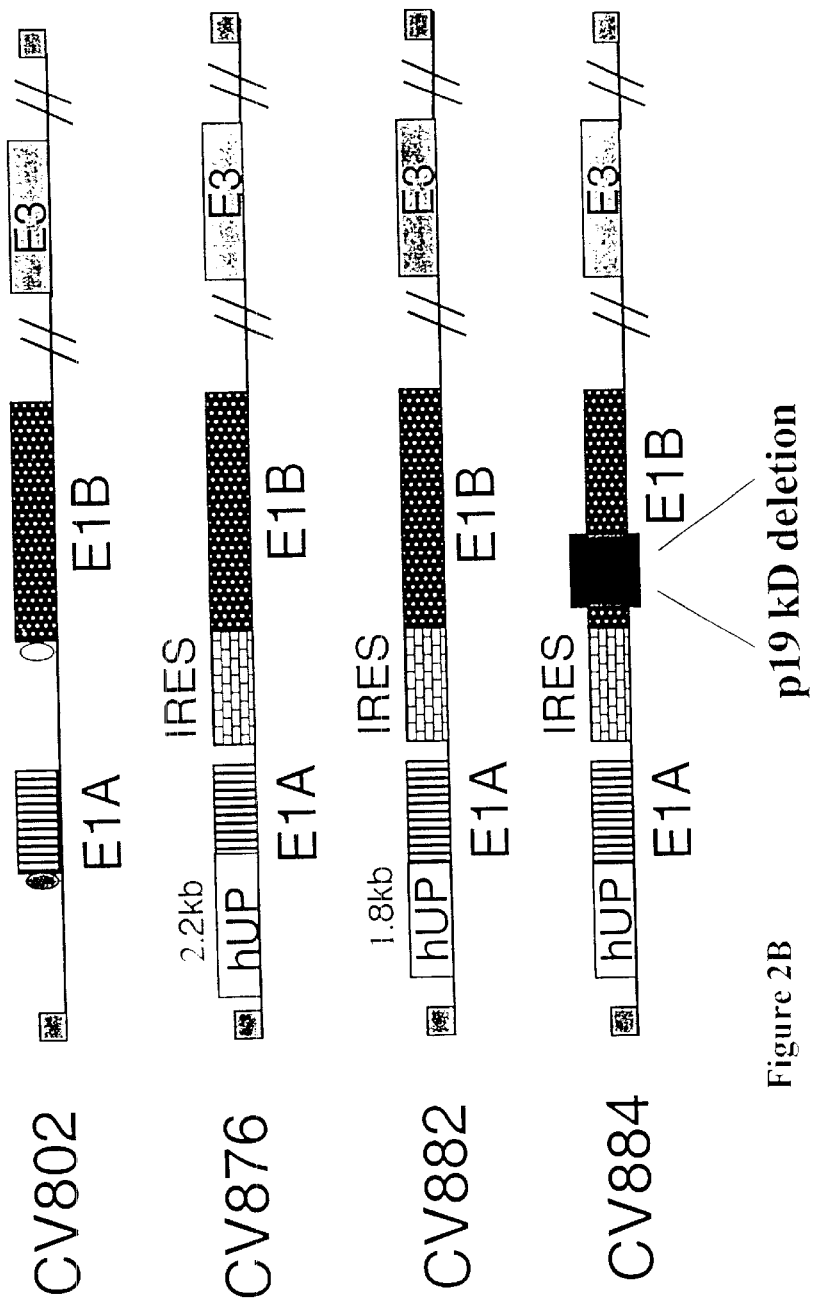

We have discovered and constructed improved adenovirus vectors comprising co-transcribed first and second genes under transcriptional control of a heterologous, target cell-specific transcriptional regulatory element (TRE), wherein the second gene is under translational control of an internal ribosome entry site (IRES). In one embodiment, the first and second genes are co-transcribed as a single mRNA and the second gene has a mutation in or deletion of its endogenous promoter. In another embodiment, at least one of the genes is an adenovirus gene and in yet another embodiment, both genes are adenovirus genes, including adenovirus genes that are essential for viral replication. The adenovirus vector may comprise a gene that contributes to cytotoxicity (whether direct and/or indirect), and/or causes cell death. An example of an adenovirus gene that contributes to cytotoxicity includes, but is not limited to, the adenovirus death protein gene.

In some aspects of the present invention, an adenovirus vector comprising co-transcribed first and second genes under transcriptional control of a target cell-specific TRE, wherein the second gene is under translational control of an IRES, exhibits greater specificity for the target cell than an adenovirus vector comprising a target cell-specific TRE operably linked to a gene and lacking an IRES. In some embodiments, specificity is conferred by preferential transcription and/or translation of the first and second genes due to the presence of a target cell specific TRE. In other embodiments, specificity is conferred by preferential replication of the adenovirus vectors in target cells due to the target cell-specific TRE driving transcription of a gene essential for replication.

Also disclosed herein are IRES containing adenovirus vectors comprising an adenovirus gene essential for viral replication wherein said essential gene has a mutation in or deletion of its endogenous promoter. In an embodiment disclosed herein, the adenovirus vectors comprise the adenovirus early gene E1A which has a deletion of its endogenous promoter. In another embodiment disclosed herein, the adenovirus vectors comprise the adenovirus early gene E1B which has a deletion of its endogenous promoter. In other embodiments disclosed herein, the 19-kDa region of E1B is deleted.

In another aspect, the adenovirus vectors disclosed herein comprise an adenovirus gene essential for viral replication wherein said essential gene has a mutation in or deletion of its endogenous enhancer. In one embodiment, the adenovirus vector comprises the adenovirus early gene E1A which has a mutation of or deletion in its endogenous promoter. In one embodiment, the adenovirus vector comprises the adenovirus early gene E1A which has a mutation of or deletion in E1A enhancer 1. In a further embodiment, the adenovirus vector comprises the adenovirus early gene E1A which has a mutation of or deletion in its endogenous promoter and a mutation of or deletion in the E1A enhancer. In an additional embodiment, the adenovirus vector comprises the adenovirus early gene E1A which has a mutation of or deletion in its endogenous promoter and the adenovirus early gene E1B which has a mutation of or deletion in its endogenous promoter. In an additional embodiment, the adenovirus vector comprises the adenovirus early gene E1A, which has a mutation of or deletion in its endogenous promoter and a mutation of or deletion in the E1A enhancer 1, and the adenovirus early gene E1B which has a mutation of or deletion in its endogenous promoter. In other embodiments disclosed herein, the 19-kDa region of E1B is deleted.

The replication-competent adenovirus vectors of the present invention take advantage of what has been heretofore considered an undesirable aspect of adenovirus vectors, namely their replication and possible concomitant immunogenicity. Runaway infection is prevented due to the cell-specific requirements for viral replication. Without wishing to be bound by any particular theory, it is noted that production of adenovirus proteins can serve to activate and/or stimulate the immune system, either generally or specifically, toward target cells producing adenoviral proteins. This type of immune stimulation can be an important consideration in the cancer context, where patients are often moderately to severely immunocompromised.

The adenovirus vectors of the present invention comprising an intergenic IRES element(s) which links the translation of two or more genes, reflects an improvement over vector constructs which use identical control regions to drive expression of two or more desired genes in that any potential for homologous recombination based on the presence of homologous control regions in the vector is removed. As demonstrated herein, adenovirus vectors comprising an IRES are stable and in some embodiments provide better specificity than vectors not containing an IRES. Another advantage of an adenovirus vector comprising an intergenic IRES is that the use of an IRES rather than a second TRE may provide additional space in the vector for an additional gene(s) such as a therapeutic gene.

Thus, the adenovirus vectors comprising a second gene under control of an IRES retain a high level of target cell specificity and remain stable in the target cell. Accordingly, in one aspect of the invention, the viral vectors disclosed herein comprise at least one IRES within a multicistronic transcript, wherein production of the multicistronic transcript is regulated by a heterologous, target cell-specific TRE. For adenovirus vectors comprising a second gene under control of an IRES, it is preferred that the endogenous promoter of a gene under translational control of an IRES be deleted so that the endogenous promoter does not interfere with transcription of the second gene. It is preferred that the second gene be in frame with the IRES if the IRES contains an initiation codon. If an initiation codon, such as ATG, is present in the IRES, it is preferred that the initiation codon of the second gene is removed and that the IRES and the second gene are in frame. Alternatively, if the IRES does not contain an initiation codon or if the initiation codon is removed from the IRES, the initiation codon of the second gene is used. In one embodiment, the adenovirus vectors comprises the adenovirus essential genes, E1A and E1B genes, under the transcriptional control of a heterologous, cell-specific TRE, and an IRES introduced between E1A and E1B. Thus, both E1A and E1B are under common transcriptional control, and translation of E1B coding region is obtained by virtue of the presence of the IRES. In one embodiment, E1A has its endogenous promoter deleted. In another embodiment, E1A has an endogenous enhancer deleted and in yet an additional embodiment, E1A has its endogenous promoter deleted and E1A enhancer I deleted. In another embodiment, E1B has its endogenous promoter deleted. In other embodiments disclosed herein, the 19-kDa region of E1B is deleted.

To provide cytotoxicity to target cells, one or more transgenes having a cytotoxic effect may be present in the vector. Additionally, or alternatively, an adenovirus gene that contributes to cytotoxicity and/or cell death, such as the adenovirus death protein (ADP) gene, can be included in the vector, optionally under the selective transcriptional control of a heterologous TRE and optionally under the translational control of an IRES.

Examples of target cells include neoplastic cells, although any cell for which it is desirable and/or tolerable to sustain a cytotoxic activity can be a target cell. By combining an adenovirus vector(s) comprising a target cell-specific TRE with a mixture of target and non-target cells, in vitro or in vivo, the vector(s) preferentially replicates in the target cells, causing cytotoxic and/or cytolytic effects. Once the target cells are destroyed due to selective cytotoxic and/or cytolytic activity, replication of the vector(s) is significantly reduced, lessening the probability of runaway infection and undesirable bystander effects. In vitro cultures can be retained to continually monitor the mixture (such as, for example, a biopsy or other appropriate biological sample) for the presence of the undesirable target cell, e.g., a cancer cell in which the target cell-specific TRE is functional. The adenovirus vectors of the present invention can also be used in ex vivo procedures wherein desirable biological samples comprising target cells are removed from the animal, subjected to exposure to an adenovirus vector of the present invention comprising a target cell-specific TRE and then replaced within the animal.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, *Molecular Cloning: A Laboratory Manual*, second edition (Sambrook et al., 1989);

*Oligonucleotide Synthesis* (M. J. Gait, ed., 1984); *Animal Cell Culture* (R. I. Freshney, ed., 1987); *Methods in Enzymology* (Academic Press, Inc.); *Handbook of Experimental Immunology* (D. M. Wei & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987 and annual updates); *PCR: The Polymerase Chain Reaction,* (Mullis et al., eds., 1994); *Current Protocols in Immunology* (J. E. Coligan et al., eds., 1991 and annual updates).

For techniques related to adenovirus, see, inter alia, Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; Bett et al. (1994) *Proc. Natl. Acad. Sci. USA* 91:8802–8806.

Definitions

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. Jackson R J, Howell M T, Kaminski A (1990) *Trends Biochem Sci* 15(12):477–83) and Jackson R J and Kaminski, A. (1995) *RNA* 1(10):985–1000). The present invention encompasses the use of any IRES element which is able to promote direct internal ribosome entry to the initiation codon of a cistron. "Under translational control of an IRES" as used herein means that translation is associated with the IRES and proceeds in a cap-independent manner. Examples of "IRES" known in the art include, but are not limited to IRES obtainable from picornavirus (Jackson et al., 1990, *Trends Biochem Sci* 15(12):477–483); and IRES obtainable from viral or cellular mRNA sources, such as for example, immunogloublin heavy-chain binding protein (BiP), the vascular endothelial growth factor (VEGF) (Huez et al. (1998) *Mol. Cell. Biol.* 18(11):6178–6190), the fibroblast growth factor 2, and insulin-like growth factor, the translational initiation factor eIF4G, yeast transcription factors TFIID and HAP4. IRES have also been reported in different viruses such as cardiovirus, rhinovirus, aphthovirus, HCV, Friend murine leukemia virus (FrMLV) and Moloney murine leukemia virus (MoMLV). As used herein, "IRES" encompasses functional variations of IRES sequences as long as the variation is able to promote direct internal ribosome entry to the initiation codon of a cistron. In preferred embodiments, the IRES is mammalian. In other embodiments, the IRES is viral or protozoan. In one illustrative embodiment disclosed herein, the IRES is obtainable from encephelomycarditis virus (ECMV) (commercially available from Novogen, Duke et al. (1992) *J. Virol* 66(3):1602–1609). In another illustrative embodiment disclosed herein, the IRES is from VEGF. Table I and Table II disclose a variety of IRES sequences useful in the present invention.

A "multicistronic transcript" refers to an mRNA molecule which contains more than one protein coding region, or cistron. A mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of a mRNA molecule.

As used herein, "co-transcribed" means that two (or more) coding regions of polynucleotides are under transcriptional control of single transcriptional control element.

A "gene" refers to a coding region of a polynucleotide. A "gene" may or may not include non-coding sequences and/or regulatory elements.

As used herein, a "transcription response element" or "transcriptional regulatory element", or "TRE" is a polynucleotide sequence, preferably a DNA sequence, which increases transcription of an operably linked polynucleotide sequence in a host cell that allows that TRE to function. A TRE can comprise an enhancer and/or a promoter. A "transcriptional regulatory sequence" is a TRE. A "target cell-specific transcriptional response element" or "target cell-specific TRE" is a polynucleotide sequence, preferably a DNA sequence, which is preferentially functional in a specific type of cell, that is, a target cell. Accordingly, a target cell-specific TRE transcribes an operably linked polynucleotide sequence in a target cell that allows the target cell-specific TRE to function. The term "target cell-specific", as used herein, is intended to include cell type specificity, tissue specificity, developmental stage specificity, and tumor specificity, as well as specificity for a cancerous state of a given target cell. "Target cell-specific TRE" includes cell type-specific and cell status-specific TRE, as well as "composite" TREs. The term "composite TRE" includes a TRE which comprises both a cell type-specific and a cell status-specific TRE. A target cell-specific TRE can also include a heterologous component, including, for example, an SV40 or a cytomegalovirus (CMV) promoter(s). An example of a target cell specific TRE which is tissue specific is a CMV TRE which contains both promoter(s) and enhancer(s).

As described in more detail herein, a target cell-specific TRE can comprise any number of configurations, including, but not limited to, a target cell-specific promoter; and target cell-specific enhancer; a heterologous promoter and a target cell-specific enhancer; a target cell-specific promoter and a heterologous enhancer; a heterologous promoter and a heterologous enhancer; and multimers of the foregoing. The promoter and enhancer components of a target cell-specific TRE may be in any orientation and/or distance from the coding sequence of interest, as long as the desired target cell-specific transcriptional activity is obtained. Transcriptional activation can be measured in a number of ways known in the art (and described in more detail below), but is generally measured by detection and/or quantitation of mRNA or the protein product of the coding sequence under control of (i.e., operably linked to) the target cell-specific TRE. As discussed herein, a target cell-specific TRE can be of varying lengths, and of varying sequence composition. As used herein, the term "cell status-specific TRE" is preferentially functional, i.e., confers transcriptional activation on an operably linked polynucleotide in a cell which allows a cell status-specific TRE to function, i.e., a cell which exhibits a particular physiological condition, including, but not limited to, an aberrant physiological state. "Cell status" thus refers to a given, or particular, physiological state (or condition) of a cell, which is reversible and/or progressive. The physiological state may be generated internally or externally; for example, it may be a metabolic state (such as in response to conditions of low oxygen), or it may be generated due to heat or ionizing radiation. "Cell status" is distinct from a "cell type", which relates to a differentiation state of a cell, which under normal conditions is irreversible. Generally (but not necessarily), as discussed herein, a cell status is embodied in an aberrant physiological state, examples of which are given below.

A "functional portion" of a target cell-specific TRE is one which confers target cell-specific transcription on an operably linked gene or coding region, such that the operably linked gene or coding region is preferentially expressed in the target cells.

By "transcriptional activation" or an "increase in transcription," it is intended that transcription is increased above basal levels in the target cell (i.e., target cell) by at least about 2 fold, preferably at least about 5 fold, preferably at least about 10 fold, more preferably at least about 20 fold, more preferably at least about 50 fold, more preferably at least about 100 fold, more preferably at least about 200 fold, even more preferably at least about 400 fold to about 500 fold, even more preferably at least about 1000 fold. Basal levels are generally the level of activity (if any) in a non-target cell (i.e., a different cell type), or the level of activity (if any) of a reporter construct lacking a target cell-specific TRE as tested in a target cell line.

A "functionally-preserved variant" of a target cell-specific TRE is a target cell-specific TRE which differs from another target cell-specific TRE, but still retains target cell-specific transcription activity, although the degree of activation may be altered (as discussed below). The difference in a target cell-specific TRE can be due to differences in linear sequence, arising from, for example, single base mutation(s), addition(s), deletion(s), and/or modification(s) of the bases. The difference can also arise from changes in the sugar(s), and/or linkage(s) between the bases of a target cell-specific TRE. For example, certain point mutations within sequences of TREs have been shown to decrease transcription factor binding and stimulation of transcription. See Blackwood, et al. (1998) *Science* 281:60–63 and Smith et al. (1997) *J. Biol. Chem.* 272:27493–27496. One of skill in the art would recognize that some alterations of bases in and around transcription factor binding sites are more likely to negatively affect stimulation of transcription and cell-specificity, while alterations in bases which are not involved in transcription factor binding are not as likely to have such effects. Certain mutations are also capable of increasing TRE activity. Testing of the effects of altering bases may be performed in vitro or in vivo by any method known in the art, such as mobility shift assays, or transfecting vectors containing these alterations in TRE functional and TRE non-functional cells. Additionally, one of skill in the art would recognize that point mutations and deletions can be made to a TRE sequence without altering the ability of the sequence to regulate transcription.

As used herein, a TRE derived from a specific gene is referred to by the gene from which it was derived and is a polynucleotide sequence which regulates transcription of an operably linked polynucleotide sequence in a host cell that expresses said gene. For example, as used herein, a "human glandular kallikrein transcriptional regulatory element", or "hKLK2-TRE" is a polynucleotide sequence, preferably a DNA sequence, which increases transcription of an operably linked polynucleotide sequence in a host cell that allows an hKLK2-TRE to function, suoh as a cell (preferably a mammalian cell, even more preferably a human cell) that expresses androgen receptor, such as a prostate cell. An hKLK2-TRE is thus responsive to the binding of androgen receptor and comprises at least a portion of an hKLK2 promoter and/or an hKLK2 enhancer (i.e., the ARE or androgen receptor binding site).

As used herein, a "probasin (PB) transcriptional regulatory element", or "PB-TRE" is a polynucleotide sequence, preferably a DNA sequence, which selectively increases transcription of an operably-linked polynucleotide sequence in a host cell that allows a PB-TRE to function, such as a cell (preferably a mammalian cell, more preferably a human cell, even more preferably a prostate cell) that expresses androgen receptor. A PB-TRE is thus responsive to the binding of androgen receptor and comprises at least a portion of a PB promoter and/or a PB enhancer (i.e., the ARE or androgen receptor binding site).

As used herein, a "prostate-specific antigen (PSA) transcriptional regulatory element", or "PSA-TRE", or "PSE-TRE" is a polynucleotide sequence, preferably a DNA sequence, which selectively increases transcription of an operably linked polynucleotide sequence in a host cell that allows a PSA-TRE to function, such as a cell (preferably a mammalian cell, more preferably a human cell, even more preferably a prostate cell) that expresses androgen receptor. A PSA-TRE is thus responsive to the binding of androgen receptor and comprises at least a portion of a PSA promoter and/or a PSA enhancer (i.e., the ARE or androgen receptor binding site).

As used herein, a "carcinoembryonic antigen (CEA) transcriptional regulatory element", or "CEA-TRE" is a polynucleotide sequence, preferably a DNA sequence, which selectively increases transcription of an operably linked polynucleotide sequence in a host cell that allows a CEA-TRE to function, such as a cell (preferably a mammalian cell, even more preferably a human cell) that expresses CEA. The CEA-TRE is responsive to transcription factors and/or co-factor(s) associated with CEA-producing cells and comprises at least a portion of the CEA promoter and/or enhancer.

As used herein, an "α-fetoprotein (AFP) transcriptional regulatory element", or "AFP-TRE" is a polynucleotide sequence, preferably a DNA sequence, which selectively increases transcription (of an operably linked polynucleotide sequence) in a host cell that allows an AFP-TRE to function, such as a cell (preferably a mammalian cell, even more preferably a human cell) that expresses AFP. The AFP-TRE is responsive to transcription factors and/or co-factor(s) associated with AFP-producing cells and comprises at least a portion of the AFP promoter and/or enhancer.

As used herein, an "a mucin gene (MUC) transcriptional regulatory element", or "MUC1-TRE" is a polynucleotide sequence, preferably a DNA sequence, which selectively increases transcription (of an operably-linked polynucleotide sequence) in a host cell that allows a MUC1-TRE to function, such as a cell (preferably a mammalian cell, even more preferably a human cell) that expresses MUC1. The MUC1-TRE is responsive to transcription factors and/or co-factor(s) associated with MUC1-producing cells and comprises at least a portion of the MUC1 promoter and/or enhancer.

As used herein, a "urothelial cell-specific transcriptional response element", or "urothelial cell-specific TRE" is polynucleotide sequence, preferably a DNA sequence, which increases transcription of an operably linked polynucleotide sequence in a host cell that allows a urothelial-specific TRE to function, i.e., a target cell. A variety of urothelial cell-specific TREs are known, are responsive to cellular proteins (transcription factors and/or co-factor(s)) associated with urothelial cells, and comprise at least a portion of a urothelial-specific promoter and/or a urothelial-specific enhancer. Methods are described herein for measuring the activity of a urothelial cell-specific TRE and thus for determining whether a given cell allows a urothelial cell-specific TRE to function.

As used herein, a "melanocyte cell-specific transcriptional response element", or "melanocyte cell-specific TRE" is polynucleotide sequence, preferably a DNA sequence, which increases transcription of an operably linked polynucleotide sequence in a host cell that allows a melanocyte-specific TRE to function, i.e., a target cell. A variety of melanocyte cell-specific TREs are known, are responsive to cellular proteins (transcription factors and/or co-factor(s)) associated with melanocyte cells, and comprise at least a portion of a melanocyte-specific promoter and/or a melanocyte-specific enhancer. Methods are described herein for measuring the activity of a melanocyte cell-specific TRE and thus for determining whether a given cell allows a melanocyte cell-specific TRE to function.

An "E1B 19-kDa region" (used interchangeably with "E1B 19-kDa genomic region") refers to the genomic region of the adenovirus E1B gene encoding the E1B 19-kDa product. According to wild-type Ad5, the E1B 19-kDa region is a 261 bp region located between nucleotide 1714 and nucleotide 2244. The E1B 19-kDa region has been described in, for example, Rao et al., *Proc. Natl. Acad. Sci. USA*, 89:7742–7746. The present invention encompasses deletion of part or all of the E1B 19-kDa region as well as embodiments wherein the E1B 19-kDa region is mutated, as long as the deletion or mutation lessens or eliminates the inhibition of apoptosis associated with E1B-19 kDa.

As used herein, a target cell-specific TRE can comprise any number of configurations, including, but not limited to, a target cell-specific promoter; a target cell-specific enhancer; a target cell-specific promoter and a target cell-specific enhancer; a target cell-specific promoter and a heterologous enhancer; a heterologous promoter and a target cell-specific enhancer; and multimers of the foregoing. The promoter and enhancer components of a target cell-specific TRE may be in any orientation and/or distance from the coding sequence of interest, as long as the desired target cell-specific transcriptional activity is obtained. Transcriptional activation can be measured in a number of ways known in the art (and described in more detail below), but is generally measured by detection and/or quantitation of mRNA or the protein product of the coding sequence under control of (i.e., operably linked to) the target cell-specific TRE.

"Replicating preferentially", as used herein, means that the adenovirus replicates more in a target cell than a non-target cell. Preferably, the adenovirus replicates at a significantly higher rate in target cells than non target cells; preferably, at least about 2-fold higher, preferably, at least about 5-fold higher, more preferably, at least about 10-fold higher, still more preferably at least about 50-fold higher, even more preferably at least about 100-fold higher, still more preferably at least about 400- to 500-fold higher, still more preferably at least about 1000-fold higher, most preferably at least about $1 \times 10^6$ higher. Most preferably, the adenovirus replicates solely in the target cells (that is, does not replicate or replicates at a very low levels in non-target cells).

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

An "adenovirus vector" or "adenoviral vector" (used interchangeably) comprises a polynucleotide construct of the invention. A polynucleotide construct of this invention may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a nonviral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1996) *Nucleic Acids Res.* 24: 2966–73. A phosphorothioate linkage can be used in place of a phosphodiester linkage. Braun et al. (1988) *J. Immunol.* 141:2084–9; Latimer et al. (1995) *Molec. Immunol.* 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18. A preferred alignment program is ALIGN Plus (Scientific and Educational Software, Pennsylvania), preferably using default parameters, which are as follows: mismatch=2; open gap=0; extend gap=2.

"Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

An "E3 region" (used interchangeably with "E3") is a term well understood in the art and means the region of the adenoviral genome that encodes the E3 products (discussed herein). Generally, the E3 region is located between about 28583 and 30470 of the adenoviral genome. The E3 region has been described in various publications, including, for example, Wold et al. (1995) *Curr. Topics Microbiol. Immunol.* 199:237–274.

A "portion" of the E3 region means less than the entire E3 region, and as such includes polynucleotide deletions as well as polynucleotides encoding one or more polypeptide products of the E3 region.

As used herein, "cytotoxicity" is a term well understood in the art and refers to a state in which a cell's usual biochemical or biological activities are compromised (i.e., inhibited). These activities include, but are not limited to, metabolism; cellular replication; DNA replication; transcription; translation; uptake of molecules. "Cytotoxicity" includes cell death and/or cytolysis. Assays are known in the art which indicate cytotoxicity, such as dye exclusion, $^3$H-thymidine uptake, and plaque assays.

The term "selective cytotoxicity", as used herein, refers to the cytotoxicity conferred by an adenovirus vector of the present invention on a cell which allows or induces a target cell-specific TRE to function (a target cell) when compared to the cytotoxicity conferred by an adenoviral vector of the present invention on a cell which does not allow a target cell-specific TRE to function (a non-target cell). Such cytotoxicity may be measured, for example, by plaque assays, by reduction or stabilization in size of a tumor comprising target cells, or the reduction or stabilization of serum levels of a marker characteristic of the tumor cells, or a tissue-specific marker, e.g., a cancer marker.

In the context of adenovirus, a "heterologous polynucleotide" or "heterologous gene" or "transgene" is any polynucleotide or gene that is not present in wild-type adenovirus. Preferably, the transgene will also not be expressed or present in the target cell prior to introduction by the adenovirus vector. Examples of preferred transgenes are provided below.

In the context of adenovirus, a "heterologous" promoter or enhancer is one which is not associated with or derived from an adenovirus gene.

In the context of adenovirus, an "endogenous" promoter, enhancer, or TRE is native to or derived from adenovirus. In the context of promoter, an "inactivation" means that there is a mutation of or deletion in part or all of the of the endogenous promoter, ie, a modification or alteration of the endogenous promoter, such as, for example, a point mutation or insertion, which disables the function of the promoter.

In the context of a target cell-specific TRE, a "heterologous" promoter or enhancer is one which is derived from a gene other than the gene from which a reference target cell-specific TRE is derived.

"Suppressing" tumor growth indicates a growth state that is curtailed when compared to growth without contact with, i.e., transfection by, an adenoviral vector described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

An "ADP coding sequence" is a polynucleotide that encodes ADP or a functional fragment thereof. In the context of ADP, a "functional fragment" of ADP is one that exhibits cytotoxic activity, especially cell lysis, with respect to adenoviral replication. Ways to measure cytotoxic activity are known in the art and are described herein.

A polynucleotide that "encodes" an ADP polypeptide is one that can be transcribed and/or translated to produce an ADP polypeptide or a fragment thereof. The anti-sense strand of such a polynucleotide is also said to encode the sequence.

An "ADP polypeptide" is a polypeptide containing at least a portion, or region, of the amino acid sequence of an ADP and which displays a function associated with ADP, particularly cytotoxicity, more particularly, cell lysis. As discussed herein, these functions can be measured using techniques known in the art. It is understood that certain sequence variations may be used, due to, for example, conservative amino acid substitutions, which may provide ADP polypeptides.

"Androgen receptor," or AR, as used herein refers to a protein whose function is to specifically bind to androgen and, as a consequence of the specific binding, recognize and bind to an androgen response element (ARE), following which the AR is capable of regulating transcriptional activity. The AR is a nuclear receptor that, when activated, binds to cellular androgen-responsive element(s). In normal cells the AR is activated by androgen, but in non-normal cells (including malignant cells) the AR may be activated by non-androgenic agents, including hormones other than androgens. Encompassed in the term "androgen receptor" are mutant forms of an androgen receptor, such as those characterized by amino acid additions, insertions, truncations and deletions, as long as the function is sufficiently preserved. Mutants include androgen receptors with amino acid additions, insertions, truncations and deletions, as long as the function is sufficiently preserved. In this context, a functional androgen receptor is one that binds both androgen and, upon androgen binding, an ARE.

A polynucleotide sequence that is "depicted in" a SEQ ID NO means that the sequence is present as an identical contiguous sequence in the SEQ ID NO. The term encompasses portions, or regions of the SEQ ID NO as well as the entire sequence contained within the SEQ ID NO.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, rodents, primates, and pets.

An "effective amount" is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

A given TRE is "derived from" a given gene if it is associated with that gene in nature.

"Expression" includes transcription and/or translation.

As used herein, the term "comprising" and its cognates are used in their inclusive sense; that is, equivalent to the term "including" and its corresponding cognates.

"A," "an" and "the" include plural references unless the context clearly dictates otherwise.

Internal Ribosome Entry Site (IRES)

IRES elements were first discovered in picornavirus mRNAs (Jackson R J, Howell M T, Kaminski A (1990) *Trends Biochem Sci* 15(12):477–83) and Jackson R J and Kaminski, A. (1995) *RNA* 1(10):985–1000). The present invention provides improved adenovirus vectors comprising co-transcribed first and second genes under transcriptional control of a heterologous, target cell-specific TRE, and wherein the second gene (i.e., coding region) is under translational control of an internal ribosome entry site (IRES). Any IRES may be used in the adenovirus vectors of the invention, as long as they exhibit requisite function in the vectors. Example of IRES which can be used in the present invention include those provided in Table I and referenced in Table II. Examples of IRES elements include the encephelomycarditis virus (EMCV) which is commercially available from Novagen (Duke et al. (1992) *J. Virol* 66(3):1602–9) the sequence for which is depicted in Table 1 (SEQ ID NO: 1). Another example of an IRES element disclosed herein is the VEGF IRES (Huez et al. (1998) *Mol Cell Biol* 18(11):6178–90). This IRES has a short segment and the sequence is depicted in Table 1 (SEQ ID NO: 2).

Figure 7:
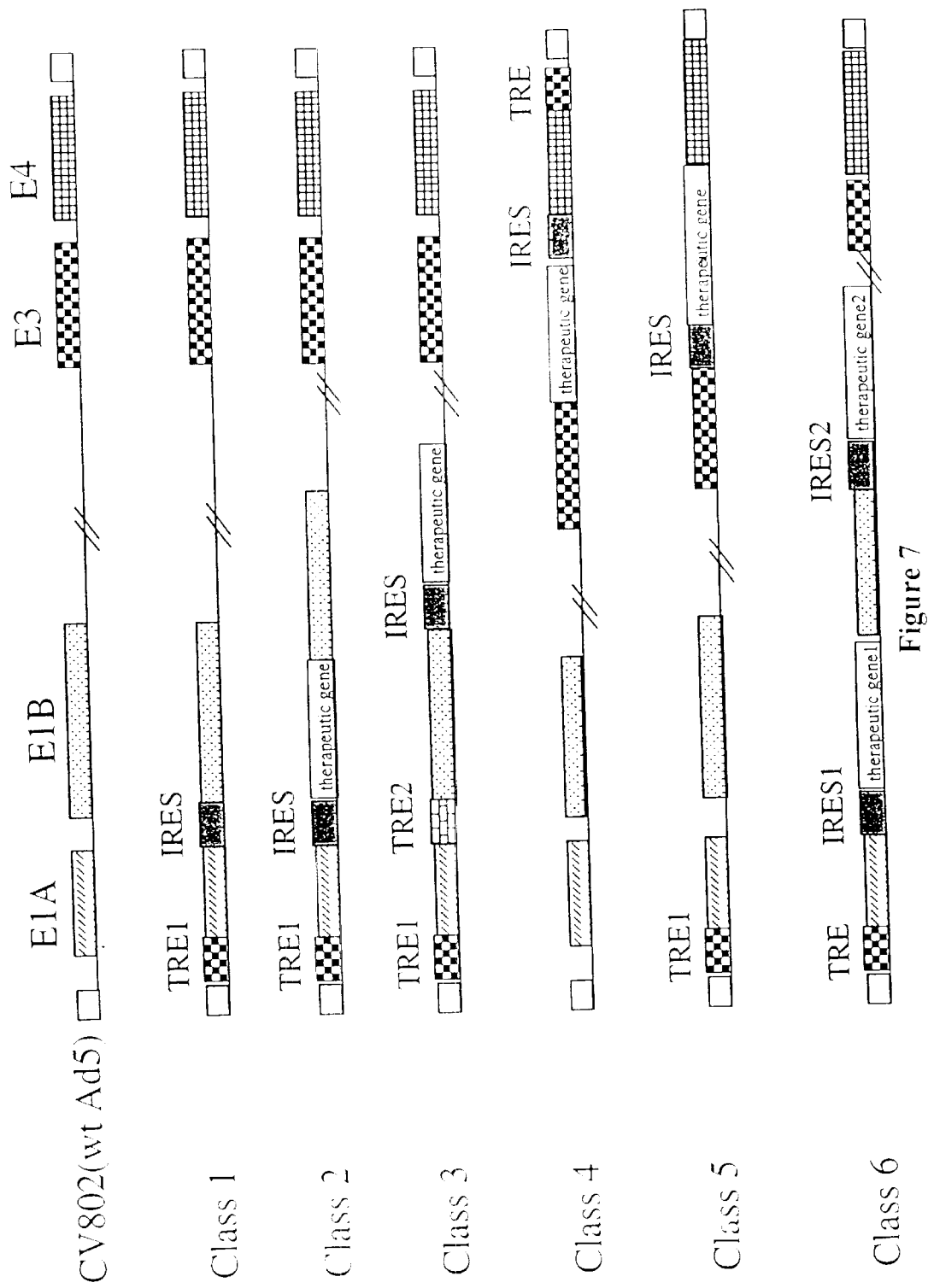
FIG. 7 is a schematic representation of adenovirus vectors described herein.

The IRES promotes direct internal ribosome entry to the initiation codon of a downstream cistron, leading to cap-independent translation. Thus, the product of a downstream cistron can be expressed from a bicistronic (or multicistronic) mRNA, without requiring either cleavage of a polyprotein or generation of a monocistronic mRNA. Therefore, in one illustrative embodiment of the present invention, an adenovirus vector comprising E1B under translational control of an IRES allows translation of E1B from a bicistronic E1A-E1B mRNA under control of a target cell-specific TRE. FIG. 7 provides a schematic representation of adenovirus constructs of the present invention.

Internal ribosome entry sites are approximately 450 nucleotides in length and are characterized by moderate conservation of primary sequence and strong conservation of secondary structure. The most significant primary sequence feature of the IRES is a pyrimidine-rich site whose start is located approximately 25 nucleotides upstream of the 3' end of the IRES. See Jackson et al.(1990).

Three major classes of picornavirus IRES have been identified and characterized: (1) the cardio- and aphthovirus class (for example, the encephelomycarditis virus, Jang et al. (1990) *Gene Dev* 4:1560–1572); (2) the entero- and rhinovirus class (for example, polioviruses, Borman et al. (1994) *EMBO J*. 13:314903157); and (3)the hepatitis A virus (HAV) class, Glass et al. (1993) *Virol* 193:842–852). For the first two classes, two general principles apply. First, most of the 450-nucleotide sequence of the IRES functions to maintain particular secondary and tertiary structures conducive to ribosome binding and translational initiation. Second, the ribosome entry site is an AUG triplet located at the 3' end of the IRES, approximately 25 nucleotides downstream of a conserved oligopyrimidine tract. Translation initiation can occur either at the ribosome entry site (cardioviruses) or at the next downstream AUG (entero/rhinovirus class). Initiation occurs at both sites in aphthoviruses.

HCV and pestiviruses such as bovine viral diarrhea virus (BVDV) or classical swine fever virus (CSFV) have 341 nt and 370 nt long 5'-UTR respectively. These 5'-UTR fragments form similar RNA secondary structures and can have moderately efficient IRES function (Tsukiyama-Kohara et al. (1992) *J Virol.* 66:1476–1483; Frolov I et al., (1998) *RNA* 4:1418–1435). Table I depicts the 5'-UTR region from HCV genome sequence (GenBank accession D14853).

Leishmania RNA virus 1 (LRV1) is a double-stranded RNA virus. Its 128 nt long 5'-UTR has IRES activity to facilitate the cap-independent translation, (Maga et al. (1995) *Mol Cell Biol* 15:4884–4889). This fragment also forms conserved stemloop secondary structure and at least the front part is essential.

Recent studies showed that both Friend-murine leukemia virus (MLV) 5'-UTR and rat retrotransposon virus-like 30S (VL30) sequences contain IRES structure of retroviral origin (Torrent et al. (1996) *Hum Gene Ther* 7:603–612). These fragments are also functional as packing signal when used in retrovirus derived vectors. Studies of avian reticuloendotheliosis virus type A (REV-A) show that its IRES maps downstream of the packaging/dimerization (E/DLS) sequence and the minimal IRES sequence appears to be within a 129 nt fragment (452–580) of the 5' leader, immediately upstream of the gag AUG codon (Lopez-Lastra et al. (1997) *Hum Gene Ther* 8:1855–1865).

In eukaryotic cells, translation is normally initiated by the ribosome scanning from the capped mRNA 5' end, under the control of initiation factors. However, several cellular mRNAs have been found to have IRES structure to mediate the cap-independent translation (van der Velde, et al. (1999) *Int J Biochem Cell Biol.* 31:87–106). Examples are immunoglobulin heavy-chain binding protein (BiP) (Macejak et al. (1991) *Nature* 353:90–94), antennapedia mRNA of Drosophilan (Oh et al. (1992) *Gene and Dev* 6:1643–1653), fibroblast growth factor-2 (FGF-2) (Vagner et al. (1995) *Mol Cell Biol* 15:35–44), platelet-derived growth factor B (PDGF-B) (Bernstein et al. (1997) *J Biol Chem* 272:9356–9362), insulin-like growth factor II (Teerink et al. (1995) *Biochim Biophys Acta* 1264:403–408), and the translation initiation factor eIF4G (Gan et al. (1996) *J Biol Chem* 271:623–626). Table 1 depicts the 5'-noncoding region for BiP and PDGF. Recently, vascular endothelial growth factor (VEGF) was also found to have IRES element (Stein et al. (1998) *Mol Cell Biol* 18:3112–3119; Huez et al. (1998) *Mol Cell Biol* 18:6178–6190).

Apart from the oligopyrimidine tract, nucleotide sequence per se does not appear to be important for IRES function. Without wishing to be bound by theory, a possible explanation for the function of an IRES is that it forms secondary and/or tertiary structures which orient particular single-stranded regions of its sequence in a three-dimensional configuration that is conducive to interaction with a mammalian ribosome (either ribosomal protein and/or ribosomal RNA components) and/or initiation factor(s) and/or RNA binding proteins which interact with ribosomes and/or initiation factors. It is also possible that the three-dimensional structure of the IRES is determined or stabilized by one or more RNA-binding proteins. Thus it is possible to devise synthetic IRES sequences having similar single-stranded regions in a similar three-dimensional configuration.

In certain cases, one or more trans-acting cellular proteins may be required for IRES function. For example, the HAV and entero/rhinovirus IRESes function inefficiently in vitro in reticulocyte lysates. Supplementation of a reticulocyte lysate with a cytoplasmic extract from HeLa, Krebs II ascites, or L-cells restores activity of entero/rhinovirus IRESes. See, for example, Brown et al. (1979) *Virology* 97:396–405; and Dorner et al. (1984) *J. Virol.* 50:507–514. Activity of the HAV IRES in vitro is stimulated by liver cytoplasmic extracts. Glass et al. (1993) *Virology* 193:1047–1050. These observations indicate that cell-specific translational regulation can be achieved through the use of a cell-specific IRES. Furthermore, coordinated cell-specific transcriptional and translational regulatory elements can be included in a vector to further increase cell specificity of viral replication. For example, the combination of an AFP-TRE and a HAV-IRES can be used to direct preferential replication of a vector in hepatic cells. Thus, in one illustrative embodiment, a vector comprises an AFP-TRE regulating the transcription of a bicistronic E1A-E1B mRNA in which E1B translation is regulated by an ECMV IRES. In another illustrative embodiment, the vector comprises a probasin-TRE regulating the transcription of a bicistronic E1A-E1B mRNA in which E1B translation is regulated by an ECMV IRES. In yet another illustrative embodiment, a vector comprises a CMV-TRE regulating the transcription of a bicistronic E1A-E1B mRNA in which E1B translation is regulated by an ECMV IRES.

Examples of IRES which can be used in the present invention include those provided in Table 1 and Table 2. An IRES sequence which may be used in the present invention may be tested as follows. A test vector is produced having a reporter gene, such as luciferase, for example, placed under translational control of an IRES to be tested. A desired cell type is transfected with the vector containing the desired IRES-reporter gene and an assay is performed to detect the presence of the reporter gene. In one illustrative example, the test vector comprises a co-transcribed chloramphenicol transferase (CAT) and luciferase encoding gene transcriptionally driven by a CMV promoter wherein the luciferase encoding gene is translationally driven by an IRES to be tested. Host cells are transiently transfected with the test vector by means known to those of skill in the art and assayed for the presence of luciferase.

IRES may be prepared using standard recombinant and synthetic methods known in the art, and as described in the Examples. For cloning convenience, restriction sites may be engineered into the ends of the IRES fragments to be used.

Transcriptional Response Elements (TREs)

The adenovirus vectors of the invention comprise target cell specific TREs which direct preferential expression of an operatively linked gene (or genes) in a particular target cell. A TRE can be tissue-specific, tumor-specific, developmental stage-specific, cell status specific, etc., depending on the type of cell present in the tissue or tumor.

Cell- and tissue-specific transcriptional regulatory elements, as well as methods for their identification, isolation, characterization, genetic manipulation and use for regulation of operatively linked coding sequences, are well known in the art. A TRE can be derived from the transcriptional regulatory sequences of a single gene, or sequences from different genes can be combined to produce a functional TRE. A cell-specific TRE is preferentially functional in a limited population (or type) of cells, e.g., prostate cells or liver cells. Accordingly, in some embodiments, the TRE used is preferentially functional in any of the following cell types: prostate; liver; breast; urothelial cells (bladder); colon; lung; ovarian; pancreas; stomach; and uterine. In other embodiments, in accordance with cell status, the TRE is functional in or during: low oxygen conditions (hypoxia); certain stages of cell cycle, such as S phase; elevated temperature; ionizing radiation.

As is known in the art, activity of TREs can be inducible. Inducible TREs generally exhibit low activity in the absence of inducer, and are up-regulated in the presence of inducer. Inducers include, for example, nucleic acids, polypeptides, small molecules, organic compounds and/or environmental conditions such as temperature, pressure or hypoxia. Inducible TREs may be preferred when expression is desired only at certain times or at certain locations, or when it is desirable to titrate the level of expression using an inducing agent. For example, transcriptional activity from the PSE-TRE, PB-TRE and hKLK2-TRE is inducible by androgen, as described herein and in PCT/US98/04090. Accordingly, in one embodiment of the present invention, an adenovirus vector comprises an inducible heterologous TRE.

TRE multimers are also useful in the disclosed vectors. For example, a TRE can comprise a tandem series of at least two, at least three, at least four, or at least five promoter fragments. Alternatively, a TRE can comprise one or more promoter regions along with one or more enhancer regions. TRE multimers can also comprise promoter and/or enhancer sequences from different genes. The promoter and enhancer components of a TRE can be in any orientation with respect to each other and can be in any orientation and/or any distance from the coding sequence of interest, as long as the desired cell-specific transcriptional activity is obtained.

The disclosed vectors are designed such that replication is preferentially enhanced in target cells in which the TRE(s) is (are) functional. More than one TRE can be present in a vector, as long as the TREs are functional in the same target cell. However, it is important to note that a given TRE can be functional in more than one type of target cell. For example, the CEA-TRE functions in, among other cell types, gastric cancer cells, colorectal cancer cells, pancreatic cancer cells and lung cancer cells.

A TRE for use in the present vectors may or may not comprise a silencer. The presence of a silencer (i.e., a negative regulatory element known in the art) can assist in shutting off transcription (and thus replication) in non-target cells. Thus, presence of a silencer can confer enhanced cell-specific vector replication by more effectively preventing replication in non-target cells. Alternatively, lack of a silencer may stimulate replication in target cells, thus conferring enhanced target cell-specificity.

As is readily appreciated by one skilled in the art, a TRE is a polynucleotide sequence, and, as such, can exhibit function over a variety of sequence permutations. Methods of nucleotide substitution, addition, and deletion are known in the art, and readily-available functional assays (such as the CAT or luciferase reporter gene assay) allow one of ordinary skill to determine whether a sequence variant exhibits requisite cell-specific transcription regulatory function. Hence, functionally preserved variants of TREs, comprising nucleic acid substitutions, additions, and/or deletions, can be used in the vectors disclosed herein. Accordingly, variant TREs retain function in the target cell but need not exhibit maximal function. In fact, maximal transcriptional activation activity of a TRE may not always be necessary to achieve a desired result, and the level of induction afforded by a fragment of a TRE may be sufficient for certain applications. For example, if used for treatment or palliation of a disease state, less-than-maximal responsiveness may be sufficient if, for example, the target cells are not especially virulent and/or the extent of disease is relatively confined.

Certain base modifications may result in enhanced expression levels and/or cell-specificity. For example, nucleic acid sequence deletions or additions within a TRE can move transcription regulatory protein binding sites closer or farther away from each other than they exist in their normal configuration, or rotate them so they are on opposite sides of the DNA helix, thereby altering spatial relationship among TRE-bound transcription factors, resulting in a decrease or increase in transcription, as is known in the art. Thus, while not wishing to be bound by theory, the present disclosure contemplates the possibility that certain modifications of a TRE will result in modulated expression levels as directed by the TRE, including enhanced cell-specificity. Achievement of enhanced expression levels may be especially desirable in the case of more aggressive forms of neoplastic growth, and/or when a more rapid and/or aggressive pattern of cell killing is warranted (for example, in an immunocompromised individual).

Transcriptional activity directed by a TRE (including both inhibition and enhancement) can be measured in a number of ways known in the art (and described in more detail below), but is generally measured by detection and/or quantitation of mRNA and/or of a protein product encoded by the sequence under control of (i. e., operably linked to) a TRE.

As discussed herein, a TRE can be of varying lengths, and of varying sequence composition. The size of a heterologous TRE will be determined in part by the capacity of the viral vector, which in turn depends upon the contemplated form of the vector (see infra). Generally minimal sizes are preferred for TREs, as this provides potential room for insertion of other sequences which may be desirable, such as transgenes (discussed infra) and/or additional regulatory sequences. In a preferred embodiment, such an additional regulatory sequence is an IRES. However, if no additional sequences are contemplated, or if, for example, an adenoviral vector will be maintained and delivered free of any viral packaging constraints, larger TRE sequences can be used as long as the resultant adenoviral vector remains replication-competent.

An adenoviral vector can be packaged with extra sequences totaling up to about 5% of the genome size, or approximately 1.8 kb, without requiring deletion of viral sequences. If non-essential sequences are removed from the adenovirus genome, an additional 4.6 kb of insert can be tolerated (i.e., for a total insertion capacity of about 6.4 kb). Examples of non-essential adenoviral sequences that can be deleted are E3, and E4 sequences other than those which encode E4 ORF6.

To minimize non-specific replication, endogenous (e. g., adenovirus) TREs are preferably removed from the vector. Besides facilitating target cell-specific replication, removal of endogenous TREs also provides greater insert capacity in a vector, which may be of special concern if an adenoviral vector is to be packaged within a virus particle. Even more importantly, deletion of endogenous TREs prevents the possibility of a recombination event whereby a heterologous TRE is deleted and the endogenous TRE assumes transcriptional control of its respective adenovirus coding sequences (thus allowing non-specific replication). In one embodiment, an adenoviral vector is constructed such that the endogenous transcription control sequences of adenoviral genes are deleted and replaced by one or more heterologous TREs. However, endogenous TREs can be maintained in the adenovirus vector(s), provided that sufficient cell-specific replication preference is preserved. These embodiments are constructed by inserting heterologous TREs between an endogenous TRE and a replication gene coding segment. Requisite cell-specific replication preference is determined by conducting assays that compare replication of the adenovirus vector in a cell which allows function of the heterologous TREs with replication in a cell which does not.

Generally, a TRE will increase replication of a vector in a target cell by at least about 2-fold, preferably at least about 5-fold, preferably at least about 10-fold more preferably at least about 20-fold, more preferably at least about 50-fold, more preferably at least about 100-fold, more preferably at least about 200-fold, even more preferably at least about 400- to about 500- fold, even more preferably at least about 1000-fold, compared to basal levels of replication in the absence of a TRE. The acceptable differential can be determined empirically (by measurement of mRNA levels using, for example, RNA blot assays, RNase protection assays or other assays known in the art) and will depend upon the anticipated use of the vector and/or the desired result.

Replication-competent adenovirus vectors directed at specific target cells can be generated using TREs that are preferentially functional in a target cell. In one embodiment of the present invention, the target cell is a tumor cell.

Non-limiting examples of tumor cell-specific heterologous TREs, and their respective target cells, include: probasin (PB), target cell, prostate cancer (PCT/US98/04132); α-fetoprotein (AFP), target cell liver cancer (PCT/US98/04084); mucin-like glycoprotein DF3 (MUC1), target cell, breast carcinoma (PCT/US98/04080); carcinoembryonic antigen (CEA), target cells, colorectal, gastric, pancreatic, breast, and lung cancers (PCT/US98/04133); plasminogen activator urokinase (uPA) and its receptor gene, target cells, breast, colon, and liver cancers (PCT/US98/04080); E2F1 (cell cycle S-phase specific promoter); target cell, tumors with disrupted retinoblastoma gene function, and HER-2/neu (c-erbB2/neu), target cell, breast, ovarian, stomach, and lung cancers (PCT/US98/04080); tyrosinase, target cell, melanoma cells as described herein and uroplakins, target cell, bladder cells as described herein. Methods for identification, isolation, characterization and utilization of additional target cell-specific TREs are readily available to those of skill in the art.

In addition, tumor-specific TREs can be used in conjunction with tissue-specific TREs from the following exemplary genes (tissue in which the TREs are specifically functional are in parentheses): hypoxia responsive element, vascular endothelial growth factor receptor (endothelium), albumin (liver), factor VII (liver), fatty acid synthase (liver), Von Willebrand factor (brain endothelium), alpha-actin and myosin heavy chain (both in smooth muscle), synthetase I (small intestine) Na+—K+—Cl⁻transporter (kidney). Additional tissue-specific TREs are known in the art.

In one embodiment of the present invention, a target cell-specific, heterologous TRE is tumor cell-specific. A vector can comprise a single tumor cell-specific TRE or multiple heterologous TREs which are tumor cell-specific and functional in the same cell. In another embodiment, a vector comprises one or more heterologous TREs which are tumor cell-specific and additionally comprises one or more heterologous TREs which are tissue specific, whereby all TREs are functional in the same cell.

Prostate-Specific TREs

In one embodiment, adenovirus vectors comprise heterologous TREs that are prostate cell specific. For example, TREs that function preferentially in prostate cells and can be used to target adenovirus replication to prostate neoplasia, include, but are not limited to, TREs derived from the prostate-specific antigen gene (PSA-TRE) (Henderson U.S. Pat. No. 5,698,443); the glandular kallikrein-1 gene (from the human gene, hKLK2-TRE) (PCT US98/16312), and the probasin gene (PB-TRE) (PCT/US98/04132). All three of these genes are preferentially expressed in prostate cells and their expression is androgen-inducible. Generally, expression of genes responsive to androgen induction is mediated by an androgen receptor (AR).

Prostate-Specific Antigen (PSA)

PSA is synthesized exclusively in prostatic epithelial cells and is synthesized in these cells whether they are normal, hyperplastic, or malignant. This tissue-specific expression of PSA has made it an excellent biomarker for benign prostatic hyperplasia (BPH) and prostatic carcinoma (CaP). Normal serum levels of PSA are typically below 5 ng/ml, with elevated levels indicative of BPH or CaP. Lundwall et al. (1987) *FEBS Lett.* 214:317; Lundwall (1989) *Biochem. Biophys. Res. Comm.* 161:1151; and Riegmann et al. (1991) *Molec. Endocrin.* 5:1921.

The region of the PSA gene that provides androgen-dependent cell specificity, particularly in prostate cells, involves approximately 6.0 kilobases (kb). Schuur et al. (1996) *J. Biol. Chem.* 271:7043–7051. An enhancer region of approximately 1.5 kb in humans is located between nt −5322 and nt −3739, relative to the transcription start site of the PSA gene. Within these enhancer sequences is an androgen response element (ARE) a sequence which binds androgen receptor. The sequence coordinates of the PSA promoter are from about nt −540 to nt +8 relative to the transcription start site. Juxtapositioning of the enhancer and promoter yields a fully functional, minimal prostate-specific TRE (PSA-TRE). Other portions of this approximately 6.0 kb region of the PSA gene can be used in the vectors described herein, as long as requisite functionality is maintained.

Human Glandular Kallikrein (hKLK2)

Human glandular kallikrein (hKLK2, encoding the hK2 protein) is expressed exclusively in the prostate and its expression is up-regulated by androgens, primarily through transcriptional activation. Wolf et al. (1992) *Molec. Endocrinol.* 6:753–762; Morris (1989) *Clin. Exp. Pharm. Physiol.* 16:345–351; Qui et al. (1990) *J. Urol.* 144:1550–1556; and Young et al. (1992) *Biochem.* 31:818–824. The levels of hK2 found in various tumors and in the serum of patients with prostate cancer indicate that hK2 antigen may be a significant marker for prostate cancer. Charlesworth et al. (1997) *Urology* 49:487–493. Expression of hK2 has been detected in each of 257 radical prostatectomy specimens analyzed. Darson et al. (1997) *Urology* 49:857–862. The intensity and extent of hK2 expression, detected using specific antibodies, was observed to increase from benign epithelium to high-grade prostatic intraepithelial neoplasia (PIN) and adenocarcinoma.

The activity of the hKLK2 promoter has been described and a region up to nt −2256 relative to the transcription start site was previously disclosed. Schedlich et al. (1987) *DNA* 6:429–437. The hKLK2 promoter is androgen responsive and, in plasmid constructs wherein the promoter alone controls the expression of a reporter gene, expression of the reporter gene is increased approximately 10-fold in the presence of androgen. Murtha et al. (1993) *Biochem.* 32:6459–6464. hKLK2 enhancer activity is found within a polynucleotide sequence approximately nt −12,014 to nt −2257 relative to the start of transcription and, when this sequence is operably linked to an hKLK2 promoter and a reporter gene, transcription of operably-linked sequences in prostate cells increases in the presence of androgen to levels approximately 30-fold to approximately 100-fold greater than the level of transcription in the absence of androgen. This induction is generally independent of the orientation and position of the enhancer sequences. Enhancer activity has also been demonstrated in the following regions (all relative to the transcription start site):about nt −3993 to about nt −3643, about nt −4814 to about nt −3643, about nt −5155 to about nt −3387, about nt −6038 to about nt −2394.

Thus, a hKLK2 enhancer can be operably linked to an hKLK2 promoter or a heterologous promoter to form a hKLK2 transcriptional regulatory element (hKLK2-TRE). A hKLK2-TRE can then be operably linked to a heterologous polynucleotide to confer hKLK2-TRE-specific transcriptional regulation on the linked gene, thus increasing its expression.

Probasin

The rat probasin (PB) gene encodes an androgen and zinc-regulated protein first characterized in the dorsolateral prostate of the rat. Dodd et al. (1983) *J. Biol. Chem.* 258:10731–10737; Matusik et al. (1986) *Biochem. Cell. Biol.* 64:601–607; and Sweetland et al. (1988) *Mol. Cell. Biochem.* 84:3–15. The dorsolateral lobes of the murine prostate are considered the most homologous to the peripheral zone of the human prostate, where approximately 68% of human prostate cancers are thought to originate.

A PB-TRE has been shown to exist in an approximately 0.5 kb fragment of sequence upstream of the probasin coding sequence, from about nt −426 to about nt +28 relative to the transcription start site. This minimal promoter sequence from the PB gene appears to provide sufficient information to direct prostate-specific developmental- and hormone-regulated expression of an operably linked heterologous gene in transgenic mice. Greenberg et al. (1994) *Mol. Endocrinol.* 8:230–239.

Alpha-Fetoprotein

α-fetoprotein (AFP) is an oncofetal protein, the expression of which is primarily restricted to developing tissues of endodermal origin (yolk sac, fetal liver, and gut), although the level of its expression varies greatly depending on the tissue and the developmental stage. AFP is of clinical interest because the serum concentration of AFP is elevated in a majority of hepatoma patients, with high levels of AFP found in patients with advanced disease. High serum AFP levels in patients appear to be due to AFP expression in hepatocellular carcinoma (HCC), but not in surrounding normal liver. Thus, expression of the AFP gene appears to be characteristic of hepatoma cells. An AFP-TRE is described in for example PCT/US98/04084.

According to published reports, the AFP-TRE is responsive to cellular proteins (transcription factors and/or co-factor(s)) associated with AFP-producing cells, such as AFP-binding protein (see, for example, U.S. Pat. No. 5,302, 698) and comprises at least a portion of an AFP promoter and/or an AFP enhancer. Cell-specific TREs from the AFP gene have been identified. For example, the cloning and characterization of human AFP-specific enhancer activity is described in Watanabe et al. (1987) *J. Biol. Chem.* 262:4812–4818. A 5' AFP regulatory region (containing the promoter, putative silencer, and enhancer) is contained within approximately 5 kb upstream from the transcription start site.

Within the APP regulatory region, a human AFP enhancer region is located between about nt −3954 and about nt −3335, relative to the transcription start site of the AFP gene. The human AFP promoter encompasses a region from about nt −174 to about nt +29. Juxtapositioning of these two genetic elements, yields a fully functional AFP-TRE. Ido et al. (1995) *Cancer Res.* 55:3105–3109 describe a 259 bp promoter fragment (nt −230 to nt +29) that is specific for expression in HCC cells. The AFP enhancer, located between nt −3954 and nt −3335 relative to the transcription start site, contains two regions, denoted A and B. The promoter region contains typical TATA and CAAT boxes. Preferably, the AFP-TRE contains at least one enhancer region. More preferably, the AFP-TRE contains both enhancer regions.

Suitable target cells for vectors containing AFP-TREs are any cell type that allow an AFP-TRE to function. Preferred are cells that express or produce AFP, including, but not limited to, tumor cells expressing AFP. Examples of such cells are hepatocellular carcinoma (HCC) cells, gonadal and other germ cell tumors (especially endodermal sinus tumors), brain tumor cells, ovarian tumor cells, acinar cell carcinoma of the pancreas (Kawamoto et al. (1992) *Hepatogastroenterology* 39:282–286), primary gall bladder tumor (Katsuragi et al. (1989) *Rinsko Hoshasen* 34:371–374), uterine endometrial adenocarcinoma cells (Koyama et al. (1996) *Jpn. J. Cancer Res.* 87:612–617), and any metastases of the foregoing (which can occur in lung, adrenal gland, bone marrow, and/or spleen). In some cases, metastatic disease to the liver from certain pancreatic and stomach cancers produce AFP. Especially preferred as target cells for an AFP-TRE are hepatocellular carcinoma cells and any of their metastases.

AFP production can be measured (and hence AFP-producing cells can be identified) using immunoassays standard in the art, such as RIA, ELISA or protein immunoblotting (Western blots) to determine levels of AFP protein production; and/or RNA blotting (Northern blots) to determine AFP mRNA levels. Alternatively, such cells can be identified and/or characterized by their ability to activate transcriptionally an AFP-TRE (i.e., allow an AFP-TRE to function).

See also co-owned PCT WO98/39465 regarding AFP-TREs. As described in more detail therein, an AFP-TRE can comprise any number of configurations, including, but not limited to, an AFP promoter; an AFP enhancer; an AFP promoter and an AFP enhancer; an AFP promoter and a heterologous enhancer; a heterologous promoter and an AFP enhancer; and multimers of the foregoing. The promoter and enhancer components of an AFP-TRE can be in any orientation and/or distance from the coding sequence of interest, as long as the desired AFP cell-specific transcriptional activity is obtained. An adenovirus vector of the present invention can comprise an AFP-TRE endogenous silencer element or the AFP-TRE endogenous silencer element can be deleted.

Urokinase Plasminogen Activator

The protein urokinase plasminogen activator (uPA) and its cell surface receptor, urokinase plasminogen activator receptor (uPAR), are expressed in many of the most frequently-occurring neoplasms and appear to represent important proteins in cancer metastasis. Both proteins are implicated in breast, colon, prostate, liver, renal, lung and ovarian cancer. Sequence elements that regulate uPA and uPAR transcription have been extensively studied. Riccio et al. (1985) *Nucleic Acids Res.* 13:2759–2771; Cannio et al. (1991) *Nucleic Acids Res.* 19:2303–2308.

Carcinoembryonic Antigen (CEA)

CEA is a 180,000 Dalton, tumor-associated, glycoprotein antigen present on endodermally-derived neoplasms of the gastrointestinal tract, such as colorectal, gastric (stomach) and pancreatic cancer, as well as other adenocarcinomas such as breast and lung cancers. CEA is of clinical interest because circulating CEA can be detected in the great majority of patients with CEA-positive tumors. In lung cancer, about 50% of total cases have circulating CEA, with high concentrations of CEA (greater than 20 ng/ml) often detected in adenocarcinomas. Approximately 50% of patients with gastric carcinoma are serologically positive for CEA.

The 5'-flanking sequence of the CEA gene has been shown to confer cell-specific activity. The CEA promoter region, approximately the first 424 nucleotides upstream of the transcriptional start site in the 5' flanking region of the gene, was shown to confer cell-specific activity by virtue of providing higher promoter activity in CEA-producing cells than in non-producing HeLa cells. Schrewe et al. (1990) *Mol. Cell. Biol.* 10:2738–2748. In addition, cell-specific enhancer regions have been found. See PCT/GB/02546 The CEA promoter, putative silencer, and enhancer elements appears to be contained within a region that extends approximately 14.5 kb upstream from the transcription start site. Richards et al. (1995); PCT/GB/02546. Further characterization of the 5'-flanking region of the CEA gene by Richards et al. (1995) supra indicated that two upstream regions (one between about −13.6 and about −10.7 kb, and the other between about −6.1 and about −4.0 kb), when linked to the multimerized promoter, resulted in high-level and selective expression of a reporter construct in CEA-producing LoVo and SW1463 cells. Richards et al. (1995) supra also localized the promoter region between about nt −90 and about nt +69 relative to the transcriptional start site, with the region between about nt −41 and about nt −18 being essential for expression. PCT/GB/02546 describes a series of 5'-flanking CEA fragments which confer cell-specific activity, including fragments comprising the following sequences: about nt −299 to about nt +69; about nt −90 to about nt +69; nt −14,500 to nt −10,600; nt −13,600 to nt −10,600; and nt −6100 to nt −3800, with all coordinates being relative to the transcriptional start point. In addition, cell-specific transcription activity is conferred on an operably linked gene by the CEA fragment from nt −402 to nt +69.

CEA-TREs for use in the vectors disclosed herein are derived from mammalian cells, including, but not limited to, human cells. Thus, any of the CEA-TREs TREs can be used as long as the requisite desired functionality is displayed by the vector.

Mucin

The protein product of the MUC1 gene (known as mucin, MUC1 protein; episialin; polymorphic epithelial mucin or PEM; EMA; DF3 antigen; NPGP; PAS-O; or CA15.3 antigen) is normally expressed mainly at the apical surface of epithelial cells lining the glands or ducts of the stomach, pancreas, lungs, trachea, kidney, uterus, salivary glands, and mammary glands. Zotter et al. (1988) *Cancer Rev.* 11–12:55–101; and Girling et al. (1989) *Int. J. Cancer* 43:1072–1076. However, mucin is overexpressed in 75–90% of human breast carcinomas. Kufe et al. (1984) *Hybridoma* 3:223–232. For reviews, see Hilkens (1988) *Cancer Rev.* 11–12:25–54; and Taylor-Papadimitriou, et al. (1990) *J. Nucl. Med. Allied Sci.* 34:144–150. Mucin protein expression correlates with the degree of breast tumor differentiation. Lundy et al. (1985) *Breast Cancer Res. Treat.* 5:269–276.

Overexpression of the MUC1 gene in human breast carcinoma cells MCF-7 and ZR-75-1 appears to occur at the transcriptional level. Kufe et al. (1984) supra; Kovarik (1993) *J. Biol. Chem.* 268:9917–9926; and Abe et al. (1990) *J. Cell. Physiol.* 143:226–231. The regulatory sequences of the MUC1 gene have been cloned, including the approximately 0.9 kb upstream of the transcription start site which contains a TRE that appears to be involved in cell-specific transcription. Abe et al. (1993) *Proc. Natl. Acad. Sci. USA* 90:282–286; Kovarik et al. (1993) supra; and Kovarik et al. (1996) *J. Biol. Chem.* 271:18140–18147.

MUC1-TREs are derived from mammalian cells, including but not limited to, human cells. Preferably, the MUC1-TRE is human. In one embodiment, the MUC1-TRE contains the entire 0.9 kb 5' flanking sequence of the MUC1 gene. In other embodiments, MUC1-TREs comprise the following sequences (relative to the transcription start site of the MUC1 gene) operably-linked to a promoter: about nt −725 to about nt +31, about nt −743 to about nt +33, about nt −750 to about nt +33, and about nt −598 to about nt +485.

c-erbB2/HER-2/neu

The c-erbB2/neu gene (HER-2/neu or HER) is a transforming gene that encodes a 185 kD epidermal growth factor receptor-related transmembrane glycoprotein. In humans, the c-erbB2/neu protein is expressed during fetal development and, in adults, the protein is weakly detectable (by immunohistochemistry) in the epithelium of many normal tissues. Amplification and/or over-expression of the c-erbB2/neu gene has been associated with many human cancers, including breast, ovarian, uterine, prostate, stomach and lung cancers. The clinical consequences of overexpression of the c-erbB2/neu protein have been best studied in breast and ovarian cancer. c-erbB2/neu protein overexpression occurs in 20 to 40% of intraductal carcinomas of the breast and 30% of ovarian cancers, and is associated with a poor prognosis in subcategories of both diseases.

Human, rat and mouse c-erbB2/neu TREs have been identified and shown to confer transcriptional activity specific to c-erbB2/neu-expressing cells. Tal et al. (1987) *Mol. Cell. Biol.* 7:2597–2601; Hudson et al. (1990) *J. Biol. Chem.* 265:4389–4393; Grooteclaes et al. (1994) *Cancer Res.* 54:4193–4199; Ishii et al. (1987) *Proc. Natl. Acad. Sci. USA* 84:4374–4378; and Scott et al. (1994) *J. Biol. Chem.* 269:19848–19858.

Melanocyte-Specific TRE

It has been shown that some genes which encode melanoma proteins are frequently expressed in melanoma/melanocytes, but silent in the majority of normal tissues. A variety of melanocyte-specific TRE are known, are responsive to cellular proteins (transcription factors and/or co-factor(s)) associated with melanocytes, and comprise at least a portion of a melanocyte-specific promoter and/or a melanocyte-specific enhancer. Known transcription factors that control expression of one or more melanocyte-specific genes include the microphthalmia associated transcription factor MITF. Yasumoto et al. (1997) *J. Biol. Chem.* 272:503–509. Other transcription factors that control expression of one or more melanocyte specific genes include MART-1/Melan-A, gp100, TRP-1 and TRP-2

Methods are described herein for measuring the activity of a melanocyte-specific TRE and thus for determining whether a given cell allows a melanocyte-specific TRE to function.

In some embodiments, the melanocyte-specific TREs used in this invention are derived from mammalian cells, including but not limited to, human, rat, and mouse. Any melanocyte-specific TREs may be used in the adenoviral vectors of the invention. Rodent and human 5' flanking sequences from genes expressed specifically or preferentially in melanoma cells have been described in the literature and are thus made available for practice of this invention and need not be described in detail herein. The following are some examples of melanocyte-specific TREs which can be used. A promoter and other control elements in the human tyrosinase gene 5' flanking region have been described and sequences have been deposited as GenBank Accession Nos. X16073 and D10751. Kikuchi et al. (1989) *Biochim. Biophys. Acta* 1009:283–286; and Shibata et al. (1992) *J. Biol. Chem.* 267:20584–20588. A cis-acting element has been defined that enhances melanocyte-specific expression of human tyrosinase gene. This element comprises a 20-bp sequence known as tyrosinase distal element (TDE), contains a CATGTG motif, and lies at positions about −1874 to about −1835 relative to the human tyrosinase gene transcription start site. Yasumoto et al. (1994) *Mol. Cell. Biol.* 14:8058–8070. A promoter region comprising sequences from about −209 to +61 of the human tyrosinase gene was found to direct melanocyte-specific expression. Shibata (1992). Similarly, the mouse tyrosinase 5' flanking region has been analyzed and a sequence deposited as GenBank Accession Nos. D00439 and X51743. Klüppel et al. (1991) *Proc. Natl. Acad. Sci. USA* 88:3777–3788. A minimal promoter has been identified for the mouse TRP-1 gene, and was reported to encompass nucleotides −44 to +107 relative to the transcription start site. Lowings et al. (1992) *Mol. Cell. Biol.* 12:3653–3662. Two regulatory regions required for melanocyte-specific expression of the human TRP-2 gene have been identified. Yokoyama et al. (1994) *J. Biol.*

Chem. 269:27080–27087. A human MART-1 promoter region has been described and deposited as GenBank Accession No. U55231. Melanocyte-specific promoter activity was found in a 233-bp fragment of the human MART-1 gene 5' flanking region. Butterfield et al. (1997) *Gene* 191:129–134. A basic-helix-loop-helix/leucine zipper-containing transcription factor, MITF (microphthalmia associated transcription factor) was reported to be involved in transcriptional activation of tyrosinase and TRP-1 genes. Yasumoto et al. (1997) *J. Biol. Chem.* 272:503–509.

In some embodiments, a melanocyte-specific TRE comprises sequences derived from the 5' flanking region of a human tyrosinase gene depicted in Table 3. In some of these embodiments, the melanocyte-specific TRE comprises tyrosinase nucleotides from about −231 to about +65 relative to the transcription start site (from about nucleotide 244 to about nucleotide 546 of SEQ ID NO: 10) and may further comprise nucleotides from about −1956 to about −1716 relative to the human tyrosinase transcription start site (from about nucleotide 6 to about nucleotide 243 of SEQ ID NO: 10). A melanocyte-specific TRE can comprise nucleotides from about−−231 to about +65 juxtaposed to nucleotides from about −1956 to about −1716. It has been reported that nucleotides from about −1956 to about −1716 relative to the human tyrosinase transcription start site can confer melanocyte-specific expression of an operably linked reporter gene with either a homologous or a heterologous promoter. Accordingly, in some embodiments, a melanocyte-specific TR-E comprises nucleotides from about −1956 to about −1716 operably linked to a heterologous promoter.

A melanocyte-specific TRE can also comprise multimers. For example, a melanocyte-specific TRE can comprise a tandem series of at least two, at least three, at least four, or at least five tyrosinase promoter fragments. Alternatively, a melanocyte-specific TRE could have one or more tyrosinase promoter regions along with one or more tyrosinase enhancer regions. These multimers may also contain heterologous promoter and/or enhancer sequences.

Cell Status-Specific TREs

Cell status-specific TREs for use in the adenoviral vectors of the present invention can be derived from any species, preferably a mammal. A number of genes have been described which are expressed in response to, or in association with, a cell status. Any of these cell status-associated genes may be used to generate a cell status-specific TRE.

An example of a cell status is cell cycle. An exemplary gene whose expression is associated with cell cycle is E2F-1, a ubiquitously expressed, growth-regulated gene, which exhibits peak transcriptional activity in S phase. Johnson et al. (1994) *Genes Dev.* 8:1514–1525. The RB protein, as well as other members of the RB family, form specific complexes with E2F-1, thereby inhibiting its ability to activate transcription. Thus, E2F-1-responsive promoters are down-regulated by RB. Many tumor cells have disrupted RB function, which can lead to de-repression of E2F-1-responsive promoters, and, in turn, de-regulated cell division.

Accordingly, in one embodiment, the invention provides an E3-containing adenoviral vector in which an adenoviral gene (preferably a gene necessary for replication) is under transcriptional control of a cell status-specific TRE, wherein the cell status-specific TRE comprises a cell cycle-activated TRE. In one embodiment, the cell cycle-activated TRE is an E2F1 TRE.

Another group of genes that are regulated by cell status are those whose expression is increased in response to hypoxic conditions. Bunn and Poyton (1996) *Physiol. Rev.* 76:839–885; Dachs and Stratford (1996) *Br. J. Cancer* 74:5126–5132; Guillemin and Krasnow (1997) *Cell* 89:9–12. Many tumors have insufficient blood supply, due in part to the fact that tumor cells typically grow faster than the endothelial cells that make up the blood vessels, resulting in areas of hypoxia in the tumor. Folkman (1989) *J. Natl. Cancer Inst.* 82:4–6; and Kallinowski (1996) *The Cancer J.* 9:37–40. An important mediator of hypoxic responses is the transcriptional complex HIF-1, or hypoxia inducible factor-1, which interacts with a hypoxia-responsive element (HRE) in the regulatory regions of several genes, including vascular endothelial growth factor, and several genes encoding glycolytic enzymes, including enolase-1. Murine HRE sequences have been identified and characterized. Firth et al. (1994) *Proc. Natl. Acad. Sci. USA* 91:6496–6500. An HRE from a rat enolase-1 promoter is described in Jiang et al. (1997) *Cancer Res.* 57:5328–5335. An HRE from a rat enolase-1 promoter is depicted in Table 3.

Accordingly, in one embodiment, an adenovirus vector comprises an adenovirus gene, preferably an adenoviral gene essential for replication, under transcriptional control of a cell status-specific TRE comprising an HRE. In one embodiment, the cell status-specific TRE comprises the HRE depicted in Table 3.

Other cell status-specific TREs include heat-inducible (i.e., heat shock) promoters, and promoters responsive to radiation exposure, including ionizing radiation and UV radiation. For example, the promoter region of the early growth response-1 (Egr-1) gene contains an element(s) inducible by ionizing radiation. Hallahan et al. (1995) *Nat. Med.* 1:786–791; and Tsai-Morris et al. (1988) *Nucl. Acids. Res.* 16:8835–8846. Heat-inducible promoters, including heat-inducible elements, have been described. See, for example Welsh (1990) in "Stress Proteins in Biology and Medicine", Morimoto, Tisseres, and Georgopoulos, eds. Cold Spring Harbor Laboratory Press; and Perisic et al. (1989) *Cell* 59:797–806. Accordingly, in some embodiments, the cell status-specific TRE comprises an element(s) responsive to ionizing radiation. In one embodiment, this TRE comprises a 5' flanking sequence of an Egr-1 gene. In other embodiments, the cell status-specific TRE comprises a heat shock responsive element.

The cell status-specific TREs listed above are provided as non-limiting examples of TREs that would function in the instant invention. Additional cell status-specific TREs are known in the art, as are methods to identify and test cell status specificity of suspected cell status-specific TREs.

Urothelial Cell-Specific TREs

Any urothelial cell-specific TRE may be used in the adenoviral vectors of the invention. A number of urothelial cell-specific proteins have been described, among which are the uroplakins. Uroplakins (UP), including UPIa and UPIb (27 and 28 kDa, respectively), UPII (15 kDa), and UPIII (47 kDa), are members of a group of integral membrane proteins that are major proteins of urothelial plaques. These plaques cover a large portion of the apical surface of mammalian urothelium and may play a role as a permeability barrier and/or as a physical stabilizer of the urothelial apical surface. Wu et al. (1994) *J. Biol. Chem.* 269:13716–13724. UPs are bladder-specific proteins, and are expressed on a significant proportion of urothelial-derived tumors, including about 88% of transitional cell carcinomas. Moll et al. (1995) *Am. J. Pathol.* 147:1383–1397; and Wu et al. (1998) *Cancer Res.* 58:1291–1297. The control of the expression of the human UPII has been studied, and a 3.6-kb region upstream of the mouse UPII gene has been identified which can confer urothelial-specific transcription on heterologous genes (Lin et al. (1995) *Proc. Natl. Acad. Sci. USA* 92:679–683).

Preferred urothelial cell-specific TREs include TREs derived from the uroplakins UPIa, UPIb, UPII, and LUPIII, as well as urohingin. A uroplakin TRE may be from any species, depending on the intended use of the adenovirus, as well as the requisite functionality is exhibited in the target or host cell. Significantly, adenovirus constructs comprising a urothelial cell-specific TREs have observed that such constructs are capable of selectively replicating in urothelial cells as opposed to smooth muscle cells, which adjoin urothelial cells in the bladder.

Uroplakin

Urothelial-specific TREs derived from the hUPII gene are described herein. Accordingly, in some embodiments, an adenovirus vector of the invention comprises an adenovirus gene, preferably an adenoviral gene essential for replication, under transcriptional control of a urothelial cell-specific TRE which comprises the 2.2 kb sequence from the 5' flanking region of hUPII gene, as shown in Table 3. In other embodiments, an adenovirus vector of the invention comprises an adenovirus gene, preferably an adenoviral gene essential for replication, under transcriptional control of a urothelial cell-specific TRE which comprises a 1.8 kb sequence from the 5' flanking region of hUPII gene, from nucleotides 430 to 2239 as shown in Table 3. In other embodiments, the urothelial cell-specific TRE comprises a functional portion of the 2.2 kb sequence depicted in Table 3, or a functional portion of the 1.8 kb sequence of nucleotides 430 to 2239 of the sequence depicted in Table 3, such as a fragment of 2000 bp or less, 1500 bp or less, or 1000 bp or less, 600 bp less, or at least 200 bp which includes the 200 bp fragment of the hUPII 5'-flanking region.

A 3.6 kb 5'-flanking sequence located from the mouse UPII (mUPII) gene which confers urothelial cell-specific transcription on heterologous genes is one urothelial cell-specific TRE useful in vectors of the instant invention (Table 3). Smaller TREs (i.e., 3500 bp or less, more preferably less than about 2000 bp, 1500 bp, or 1000 bp) are preferred. Smaller TREs derived from the mUPII 3.6 kb fragment are one group of preferred urothelial cell-specific TREs. In particular, Inventors have identified an approximately 600 bp fragment from the 5' flanking DNA of the mUPII gene, which contains 540 bp of 5' untranslated region (UTR) of the mUPII gene, that confers urothelial cell-specific expression on heterologous genes.

Accordingly, in some embodiments, an adenovirus vector of the invention comprises an adenovirus gene, preferably an adenoviral gene essential for replication, under transcriptional control of a urothelial cell-specific TRE which comprises the 3.6 kb sequence from the 5' flanking region of mouse UPII gene, as shown in Table 3. In other embodiments, the urothelial cell-specific TRE comprises a functional portion of the 3.6 kb sequence depicted in Table 3, such as a fragment of 3500 bp or less, 2000 bp or less, 1500 bp or less, or 1000 bp or less which includes the 540 bp fragment of 5' UTR. The urothelial cell-specific TRE may also be a sequence which is substantially identical to the 3.6 kb mUPII 5'-flanking region or any of the described fragments thereof.

As an example of how urothelial cell-specific TRE activity can be determined, a polynucleotide sequence or set of such sequences can be generated using methods known in the art, such as chemical synthesis, site-directed mutagenesis, PCR, and/or recombinant methods. The sequence(s) to be tested is inserted into a vector containing an appropriate reporter gene, including, but not limited to, chloramphenicol acetyl transferase (CAT), β-galactosidase (encoded by the lacZ gene), luciferase (encoded by the luc gene), a green fluorescent protein, alkaline phosphatase, and horse radish peroxidase. Such vectors and assays are readily available, from, inter alia, commercial sources. Plasmids thus constructed are transfected into a suitable host cell to test for expression of the reporter gene as controlled by the putative target cell-specific TRE using transfection methods known in the art, such as calcium phosphate precipitation, electroporation, liposomes (lipofection) and DEAE dextran. Suitable host cells include any urothelial cell type, including but not limited to, KU-1, MYP3 (a non-tumorigenic rat urothelial cell line), 804G (rat bladder carcinoma cell line), cultured human urothelial cells (HUC), HCV-29, UM-UC-3, SW780, RT4, HL60, KG-1, and KG1A. Non-urothelial cells, such as LNCaP, HBL-100, HLF, HLE, 3T3, Hep3B, HuH7, CADO-LC9, and HeLa are used as a control. Results are obtained by measuring the level of expression of the reporter gene using standard assays. Comparison of expression between urothelial cells and control indicates presence or absence of transcriptional activation.

Comparisons between or among various urothelial cell-specific TREs can be assessed by measuring and comparing levels of expression within a single urothelial cell line. It is understood that absolute transcriptional activity of a urothelial cell-specific TRE will depend on several factors, such as the nature of the target cell, delivery mode and form of the urothelial cell-specific TRE, and the coding sequence that is to be selectively transcriptionally activated. To compensate for various plasmid sizes used, activities can be expressed as relative activity per mole of transfected plasmid. Alternatively, the level of transcription (i.e., mRNA) can be measured using standard Northern analysis and hybridization techniques. Levels of transfection (i.e., transfection efficiencies) are measured by co-transfecting a plasmid encoding a different reporter gene under control of a different TRE, such as the CMV immediate early promoter. This analysis can also indicate negative regulatory regions, i.e., silencers.

Alternatively a putative urothelial cell-specific TRE can be assessed for its ability to confer adenoviral replication preference for cells that allow a urothelial cell-specific TRE to function. For this assay, constructs containing an adenovirus gene essential to replication operatively linked to a putative urothelial cell-specific TRE are transfected into urothelial cells. Viral replication in those cells is compared, for example, to viral replication by wild type adenovirus in those cells and/or viral replication by the construct in non-urothelial cells.

TRE Configurations

A TRE as used in the present invention can be present in a variety of configurations. A TRE can comprise multimers. For example, a TRE can comprise a tandem series of at least two, at least three, at least four, or at least five target cell-specific TREs. These multimers may also contain heterologous promoter and/or enhancer sequences.

Optionally, a transcriptional terminator or transcriptional "silencer" can be placed upstream of the target cell-specific TRE, thus preventing unwanted read-through transcription of the coding segment under transcriptional control of the target cell-specific TRE. Also, optionally, the endogenous promoter of the coding segment to be placed under transcriptional control of the target cell-specific TRE can be deleted.

A target cell-specific TRE may or may not lack a silencer. The presence of a silencer (i.e., a negative regulatory element) may assist in shutting off transcription (and thus replication) in non-permissive cells (i.e., a non-target cell). Thus, presence of a silencer may confer enhanced target cell-specific replication by more effectively preventing adenoviral vector replication in non-target cells. Alternatively, lack of a silencer may assist in effecting replication in target cells, thus conferring enhanced target cell-specific replication due to more effective replication in target cells.

It is also understood that the invention includes a target cell-specific TRE regulating the transcription of a bicistronic mRNA in which translation of the second mRNA is associated by an IRES. An adenovirus vector may further include an additional heterologous TRE which may or may not be operably linked to the same gene(s) as the target cell-specific TRE. For example a TRE (such as a cell type-specific or cell status-specific TRE) may be juxtaposed to a second type of target-cell-specific TRE. "Juxtaposed" means a target cell-specific TRE and a second TRE transcriptionally control the same gene. For these embodiments, the target cell-specific TRE and the second TRE may be in any of a number of configurations, including, but not limited to, (a) next to each other (i.e., abutting); (b) both 5' to the gene that is transcriptionally controlled (i.e., may have intervening sequences between them); (c) one TRE 5' and the other TRE 3' to the gene.

As is readily appreciated by one skilled in the art, a target cell-specific TRE is a polynucleotide sequence, and, as such, can exhibit function over a variety of sequence permutations. Methods of nucleotide substitution, addition, and deletion are known in the art, and readily available functional assays (such as the CAT or luciferase reporter gene assay) allow one of ordinary skill to determine whether a sequence variant exhibits requisite target cell-specific transcription function. Hence, the invention also includes functionally-preserved variants of the TRE nucleic acid sequences disclosed herein, which include nucleic acid substitutions, additions, and/or deletions. The variants of the sequences disclosed herein may be 80%, 85%, 90%, 95%, 98%, 99% or more identical, as measured by, for example, ALIGN Plus (Scientific and Educational Software, Pennsylvania), preferably using efault parameters, which are as follows: mismatch=2; open gap=0; extend gap=2 to any of the urothelial cell-specific TRE sequences disclosed herein. Variants of target cell-specific TRE sequences may also hybridize at high stringency, that is at 68° C. and 0.1×SSC, to any of the target cell-specific TRE sequences disclosed herein.

In terms of hybridization conditions, the higher the sequence identity required, the more stringent are the hybridization conditions if such sequences are determined by their ability to hybridize to a sequence of TRE disclosed herein. Accordingly, the invention also includes polynucleotides that are able to hybridize to a sequence comprising at least about 15 contiguous nucleotides (or more, such as about 25, 35, 50, 75 or 100 contiguous nucleotides) of a TRE disclosed herein. The hybridization conditions would be stringent, i.e., 80° C. (or higher temperature) and 6M SSC (or less concentrated SSC). Another set of stringent hybridization conditions is 68° C. and 0.1×SSC. For discussion regarding hybridization reactions, see below.

Hybridization reactions can be performed under conditions of different "stringency". Conditions that increase stringency of a hybridization reaction of widely known and published in the art. See, for example, Sambrook et al. (1989) at page 7.52. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. An exemplary set of stringent hybridization conditions is 68° C. and 0.1×SSC.

"$T_m$" is the temperature in degrees Celcius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6 \log[X^+] + 0.41(\% \ G/C) - 0.61(\% \ F) - 600/L$$

where [$X^+$] is the cation concentration (usually sodium ion, $Na^+$) in mol/L; (% G/C) is the number of G and C residues as a percentage of total residues in the duplex; (% F) is the percent formamide in solution (wt/vol); and L is the number of nucleotides in each strand of the duplex.

While not wishing to be bound by a single theory, the inventors note that it is possible that certain modifications will result in modulated resultant expression levels, including enhanced expression levels. Achievement of modulated resultant expression levels, preferably enhanced expression levels, may be especially desirable in the case of certain, more aggressive forms of cancer, or when a more rapid and/or aggressive pattern of cell killing is warranted (due to an immunocompromised condition of the individual, for example).

Determination of TRE Activity

Activity of a TRE can be determined, for example, as follows. A TRE polynucleotide sequence or set of such sequences can be generated using methods known in the art, such as chemical synthesis, site-directed mutagenesis, PCR, and/or recombinant methods. The sequence(s) to be tested can be inserted into a vector containing a promoter (if no promoter element is present in the TRE) and an appropriate reporter gene encoding a reporter protein, including, but not limited to, chloramphenicol acetyl transferase (CAT), β-galactosidase (encoded by the lacZ gene), luciferase (encoded by the luc gene), alkaline phosphatase (AP), green fluorescent protein (GFP), and horseradish peroxidase (HRP). Such vectors and assays are readily available, from, inter alia, commercial sources. Plasmids thus constructed are transfected into a suitable host cell to test for expression of the reporter gene as controlled by the putative TRE using transfection methods known in the art, such as calcium phosphate precipitation, electroporation, liposomes, DEAE dextran-mediated transfer, particle bombardment or direct injection. TRE activity is measured by detection and/or quantitation of reporter gene-derived mRNA and/or protein. Reporter protein product can be detected directly (e.g., immunochemically) or through its enzymatic activity, if any, using an appropriate substrate. Generally, to determine cell specific activity of a TRE, a TRE-reporter gene construct is introduced into a variety of cell types. The amount of TRE activity is determined in each cell type and compared to that of a reporter gene construct lacking the TRE. A TRE is determined to be cell-specific if it is preferentially functional in one cell type, compared to a different type of cell.

Adenovirus Early Genes

The adenovirus vectors of the invention comprise two or more genes which are co-transcribed under the control of a target cell-specific TRE wherein the second gene is under translational control of an IRES. One or more of the genes can be an adenovirus gene, preferably an adenovirus gene essential for replication. Any gene that is essential for adenovirus replication, such as E1A, E1B, E2, E4 or any of the late genes, is useful. The adenovirus may also comprise E3. In addition, one or more of the genes can be a transgene or heterologous gene. Any of the various adenovirus serotypes can be used, such as, for example, Ad2, Ad5, Ad12 and Ad40. For purposes of illustration, the Ad5 serotype is exemplified herein.

The E1A gene is expressed immediately (between 0 and 2 hours) after viral infection, before any other viral genes. E1A protein is a trans-acting positive transcriptional regulatory factor, and is required for the expression of the other early viral genes E1B, E2, E3, E4, and the promoter-proximal major late genes. Despite the nomenclature, the promoter proximal genes driven by the major late promoter are also expressed during early times after Ad5 infection. Flint (1982) Biochem. Biophys. Acta 651:175–208; Flint (1986) Advances Virus Research 31:169–228; and Grand (1987) Biochem. J. 241:25–38. In the absence of a functional E1A gene, viral infection does not proceed, because the gene products necessary for viral DNA replication are not produced. Nevins (1989) Adv. Virus Res. 31:35–81. The transcription start site of Ad5 E1A is at coordinate 498 and the ATG start site of the E1A protein is at coordinate 560 in the virus genome.

The E1B protein is necessary in trans for transport of late mRNA from the nucleus to the cytoplasm. Defects in E1B expression result in poor expression of late viral proteins and an inability to shut off host cell protein synthesis. The promoter of E1B has been implicated as the defining element of difference in the host range of Ad40 and Ad5: clinically Ad40 is an enterovirus, whereas Ad5 causes acute conjunctivitis. Bailey et al. (1993) Virology 193:631; Bailey et al. (1994) Virology 202:695–706. The E1B promoter of Ad5 consists of a single high-affinity recognition site for Sp1 and a TATA box, and extends from Ad5 nt 1636 to 1701.

Adenovirus E1B 19-kDa (19K) protein is a potent inhibitor of apoptosis and cooperates with E1A to produce oncogenic transformation of primary cells (Rao, et al., 1992, Cell Biology, 89:7742–7746). During productive adenovirus infection, E1A stimulates host cell DNA synthesis, thereby causing cells to aberrantly go through the cell cycle. In response to cell cycle deregulation, the host cell undergoes apoptosis. As a defense mechanism, the E1B 19-kDa protein inhibits this E1A-induced apoptosis and allows assembly of viral progeny to be completed before the cell commits suicide. E1B 19-kDa conducts anti-apoptotic function by multiple mechanisms. E1B 19-kDa inhibits the apoptosis of multiple stimuli, including E1a, 53 and TNF, for example. According to wild-type Ad5, the E1B 19-kDa region is located between nucleotide 1714 and nucleotide 2244. The E1B 19-kDa region has been described in, for example, Rao et al., Proc. Natl. Acad. Sci. USA, 89:7742–7746.

In a preferred embodiment, expression of the E1A and E1B regions of the Ad genome is facilitated in a cell-specific fashion by placing a cell-specific TRE upstream of E1A and a internal ribosome entry site between E1A and E1B.

The E2 region of adenovirus encodes proteins related to replication of the adenoviral genome, including the 72 kD DNA-binding protein, the 80 kD precursor terminal protein and the viral DNA polymerase. The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the E1A transactivator protein, the E2 early promoter is crucial during the early phases of viral replication.

The E2 early promoter of Ad5 is located between nucleotides 27,050 and 27,150, and consists of a major and a minor transcription initiation site (the latter accounting for about 5% of E2 transcripts), two non-canonical TATA boxes, two E2F transcription factor binding sites and an ATF transcription factor binding site. For a detailed review of E2 promoter architecture see Swaminathan et al. (1995) Curr. Topics in Micro. and Imm. 199 part 3:177–194.

The E2 late promoter overlaps with the coding sequences of a gene encoded by the counterstrand and is therefore not amenable for genetic manipulation. However, the E2 early promoter overlaps by only a few base pairs with sequences on the counterstrand which encode a 33 kD protein. Notably, an SpeI restriction site (Ad5 position 27,082) is part of the stop codon for the above mentioned 33 kD protein and conveniently separates the major E2 early transcription initiation site and TATA box from the upstream E2F and ATF binding sites. Therefore, insertion of a heterologous TRE having SpeI ends into the SpeI site disrupts the endogenous E2 early promoter of Ad5 and allows TRE-regulated expression of E2 transcripts.

An E3 region refers to the region of the adenoviral genome that encodes the E3 products. The E3 region has been described in various publications, including, for example, Wold et al. (1995) Curr. Topics Microbiol. Immunol. 199:237–274. Generally, the E3 region is located between about 28583 and about 30470 of the adenoviral genome. An E3 region for use in the present invention may be from any adenovirus serotype. An E3 sequence is a polynucleotide sequence that contains a sequence from an E3 region. In some embodiments, the sequence encodes ADP. In other embodiments, the sequence encodes other than ADP and excludes a sequence encoding only ADP. As is well known in the art, the ADP coding region is located in the E3 region within the adenoviral genome from about 29468 bp to about 29773 bp; including the Y leader, the location of ADP is from about 28375 bp to about 29773 bp for Ad5. Other ADP regions for other serotypes are known in the art. An E3 sequence includes, but is not limited to, deletions; insertions; fusions; and substitutions. An E3 sequence may also comprise an E3 region or a portion of the E3 region. It is understood that, as an "E3 sequence" is not limited to an "E3 region", alternative references herein to an "E3 region" or "E3 sequence" do not indicate that these terms are interchangeable. Assays for determining a functional E3 sequence for purposes of this invention are described herein.

The E4 gene has a number of transcription products and encodes two polypeptides (the products of open reading frames (ORFs) 3 and 6) which are responsible for stimulating the replication of viral genomic DNA and stimulating late gene expression, through interaction with heterodimers of cellular transcription factors E2F-1 and DP-1. The ORF 6 protein requires interaction with the E1B 55 kD protein for activity while the ORF 3 protein does not. In the absence of functional ORF 3- and ORF 6-encoded proteins, efficiency of plaque formation is less than $10^{-6}$ that of wild type virus.

To further increase cell-specificity of replication, it is possible to take advantage of the interaction between the E4 ORF 6 gene product and the E1B 55 kD protein. For example, if E4 ORFs 1–3 are deleted, viral DNA replication and late gene synthesis becomes dependent on E4 ORF6 protein. By generating such a deletion in a vector in which the E1B region is regulated by a cell-specific TRE, a virus is obtained in which both E1B and E4 functions are dependent on the cell-specific which regulates E1B.

Late genes relevant to the disclosed vectors are L1, L2 and L3, which encode proteins of the virion. All of these genes (typically coding for structural proteins) are probably required for adenoviral replication. All late genes are under the control of the major late promoter (MLP), which is located in Ad5 between nucleotides 5986 and 6048.

In one embodiment, an adenovirus early gene is under transcriptional control of a cell specific, heterologous TRE. In additional embodiments, the early gene is selected from the group including E1A, E1B, E2, E3, E4. In another embodiment, an adenovirus late gene is under transcriptional control of a cell specific, heterologous TRE. In further embodiments, two or more early genes are under the control of heterologous TREs that function in the same target cell. The heterologous TREs can be the same or different, or one can be a variant of the other. In additional embodiments, two or more late genes are under the control of heterologous TREs that function in the same target cell. The heterologous TREs can be the same or different, or one can be a variant of the other. In yet another embodiment, one or more early gene(s) and one or more late gene(s) are under transcriptional control of the same or different heterologous TREs, wherein the TREs function in the same target cell.

In some embodiments of the present invention, the adenovirus vector comprises the essential gene E1A and the E1A promoter is deleted. In other embodiments, the adenovirus vector comprises the essential gene E1A and the E1A enhancer I is deleted. In yet other embodiments, the E1A promoter is deleted and E1A enhancer I is deleted. In other embodiments, an internal ribosome entry site (IRES) is inserted upstream of E1B (so that E1B is translationally linked), and a target cell-specific TRE is operably linked to E1A. In still other embodiments, an (IRES) is inserted upstream of E1B (so that E1B is translationally linked), and target cell-specific TRE is operably linked to E1A, which may or may not maintain the E1A promoter and/or enhancer I (i.e., the E1A promoter and/or enhancer I may be, but not necessarily be, deleted). In yet other embodiments, the 19-kDa region of E1B is deleted.

For adenovirus vectors comprising a second gene under control of an IRES, it is preferred that the endogenous promoter of a gene under translational control of an IRES be deleted so that the endogenous promoter does not interfere with transcription of the second gene. It is preferred that the second gene be in frame with the IRES if the IRES contains an initiation codon. If an initiation codon, such as ATG, is present in the IRES, it is preferred that the initiation codon of the second gene is removed and that the IRES and second gene are in frame. Alternatively, if the IRES does not contain an initiation codon or if the initiation codon is removed from the IRES, the initiation codon of the second gene is used.
Adenovirus Death Protein (ADP) Gene and Gene Product In the construction of adenovirus vectors, the E3 region is often deleted to facilitate insertion of one or more TREs and/or transgenes. In some embodiments, however, the adenovirus death protein (ADP), encoded within the E3 region, is retained in an adenovirus vector. The ADP gene, under control of the major late promoter (MLP), appears to code for a protein (ADP) that is important in expediting host cell lysis. Tollefson et al. (1992) *J. Virol.* 66:3633; and Tollefson et al. (1996) *J. Virol.* 70:2296. Thus, inclusion of an ADP gene in a viral vector can render the vector more potent, making possible more effective treatment and/or a lower dosage requirement.

Figure 6:
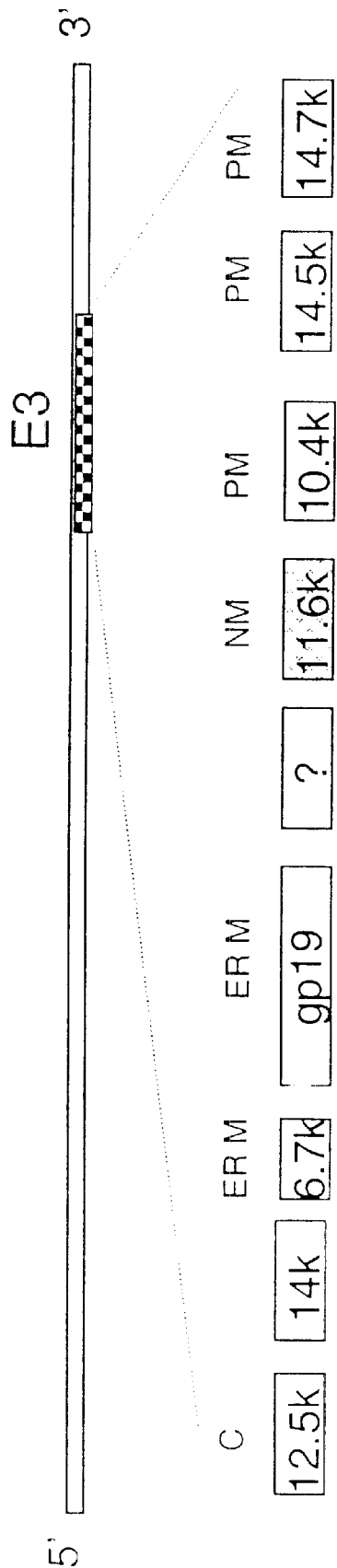
FIG. 6 depicts an E3 region.

An ADP coding sequence is obtained preferably from Ad2 (since this is the strain in which the ADP has been most fully characterized) using techniques known in the art, such as PCR. Preferably, the Y leader (which is an important sequence for correct expression of late genes) is also obtained and placed in operative linkage to the ADP coding sequence. The ADP coding sequence (with or without the Y leader) is then introduced into an adenoviral genome, for example, in the E3 region, where expression of the ADP coding sequence will be driven by the MLP. The ADP coding sequence can, of course, also be inserted in other locations of the adenovirus genome, such as the E4 region. Alternatively, the ADP coding sequence can be operably linked to a heterologous TRE, including, but not limited to, another viral TRE or a target cell-specific TRE (see infra). In another embodiment, the ADP gene is present in a viral genome such that it is transcribed as part of a multi-cistronic mRNA in which its translation is associated with an IRES.
E3-Containing Target Cell-Specific Adenoviral Vectors In some embodiments, the adenovirus vectors contain an E3 region, or a portion of an E3 region. Inclusion of the E3 region of adenovirus can enhance cytotoxicity of the target cell-specific adenoviral vectors of the present invention. Adenoviral vectors containing an E3 region may maintain their high level of specificity and can be (a) significantly more cytotoxic; (b) produce higher virus yield including extracellular virus yield; (c) form larger plaques; (d) produce rapid cell death; and (e) kill tumors more efficiently in vivo than vectors lacking the E3 region. The adenoviral vectors of this invention may contain the E3 region or a portion of the E3 region. It is understood that, as inclusion of E3 confers observable and measurable functionality on the adenoviral vectors, for example, increased replication and production, functionally equivalent (in which functionality is essentially maintained, preserved, or even enhanced or diminished) variants of E3 may be constructed. For example, portions of B3 may be used. A portion may be, non-inclusively, either of the following: (a) deletion, preferably at the 3' end; (b) inclusion of one or more various open reading frames of E3. Five proteins which are encoded by the Ad-E3 region have been identified and characterized: (1) a 19-kDa glycoprotein (gp19 k) is one of the most abundant adenovirus early proteins, and is known to inhibit transport of the major histocompatibility complex class I molecules to the cell surface, thus impairing both peptide recognition and clearance of Ad-infected cells by cytotoxic T lymphocytes (CTLs); (2) E3 14.7 k protein and the E3 10.4k/14.5 k complex of proteins inhibit the cytotoxic and inflammatory responses mediated by tumor necrosis factor (TNF); (3) E3 10.4 k/14.5 k protein complex down regulates the epidermal growth factor receptor, which may inhibit inflammation and activate quiescent infected cells for efficient virus replication; (4) E3 11.6 k protein (adenoviral death protein, ADP) from adenovirus 2 and 5 appears to promote cell death and release of virus from infected cells. The functions of three E3-encoded proteins—3.6 k, 6.7 k and 12.5 k—are unknown. A ninth protein having a molecular weight of 7.5 kDa has been postulated to exist, but has not been detected in cells infected with wild-type adenovirus. Wold et al. (1995) *Curr. Topics Microbiol. Immunol.* 199:237–274. The E3 region is schematically depicted in FIG. 6. These intact, portions, or variants of E3 may be readily constructed using standard knowledge and techniques in the art. Preferably, an intact E3 region is used.

In the adenovirus vectors of the present invention, E3 may or may not be under transcriptional control of native adenoviral transcriptional control element(s). The E3 promoter is located within the coding sequence for virion protein VIII, an essential protein which is highly conserved among adenovirus serotypes. In some embodiments, E3 is under transcriptional control of a heterologous TRE, including, but not limited to, a target cell-specific TRE. Accordingly, in one embodiment, the invention provides an adenoviral vector, preferably replication competent, that comprises E3 region (or a portion of E3) under transcriptional control of a target cell-specific TRE. In other embodiments, the E3 region is under transcriptional control of a native adenoviral TRE, and the vector further comprises an adenoviral gene essential for replication under transcriptional control of a target cell-specific TRE. In other embodiments, the E3 region is under transcriptional control of a target cell-specific TRE, and the vector further comprises an adenoviral gene essential for replication under transcriptional control of a target cell-specific TRE.

Transgenes Under Transcriptional Control of a Target Cell-Specific TRE

Various other replication-competent adenovirus vectors can be made according to the present invention in which, in addition to having a single or multiple adenovirus gene(s) under control of a target cell-specific TRE, a trans gene(s) is/are also under control of a target cell-specific TRE and optionally under translational control of an IRES. Transgenes include, but are not limited to, therapeutic transgenes and reporter genes.

Reporter Genes

For example, a target cell-specific TRE can be introduced into an adenovirus vector immediately upstream of and operably linked to an early gene such as E1A or E1B, and this construct may further comprise a second co-transcribed gene under translational control of an IRES. The second gene may be a reporter gene. The reporter gene can encode a reporter protein, including, but not limited to, chloramphenicol acetyl transferase (CAT), β-galactosidase (encoded by the lacZ gene), luciferase, alkaline phosphatase, a green fluorescent protein, and horse radish peroxidase. For detection of a putative cancer cell(s) in a biological sample, the biological sample may be treated with modified adenoviruses in which a reporter gene (e.g., luciferase) is under control of a target cell-specific TRE. The target cell-specific TRE will be transcriptionally active in cells that allow the target cell-specific TRE to function, and luciferase will be produced. This production will allow detection of target cells, including cancer cells in, for example, a human host or a biological sample. Alternatively, an adenovirus can be constructed in which a gene encoding a product conditionally required for survival (e.g., an antibiotic resistance marker) is under transcriptional control of a target cell-specific TRE. When this adenovirus is introduced into a biological sample, the target cells will become antibiotic resistant. An antibiotic can then be introduced into the medium to kill the non-cancerous cells.

Therapeutic Transgenes

Transgenes also include genes which may confer a therapeutic effect, such as enhancing cytotoxicity so as to eliminate unwanted target cells. In this way, various genetic capabilities may be introduced into target cells, particularly cancer cells. For example, in certain instances, it may be desirable to enhance the degree and/or rate of cytotoxic activity, due to, for example, the relatively refractory nature or particular aggressiveness of the cancerous target cell. This could be accomplished by coupling the target cell-specific cytotoxic activity with cell-specific expression of, for example, HSV-tk and/or cytosine deaminase (cd), which renders cells capable of metabolizing 5-fluorocytosine (5-FC) to the chemotherapeutic agent 5-fluorouracil (5-FU). Using these types of transgenes may also confer a bystander effect.

Other desirable transgenes that may be introduced via an adenovirus vector(s) include genes encoding cytotoxic proteins, such as the A chains of diphtheria toxin, ricin or abrin (Palmiter et al. (1987) *Cell* 50: 435; Maxwell et al. (1987) *Mol. Cell. Biol.* 7: 1576; Behringer et al. (1988) *Genes Dev.* 2: 453; Messing et al. (1992) *Neuron* 8: 507; Piatak et al. (1988) *J. Biol. Chem.* 263: 4937; Lamb et al. (1985) *Eur. J Biochem.* 148: 265; Frankel et al. (1989) *Mol. Cell. Biol.* 9: 415), genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly; genes that encode an engineered cytoplasmic variant of a nuclease (e.g. RNase A) or protease (e.g. awsin, papain, proteinase K, carboxypeptidase, etc.), or encode the Fas gene, and the like. Other genes of interest include cytokines, antigens, transmembrane proteins, and the like, such as IL-1, -2, -6, -12, GM-CSF, G-CSF, M-CSF, IFN-α, -β, -χ, TNF-α, -β, TGF-α, -β, NGF, and the like. The positive effector genes could be used in an earlier phase, followed by cytotoxic activity due to replication.

Host Cells

The present invention also provides host cells comprising (i.e., transformed with) the adenoviral vectors described herein. Both prokaryotic and eukaryotic host cells can be used as long as sequences requisite for maintenance in that host, such as appropriate replication origin(s), are present. For convenience, selectable markers are also provided. Host systems are known in the art and need not be described in detail herein. Prokaryotic host cells include bacterial cells, for example, *E. coli, B. subtilis*, and mycobacteria. Among eukaryotic host cells are yeast, insect, avian, plant, *C. elegans* (or nematode) and mammalian host cells. Examples of fungi (including yeast) host cells are *S. cerevisiae, Kluyveromyces lactis* (*K. lactis*), species of Candida including *C. albicans and C. glabrata, Aspergillus nidulans, Schizosaccharomyces pombe* (*S. pombe*), *Pichia pastoris*, and *Yarrowia lipolytica*. Examples of mammalian cells are cultured human target cells (HUC), KU-1, MYP3 (a non-tumorigenic rat target cell line), 804G (rat bladder carcinoma cell line), HCV-29, UM-UC-3, SW780, RT4, HL60, KG-1, and KG-1A. COS cells, mouse L cells, LNCaP cells, Chinese hamster ovary (CHO) cells, human embryonic kidney (HEK) cells, and African green monkey cells. *Xenopus laevis* oocytes, or other cells of amphibian origin, may also be used.

Compositions and Kits

The present invention also includes compositions, including pharmaceutical compositions, containing the adenoviral vectors described herein. Such compositions are useful for administration in vivo, for example, when measuring the degree of transduction and/or effectiveness of cell killing in an individual. Compositions can comprise an adenoviral vector(s) of the invention and a suitable solvent, such as a physiologically acceptable buffer. These are well known in the art. In other embodiments, these compositions further comprise a pharmaceutically acceptable excipient. These compositions, which can comprise an effective amount of an adenoviral vector of this invention in a pharmaceutically acceptable excipient, are suitable for systemic or local administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in *Remington's Pharmaceutical*

*Sciences,* 19th Edition, Mack Publishing (1995). Compositions also include lyophilized and/or reconstituted forms of the adenoviral vectors (including those packaged as a virus, such as adenovirus) of the invention.

The present invention also encompasses kits containing an adenoviral vector(s) of this invention. These kits can be used for diagnostic and/or monitoring purposes, preferably monitoring. Procedures using these kits can be performed by clinical laboratories, experimental laboratories, medical practitioners, or private individuals. Kits embodied by this invention allow someone to detect the presence of bladder cancer cells in a suitable biological sample, such as biopsy specimens.

The kits of the invention comprise an adenoviral vector described herein in suitable packaging. The kit may optionally provide additional components that are useful in the procedure, including, but not limited to, buffers, developing reagents, labels, reacting surfaces, means for detection, control samples, instructions, and interpretive information.
Preparation of the Adenovirus Vectors of the Invention The adenovirus vectors of this invention can be prepared using recombinant techniques that are standard in the art. Generally, a target cell-specific TRE is inserted 5' to the adenoviral gene of interest, preferably an adenoviral replication gene, more preferably one or more early replication genes (although late gene(s) can be used). A target cell-specific TRE can be prepared using oligonucleotide synthesis (if the sequence is known) or recombinant methods (such as PCR and/or restriction enzymes). Convenient restriction sites, either in the natural adeno-DNA sequence or introduced by methods such as PCR or site-directed mutagenesis, provide an insertion site for a target cell-specific TRE. Accordingly, convenient restriction sites for annealing (i.e., inserting) a target cell-specific TRE can be engineered onto the 5' and 3' ends of a UP-TRE using standard recombinant methods, such as PCR.

Polynucleotides used for making adenoviral vectors of this invention may be obtained using standard methods in the art, such as chemical synthesis, recombinant methods and/or obtained from biological sources.

Adenoviral vectors containing all replication-essential elements, with the desired elements (e.g., E1A) under control of a target cell-specific TRE, are conveniently prepared by homologous recombination or in vitro ligation of two plasmids, one providing the left-hand portion of adenovirus and the other plasmid providing the right-hand region, one or more of which contains at least one adenovirus gene under control of a target cell-specific TRE. If homologous recombination is used, the two plasmids should share at least about 500 bp of sequence overlap. Each plasmid, as desired, may be independently manipulated, followed by cotransfection in a competent host, providing complementing genes as appropriate, or the appropriate transcription factors for initiation of transcription from a target cell-specific TRE for propagation of the adenovirus. Plasmids are generally introduced into a suitable host cell such as 293 cells using appropriate means of transduction, such as cationic liposomes. Alternatively, in vitro ligation of the right and left-hand portions of the adenovirus genome can also be used to construct recombinant adenovirus derivative containing all the replication-essential portions of adenovirus genome. Berkner et al. (1983) *Nucleic Acid Research* 11: 6003–6020; Bridge et al. (1989) *J. Virol* 63: 631–638.

For convenience, plasmids are available that provide the necessary portions of adenovirus. Plasmid pXC.1 (McKinnon (1982) *Gene* 19:33–42) contains the wild-type left-hand end of Ad5. pBHG10 (Bett et al. (1994); Microbix Biosystems Inc., Toronto) provides the right-hand end of Ad5, with a deletion in E3. The deletion in E3 provides room in the virus to insert a 3 kb target cell-specific TRE without deleting the endogenous enhancer/promoter. The gene for E3 is located on the opposite strand from E4 (r-strand). pBHG11 provides an even larger E3 deletion (an additional 0.3 kb is deleted). Bett et al. (1994). Alternatively, the use of pBHGE3 (Microbix Biosystems, Inc.) provides the right hand end of Ad5, with a full-length of E3.

For manipulation of the early genes, the transcription start site of Ad5 E1A is at 498 and the ATG start site of the E1A coding segment is at 560 in the virus genome. This region can be used for insertion of a target cell-specific TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a nucleotide sequence change resulting in a unique restriction site, one can provide for insertion of target cell-specific TRE at that site.

A similar strategy may also be used for insertion of a target cell-specific TRE element to regulate E1B. The E1B promoter of Ad5 consists of a single high-affinity recognition site for Sp1 and a TATA box. This region extends from Ad5 nt 1636 to 1701. By insertion of a target cell-specific TRE in this region, one can provide for cell-specific transcription of the E1B gene. By employing the left-hand region modified with the cell-specific response element regulating E1A, as the template for introducing a target cell-specific TRE to regulate E1B, the resulting adenovirus vector will be dependent upon the cell-specific transcription factors for expression of both E1A and E1B. In additional embodiments, the 19-kDa region of E1B is deleted.

Similarly, a target cell-specific TRE can be inserted upstream of the E2 gene to make its expression cell-specific. The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan et al., *Curr. Topics in Micro. and Immunol.* (1995) 199(part 3):177–194.

The E2 late promoter overlaps with the coding sequences of a gene encoded by the counterstrand and is therefore not amenable for genetic manipulation. However, the E2 early promoter overlaps only for a few base pairs with sequences coding for a 33 kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor binding sites E2F and ATF. Therefore, insertion of a target cell-specific TRE having SpeI ends into the SpeI site in the 1-strand would disrupt the endogenous E2 early promoter of Ad5 and should allow target cell-restricted expression of E2 transcripts.

For E4, one must use the right hand portion of the adenovirus genome. The E4 transcription start site is predominantly at about nt 35605, the TATA box at about nt 35631 and the first AUG/CUG of ORF I is at about nt 35532. Virtanen et al. (1984) *J. Virol.* 51: 822–831. Using any of the above strategies for the other genes, a UP-TRE may be introduced upstream from the transcription start site. For the construction of full-length adenovirus with a target cell-specific TRE inserted in the E4 region, the co-transfection and homologous recombination are performed in W162 cells (Weinberg et al. (1983) *Proc. Natl. Acad. Sci.* 80:5383–5386) which provide E4 proteins in trans to complement defects in synthesis of these proteins.

Adenoviral constructs containing an E3 region can be generated wherein homologous recombination between an E3-containing adenoviral plasmid, for example, BHGE3 (Microbix Biosystems Inc., Toronto) and a non-E3-containing adenoviral plasmid, is carried out.

Alternatively, an adenoviral vector comprising an E3 region can be introduced into cells, for example 293 cells, along with an adenoviral construct or an adenoviral plasmid construct, where they can undergo homologous recombination to yield adenovirus containing an E3 region. In this case, the E3-containing adenoviral vector and the adenoviral construct or plasmid construct contain complementary regions of adenovirus, for example, one contains the left-hand and the other contains the right-hand region, with sufficient sequence overlap as to allow homologous recombination.

Alternatively, an E3-containing adenoviral vector of the invention can be constructed using other conventional methods including standard recombinant methods (e.g., using restriction nucleases and/or PCR), chemical synthesis, or a combination of any of these. Further, deletions of portions of the E3 region can be created using standard techniques of molecular biology.

Insertion of an IRES into a vector is accomplished by methods and techniques that are known in the art and described herein supra, including but not limited to, restriction enzyme digestion, ligation, and PCR. A DNA copy of an IRES can be obtained by chemical synthesis, or by making a cDNA copy of, for example, a picornavirus IRES. See, for example, Duke et al. (1995) *J. Vvirol.* 66(3):1602–9) for a description of the EMCV IRES and Huez et al. (1998), *Mol. Cell. Biol.* 18(11):6178–90) for a description of the VEGF IRES. The internal translation initiation sequence is inserted into a vector genome at a site such that it lies upstream of a 5'-distal coding region in a multicistronic mRNA. For example, in a preferred embodiment of an adenovirus vector in which production of a bicistronic E1A-E1B mRNA is under the control of a target cell-specific TRE, the E1B promoter is deleted or inactivated, and an IRES sequence is placed between E1A and E1B. IRES sequences of cardioviruses and certain aphthoviruses contain an AUG codon at the 3' end of the IRES that serves as both a ribosome entry site and as a translation initiation site. Accordingly, this type of IRES is introduced into a vector so as to replace the translation initiation codon of the protein whose translation it regulates. However, in an IRES of the entero/rhinovirus class, the AUG at the 3' end of the IRES is used for ribosome entry only, and translation is initiated at the next downstream AUG codon. Accordingly, if an entero/rhinovirus IRES is used in a vector for translational regulation of a downstream coding region, the AUG (or other translation initiation codon) of the downstream gene is retained in the vector construct.

Methods of packaging polynucleotides into adenovirus particles are known in the art and are also described in co-owned PCT PCT/US98/04080.

Delivery of Adenovirus Vectors

The adenoviral vectors can be used in a variety of forms, including, but not limited to, naked polynucleotide (usually DNA) constructs. Adenoviral vectors can, alternatively, comprise polynucleotide constructs that are complexed with agents to facilitate entry into cells, such as cationic liposomes or other cationic compounds such as polylysine; packaged into infectious adenovirus particles (which may render the adenoviral vector(s) more immunogenic); packaged into other particulate viral forms such as HSV or AAV; complexed with agents (such as PEG) to enhance or dampen an immune response; complexed with agents that facilitate in vivo transfection, such as DOTMA™, DOTAP™, and polyamines.

If an adenoviral vector comprising an adenovirus polynucleotide is packaged into a whole adenovirus (including the capsid), the adenovirus itself may also be selected to further enhance targeting. For example, adenovirus fibers mediate primary contact with cellular receptor(s) aiding in tropism. See, e.g., Amberg et al. (1997) *Virol.* 227:239–244. If a particular subgenus of an adenovirus serotype displayed tropism for a target cell type and/or reduced affinity for non-target cell types, such subgenus(or subgenera) could be used to further increase cell-specificity of cytotoxicity and/or cytolysis.

The adenoviral vectors may be delivered to the target cell in a variety of ways, including, but not limited to, liposomes, general transfection methods that are well known in the art, such as calcium phosphate precipitation, electroporation, direct injection, and intravenous infusion. The means of delivery will depend in large part on the particular adenoviral vector (including its form) as well as the type and location of the target cells (i.e., whether the cells are in vitro or in vivo).

If used in packaged adenoviruses, adenovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 $\mu$g to about 1000 $\mu$g of an adenoviral vector can be administered. The adenoviral vector(s) may be administered one or more times, depending upon the intended use and the immune response potential of the host or may be administered as multiple, simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

Methods Using the Adenovirus Vectors of the Invention

The subject vectors can be used for a wide variety of purposes, which will vary with the desired or intended result. Accordingly, the present invention includes methods using the adenoviral vectors described above.

In one embodiment, methods are provided for conferring selective cytotoxicity in cells that allow a target cell-specific TRE to function, preferably target cells, comprising contacting such cells with an adenovirus vector described herein. Cytotoxicity can be measured using standard assays in the art, such as dye exclusion, $^3$H-thymidine incorporation, and/or lysis.

In another embodiment, methods are provided for propagating an adenovirus specific for cells which allow a target cell-specific TRE to function, preferably target cells, preferably cancer cells. These methods entail combining an adenovirus vector with the cells, whereby said adenovirus is propagated.

Another embodiment provides methods for killing cells that allow a target cell-specific TRE to function in a mixture of cells, comprising combining the mixture of cells with an adenovirus vector of the present invention. The mixture of cells is generally a mixture of normal cells and cancerous cells that allow a target cell-specific TRE to function, and can be an in vivo mixture or in vitro mixture.

The invention also includes methods for detecting cells which allow a target cell-specific TRE to function, such as cancer cells, in a biological sample. These methods are particularly useful for monitoring the clinical and/or physiological condition of an individual (i.e., mammal), whether in an experimental or clinical setting. In one method, cells of a biological sample are contacted with an adenovirus vector, and replication of the adenoviral vector is detected. Alternatively, the sample can be contacted with an adenovirus in which a reporter gene is under control of a target cell-specific TRE. When such an adenovirus is introduced into a biological sample, expression of the reporter gene indicates the presence of cells that allow a target cell-specific TRE to function. Alternatively, an adenovirus can be constructed in which a gene conditionally required for cell survival is placed under control of a target cell-specific TRE. This gene may encode, for example, antibiotic resistance. Later the biological sample is treated with an antibiotic. The presence of surviving cells expressing antibiotic resistance indicates the presence of cells capable of target cell-specific TRE function. A suitable biological sample is one in which cells that allow a target cell-specific TRE to function, such as cancer cells, may be or are suspected to be present. Generally, in mammals, a suitable clinical sample is one in which cancerous cells that allow a target cell-specific TRE to function, such as carcinoma cells, are suspected to be present. Such cells can be obtained, for example, by needle biopsy or other surgical procedure. Cells to be contacted may be treated to promote assay conditions, such as selective enrichment, and/or solubilization. In these methods, cells that allow a target cell-specific TRE to function can be detected using in vitro assays that detect adenoviral proliferation, which are standard in the art. Examples of such standard assays include, but are not limited to, burst assays (which measure virus yield) and plaque assays (which measure infectious particles per cell). Propagation can also be detected by measuring specific adenoviral DNA replication, which are also standard assays.

The invention also provides methods of modifying the genotype of a target cell, comprising contacting the target cell with an adenovirus vector described herein, wherein the adenoviral vector enters the cell.

The invention further provides methods of suppressing tumor cell growth, preferably a tumor cell that allows a target cell-specific TRE to function, comprising contacting a tumor cell with an adenoviral vector of the invention such that the adenoviral vector enters the tumor cell and exhibits selective cytotoxicity for the tumor cell. For these methods, the adenoviral vector may or may not be used in conjunction with other treatment modalities for tumor suppression, such as chemotherapeutic agents (such as those listed below), radiation and/or antibodies.

The invention also provides methods of lowering the levels of a tumor cell marker in an individual, comprising administering to the individual an adenoviral vector of the present invention, wherein the adenoviral vector is selectively cytotoxic toward cells that allow a target cell-specific TRE to function. Tumor cell markers include, but are not limited to, CK-20. Methods of measuring the levels of a tumor cell marker are known to those of ordinary skill in the art and include, but are not limited to, immunological assays, such as enzyme-linked immunosorbent assay (ELISA), using antibodies specific for the tumor cell marker. In general, a biological sample is obtained from the individual to be tested, and a suitable assay, such as an ELISA, is performed on the biological sample. For these methods, the adenoviral vector may or may not be used in conjunction with other treatment modalities for tumor suppression, such as chemotherapeutic agents (such as those listed below), radiation and/or antibodies.

The invention also provides methods of treatment, in which an effective amount of an adenoviral vector(s) described herein is administered to an individual. Treatment using an adenoviral vector(s) is indicated in individuals with cancer as described above. Also indicated are individuals who are considered to be at risk for developing cancer (including single cells), such as those who have had disease which has been resected and those who have had a family history of cancer. Determination of suitability of administering adenoviral vector(s) of the invention will depend, inter alia, on assessable clinical parameters such as serological indications and histological examination of tissue biopsies. Generally, a pharmaceutical composition comprising an adenoviral vector(s) in a pharmaceutically acceptable excipient is administered. Pharmaceutical compositions are described above. For these methods, the adenoviral vector may or may not be used in conjunction with other treatment modalities for tumor suppression, such as chemotherapeutic agents (such as those listed below), radiation and/or antibodies.

The amount of adenoviral vector(s) to be administered will depend on several factors, such as route of administration, the condition of the individual, the degree of aggressiveness of the disease, the particular target cell-specific TRE employed, and the particular vector construct (i.e., which adenovirus gene(s) is under target cell-specific TRE control) as well as whether the adenoviral vector is used in conjunction with other treatment modalities.

If administered as a packaged adenovirus, from about $10^4$ to about $10^{14}$, preferably from about $10^4$ to about $10^{12}$, more preferably from about $10^4$ to about $10^{10}$. If administered as a polynucleotide construct (i.e., not packaged as a virus), about 0.01 $\mu$g to about 100 $\mu$g can be administered, preferably 0.1 $\mu$g to about 500 $\mu$g, more preferably about 0.5 $\mu$g to about 200 $\mu$g. More than one adenoviral vector can be administered, either simultaneously or sequentially. Administrations are typically given periodically, while monitoring any response. Administration can be given, for example, intratumorally, intravenously or intraperitoneally.

The adenoviral vectors of the invention can be used alone or in conjunction with other active agents, such as chemotherapeutics, that promote the desired objective. Examples of chemotherapeutics which are suitable for suppressing bladder tumor growth are BGC (bacillus Calmett-Guerin); mitomycin-C; cisplatin; thiotepa; doxorubicin; methotrexate; paclitaxel (TAXOL™); ifosfamide; gallium nitrate; gemcitabine; carboplatin; cyclosphasphamid; vinblastine; vincristin; fluorouracil; etoposide; bleomycin. Examples of combination therapies include (CISCA (cyclophosphamide, doxorubicin, and cisplatin); CMV (cisplatin, methotrexate, vinblastine); MVMJ (methodtrextate, vinblastine, mitoxantrone, carboplain); CAP (cyclophosphamide, doxorubicin, cisplatin); MVAC (methotrexate, vinblastine, doxorubicin, cisplatin). Radiation may also be combined with chemotherapeutic agent(s), for example, radiation with cisplatin. Administration of the chemotherapeutic agents is generally intravesical (directly into the bladder) or intravenous.

The following examples are provided to illustrate but not limit the invention.

EXAMPLES

Example 1
Construction of a Replication-Competent Adenovirus Vector Comprising an AFP-TRE and an EMCV IRES The encephalomyocarditis virus (ECMV) IRES as depicted in Table 1 was introduced between the E1A and E1B regions of a replication-competent adenovirus vector specific for cells expressing AFP as follows. Table 1 shows the 519 base pair IRES segment which was PCR amplified from Novagen's pCITE vector by primers A/B as listed in Table 4. A 98 base pair deletion in the E1A promoter region was created in PXC.1, a plasmid which contains the leftmost 16 mu of Ad5. Plasmid pXC.1 (McKinnon (1982) *Gene* 19:33–42) contains the wild-type left-hand end of Ad5, from Adenovirus 5 nt 22 to 5790 including the inverted terminal repeat, the packaging sequence, and the E1a and E1b genes in vector pBR322. pBHG10 (Bett. et al. (1994) *Proc. Natl. Acad. Sci. USA* 91:8802–8806; Microbix Biosystems Inc., Toronto) provides the right-hand end of Ad5, with a deletion in E3. The resultant plasmid, CP306 (PCT/US98/16312), was used as the backbone in overlap PCR to generate CP624. To place a SalI site between E1a and E1b, primers C/D, E/F (Table 4) were used to amplify CP306, plasmid derived from pXC.1 and lacking the E1a promoter. After first round PCR using CP306 as template and primers C/D, E/F, the resultant two DNA fragments were mixed together for another round of overlapping PCR with primers C/F. The overlap PCR product was cloned by blunt end ligation to vector. The resultant plasmid, CP624 (Table 5), contains 100 bp deletion in E1a/E1b intergenic region and introduces Sal1 site into the junction. On this plasmid, the endogenous E1a promoter is deleted, and the E1a polyadenylation signal and the E1b promoter are replaced by the Sal1 site. Next, the Sal1 fragment of CP625 was cloned into the Sal1site in CP624 to generate CP627 (Table 5). CP627 has an EMCV IRES connecting adenovirus essential genes E1a and E1b. In CP627, a series of different tumor-specific promoters can be placed at the PinA1 site in front of E1a to achieve transcriptional control on E1 expression.

The virus obtained by recombination of CP686 with a right arm containing an intact E3 region was named CV890. The virus obtained by recombination of CP686 with a right arm containing a deleted E3 region (pBHG 10) was named CV840. The structure of all viral genomes was confirmed by conducting PCR amplifications that were diagnostic for the corresponding specific regions.

Therefore, adenovirus vector designated CV890 comprises 0.8 kb AFP promoter, E1A, a deletion of the E1A promoter, EMCV IRES, E1B a deletion of the E1B promoter and an intact E3 region. Adenovirus vector CV840 comprises AFP promoter, E1A, a deletion of the E1A promoter, EMCV IRES, E1B, a deletion of the E1B promoter and a deleted E3 region.

TABLE 4

| Primer | Sequence | | Note |
| --- | --- | --- | --- |
| A. | 5'-GACGTCGACTAATTCCGGTTATTTTCCA | SEQ ID NO: 19 | For PCR EMCV IRES, GTCGAC is a SaII site. |
| B. | 5'-GACGTCGACATCGTGTTTTTCAAAGGAA | SEQ ID NO: 20 | For PCR EMCV IRES, GTCGAC is a SaII site. |
| C. | 5'-CCTGAGACGCCCGACATCACCTGTG | SEQ ID NO: 21 | Ad5 sequence to 1314 to 1338. |
| D. | 5'-<u>GTCGAC</u>CATTCAGCAAACAAAGGCGTTAAC | SEQ ID NO: 22 | Antisense of Ad5 sequence 1572 to 1586. GTCGAC is SaII site. Underline region overlaps with E. |
| E. | 5'-<u>TGCTGAATG</u>GTCGACATGGAGGCTTGGGAG | SEQ ID NO: 23 | Ad5 sequence 1714 to 1728. GTCGAC is a SaII site. Underline region overlaps with D. |
| F. | 5'-CACAAACCGCTCTCCACAGATGCATG | SEQ ID NO: 24 | Antisense of Ad5 sequence 2070 to 2094. |

For generating a liver cancer-specific virus, an about 0.8 kb AFP promoter fragment as shown in Table 3 was placed into the PinA1 site of CP627 thereby yielding plasmid

TABLE 5

| Plasmid designation | Brief description |
| --- | --- |
| CP306 | An E1A promoter deleted plasmid derived from pXC.1 |
| CP624 | Overlap PCR product from CP306 to generate 100 bp deletion and introduce a Sal1 site at E1A and E1B junction; E1A and E1B promoter deleted in E1A/E1B intergenic region. |
| CP625 | EMCV IRES element ligated to PCR-blunt vector (Invitrogen pCR ® blunt vector). |
| CP627 | IRES element derived from CP625 by Sal1 digestion and ligated to CP624 Sal1 site placing IRES upstream from E1B. |
| CP628 | Probasin promoter derived from CP251 by PinA1 digestion and cloned into PinA1 site on CP627. |
| CP629 | HCMV IE promoter amplified from pCMV beta (Clontech) with PinA1 at 5' and 3' ends ligated into CP627 PinA1 site. |
| CP630 | A 163 bp long VEGF IRES fragment (Table 1) cloned into the Sal1 site on CP628. |
| CP686 | AFP promoter from CP219 digested with PinA1 and cloned into PinA1 site on CP627. |

CP686. Full-length viral genomes were obtained by recombination between CP686 and a plasmid containing a right arm of an adenovirus genome. The right arms used in virus recombination were pBHGE3 (Microbix Biosystems Inc.), containing an intact E3 region, and pBHG11 or pBHG10 (Bett et al. (1994) containing a deletion in the E3 region.

Example 2

Construction of a Replication-Competent Adenovirus Vector with a Probasin TRE and an EMCV IRES The probasin promoter as shown in Table 3 was inserted at the PinAI site of plasmid CP627 (see Example 1) to generate CP628, which contains a probasin promoter upstream of E1A and an EMCV IRES between E1A and E1B. Full-length viral genomes were obtained by recombination between CP628 and a plasmid containing a right arm of an adenovirus genome. The right arms used in virus recombination were pBHGE3, containing an intact E3 region, and pBHG11 or pBHG10 containing a deletion in the E3 region. The structure of all viral genomes was confirmed by conducting PCR amplifications that were diagnostic for the corresponding specific regions.

Therefore, adenovirus designated CV 834 comprises probasin promoter, E1A, a deletion of the E1A promoter, EMCV IRES, E1B, a deletion of the E1B endogenous promoter and a deleted E3 region.

Example 3
Construction of a Replication-Competent Adenovirus Vector with a hCMV-TRE and an EMCV IRES The hCMV immediate early gene (IE) promoter from plasmid CP629, originally derived from pCMVBeta (Clonetech, Palo Alto) was inserted at the PinAI site of plasmid CP627 (see Example 1) to generate CP629, containing a CMV IE promoter upstream of E1A and an IRES between E1A and E1B. Full-length viral genomes were obtained by recombination between CP629 and a plasmid containing a right arm of an adenovirus genome. The right arms used in virus recombination were pBHGE3, containing an intact E3 region, and pBHG11 or pBHG10 containing a deletion in the E3 region. The structure of all viral genomes was confirmed by conducting PCR amplifications that were diagnostic for the corresponding specific regions.

Therefore, adenovirus vector designated CV835 comprises hCMV-IE promoter, E1A, a deletion of the E1A promoter, EMCV IRES, E1B a deletion in the E1B endogenous promoter and a deleted E3 region. CV835 lacks the hCMV enhancer and is therefore not tissue specific. By adding the hCMV IE enhancer sequence to CV835, the vector is made tissue specific.

Example 4
Replication of IRES-Containing Adenovirus Vectors with Different TREs Controlling E1 Expression The viral replication of adenovirus vectors comprising the probasin promoter (CV836 and CV834) generally considered a weak promoter, and the human cytomegalovirus immediate early gene (HCMV-IE) promoter (CV837 and CV835), generally considered a strong promoter, were characterized in the virus yield assay.

Probasin promoter containing adenovirus vectors (see PCT/US98/04132), CV836 and CV834, and HCMV-IE promoter containing adenovirus vectors, CV837 and CV835, were tested against a panel of cell lines for viral replication (indicative of lethality) and specificity. Cell lines 293 (the producer line), LNCap and HepG2 were plated at $0.5 \times 10^6$ per well in 6 well tissue culture plates, incubated for 24 hours at 37° C., then infected with CV836, CV834 or CV837 and CV835 at a multiplicity of infection (MOI) of 2 plaque forming units per cell (PFU/cell) for 4 hours at 37° C. At the end of the infection period, the medium was replaced and the cells were incubated at 37° C. for a further 72 hours before harvesting for a viral yield assay as described in Yu et al. (1999) *Cancer Res.* 59:1498–1504. The results are shown in FIG. 3.

The data demonstrate that the presence of an IRES element in the intergenic region between E1A and E1B does not significantly affect viral replication, as compared to control viruses lacking an IRES, such as a wild-type AD5 with a deletion in the E3 region. In CV834, the loss of tissue cytotoxicity could be caused by the weakness of the probasin promoter in the virus structure.

Example 5
Comparison of Dual TRE Vectors with Single TRE/IRES-Containing Vectors Two liver cancer-specific adenovirus vectors, CV790 and CV733 (also designated CN790 and CN733, respectively), were generated and characterized. See PCT/US98/04084. These viruses contain two AFP TREs, one upstream of E1A and one upstream of E1B. They differ in that CV790 contains an intact E3 region, while the E3 region is deleted in CV733. Replication of these two viruses was compared with that of the newly generated IRES-containing viruses, CV890 and CV840 (see Example 1).

Figure 4B:
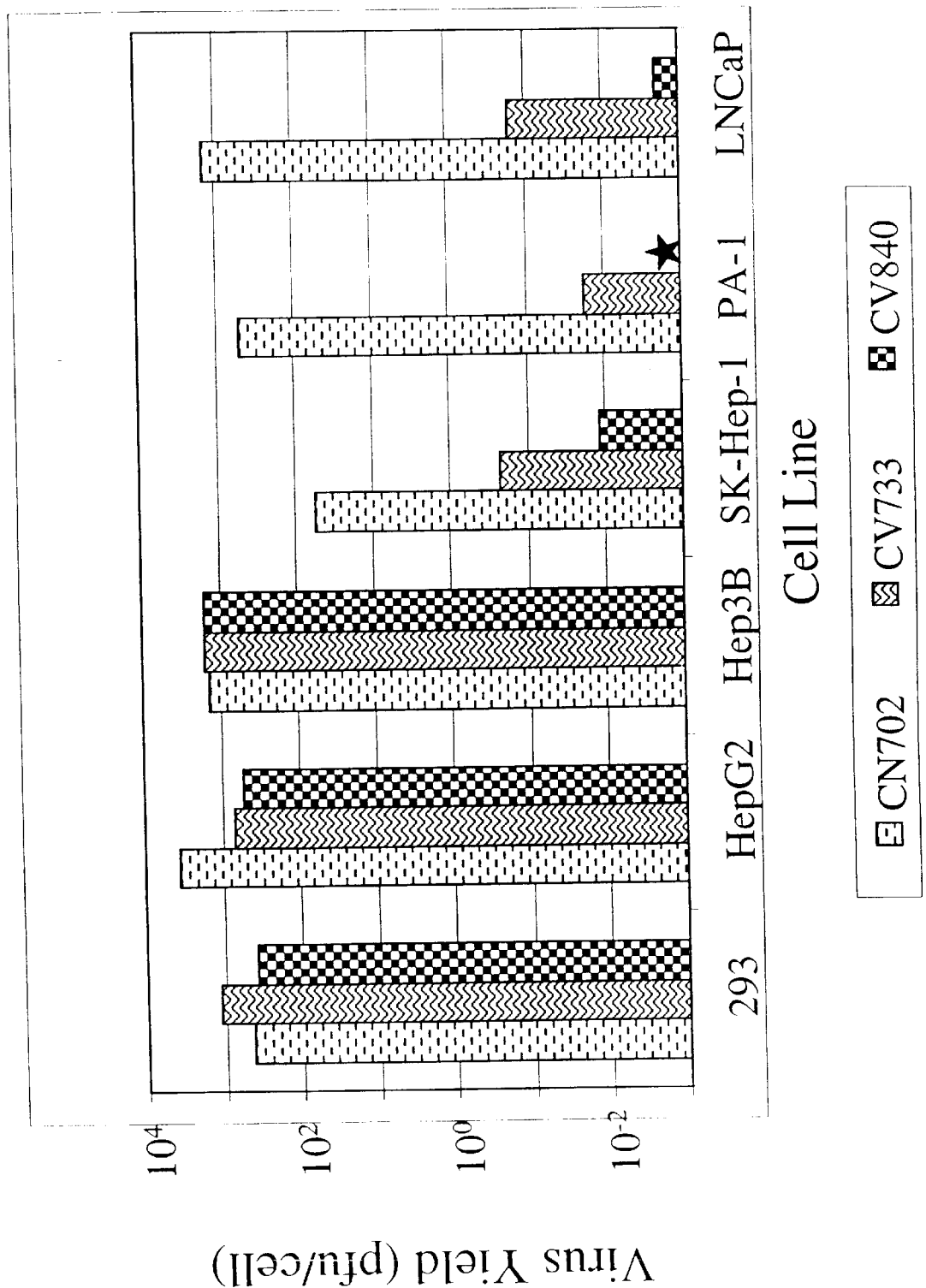
Figure 5:
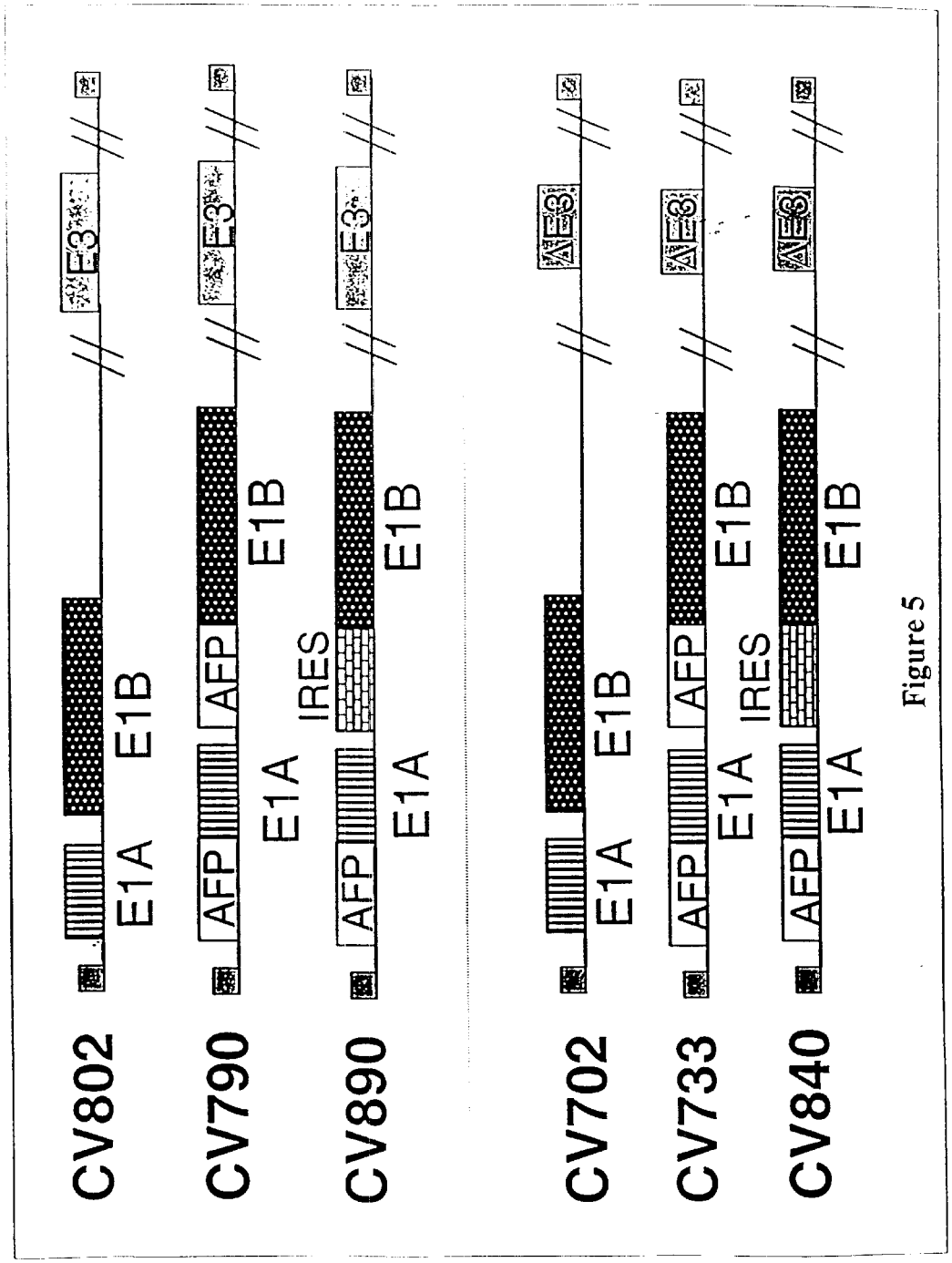
FIG. 5 is a schematic representation of adenovirus vectors comprising AFP-TRE with and without IRES.

Virus replication was compared, in different cell types, using a virus yield assay as described in Example 4. Cells were infected with each type of virus and, 72 hrs after infection, virus yield was determined by a plaque assay. FIGS. 4A and 4B show viral yield for different viruses in different cell types. The results indicate that vectors containing an IRES between E1A and E1B (CV890 and CV840), in which E1B translation is regulated by the IRES, replicate to similar extents as normal adenovirus and viruses with dual AFP TREs, in AFP-producing cells such as 293 cells and hepatoma cells. In SK-Hep-1 (liver cells), PA-1 (ovarian carcinoma) and LNCaP cells (prostate cells) the IRES-containing viruses do not replicate as well as dual TRE or wild-type adenoviruses, indicating that the IRES-containing viruses have higher specificity for hepatoma cells. Based on these results, it is concluded that IRES-containing vectors have unaltered replication levels, but are more stable and have better target cell specificity, compared to dual-TRE vectors.

Example 6
Uroplakin Adenoviral Constructs Containing an EMCV IRES

A number of E3-containing viral constructs were prepared which contained uroplakin II sequences (mouse and/or human) as well as an EMCV internal ribosome entry site (IRES). The viral constructs are summarized in Table 6. All of these vectors lacked an E1A promoter and retained the E1A enhancer.

The 519 base pair EMCV IRES segment was PCR amplified from Novagen's pCITE vector by primers A/B:

primer  A:
5'-GACGTCGACTAATTCCGGTTATTTTCCA SEQ ID NO: 19 primer  B
5'-GACGTCGACATCGTGTTTTTCAAAGGAA SEQ ID NO: 20 (GTCGAC is a SaiI site).

The EMCV IRES element was ligated to PCR blunt vector (Invitrogen pCR® blunt vector).
CP1066

The 1.9 kb-(−1885 to +1) fragment of mouse UPII from CP620 was digested with AflIII (blunted) and HindIII and inserted into pGL3-Basic from CP620 which had been digested with XhoI (blunted) and HindlII to generate CP1066.
CP1086

The 1.9kb mouse UPII insert was digested with PinAI and ligated with CP269 (CMV driving E1A and IRES driving E1B with the deletions of E1A/E1B endogenous promoter) which was similarly cut by PinAI.
CP1087

The 1 kb (−1128 to +1) human UPII was digested with PinAI from CP665 and inserted into CP629 which had been cut by PinAI and purified (to elute CMV).
CP 1088

The 2.2 kb (-2225 to +1) human UPII was amplified from CP657 with primer 127.2.1 (5'-AGGACCGGTCACTATAGGGCACGCGTGGT-3' (SEQ ID NO: 25)) PLUS 127.2.2 (5'-AGGACCGGTGGGATGCTGGGCTGGGAGGTGG-3' (SEQ ID NO: 26')) and digested with PinAI and ligated with CP629 cut with PinAI.

CP627 is an Ad5 plasmid with an internal ribosome entry site (IRES) from encephelomycarditis virus (EMCV) at the junction of E1A and E1B. First, CP306 (Yu et al., 1999) was amplified with primer pairs 96.74.3/96.74.6 and 96.74.4/96.74.5.

The two PCR products were mixed and amplified with primer pairs 96.74.3 and 96.74.5. The resultant PCR product contains a 100 bp deletion in E1A-E1B intergenic region and a new SalI site at the junction. EMCV IRES fragment was amplified from pCITE-3a(+) (Novagen) using primers 96.74.1 and 96.74.2. The SalI fragment containing IRES was placed into SalI site to generate CP627 with the bicistronic E1A-IRES-E1B cassette. CP629 is a plasmid with CMV promoter amplified from pCMVbeta (Clontech) with primer 99.120.1 and 99.120.2 and cloned into PinAI site of CP627.

CP657 is a plasmid with 2.2 kb 5' flanking region of human UP II gene in pGL3-Basic (Promega). The 2.2 kb hUPII was amplified by PCR from GenomeWalker product with primer 100.113.1 and 100.113.2 and TA-cloned into pGEM-T to generate CP655.

The 2.2 kb insert digested from SacII (blunt-ended) and KpnI was cloned into pGL3-Basic at HindIII (blunted) and KpnI to create CP657.

CP1089

The 1 kb (-965 to +1) mouse LTPII was digested by PinAI from CP263 and inserted into CN422 (PSE driving E1A and GKE driving E1B with the deletions of E1A/E1B endogenous promoter) cut by PinAI and purified and farther digested with EagI and ligated with 1 kb (-1128 to +1) human UPII cut from CP669 with EagI.

CP1129

The 1.8 kb hUPII fragment with PinAI site was amplified from CP657 with primer 127.50.1 and 127.2.2 and cloned into PinAI site of CP629.

CP1131

CP686 was constructed by replacing the CMV promoter in CP629 with an AFP fragment from CP219. A 1.4 kb DNA fragment was released from CP686 by digesting it with BssHII, filling with Klenow, then digesting with BglII. This DNA fragment was then cloned into a similarly cut CP686 to generate CP1199. In CP1199, most of the E1B 19-KDa region was deleted. The 1.8 kb hUPII fragment with PinAI site was amplified from CP657 by PCR with primer 127.50.1 and 127.2.2 and inserted into similarly digested CP1199 to create CP1131.

The plasmids above were all co-transfected with pBHGE3 to generate CV874 (from CP1086), CV875 (from CP1087), CV876 (from 1088) and CV877 (from CP1089), CV882 (from CP1129) and CV884 (from CP1131). CP1088, CP1129 and CP1131 were cotransfected with pBHGE3 for construction of CV876, CV892 and CV884, respectively by lipofectAMINE (Gibco/BRL) for 11–14 days. pBHGE3 was purchased from Microbix, Inc., and was described previously. The cells were lysed by three freeze-thaw cycles and plaqued on 293 cells for a week. The single plaques were picked and amplified by infection in 293 cells for 3–5 days. The viral DNAs were isolated from the lysates and the constructs were confirmed by PCR with primer 31.166.1/51.176 for CV876 and primer 127.50.1/51.176 for CV882 and CV884 at E1 region and primer 32.32.1/2 for all three viruses at E3 region.

TABLE 6

| Name | Vector | Ad 5 Vector | E1A TRE | E1B TRE | E3 |
|---|---|---|---|---|---|
| CV874 | CP1086 | pBHGE3 | 1.9 kb mUPII | IRES | intact |
| CV875 | CP1087 | pBHGE3 | 1.0 kb hUPII | IRES | intact |
| CV876 | CP1088 | pBHGE3 | 2.2 kb hUPII | IRES | intact |
| CV877 | CP1089 | pBHGE3 | 1.0 kb mUPII | 1.0 kb hUPII (E1B promoter deleted) | intact |
| CV882 | CP1129 | pBHGE3 | 1.8 kb hUPII | IRES | intact |
| CV884 | CP1131 | pBHGE3 | 1.8 kb hUPii | IRES (E1B 19-kDa deleted) | intact |

Viruses are tested and characterized as described above.

Primer sequences:

| | | |
|---|---|---|
| 96.74.1 | GACGTCGACATCGTGTTTTTCAAAGGAA | SEQ ID NO: 20 |
| 96.74.2 | GACGTCGACTAATTCCGGTTATTTTCCA | SEQ ID NO: 19 |
| 96.74.3 | CCTGAGACGCCCGACATCACCTGTG | SEQ ID NO: 21 |
| 96.74.4 | TGCTGAATGGTCGACATGGAGGCTTGGGAG | SEQ ID NO: 23 |
| 96.74.5 | CACAACCGCTCTCCACAGATGCATG | SEQ ID NO: 24 |
| 96.74.6 | GTCGACCATTCAGCAAACAAAGGCGTTAAC | SEQ ID NO: 22 |
| 100.113.1 | AGGGGTACCCACTATAGGGCACGCGTGGT | SEQ ID NO: 27 |
| 100.113.2 | ACCCAAGCTTGGGATGCTGGGCTGGGAGGTGG | SEQ ID NO: 28 |
| 127.2.2 | AGGACCGGTGGGATGCTGGGCTGGGAGGTGG | SEQ ID NO: 26 |
| 127.50.1 | AGGACCGGTCAGGCTTCACCCCAGACCCAC | SEQ ID NO: 29 |
| 31.166.1 | TGCGCCGGTGTACACAGGAAGTGA | SEQ ID NO: 30 |
| 32.32.1 | GAGTTTGTGCCATCGGTCTAC | SEQ ID NO: 31 |

-continued

Primer sequences:

| | | |
|---|---|---|
| 32.32.2 | AATCAATCCTTAGTCCTCCTG | SEQ ID NO: 32 |
| 51.176 | GCAGAAAAATCTTCCAAACACTCCC | SEQ ID NO: 33 |
| 99.120.1 | ACGTACACCGGTCGTTACATAACTTAC | SEQ ID NO: 34 |
| 99.120.2 | CTAGCAACCGGTCGGTTCACTAAACG | SEQ ID NO: 35 |

Example 7
Construction of a Replication-Competent Adenovirus Vector with a Tyrosinase TRE and EMCV IRES CP621 is a plasmid containing a human tyrosinase enhancer and promoter elements in a PinA1 fragment. This fragment is ligated to the PinA1 site on CP627 to generate CP1078. CP1078 is combined with pBHGE3 to generate a new melanoma specific virus, CV859. Table 3 depicts the polynucleotide sequence of the PinA1 fragment which contains a tyrosinase promoter and enhancer.

Example 8
Construction of a Replication-Competent Adenovirus Vector with a Probasin-TRE and a VEGF IRES Using a strategy similar to that described in Example 1, the IRES fragment from the mouse vascular endothelial growth factor (VEGF) gene is amplified and cloned into CP628 at the SalI site. Table 1 depicts the IRES fragment obtainable from vascular endothelial growth factor (VEGF) mRNA. In order to clone this fragment into the E1a/E1b intergenic region, two pieces of long oligonucleotide are synthesized. The sense oligonucleotide is shown in the Table, whereas the second piece is the corresponding antisense one. After annealing the two together to create a duplex, the duplex is subjected to SalI digestion and the resulting fragment is cloned into the SalI site on CP628. The resulting plasmid, CP630, has a probasin promoter in front of E1a and an VEGF IRES element in front of E1b. This plasmid is used to construct a prostate cancer-specific virus comprising the VEGF IRES element.

Example 9
Construction of a Replication-Competent Adenovirus Vector with an AFP-TRE and a VEGF IRES Using a strategy similar to Example 1, a PinAI fragment which contains AFP TRE can be obtained. This AFP TRE is cloned into the PinA1 site in front of E1A on CP628 yielding plasmid CP1077. This plasmid has the AFP TRE for E1 transcriptional control and the VEGF IRES element before E1b. CP1077 can be recombined with pBHGE3 to generate a liver-specific adenovirus, designated as CV858.

Example 10
Construction of a Replication-Competent Adenovirus Vector with a hKLK2-TRE and a EMCV IRES Using a strategy similar to Example 1, the TRE fragment from human glandular kallikrein II as shown in Table 3 was cloned into the PinAI site in CP627. The resultant plasmid, CP1079, is cotransfected with pBHGE3 to create CV860.

Example 11
Treatment of Hep3B Tumor Xenografts with Replication-Competent Hepatoma Specific CV790 and Doxorubicin and Hepatoma Specific CV890 and Doxorubicin CV790 is an AFP producing hepatocellular carcinoma specific adenovirus, with E1A and E1B under the control of an identical AFP promoter and enhancer (822 base pair promoter shown in Table 3) with an E3 region. The CV890 adenovirus construct is also a hepatoma or liver-specific adenoviral mutant with the E1A and E1B genes under transcriptional control of 822 bp AFP promoter (827 bp including nucleotides for restriction site), wherein E1B is under translational control of EMCV IRES and having an intact E3 region. The structure of CV890 therefore reads as AFP/E1A, IRES/E1B, E2, E3, E4. In vivo studies of the efficacy of combinations of CV790 and doxorubicin and CV890 and doxorubicin were performed according to the protocols described in detail in Example 4, with minor alterations which are described below.

Xenografts in the study of CV790 and CV890 combined with chemotherapeutic agents utilized liver carcinoma Hep3B cells. Virus, CV790 or CV890, was administered by a single intravenous injection of $1\times10^{11}$ particles through the tail veins of the nude mice. One day after virus delivery, a single dose of doxorubicin was given to each animal by i.p. injection. The doxorubicin dose was 10 mg/kg for both doxorubicin alone and doxorubicin combined with virus treatments. Tumor volume was measured once a week for six weeks. Tumors were measured weekly in two dimensions by external caliper and volume was estimated by the formula [length (mm)×width $(mm)^2$]/2.

Figure 8:
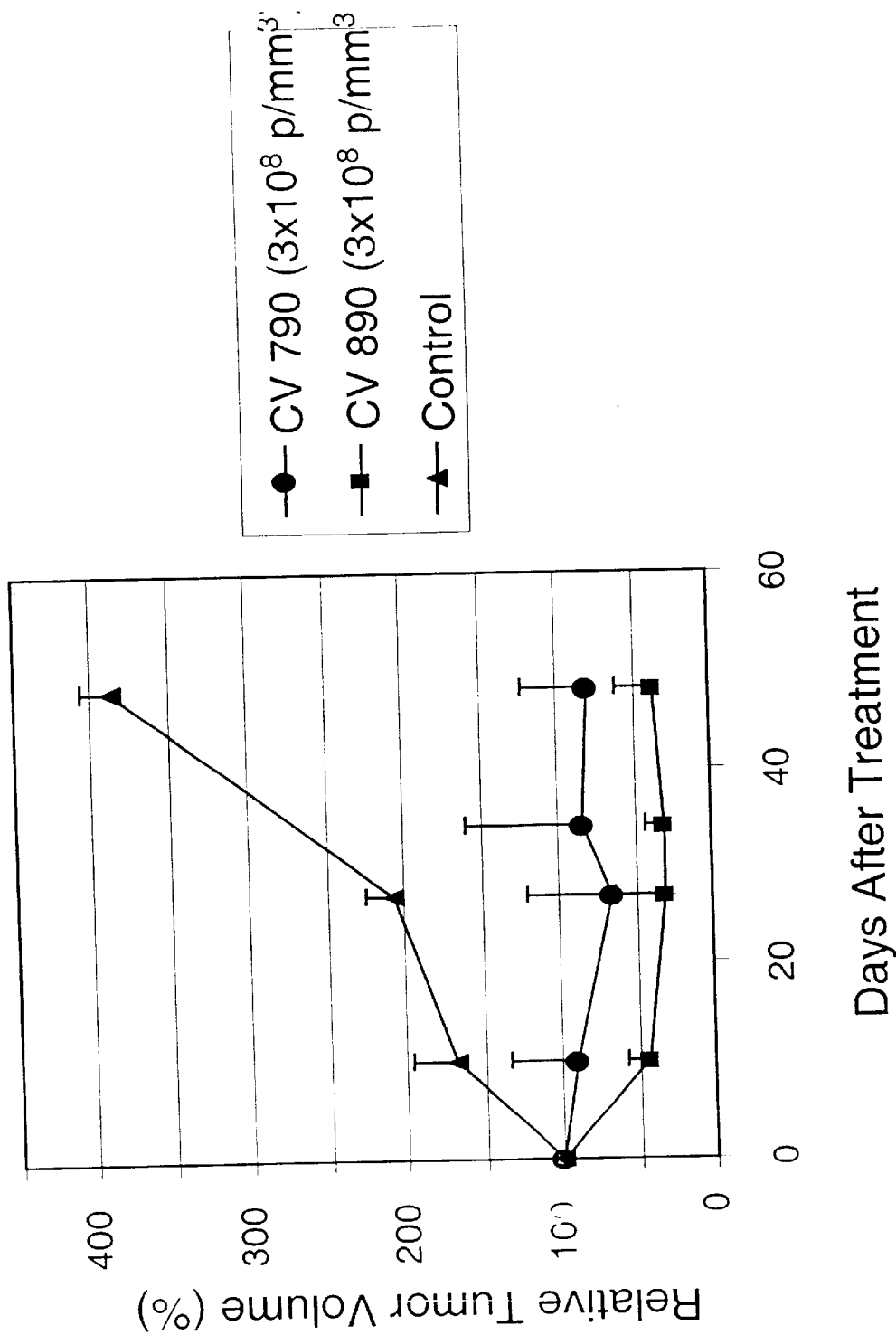
FIG. 8 depicts in vivo antitumor activity of CV890 containing an IRES. This figure depicts the results of a HepG2 Xenograph treated with CV790 or CV890.

FIG. 8 depicts the anti-tumor activity of CV890 containing an IRES as compared to CV 790 containing dual TREs. As FIG. 8 demonstrates, relative tumor volume was less with administration of CV890 than administration of CV790.

Furthermore, both CV790/doxorubicin and CV890/doxorubicin treatment of the hepatoma showed synergistic results. Four days after treatment with either CV790/doxorubicin or CV890/doxorubicin the relative tumor volume was less than 10%. Unlike mice treated with either virus alone or doxorubicin alone, after day 4, the relative tumor volume did not increase for either the either CV790/doxorubicin or CV890/doxorubicin treated mice. At day 6 in the control mice, the relative tumor volume was approximately 1000% in the CV790 study and approximately 600% in the CV890 study. The relative tumor volumes of mice treated with virus alone were 250% (CV790) and 520% (CV890) while the relative tumor volumes for mice treated with doxorubicin alone were 450% with 280% in the CV790 study and 500% in the CV890 study.

Example 12
In Vitro Characterization of Melanocyte-Specific TRE-Containing Adenoviral Constructs An especially useful objective in the development of melanocyte cell-specific adenoviral vectors is to treat patients with melanoma. Methods are described below for measuring the activity of a melanocyte-specific TRE and thus for determining whether a given cell allows a melanocyte-specific TRE to function.

Cells and Culture Methods

Host cells such as, HepG2 (liver); Lovo (colon); LNCaP (prostate); PMEL (melanoma); SKMel (melanoma); G361 (melanoma) and MeWo cells are obtained at passage 9 from the American Type Culture Collection (Rockville, Md.). MeWo cells are maintained in RPMI 1640 medium (RPMI) supplemented with 10% fetal bovine serum (FBS; Intergen Corp.), 100 units/mL of penicillin, and 100 units/mL streptomycin. MeWo cells being assayed for luciferase expression are maintained in 10% strip-serum (charcoal/dextran treated fetal bovine serum to remove T3, T4, and steroids; Gemini Bioproduct, Inc., Calabasas, Calif.) RPMI.

Transfections of MeWo Cells

For transfections, MeWo cells are plated out at a cell density of $5 \times 10^5$ cells per 6-cm culture dish (Falcon, N.J.) in complete RPMI. DNAs are introduced into MeWo cells after being complexed with a 1:1 molar lipid mixture of N-[1-(2,3-dioleyloxy)propyl-N,N,N-trimethylammonium chloride (DOTAP™; Avanti Polar Lipids, AL) and dioleoyl-phosphatidylethanolamine (DOPE™; Avanti Polar Lipids, AL); DNA/lipid complexes are prepared in serum-free RPMI at a 2:1 molar ratio. Typically, 8 μg (24.2 nmole) of DNA is diluted into 200 μL of incomplete RPMI and added dropwise to 50 nmole of transfecting, lipids in 200 μL of RPMI with gentle vortexing to insure homogenous mixing of components. The DNA/lipid complexes are allowed to anneal at room temperature for 15 minutes prior to their addition to MeWo cells. Medium is removed from MeWo cells and replaced with 1 mL of serum-free RPMI followed by the dropwise addition of DNA/lipid complexes. Cells are incubated with complexes for 4–5 hours at 37° C., 5% $CO_2$. Medium was removed and cells washed once with PBS. The cells were then trypsinized and resuspended in 10% strip-serum RPMI (phenol red free). Cells were replated into an opaque 96-well tissue culture plate (Falcon, N.J.) at a cell density of 40,000 cells/well per 100 μL media and assayed.

Plague Assays

To determine whether the adenoviral constructs described above replicate preferentially in melanocytes, plaque assays are performed. Plaquing efficiency is evaluated in the following cell types: melanoma cells (MeWo), prostate tumor cell lines (LNCaP), breast normal cell line (HBL-100), ovarian tumor cell line (OVCAR-3, SK-OV-3), and human embryonic kidney cells (293). 293 cells serve as a positive control for plaquing efficiency, since this cell line expresses Ad5 E1A and E1B proteins. For analyzing constructs comprising a melanocyte-specific TRE, cells that allow a melanocyte-specific TRE to function, such as the cell lines provided above and cells that do not allow such function, such as HuH7, HeLa, PA-1, or G361, are used. The plaque assay is performed as follows: Confluent cell monolayers are seeded in 6-well dishes eighteen hours before infection. The monolayers are infected with 10-fold serial dilutions of each virus. After infecting monolayers for four hours in serum-free media (MEM), the medium is removed and replaced with a solution of 0.75% low melting point agarose and tissue culture media. Plaques are scored two weeks after infection.

Example 13

Construction of a Replication-competent Adenovirus Vector With a CEA-TRE and a EMCV IRES Using a strategy similar to Example 1, the TRE fragment from Carcinembryonic antigen (CEA)(Table 3, SEQ ID NO: 14) is used to construct virus designated CV873. A PinAI fragment containing the CEA-TRE was cloned into the PinAI site in front of E1A CP627 for the transcriptional control. The resultant plasmid CP1080 is used together with pBHGE3 to generate CV873.

Example 14

In Vitro and In Vivo Assays of Anti-Tumor Activity An especially useful objective in the development of urothelial cell-specific adenoviral vectors is to treat patients with bladder cancer. An initial indicator of the feasibility is to test the vector(s) for cytotoxic activity against cell lines and tumor xenografts grown subcutaneously in Balb/c nu/nu mice.

In Vitro Characterization of CV876

Virus Yield Assay for CV876

$5 \times 10^5$ 293, RT-4, SW780, PA-1, G361, MKN1, HBL-100, Fibroblast (from lung) and Smooth muscle cells (from bladder) were plated into each well of six-well plates. Twenty-four hours later, medium was aspirated and replaced with 1 ml of serum-free RPMI 1640 containing CV802 (wt.Ad5 with E3) or CV876 at a MOI of 2 pfu/cell. After a 4-h incubation at 37° C., cells were washed with prewarmed PBS, and 2 ml of complete RPMI 1640 were added to each well. After an additional 72 h at 37° C., the cells were scraped into medium and lysed by three freeze-thaw cycles. The lysates were tested for virus production by triplicate plaque assay for 8–10 days under semisolid agarose on 293 cells.

Unlike wt. Ad5, CV802 which grows well in all of the cells tested, CV876 replicates much better in permissive cells (293, RT-4 and SW780) than in non-permissive cells (PA-1, G361, MKN1, HBL-100 and primary cells) by about 100–10000 fold. Noticeably, the replication in SW780 for CV876 is about 100 fold less than CV802, which indicates the limitation of this virus in efficacy.

Growth Curve Experiment for CV876

$5 \times 10^5$ RT-4, PA-1, Smooth muscle and Fibroblast cells were plated into each well of six-well plates. Twenty-four hours later, medium was aspirated and replaced with 1 ml of serum-free RPMI 1640 containing CV802 (wt.Ad5 with 133) or CV876 at a MOI of 2 pfu/cell. After a 4-h incubation at 37° C., cells were washed with prewarmed PBS, and 2 ml of complete RPMI 1640 were added to each well. At different time points of 0, 12, 24, 36, 48, 72, 96 and 120h, the cells were scraped into medium and lysed by three freeze-thaw cycles. The lysates were tested for virus production by triplicate plaque assay for 8–10 days under semisolid agarose on 293 cells.

Very similar as in virus yield assay, CV876 replicates well only in RT-4 but not in primary cells and PA-1 over a 120 h period of time. However, CV876 does show a delay of replication in RT-4 compared to CV802.

Cytopathic Effect Assay for CV876

$5 \times 10^5$ 293, RT-4, SW780, PA-1, MKN1 and LNCap were plated into each well of six-well plates. Twenty-four hours later, medium was aspirated and replaced with 1 ml of serum-free RPMI 1640 containing CV802 (wt.Ad5 with E3) or CV876 at increasing MOI from 0.001 to 10 (the data shown was at MOI 1). After a 4-h incubation at 37° C., medium was replaced with 3 ml of complete RPMI 1640 and incubated at 37° C. for 6–8 days when cytopathic effect was observed for CV802 at MOI 0.01.

CV802 shows efficacy in all the cells tested while CV876 only kills the permissive cells (293, RT-4 and SW780) but not the non-permissive cells (PA-1, MKN-1 and LNCap).

MTT Assay for CV876

$2 \times 10^4$ 293, RT-4, SW780, MKN1, PA-1, HBL-100, Smooth muscle cells (from bladder) and Fibroblast (from lung) were plated into each well of 96-well plates. Twenty-four hours later, the cells were infected with CV802 and CV876 at increasing MOI from 0.001 to 10 in complete RPMI 1640. A rapid colorimetric assay for cell growth and survival was run at different time point of day 1, 3,5,7 and 10. The medium was replaced by 50 ul of MTT at 1 mg/ml solution, which is converted to an insoluble purple formazan by dehydrogenase enzymes present in active mitochondria of live cells. After 3–4h incubation at 37° C., the solution was replaced by isopropanol and the plates were incubated at 30° C. for 1 h and read at 560 nm test wavelength and 690 nm reference wavelength.

Similar as the results in CPE assay, CV876 shows efficacy only in permissive cells but not in non-permissive cells. Again, in RT-4 and SW780, CV876 kills the cells much slower than CV802.

In Vitro Characterization of CV882

Virus Yield Assay for CV882

$5 \times 10^5$ 293, RT-4, SW780, G361, LNCap, HBL-100, MKN1, PA-1, Fibroblast and Smooth muscle cells were plated into each well of six-well plates. Twenty-four hours later, medium was aspirated and replaced with 1 ml of serum-free RPMI 1640 containing CV802 (wt.Ad5 with E3) or CV882 at a MOI of 2 pfu/cell. After a 4-h incubation at 37° C., cells were washed with prewarmed PBS, and 2 ml of complete RPMI 1640 were added to each well. After an additional 72 h at 37° C., the cells were scraped into medium and lysed by three freeze-thaw cycles. The lysates were tested for virus production by triplicate plaque assay for 8–10 days under semisolid agarose on 293 cells.

The replication of CV882 in permissive cells (293, RT-4 and SW780) is comparable to CV802 (the difference is less than 100 fold) while it shows over 1000–1000000 fold difference in non-permissive cells (G361, LNCap, HBL-100, MKN1, PA-1 and primary cells).

Growth Curve Experiment for CV882

$5 \times 10^5$ RT-4, PA-1, and Fibroblast cells were plated into each well of six-well plates. Twenty-four hours later, medium was aspirated and replaced with 1 ml of serum-free RPMI 1640 containing CV802 (wt.Ad5 with E3) or CV882 at a MOI of 2 pfu/cell. After a 4-h incubation at 37° C., cells were washed with prewarmed PBS, and 2 ml of complete RPMI 1640 were added to each well. At different time points of 0, 12, 24, 36, 48, 72, 96 and 120 h, the cells were scraped into medium and lysed by three, freeze-thaw cycles. The lysates were tested for virus production by triplicate plaque assay for 8–10 days under semisolid agarose on 293 cells.

Very similar as in virus yield assay, CV882 replicates well only in RT-4 but not in primary cells and PA-1 over a 120 h period of time. Additionally, CV882 shows better replication in RT-4 compared to CV876.

Cytopathic Effect Assay for CV882

$5 \times 10^5$ 293, RT-4, SW780, HBL-100, G361, PA-1 and Fibroblast cells were plated into each well of six-well plates. Twenty-four hours later, medium was aspirated and replaced with 1 ml of serum-free RPNI 1640 containing CV802 (wt.Ad5 with E3) or CV882 at increasing MOI from 0.001 to 10 (the data shown was at MOI 1). After a 4-h incubation at 37° C., medium was replaced with 3 ml of complete RPMI 1640 and incubated at 37° C. for 6–8 days when cytopathic effect was observed for CV802 at MOI 0.01.

CV802 shows efficacy in all the cells tested while CV882 only kills the permissive cells (293, RT-4 and SW780) but not the non-permissive cells (HBL-100, G361, PA-1 and Fibroblast cells).

MTT Assay for CV882

$2 \times 10^4$ RT-4, SW780, PA-1, HBL-100, U118 and Fibroblast were plated into each well of 96-well plates. Twenty-four hours later, the cells were infected with CV802 and CV882 at increasing MOI from 0.001 to 10 in complete RPMI 1640. A rapid colorimetric assay for cell growth and survival was run at different time points of day 1, 3, 5, 7 and 10. The medium was replaced by 50 ul of MTT at 1 mg/ml solution, which is converted to an insoluble purple formazan by dehydrogenase enzymes present in active mitochondria of live cells. After 3–4 h incubation at 37° C., the solution was replaced by isopropanol and the plates were incubated at 30° C. for 1 h and read at 560 nm test wavelength and 690 nm reference wavelength.

Similar as the results in CPE assay, CV882 shows efficacy only in permissive cells but not in non-permissive cells.

In Vitro Characterization of CV884

Virus Yield Assay for CV884

$5 \times 10^5$ 293, RT-4, SW780, G361, LNCap, HBL-100, MKN1, PA-1, Fibroblast and Smooth muscle cells were plated into each well of six-well plates. Twenty-four hours later, medium was aspirated and replaced with 1 ml of serum-free RPMI 1640 containing CV802 (wt.Ad5 with E3) or CV984 at a MOI of 2 pfu/cell. After a 4-h incubation at 37° C., cells were washed with prewarmed PBS, and 2 ml of complete RPMI 1640 were added to each well. After an additional 72 h at 37° C., the cells were scraped into medium and lysed by three freeze-thaw cycles. The lysates were tested for virus production by triplicate plaque assay for 8–10 days under semisolid agarose on 293 cells.

The replication of CV884 is very similar as CV802 in permissive cells (293, RT-4 and SW780) but shows over 1000 fold difference with CV802 in non-permissive cells (G361, LNCap, HBL-100, MKN1, PA-1 and primary cells). CV884 shows better efficacy than CV876 and CV882 without losing much specificity.

Growth Curve Experiment for CV884

$5 \times 10^5$ RT-4, PA-1, Smooth muscle and Fibroblast cells were plated into each well of six-well plates. Twenty-four hours later, medium was aspirated and replaced with 1 ml of serum-free RPMI 1640 containing CV802 (wt.Ad5 with E3) or CV884 at a MOI of 2 pfu/cell. After a 4-h incubation at 37° C., cells were washed with prewarmed PBS, and 2 ml of complete RPMI 1640 were added to each well. At different time points of 0, 12, 24, 36, 48, 72, 96 and 120 h, the cells were scraped into medium and lysed by three freeze-thaw cycles. The lysates were tested for virus production by triplicate plaque assay for 8–10 days under semisolid agarose on 293 cells.

Very similar as in virus yield assay, CV884 replicates very well only in RT-4 (similar as CV802) but not in primary cells and PA-1. Again, the replication of CV884 is better than CV882 and CV876.

Cytopathic Effect Assay for CV884

$5 \times 10^5$ 293, RT-4, SW780, G361, PA-1 and Fibroblast cells were plated into each well of six-well plates. Twenty-four hours later, medium was aspirated and replaced with 1 ml of serum-free RPMI 1640 containing CV802 (wt.Ad5 with E3) or CV884 at increasing MOI from 0.001 to 10 (the data shown was at MOI 1). After a 4-h incubation at 37° C., medium was replaced with 3 ml of complete RPMI 1640 and incubated at 37° C. for 6–8 days when cytopathic effect was observed for CV802 at MOI 0.01.

CV802 shows efficacy in all the cells tested while CV884 only kills the permissive cells (293, RT-4 and SW780) but not the non-permissive cells (G361, PA-I and Fibroblast cells).

MTT Assay for CV884

$2 \times 10^4$ 293, RT-4, SW780, U118, Fibroblast and Smooth muscle cells were plated into each well of 96-well plates. Twenty-four hours later, the cells were infected with CV802 and CV884 at increasing MOI from 0.001 to 10 in complete RPMI 1640. A rapid colorimetric assay for cell growth and survival was run at different time points of day 1, 3, 5, 7 and 10. The medium was replaced by 50 ul of MTT at 1 mg/ml solution which is converted to an insoluble purple formazan by dehydrogenase enzymes present in active mitochondria of live cells. After 3–4 h incubation at 37° C., the solution was replaced by isopropanol and the plates were incubated at 30° C. for 1 h and read at 560 nm test wavelength and 690 nm reference wavelength.

Similar as the results in CPE assay, CV884 shows strong efficacy (similar as wt. Ad5) only in permissive cells but not in non-permissive cells.

In Vivo Activity of CV808

Figure 11:
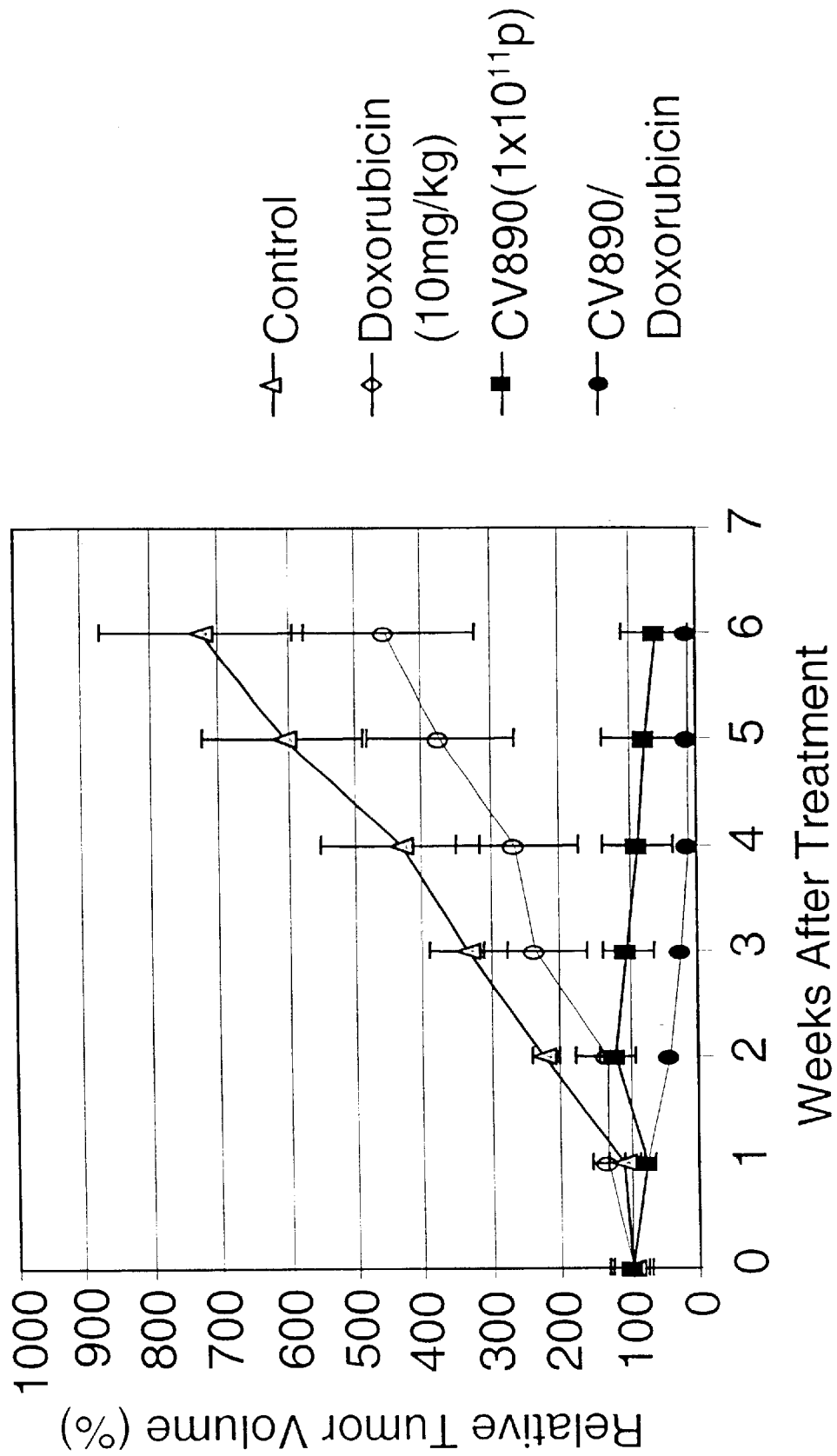
FIG. 11 depicts in vivo efficacy of CV890 with doxorubicin. Hep3B nude mouse xenografts were grouped (n=6) and treated with CV890 alone ($1 \times 10^{11}$ particles/dose, iv), doxorubicin alone (10 mg/kg, ip), CV890 and doxorubicin combination ($1 \times 10_{11}$ particles of CV890 through tail vein and 10 mg/kg doxorubicin ip), or vehicle control. Tumor size was measured weekly and the tumor volume were normalized as 100% at the day of treatment. Error bars represent the standard error of the mean.
Figure 12:
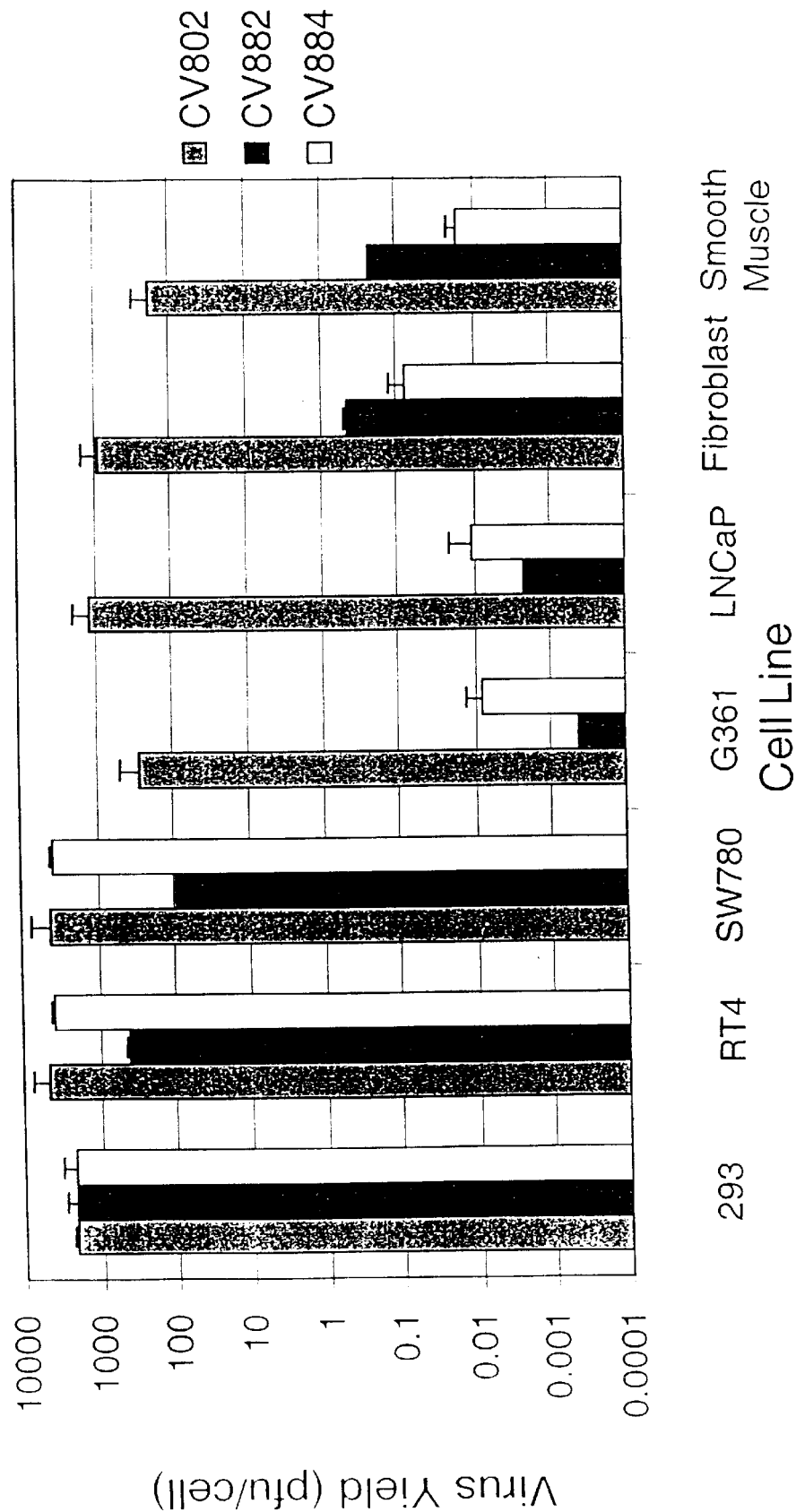
FIG. 12 shows the virus yield of CV802, CV882 and CV884 in cell lines.

Mice were given subcutaneous (SC) injections of $1\times10^6$ sW780 cells. When tumors grew to about 500 mm$^3$, CV808 was introduced into the mice ($5\times10^7$ PFU of virus in 0.1 ml PBS and 10% glycerol) intratumorally. Control mice received vehicle alone. Tumor sizes were measured weekly. The results are shown in FIG. 11. The data indicate that CV808 was effective at suppressing tumor growth.

While it is highly possible that a therapeutic based on the viruses described here would be given intralesionally (i.e., direct injection), it would also be desirable to determine if intravenous (IV) administration of adenovirus vector can affect tumor growth. If so, then it is conceivable that the virus could be used to treat metastatic tumor deposits inaccessible to direct injection. For this experiment, groups of mice bearing bladder epithelial tumors are inoculated with $10^8$ to $10^{10}$ PFU of an adenoviral vector by tail vein injection, or with buffer used to carry the virus as a negative control. The effect of IV injection of the adenoviral vector on tumor size is compared to vehicle treatment.

Example 15
Synergistic Effect of CV 890 with Chemotherapeutics
Materials and Methods Cells. Hepatocellular carcinoma cell lines HepG2, Hep3B, PLC/PRF/5, SNU449, and Sk-Hep-1, Chang liver cell (human normal liver cells), as well as other tumor cell lines PA-1 (ovarian carcinoma), UM-UC-3 (bladder carcinoma), SW 780 (bladder carcinoma), HBL100 (breast epithelia), Colo 201 (Colon adenocarcinoma), U 118 MG (glioblastoma) and LNCaP (prostate carcinoma) were obtained from the American Type Culture Collection. HuH-7 (liver carcinoma) was a generous gift of Dr. Patricia Marion (Stanford University). 293 cells (human embryonic kidney containing the E1 region of Adenovirus) were purchased from Microbix, Inc. (Toronto, Canada). The primary cells nBdSMC (normal human bladder smooth muscle cells), nHLFC (normal human lung fibroblast cells), and nHMEC (normal human mammary epithelial cells) were purchased from Clonetics (San Diego, Calif.). All tumor cell lines were maintained in RPMI 1640 (Bio Whittaker, Inc.) supplemented with 10% fetal bovine serum (Irvine Scientific), 100 U/ml penicillin and 100 ug/ml streptomycin. Primary cells were maintained in accordance with vendor instructions (Clonetics, San Diego). Cells were tested for the expression of AFP by immunoassay (Genzyme Diagnostics, San Carlos, Calif.).

Virus yield and one-step growth curves. Six well dishes (Falcon) were seeded with $5\times10^5$ cells per well of calls of interest 24 hrs prior to infection. Cells were infected at an multiplicity of infection (MOI) of 2 PFU/cell for three hours in serum-free media. After 3 hours, the virus containing media was removed, monolayers were washed three times with PBS, and 4 ml of complete media (RPMI1640+10% FBS) was added to each well. 72 hours post infection, cells were scraped into the culture medium and lysed by three cycles of freeze-thaw.

The one-step growth curves time points were harvested at various time points after infection. Two independent infections of each virus cell-combination were titered in duplicate on 293 cells (Yu et al., 1999, *Cancer Research*, 59:1498–1504.

Northern blot analysis. Hep3B or HBL100 cells were infected at an MOI of 20 PFU/cell (plaque forming unit per cell) with either CV802 or CV890 and harvested 24 hours post infection. Total cell RNA was purified using the RNeasy protocol (Qiagen). The Northern blot was conducted using NorthernMax Plus reagents (Ambion, Austin, Tex.). 5 ug of RNA was fractionated on a 1% agarose, formaldehyde-based denaturing gel and transferred to a BrightStar-Plus (Ambion) positively charged membrane by capillary transfer. The antisense RNA probes for E1A (adenovirus genome 501 bp to 1141 bp) or E1B (1540 bp–3910 bp) were PCR products cloned in pGEM-T easy (Promega) and transcription labeled with [$\alpha$ $^{32}$P] UTP. Blots were hybridized at 68° C. for 14 hours with ZipHyb solution and washed using standard methods (Ambion). Membranes were exposed to BioMax film (Kodak).

Western blot analysis. Hep3B or HBL100 cells were infected at MOI of 20 PFU/cell with either CV802 or CV890 and harvested 24 hours post infection. Cells were washed with cold PBS and lysed for 30 min on ice in (50 mM Tris, pH8.0, 150 mM NaCl, 1% IGEPAL CA360 a NP40 equivalent (Sigma), 0.5% sodium deoxycholate, and protease inhibitor cocktail from (Roche, Palo Alto, Calif.). After 30 min centrifugation at 4C, the supernatant was harvested and the protein concentration determined with protein assay ESL kit (Roche). Fifty micrograms of protein per lane were separated on 816% SDS-PAGE and electroblotted onto Hybond ECL membrane (Amersham Pharmacia, Piscataway, N.J.). The membrane was blocked overnight in PBST (PBS with 0.1% Tween-20) supplemented with 5% nonfat dry milk. Primary antibody incubation was done at room temperature for 2–3 hrs with PBST/1% milk diluted antibody, followed by wash and 1 hr incubation with diluted horseradish peroxidase-conjugated secondary antibody (Santa Cruz Biotechnology Inc., Santa Cruz, Calif.). Enhanced chemiluminescence (ECL; Amersham Pharmacia) was used for the detection. E1A antibody (clone M58) was from NeoMarkers (Fremont, Calif.), E1B-21 kD antibody was from Oncogene (Cambridge, Mass.). All antibodies were used according manufacturer's instruction.

Cell viability assay and statistical analysis. To determine the cell killing effect of virus and chemotherapeutic agent in combination treatment, a cell viability assay was conducted as previously described with modifications (Denizot, 1986, Journal Immunology. Methods, 89:271–277). On 96 well plates, cells of interest were seeded at 10,000 calls per well 48 hr prior to infection. Cells were then treated with virus alone, drug alone, or in combination. Cell viability was measured at different time points by removing the media, adding 50 $\mu$l of 1 mg/ml solution of MTT (3-(4,5-Dimethylthiazol-2-yl)-2,5-diphenyl-$^2$H-tetrazolium bromide) (Sigma, St. Louis, Mo.) and incubating for 3 hrs at 37° C. After removing the MTT solution, the crystals remaining in the wells were solubilized by the addition of 50 $\mu$l of isopropanol followed by 30C incubation for 0.5 hr. The absorbency was determined on a microplate reader (Molecular Dynamics) at 560 nm (test wavelength) and 690 nm (reference wavelength). The percentage of surviving cells was estimated by dividing the OD$_{550}$–OD$_{650}$ of virus or drug treated cells by the OD$_{550}$–OD$_{650}$ of control cells. 6 replica samples were taken for each time point and each experiment was repeated at least three times.

For statistical analysis, CurveExpert (shareware by Daniel Hyams, version 1.34) was used to plot the dose-response curves for virus and drugs. Based upon the dose-response curves, the isobolograms were made according to the original theory of Steel and Peckham (1993, *Int. J Rad. Onc. Biol. Phys.*, 5:85) and method described in Aoe et al. (1999, *Anticancer Res.* 19:291–299).

Animal studies. Six to eight week old athymic BALB/C nu/nu mice were obtained from Simonson Laboratories (Gilroy, Calif.) and acclimated to laboratory conditions one week prior to tumor implantation. Xenografts were established by injecting $1 \times 10^6$ Hep3B, HepG2 or LNCaP cells suspended in 100 μl of RPMI 1640 media subcutaneously. When tumors reached between 200 mm$^3$ and 300 mm$^3$, mice were randomized and dosed with 100 μl of test article via intratumoral or the tail vein injection. Tumors were measured in two dimensions by external caliper and volume was estimated by the formula [length (mm)×width (mm)$^2$]/2. Animals were humanely killed when their tumor burden became excessive. Serum was harvested weekly by retroorbital bleed. The level of AFP in the serum was determined by AFP Immunoassay kit (Genzyme Diagnostics, San Carlos, Calif.). The difference in mean tumor volume and mean serum AFP concentration between treatment groups was compared for statistical significance using the unpaired, two-tailed t-test.

Transcription and Translation of E1A/E1B Bicistronic Cassette of CV890 in Different Cells.

In wild type adenovirus infection, E1A and E1B genes produce a family of alternatively spliced products. It has been found that there are five E1A mRNAs, among them 12S (880 nucleotides, nts) and 13S (1018 nts) mRNAs are the dominant ones that are expressed both early and late after infection. The 12S and 13S mRNAs encode the gene product of 243 amino acids (243R) and 289 amino acids (289R) respectively (reviewed by Shenk, 1996). The two major E1B transcripts that code for 19 kD and 55 kD proteins are 12S (1031 nts) and 22S (2287 nts) mRNAs. E1B 12S mRNA only codes the 19 kD product, whereas the 22S mRNA codes for both 19 kD and 55 kD products due to different initiation sites during translation. In the current study, the generation of E1A-IRES-E1B bicistronic cassette was expected to change the pattern of E1A and E1B transcripts in viral infection. Therefore, Northern blot analysis was conducted to evaluate the steady-state level of E1A and E1B transcripts. First, CV802 or CV890 were infected to Hep3B (AFP) or HBL100 (AFP) cells for 24 hours. The total RNA samples were separated on agarose gels and processed for Northern blot by hybridizing to antisense RNA probes. The Northern blot with E1A probe visualized the 12S and 13S mRNAs in both wild type CV802 infected cells. For CV890, E1A transcripts can only be seen in Hep3B cells, indicating the conditional transcription of E1A. It is of interest to find that in CV890, there is only one large transcript (about 3.51 Kb), whereas the 12S and 13S mRNAs are no longer present. This large transcript indicates the continuous transcription of E1A-IRES-E1B bicistronic cassette, suggesting an alteration of viral E1A splicing pattern in CV890. Transcription of E1B from CV890 also appears to be AFP-dependent. It is clear that both 12S and 22S mRNAs of EBB were present in wild type CV802 samples, whereas the 12S mRNA and an enlarged 22S mRNA (3.5 Kb) appeared in CV890 infected cells. Obviously, the identity of this enlarged mRNA is the same 3.5 Kb transcript as visualized in E1A blot, which is from the transcription of E1A/E1B bicistronic cassette. Therefore, the E1B mRNA is tagged after E1A mRNA in this large transcript. This large transcript contains all the coding information for E1A, E1B 19 kD and E1B 55 kD. The mRNA splice pattern that appears in CV802 is not valid in CV890, the 12S mRNA with E1B probe disappeared. Meanwhile, in the E1B Northern blot, due to the selection of our E1B probe (1540 bp–3910 bp), mRNA of the Adenovirus gene IX (3580 bp–4070 bp), the hexon-associated protein, was also detected. In CV890 infected Hep3B cells, gene IX expression is equivalent to that of CV802, whereas in CV890 infected HBL100, its expression was also completely shut down. This result further demonstrated that the AFP controlled E1A/E1B expression is the key for late gene expression as well as viral replication.

Results of the same samples in the Western blot also indicate that CV890 has AFP dependent expression of E1A and E1B. Under our experimental conditions, E1A expression level of CV890 in Hep3B cells is similar to that of CV802. However, when E1B 19 kD protein was detected, it was found that the expression level was much lower than CV802 E1A. Previously, it has been addressed that IRES-mediated second gene has less expression (Mizuguchi et al., 2000, *Mol. Ther.* 1:376–382). Taken together, CV890 infection in permissive Hep3B cells can produce normal amounts of E1A and lesser amounts of E1B proteins capable of initiating a normal productive infection. In AFP$^-$ cells, however, this process was attenuated due to a lack of E1A and E1B gene transcription and translation. These data demonstrated that the expression of both E1A and E1B genes are under the control of AFP TRE and the artificial E1A/E1B bicistronic cassette is functioning properly in CV890.

In Vitro Replication Specificity of CV890 in Tumor Cells and Primary Cells.

From in vitro comparison of virus yield, CV890 has a better specificity profile than CV732 (CV732 is an AFP-producing, cell-specific adenovirus variant in which the E1A gene is under control of AFP-TRE). In order to gain further insights of using CV890 in liver cancer therapy, more tumor cell lines and primary cells were tested to characterize in vitro virus replication. First, all cells in the study were analyzed for their AFP status by AFP immune assay. Based on AFP produced in the cells and media, all the cells were divided into three groups, high (>2.5 μg/10$^6$ cells/10 days), low (<0.6 μg/10$^6$ cells/10 days) and none (undetectable in our study) (Table 7). It was confirmed that replication of CV890 in different cell lines correlates well with the AFP status of the host cell. Among the group of liver cell lines, CV890 only replicates well in AFP$^+$ cells, including Hep3B, HepG2, Huh7, SNU449 and PLC/PRF/5. The amount of AFP required for the promoter activity seems very low as one of the hepatoma cell lines, SNU449, a previous reported AFP$^-$ cell (Park et al., 1995, *Int. J. Cancer* 62:276–282), produces very low AFP (about 60 ng/10$^6$ cells/10 days) compared to other cells. Nevertheless, even with very low amount of AFP, SNU449 cells can still support CV890 replication to the extent comparable to cells producing significantly higher levels of AFP such as HepG2. Compared to CV802, CV890 is attenuated 5,000 to 100,000 fold in cells that do not produce AFP, including the hepatoma cell Sk-Hep1 and Chang liver cell, other tumor cells and primary cells. Taken together the results indicate that CV890 has shown a good specificity profile from a broad spectrum of tumor cells. Among them, only the AFP+ liver cells, AFP production level from high to low, are permissive for CV890.

In another experiment, CV890 was compared to CV802 for their single step growth curves on different cells. Results demonstrated that CV890 has a similar growth kinetics to wild-type CV802 in AFP+ cells except that virus yields are slightly lower (2–8 fold) in low AFP producing cells. In consideration of experimental error, there is no dramatic difference in the replication of CV890 and CV802 in AFP+ hepatoma cells. However, the growth curves of CV890 in AFP− cells showed clear attenuation. During a 5 day experiment, CV890 failed to replicate in AFP− cells including hepatoma cell (Change liver) and primary cells (nHLFC). From all the in vitro virus replication studies, it is clear that replication of CV890 is under the tight control of AFP-TRE and this adenovirus variant has an excellent specificity profile of preferentially targeting AFP producing hepatocellular carcinoma cells.

In Vivo Specificity and Efficacy of CV890.

CV890 specificity was also evaluated in animals bearing prostate cancer LNCaP xenografts. In this in vivo test, nude mice with prostate xenograft were intravenously injected with either CV890 or CV787, a prostate cancer specific adenovirus variant (Yu et al., 1999, *Cancer Research*, 59:4200–4203). Tumor volumes were documented and indicated that only CV787 had a significant antitumor efficacy in LNCaP xenografts, while tumors in the animals treated with CV890 grew, from 400 mm3 to approximately 1200 mm3 in six weeks, similar to the group treated with vehicle. This study indicates that CV890 does not attack LNCaP xenograft and keeps the good specificity profile under in vivo conditions.

To evaluate in vivo antitumor efficacy of CV890, different studies were carried out in the nude mouse model harboring human hepatoma xenografts. First, BALB/c nu/nu mice with HepG2 or Hep3B xenografts were established, animals were further challenged with single dose or multiple doses of CV890 into the tumor mass (intratumoral administration, IT) or via their tail vein (intravenous administration, IV). Tumor volume and the level of serum AFP were monitored weekly after the start of treatment, and hence the efficacy of the treatment was determined. The in vitro cytotoxicity study has demonstrated that CV890 has a better cytolytic effect than CV732. In order to further examine their antitumor activity, we first conducted animal study to compare CV890 to CV732. Animals harboring 300 mm³ Hep3B xenograft were grouped (n=6) and injected with vehicle alone (control group), CV890 (1×10$^{11}$ particles/dose, CV890 group), or CV732 (1×10$^{11}$ particles/dose, CV732 group). The Hep3B xenograft is a very aggressive tumor model and tumors grow very fast. Most animals can not survive long because of excessive tumor burden. During a six week study, single intravenous administration of CV890 have shown significant tumor growth inhibition, whereas control mice had over 10 fold tumor growth at week 5. In the group treated with CV732, single dose IV injection also reduced the tumor growth as compared to control group, however, it was much less effective compared to CV890. For example, the average tumor volume of the CV890 treated group dropped from 312 mm³ to 219 mm³, while tumor volume increased from 308 mm³ to 1542 mm³ 5 weeks after treatment in control. Both control group and the CV732 group were terminated at week 5 because excessive tumor size. Previously, CV732 has been demonstrated to restrict the hepatoma tumor from growth after 5 doses of intravenous administration. Similar efficacy can be achieved with just a single intravenous administration of CV890, indicating that under in vivo conditions, CV890 has better efficacy than CV732 in hepatoma xenografts. In this experiment, 4 out of five CV890 treated mice were tumor free three weeks after treatment. However, in CV732 group, xenografts in two mice stopped growing but none of treated animals were tumor free through the six-week experiment. There was no tumor reduction in this group or the control group of animals. By statistical analysis, the differences in mean relative tumor volumes and serum AFP concentrations between CV890 treated and CV732 treated or vehicle treated tumors are significant ($p<0.01$)). Taken together, these studies suggest that CV890 has a significant antitumor activity and its oncolytic efficacy is better than CV732, an adenovirus variant similar to AvE1a04I, in which the AFP TRE was applied to control E1A alone (Hallenback et al, 1999, Hum. Gene. Ther., 10:1721–1733).

Figure 10:
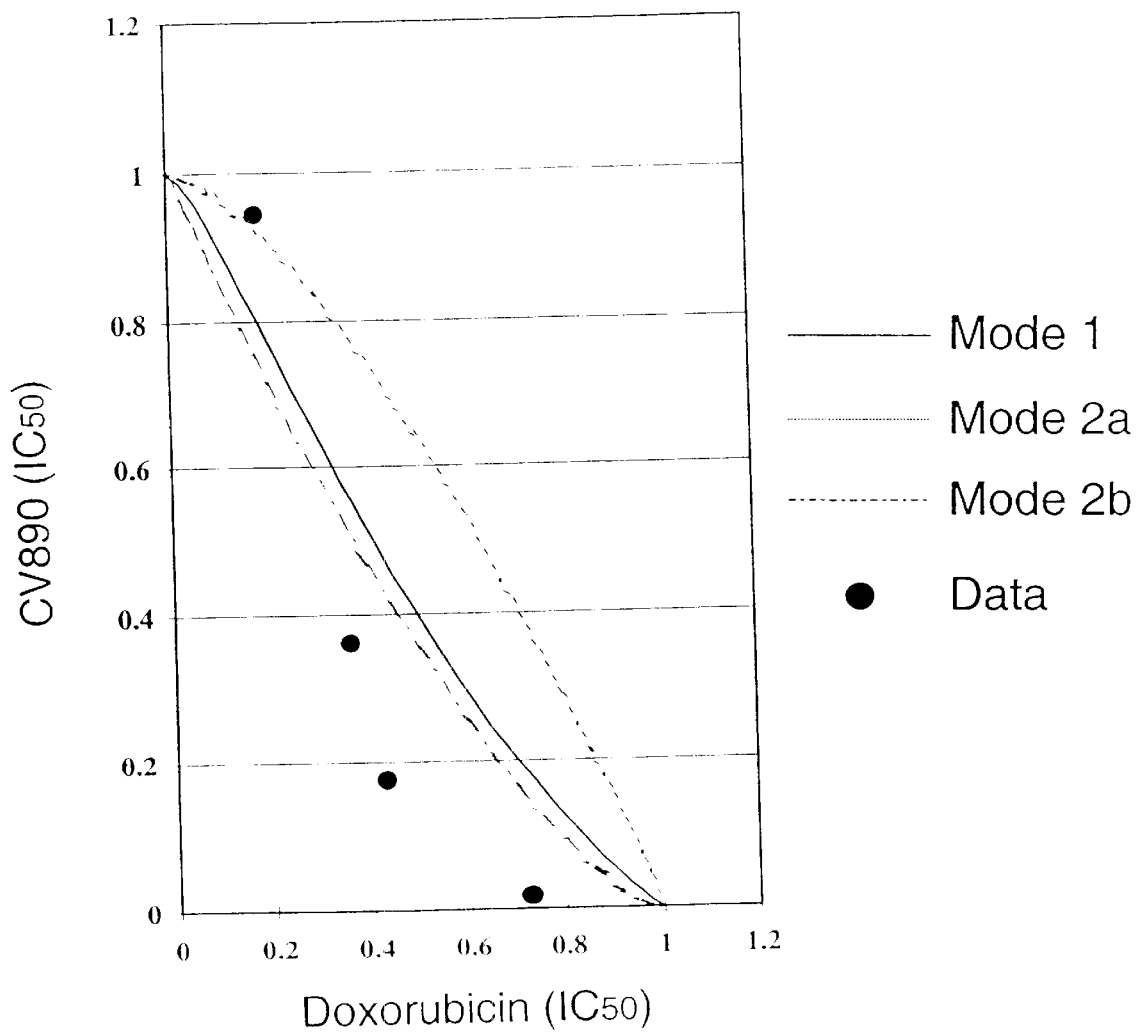
FIG. 10 depicts an $IC_{50}$ isobologram of doxorubicin and CV 890 on Hep3B cells at day 5.

Synergistic Antitumor Efficacy of CV890 in Combination with Chemotherapeutic Agents In this example, different chemotherapeutic agents were tested in combination with CV890 for their in vitro killing effect in Hep3B or HepG2 cells. Drug concentrations were optimized to the extent that they would not generate extensive cytotoxic effect on their own. Under such conditions, some agents had shown higher cell killing effect in combination with CV890. Among them, doxorubicin, a drug currently used in treatment of HCC showed synergistic cytotoxicity with CV890. In experiments using doxorubicin together with CV890 on Hep3B cells, doxorubicin at 10 ng/ml did not generate cytotoxicity, whereas CV890 at an MOI of 0.01 (pfu/cell) only had about 35% of cell killed at day 9. However, when both were applied together, 90% cells were killed 9 days after treatment. In order to determine the potential synergistic effect from the combination treatment, the MTT cell viability data were subjected to further statistical analysis. FIG. 10 shows a representative IC$_{50}$ isobologram of doxorubicin and CV890 on Hep3B cells at day 5. First, the dose-response curves of doxorubicin alone or CV890 alone were made. Based on the original theory of Steel and Peckham (1993) and method by Aoe et al. (1999), three isoeffect curves (mode I and mode 2a, 2b) were constructed. From this isobologram, several data points were in the synergy or additive area, indicating that combination of CV890 and doxorubicin provides synergistic effect on killing of Hep3B cells.

Although CV890 alone has good antitumor activity, we applied combination therapy with doxorubicin for in vivo evaluation of synergy. Animals harboring 300 mm³ Hep3B xenografts were grouped (n=6) and injected with vehicle alone (control group), CV890 alone (1×10$^{11}$ particles/dose, CV890 group), doxorubicin alone (10 mg/kg, doxorubicin group), or CV890 in combination with doxorubicin (combination group). FIG. 11 shows weekly change of the relative tumor size normalized to 100% at day 1. In this experiment, by week six, all animals in the control group had excessive tumor which has increased by 700% of baseline, whereas in CV890 group and combination group, animals had either tumor free or tumor reduction. Of the eight Hep3B xenografts, treated with CV890, three animals (37.5%) had no palpable tumor at week 5, another three animals had tumor regressed by more than 60%. In combination group, four out of eight animals were tumor free from week 5, another four animals had tumor reduction about 90%. All the animals in the CV890 and combination group were alive and tumor was suppressed even ten weeks following treatment whereas the control animals were sacrificed for excessive tumor burden after week 6. Furthermore, CV890 also caused a drop in the serum AFP concentration in these mice. Statistical analysis shows that differences in mean relative tumor volumes and serum AFP concentrations between CV890 and vehicle treated group or combination and doxorubicin treated group are significant at different times (p<0.005).

The strong efficacy in the combination treatment shows that single IV injection of CV890 in combination of doxorubicin can eradicate aggressive Hep3B xenografts in most of the animals.

TABLE 7

AFP production in different tumor cells

| CELLS | AFP (ng/$10^6$ cells/10 days) | |
|---|---|---|
| Hep3B | 2645 | High |
| HepG2 | 3140 | |
| HuH7 | 4585 | |
| SNU449 | 60 | Low |
| PLC/PRF/5 | 600 | |
| Chang | 0 | None |
| SK-Hep1 | 0 | |
| HBL100 | 0 | |
| PA-1 | 0 | |
| LoVo | 0 | |

TABLE 1

IRES SEQUENCES

A 519 base pair TIRES obtainable from encephelomycarditis virus (EMCV).
```
  1 GACGTCGACTAATTCCGGTTATTTTCCACCATATTGCCGTCTTTTCGCAA      SEQ ID NO:1
       SalI

51 TGTGAGGGCCCGGAAACCTGGCCCTGTCTTCTTGACGAGCATTCCTAGGG

101 GTCTTTCCCCTCTCGCCAAAGGAATGCAAGGTCTGTTGAATGTCGTGAAG

151 GAAGCAGTTCCTCTGGAAGCTTCTTGAAGACAAACAACGTCTGTAGCGAC

201 CCTTTGCAGGCAGCGGAACCCCCCACCTGGCGACAGGTGCCTCTGCGGCC

251 AAAAGCCACGTGTATAAGATACACCTGCAAAGGCGGCACAACCCCAGTGC

301 CACGTTGTGAGTTGGATAGTTGTGGAAAGAGTCAAATGGCTCTCCTCAAG

351 CGTATTCAACAAGGGGCTGAAGGATGCCCAGAAGGTACCCCATTGTATGG

401 GATCTGATCTGGGGCCTCGGTGCACATGCTTTACATGTGTTTAGTCGAGG

451 TTAAAAAACGTCTAGGCCCCCCGAACCACGGGGACGTGGTTTTCCTTTGA
       SalI

501 AAAACACGATGTCGACGTC
```

An IRES obtainable from vascular endothelial growth factor (VEGF).
```
  1 ACCTAGTCGACAGCGCAGAGGCTTGGGGCAGCCGAGCGGCAGCCAGGCCC     SEQ ID NO:2
         Sal I

51 CGGCCCGGGCCTCGGTTCCAGAAGGGAGAGGAGCCCGCCAAGGCGCGCAA

101 GAGAGCGGGCTGCCTCGCAGTCCGAGCCGGAGAGGGAGCGCGAGCCGCGC

151 CGGCCCCGGACGGCCTCCGAAACCATGGTCGACACGTA
                                  Sal I
```

A 5'UTR region of HCV.
```
  1 GCCAGCCCCCTGATGGGGCGACACTCCGCCATGAATCACTCCCCTGTGAGGAACTACTG    SEQ ID NO:3

61 TCTTCACGCAGAAAGCGTCTAGCCATGGCGTTAGTATGAGTGTCGTGCAGCCTCCAGGAC

121 CCCCCCTCCCGGGAGAGCCATAGTGGTCTGCGGAACCGGTGAGTACACCGGAATTGCCAG
```

TABLE 1-continued

IRES SEQUENCES

181 GACGACCGGGTCCTTTCTTGGATTAACCCGCTCAATGCCTGGAGATTTGGGCGTGCCCCC

241 GCAAGACTGCTAGCCGAGTAGTGTTGGGTCGCGAAAGGCCTTGTGGTACTGCCTGATAGG

301 GTGCTTGCGAGTGCCCCGGGAGGTCTCGTAGACCGTGCACC (341)

5'UTR region of BiP SEQ ID NO:4
1 CCCGGGGTCACTCCTGCTGGACCTACTCCGACCCCCTAGGCCGGGAGTGAAGGCGGGACT  SEQ ID NO:4A

61 TCTGCGGTTACCAGCGGAAATGCCTCGGGGTCAGAAGTCGCAGGAGAGATAGACAGCTGC

121 TGAACCAATGGGACCAGCGGATGGGGCGGATGTTATCTACCATTGGTGAACGTTAGAAAC

181 GAATAGCAGCCAATGAATCAGCTGGGGGGGCGGAGCAGTGACGTTTATTGCGGAGGGGGC

241 CGCTTCGAATCGGCGGCGGCCAGCTTGGTGGCCTGGGCCAATGAACGGCCTCCAACGAGC

301 AGGGCCTTCACCAATCGGCGGCCTCCACGACGGGGCTGGGGGAGGGTATATAAGCCGAGT

361 AGGCGACGGTGAGGTCGACGCCGGCCAAGACAGCACAGACAGATTGACCTATTGGGGTGT

421 TTCGCGAGTGTGAGAGGGAAGCGCCGCGGCCTGTATTTCTAGACCTGCCCTTCGCCTGGT

481 TCGTGGCGCCTTGTGACCCCGGGCCCTGCCGCCTGCAAGTCGAAATTGCGCTGTGCTCC

541 TGTGCTACGGCCTGTGGCTGGACTGCCTGCTGCTGCCCAACTGGCTGGCAAGATG (595)

A 5'UTR of PDGF SEQ ID NO:5
1 GTTTGCACCTCTCCCTGCCCGGGTGCTCGAGCTGCCGTTGCAAAGCCAACTTTGGAAAAA  SEQ ID NO:5

61 GTTTTTTGGGGGAGACTTGGGCCTTGAGGTGCCCAGCTCCGCGCTTTCCGATTTTGGGGG

121 CTTTCCAGAAAATGTTGCAAAAAAGCTAAGCCGGCGGGCAGAGGAAAACGCCTGTAGCCG

181 GCGAGTGAAGACGAACCATCGACTGCCGTGTTCCTTTTCCTCTTGGAGGTTGGAGTCCCC

241 TGGGCGCCCCCACACCCCTAGACGCCTCGGCTGGTTCGCGACGCAGCCCCCCGGCCGTGG

301 ATGCTGCACTCGGGCTCGGGATCCGCCCAGGTAGCCGGCCTCGGACCCAGGTCCTGCGCC

361 CAGGTCCTCCCCTGCCCCCCAGCGACGGAGCCGGGGCCGGGGCGGCGGCGCCGGGGCA

421 TGCGGGTGAGCCGCGGCTGCAGAGGCCTGAGCGCCTGATCGCCGCGGACCTGAGCCGAGC

481 CCACCCCCCTCCCCAGCCCCCCACCCTGGCCGCGGGGCGGCGCGCTCGATCTACGCGTC

541 CGGGGCCCCGCGGGGCCGGGCCCGGAGTCGGCATG (575)

TABLE 2

LITERATURE REFERENCES FOR IRES

| IRES Host | Example | Reference |
|---|---|---|
| Picornavirus | HAV | Glass et al., 1993. Virol 193:842–852 |
| | EMCV | Jang & Wimmer, 1990. Gene Dev 4:1560–1572 |
| | Poliovirus | Borman et al., 1994. EMBO J 13:3149–3157 |
| HCV and pestivirus | HCV | Tsukiyama-Kohara et al., 1992. J Virol 66:1476–1483 |
| | BVDV | Frolov I et al., 1998. RNA. 4:1418–1435 |
| Leishmania virus | LRV-1 | Maga et al., 1995. Mol Cell Biol 15:4884–4889 |
| Retroviruses | MoMLV | Torrent et al., 1996. Hum Gene Ther 7:603–612 |
| | VL30 (Harvey murine sarcoma virus) | |
| | REV | Lopez-Lastra et al., 1997. Hum Gene Ther 8:1855–1865 |
| Eukaryotic mRNA | BiP | Macejak & Sarnow, 1991. Nature 353:90–94 |
| | antennapedia mRNA | Oh et al., 1992. Gene & Dev 6:1643–1653 |
| | FGF-2 | Vagner et al., 1995. Mol Cell Biol 15:35–44 |

TABLE 2-continued

LITERATURE REFERENCES FOR IRES

| IRES Host | Example | Reference |
|---|---|---|
| | PDGF-B | Bernstein et al., 1997. J Biol Chem 272:9356–9362 |
| | IGFII | Teerink et al., 1995. Biochim Biophys Acta 1264:403–408 |
| | eIF4G | Gan & Rhoads, 1996. J Biol Chem 271:623–626 |
| | VEGF | Stein et al., 1998. Mol Cell Biol 18:3112–3119; Huez et al., 1998. Mol Cell Biol 18:6178–6190 |

TABLE 3

TRE SEQUENCES

Nucleotide sequence of a human uroplakin II 5'flanking region. Position +1 (the translational start site) is denoted with an asterisk. SEQ ID NO:6 (number 1 of SEQ ID NO:6 corresponds to position -2239 with respect to the translational start site).

```
TCGATAGGTA CCCACTATAG GGCACGCGTG GTCGACGGCC CGGGCTGGTC
1                                                    50

TGGCAACTTC AAGTGTGGGC CTTTCAGACC GGCATCATCA GTGTTACGGG
51                                                  100

GAAGTCACTA GGAATGCAGA ATTGATTGAG CACGGTGGCT CACACCTGTA
101                                                 150

ATCCCAACAC TCTGGGAGGC CAAGGCAGGT GGATCACTTG TGGTCAGGAG
151                                                 200

TTTGAGACCA GCCTGGCCAA CATGGTGAAA CCTCATCTCT ACTAAAAATA
201                                                 250

CAAAAATTAG CTGGGAATGG TGGCACATGC CTATAATCCC AGTTACTCAG
251                                                 300

GAGGCTGAGG CAGGAGAATC ATTTGAACCT GGGAGGCAGA GGTTGCAGTG
301                                                 350

AGCCGAGATC ACGCCACTGC ACTCCAGCCT GGGTGACACA GCGAGACTCT
351                                                 400

GTCTCAAAAA AAAAAAAATG CAGAATTTCA GGCTTCACCC CAGACCCACT
401                                                 450

GCATGACTGC ATGAGAAGCT GCATCTTAAC AAGATCCCTG GTAATTCATA
451                                                 500

CGCATATTAA ATTTGGAGAT GCACTGGCGT AAGACCCTCC TACTCTCTGC
501                                                 550

TTAGGCCCAT GAGTTCTTCC TTTACTGTCA TTCTCCACTC ACCCCAAACT
551                                                 600

TTGAGCCTAC CCTTCCCACC TTGGCGGTAA GGACACAACC TCCCTCACAT
601                                                 650

TCCTACCAGG ACCCTAAGCT TCCCTGGGAC TGAGGAAGAT AGAATAGTTC
651                                                 700

GTGGAGCAAA CAGATATACA GCAACAGTCT CTGTACAGCT CTCAGGCTTC
701                                                 750

TGGAAGTTCT ACAGCCTCTC CCGACAAAGT ATTCCACTTT CCACAAGTAA
751                                                 800

CTCTATGTGT CTGAGTCTCA GTTTCCACTT TTCTCTCTCT CTCTCTCTCT
801                                                 850

CAACTTTCTG AGACAGAGTT TCACTTAGTC GCCCAGGCTG GAGTGCAGGG
851                                                 900

GCACAATCTC GGCTCACTGC AACCTCCACC TCCTGGGTTC AAGTGTTTCT
```

TABLE 3-continued

| TRE SEQUENCES |
|---|

```
901                                              950
CCTGTCTCAG CCTCCCGAGT AGCTGGGATT ACAGGCACAC ACCACCGCGT
951                                              1000
TAGTTTTTGT ATTTTTGGTA GAGATGGTGT TTCGCCATAT TGGCCAGGCT
1001                                             1050
GATCTCGAAC TCCTGACCTC AGGTGATCCG CCCACCTCGG CCTCCCAAAG
1051                                             1100
TGCTGGGATT ACAGGCATGA GCCACCACGC CCGGCTGATC TCTTTTCTAT
1101                                             1150
TTTAATAGAG ATCAAACTCT CTGTGTTGCC TAGGCTGGTC TTGAACTCCT
1151                                             1200
GGCCTCCAGT GATCCTCCCA CCTTGGCCTC CCAAAGTGTT GACATTACAG
1201                                             1250
GCATGAGCCA CTGTGCCTGG CCTCAGTTCT ACTACAAAAG GAAGCCAGTA
1251                                             1300
CCAGCTACCA CCCAGGGTGG CTGTAGGGCT ACAATGGAGC ACACAGAACC
1301                                             1350
CCTACCCAGG GCCCGGAAGA AGCCCCGACT CCTCTCCCCT CCCTCTGCCC
1351                                             1400
AGAACTCCTC CGCTTCTTTC TGATGTAGCC CAGGGCCGGA GGAGGCAGTC
1401                                             1450
AGGGAAGTTC TGTCTCTTTT TCATGTTATC TTACGAGGTC TCTTTTCTCC
1451                                             1500
ATTCTCAGTC CAACAAATGG TTGCTGCCCA AGGCTGACTG TGCCCACCCC
1501                                             1550
CAACCCCTGC TGGCCAGGGT CAATGTCTGT CTCTCTGGTC TCTCCACAAG
1551                                             1600
TCTTCCATGG CCACCTTCGT CCCCACCCTC CAGAGGAATC TGAAACCGCA
1601                                             1650
TGTGCTCCCT GGCCCCCACA GCCCCTGCCT CTCCCAGAGC AGCAGTACCT
1651                                             1700
AAGCCTCAGT GCACTCCAAG AATTGAAACC CTCAGTCTGC TGCCCCTCCC
1701                                             1750
CACCAGAATG TTTCTCTCCC ATTCTTACCC ACTCAAGGCC CTTTCAGTAG
1751                                             1800
CCCCTTGGAG TATTCTCTTC CTACATATCA GGGCAACTTC CAAACTCATC
1801                                             1850
ACCCTTCTGA GGGGTGGGGG AAAGACCCCC ACCACATCGG GGGAGCAGTC
1851                                             1900
CTCCAAGGAC TGGCCAGTCT CCAGATGCCC GTGCACACAG GAACACTGCC
1901                                             1950
TTATGCACGG GAGTCCCAGA AGAAGGGGTG ATTTCTTTCC CCACCTTAGT
1951                                             2000
TACACCATCA AGACCCAGCC AGGGCATCCC CCCTCCTGGC CTGAGGGCCA
2001                                             2050
GCTCCCCATC CTGAAAAACC TGTCTGCTCT CCCCACCCCT TTGAGGCTAT
2051                                             2100
AGGGCCCAAG GGGCAGGTTG GACTGGATTC CCCTCCAGCC CCTCCCGCCC
2101                                             2150
CCAGGACAAA ATCAGCCACC CCAGGGGCAG GGCCTCACTT GCCTCAGGAA
2151                                             2200
```

TABLE 3-continued

TRE SEQUENCES

```
CCCCAGCCTG CCAGCACCTA TTCCACCTCC CAGCCCAGCA
2201                                    2239
```

---

Nucleotide sequence of a mouse uroplakin II 5'flanking region. The translational start site is denoted with an asterisk. SEQ ID NO:7 (number 1 of SEQ ID NO:7 corresponds to position -3592 with respect to the translational start site).

```
CTCGAGGATCTCGGCCCTCTTTCTGCATCCTTGTCCTAAATCATTTTCAT
1                                                50

ATCTTGCTAGACCTCAGTTTGAGAGAAACGAACCTTCTCATTTTCAAGTT
51                                              100

GAAAAAAAAAAGAGGTTCAAAGTGGCTCACTCAAAGTTACAAGCCAACAC
101                                             150

TCACCACTACGAGTACAATGGCCACCATTAGTGCTGGCATGCCCCAGGAG
151                                             200

ACAGGCATGCATATTATTCTAGATGACTGGGAGGCAGAGGGGTGGCCTAG
201                                             250

TGAGGTCAGACTGTGGACAGATCAGGCAGATGTGGGTTCTGATCCCAATT
251                                             300

CCTCAGGCCGCAGAACTACTGTGGTTCAAGAAGGGGACAAAAGGACTGCA
301                                             350

GTCCGGAACAGGAGGTCCATTTGAGAGCTGACTGAGCAGAAGAGGAAAGT
351                                             400

GAAGAACTTCTGGGGCAAGAGCTTACCCTACTTTACAGCTTTGTTGTCTT
401                                             450

CTTTACTCCAGGGGCGTCCCTGGTACTCAGTAAATGTCTGTTGGCTTGAG
451                                             500

GAACATATGTGTAAGGAGGAAGGAGAGGGAACTTGAGGGAGTTAAGACTC
501                                             550

AAGAATCAATCAAGGAGAGGACAGCAGAGAAGACAGGGTTTGGGAGAGAG
551                                             600

ACTCCAGACATTGGCCCTGGTTCCCTTCTTGGCCACTGTGAAACCCTCCA
601                                             650

GAGGAACTGAGTGCTGTGGCTTTAAATGATCTCAGCACTGTCAGTGAAGC
651                                             700

GCTCTGCTCAAAGAGTTATCCTCTTGCTCCTGTGCCGGGGCCTCCCCCTC
701                                             750

CTCTCAGCTCCCAAACCCTTCTCAGCCACTGTGATGGCATAATTAGATGC
751                                             800

GAGAGCTCAGACCGTCAGGTCTGCTCCAGGAACCACCCATTTTCCCCAAC
801                                             850

CCCAGAGAAAGGTCCTAGTGGAAAAGTGGGGGCCACTGAAGGGCTGATGG
851                                             900

GGTTCTGTCCTTTCCCCCATGCTGGGTGGACTTAAAGTCTGCGATGTGTG
900                                             950

TAGGGGGTAGAAGACAACAGAACCTGGGGGCTCCGGCTGGGAGCAGGAGG
951                                            1000

AACTCTCACCAGACGATCTCCAAATTTACTGTGCAATGGACGATCAGGAA
1001                                           1050

ACTGGTTCAGATGTAGCTTCTGATACAGTGGGTCTGAGGTAAAACCCGAA
```

```
                              -continued
1051                                                        1100
ACTTAATTTCTTTCAAAAATTTAAAGTTGCATTTATTATTTTATATGTGT
1101                                                        1150

GCCCATATGTGTGCCACAGTGTCTATGTGGAGGTCAGAGGGCAAGTTGTG
1151                                                        1200

GGCATTGGCTCTCTCCTTTCATAATGTGGCTTCTGGGGACCAAAATGTCA
1201                                                        1250

GGCATGGTGGCAAGAGCTTTTACCTGTTGAGCCATCTCATGGTTTCGTAA
1251                                                        1300

AACTTCCTATGACGCTTACAGGTAACGCAGAGACACAGACTCACATTTGG
1301                                                        1350

AGTTAGCAGATGCTGTATTGGTGTAAACACTCATACACAGACACACACAC
1351                                                        1400

ATACTCATACACACACACACACTTATCACATGCACACACATACTCGTA
1401                                                        1450

TACACACAGACACACACACATGCACTCTCACATTCACATATTCATACACA
1451                                                        1500

TCCACACACACACTCATCCACACACACAGACACACATACTCATCCACACA
1501                                                        1550

CACACACACACATACTCATACACACACACAGACACACATACTCATACACA
1551                                                        1600

CACACAGACACACACATATAATCATACATACACAGACACACTCATACATG
1601                                                        1650

TGCACACACACACTCATCCACACACACACACTCATACACACACACACTCA
1651                                                        1700

TACACACACACACTCATACACACACACACGAGGTTTTCTCAGGCTGCCT
1701                                                        1750

TTGGGTGGAGACTGGAACTGATTTCTGTTTTTCAGCTCCTTGGCTTTTTG
1751                                                        1800

TCCCTTTAGATGAGATCTCCTCCTCACTTTACACACAGAAAGATCACACA
1801                                                        1850

CGAGGGAGAACTGGCGGTGCGGAAGAGGGCTACACGGTAGGGTGTCAGGG
1851                                                        1900

TCAGGAGATCTTCCTGGCAAGTCTCAAACCTCCACATAGCACAGTGTTTA
1901                                                        1950

CGTGAGGATTTAGGAGGAATCAGGAAGAGGATTGGTTTACTGCAGAGCAG
1951                                                        2000

ACCATATAGGTCCACTCCTAAGCCCCATTTGAAATTAGAAGTGAGACAGT
2001                                                        2050

GTGGGATAAAAAGAGCAGATCTCTGGTCACATTTTTAAAGGGATATGAGG
2051                                                        3000

GTCCTGTGCCTTTAAGCCTTCCCATCTCCCTCCAATCCCCCCTCACCTTC
2101                                                        2150

CCCACCCTAACCCTCCCCAGGTTTCTGGAGGAGCAGAGTTGCGTCTTCTC
2151                                                        2200

CCTGCCCTGCCGAGCTGCTCACTGGCTGCTCTAGAGGCTGTGCTTTGCGG
2201                                                        2250

TCTCCATGGAAACCATTAGTTGCTAAGCAACTGGAGCATCATCTGTGCTG
2251                                                        2300

AGCTCAGGTCCTATCGAGTTCACCTAGCTGAGACACCCACGCCCCTGCAG
2301                                                        2350

CCACTTTGCAGTGACAAGCCTGAGTCTCAGGTTCTGCATCTATAAAAACG
2351                                                        2400
```

```
AGTAGCCTTTCAGGAGGGCATGCAGAGCCCCCTGGCCAGCGTCTAGAGGA
2401                                             2450

GAGGTGACTGAGTGGGCCATGTCACTCGTCCATGGCTGGAGAACCTCCA
2451                                             2500

TCAGTCTCCCAGTTAGCCTGGGGCAGGAGAGAACCAGAGGAGCTGTGGCT
2501                                             2550

GCTGATTGGATGATTTACGTACCCAATCTGTTGTCCCAGGCATCGAACCC
2551                                             2600

CAGAGCGACCTGCACACATGCCACCGCTGCCCCGCCCTCCACCTCCTCTG
2601                                             2650

CTCCTGGTTACAGGATTGTTTTGTCTTGAAGGGTTTTGTTGTTGCTACTT
2651                                             2700

TTTGCTTTGTTTTTTCTTTTTTAACATAAGGTTTCTCTGTGTAGCCCTAG
2701                                             2750

CTGTCCTGGAACTCACTCTGTAGACCAGGCTGGCCTCAAACTCAGAAATC
2751                                             2800

CACCTTCCTCCCAAGTGCTGGGATTAAAGGCATTCGCACCATCGCCCAGC
2801                                             2850

CCCCGGTCTTGTTTCCTAAGGTTTTCCTGCTTTACTCGCTACCCGTTGCA
2851                                             2900

CAACCGCTTGCTGTCCAAGTCTGTTTGTATCTACTCCACCGCCCACTAGC
2901                                             2950

CTTGCTGGACTGGACCTACGTTTACCTGGAAGCCTTCACTAACTTCCCTT
2951                                             3000

GTCTCCACCTTCTGGAGAAATCTGAAGGCTCACACTGATACCCTCCGCTT
3001                                             3050

CTCCCAGAGTCGCAGTTTCTTAGGCCTCAGTTAAATACCAGAATTGGATC
3051                                             3100

TCAGGCTCTGCTATCCCCACCCTACCTAACCAACCCCTCCTCTCCCATC
3101                                             3150

CTTACTAGCCAAAGCCCTTTCAACCCTTGGGGCTTTTCCTACACCTACAC
3151                                             3200

ACCAGGGCAATTTTAGAACTCATGGCTCTCCTAGAAAACGCCTACCTCCT
3201                                             3250

TGGAGACTGACCCTCTACAGTCCAGGAGGCAGACACTCAGACAGAGGAAC
3251                                             3300

TCTGTCCTTCAGTCGCGGGAGTTCCAGAAAGAGCCATACTCCCCTGCAGA
3301                                             3350

GCTAACTAAGCTGCCAGGACCCAGCCAGAGCATCCCCCTTTAGCCGAGGG
3351                                             3400

CCAGCTCCCCAGAATGAAAAACCTGTCTGGGGCCCCTCCCTGAGGCTACA
3401                                             3450

GTCGCCAAGGGGCAAGTTGGACTGGATTCCCAGCAGCCCCTCCCACTCCG
3451                                             3500

AGACAAAATCAGCTACCCTGGGGCAGGCCTCATTGGCCCCAGGAAACCCC
3501                                             3550

AGCCTGTCAGCACCTGTTCCAGGATCCAGTCCCAGCGCAGTA
3551                                    3592

AFP-TRE
  1 GCATTGCTGTGAACTCTGTACTTAGACTAAACTTTGAGCAATAACACACATAGATTGAG       SEQ ID NO:8

61 GATTGTTTGCTGTTAGCATACAAACTCTGGTTCAAAGCTCCTCTTTATTGCTTGTCTTGG

121 AAAATTGCTGTTCTTCATGGTTTCTCTTTTCACTGCTATCTATTTTTCTCAACCACTCA
```

```
181 CATGGCTACAATAACTGTCTGCAAGCTTATGATTCCCAAATATCTATCTCTAGCCTCAAT

241 CTTGTTCCAGAAGATAAAAAGTAGTATTCAAATGCACATCAACGTCTCCACTTGGAGGGC

301 TTAAAGACGTTTCAACATACAAACCGGGGAGTTTTGCCTGGAATGTTTCCTAAAATGTGT

361 CCTGTAGCACATAGGGTCCTCTTGTTCCTTAAAATCTAATTACTTTTAGCCCAGTGCTCA

421 TCCCACCTATGGGGAGATGAGAGTGAAAAGGGAGCCTGATTAATAATTACACTAAGTCAA

481 TAGGCATAGAGCCAGGACTGTTTGGGTAAACTGGTCACTTTATCTTAAACTAAATATATC

541 CAAAACTGAACATGTACTTAGTTACTAAGTCTTTGACTTTATCTCATTCATACCACTCAG

601 CTTTATCCAGGCCACTTATGAGCTCTGTGTCCTTGAACATAAAATACAAATAACCGCTAT

661 GCTGTTAATTATTGGCAAATGTCCCATTTTCAACCTAAGGAAATACCATAAAGTAACAGA

721 TATACCAACAAAAGGTTACTAGTTAACAGGCATTGCCTGAAAAGAGTATAAAAGAATTTC

781 AGCATGATTTTCCATATTGTGCTTCCACCACTGCCAATAACA (822)
```

```
Probasin-TRE
 -426
5'-AAGCTTCCACAAGTGCATTTAGCCTCTCCAGTATTGCTGATGAATCCACAGT          SEQ ID NO:9

TCAGGTTCAATGGCGTTCAAAACTTGATCAAAAATGACCAGACTTTATATTTA

CACCAACATCTATCTGATTGGAGGAATGGATAATAGTCATCATGTTTAAACAT

CTACCATTCCAGTTAAGAAAATATGATAGCATCTTGTTCTTAGTCTTTTTCTTA
                                 ARE-1

ATAGGGACATAAAGCCCACAAATAAAAATATGCCTGAAGAATGGGACAGGC

ATTGGGCATTGTCCATGCCTAGTAAAGTACTCCAAGAACCTATTTGTATACTA
                         ARE-2

GATGACACAATGTCAATGTCTGTGTACAACTGCCAACTGGGATGCAAGACAC

TGCCCATGCCAATCATCCTGAAAAGCAGCTATAAAAAGCAGGAAGCTACTCT
        CAAT box             TATAA box
    +1                    +28
GCACCTTGTCAGTAGGTCCAGATACCTACAG-3'
Transcription site
```

```
Tyrosinase-TRE
         PinA1 end
    1 CCGGTTGAAAATGATAAGTTGAATTCTGTCTTCGAGAACATAGAAAAGAA           SEQ ID NO:10

51 TTATGAAATGCCAACATGTGGTTACAAGTAATGCAGACCCARGGCTCCCC

101 AGGGACAAGAAGTCTTGTGTTAACTCTTTGTGGCTCTGAAAGAAAGAGAG

151 AGAGAAAAGATTAAGCCTCCTTGTGGAGATCATGTGATGACTTCCTGATT

201 CCAGCCAGAGCGAGCATTTCCATGGAAACTTCTCTTCCTCTTCACTCGAG

251 ATTACTAACCTTATTGTTAATATTCTAACCATAAGAATTAAACTATTAAT

301 GGTGAATAGAGTTTTTCACTTTAACATAGGCCTATCCCACTGGTGGGATA

351 CGAGCCAATTCGAAAGAAAAAGTCAGTCATGTGCTTTTCAGAGGATGAAA

401 GCTTAAGATAAAGACTAAAAGTGTTTGATGCTGGAGGTGGGAGTGGTATT

451 ATATAGGTCTCAGCCAAGACATGTGATAATCACTGTAGTAGTAGCTGGAA

501 AGAGAAATCTGTGACTCCAATTAGCCAGTTCCTGCAGACCTTGTGA
PinA1
  end
```

```
Human glandular kallikrein-TRE
gaattcagaa ataggggaag gttgaggaag gacactgaac tcaaagggga tacagtgatt 60     SEQ ID NO:11 ggtttatttg tcttctcttc acaacattgg tgctggagga attcccaccc tgaggttatg
120
```

-continued

```
aagatgtctg aacacccaac acatagcact ggagatatga gctcgacaag agtttctcag     180
ccacagagat tcacagccta gggcaggagg acactgtacg ccaggcagaa tgacatggga     240
attgcgctca cgattggctt gaagaagcaa ggactgtggg aggtgggctt tgtagtaaca     300
agagggcagg gtgaactctg attcccatgg gggaatgtga tggtcctgtt acaaattttt     360
caagctggca gggaataaaa cccattacgg tgaggacctg tggagggcgg ctgccccaac     420
tgataaagga aatagccagg tgggggcctt tcccattgta gggggacat atctggcat      480 agaagccttt gagacccttt agggtacaag tactgaggca gcaaataaaa tgaaatctta    540
tttttcaact ttatactgca tgggtgtgaa gatatatttg tttctgtaca gggggtgagg    600
gaaaggaggg gaggaggaaa gttcctgcag gtctggtttg gtcttgtgat ccagggggtc    660
ttggaactat ttaaattaaa ttaaattaaa acaagcgact gttttaaatt aaattaaatt    720
aaattaaatt ttactttatt ttatcttaag ttctgggcta catgtgcagg acgtgcagct    780
ttgttacata ggtaaacgtg tgccatggtg gtttgctgta cctatcaacc catcacctag    840
gtattaagcc cagcatgcat tagctgtttt tcctgacgct ctccctctcc ctgactccca    900
caacaggccc cagtgtgtgt tgttccsctc cctgtgtcca tgtgttctca ttgttcagct    960
cccacttata agtgagaaca tgtggtgttt ggttttctgt ttctgtgtta gtttgctgag    1020
gataatggct tccacctcca tccatgttcc tgcaaaggac gtgatcttat tctttttat    1080 ggttgcatag aaattgtttt tacaaatcca attgatattg tatttaatta caagttaatc   1140
taattagcat actagaagag attacagaag atattaggta cattgaatga ggaaatatat   1200
aaaataggac gaaggtgaaa tattaggtag gaaaagtata atagttgaaa gaagtaaaaa   1260
aaaatatgca tgagtagcag aatgtaaaag aggtgaagaa cgtaatagtg acttttaga    1320 ccagattgaa ggacagagac agaaaaattt taaggaattg ctaaaccatg tgagtgttag   1380
aagtacagtc aataacatta aagcctcagg aggagaaaag aataggaaag gaggaaatat   1440
gtgaataaat agtagagaca tgtttgatgg attttaaaat atttgaaaga cctcacatca   1500
aaggattcat accgtgccat tgaagaggaa gatggaaaag ccaagaagcc agatgaaagt   1560
tagaaatatt attggcaaag cttaaatgtt aaaagtccta gagagaaagg atggcagaaa   1620
tattggcggg aaagaatgca gaacctagaa tataaattca tcccaacagt ttggtagtgt   1680
gcagctgtag cctttctag ataatacact attgtcatac atcgcttaag cgagtgtaaa
```

```
                                                          1740
atggtctcct cactttattt atttatatat ttatttagtt ttgagatgga gcctcgctct
                                                          1800
gtctcctagg ctggagtgca atagtgcgat accactcact gcaacctctg cctcctctgt
                                                          1860
tcaagtgatt ttcttacctc agcctcccga gtagctggga ttacaggtgc gtgccaccac
                                                          1920
acccggctaa ttttttgtatt ttttgtagag acggggtttt gccatgttgg ccaggctggt
                                                          1980
cttgaactcc tgacatcagg tgatccacct gccttggcct cctaaagtgc tgggattaca
                                                          2040
ggcatgagcc accgtgccca accactttat ttatttttta tttttatttt taaatttcag
                                                          2100
cttctatttg aaatacaggg ggcacatata taggattgtt acatgggtat attgaactca
                                                          2160
ggtagtgatc atactaccca acaggtaggt tttcaaccca ctcccctct tttcctcccc
                                                          2220
attctagtag tgtgcagtgt ctattgttct catgtttatg tctatgtgtg ctccaggttt
                                                          2280
agctcccacc tgtaagtgag aacgtgtggt atttgatttt ctgtccctgt gttaattcac
                                                          2340
ttaggattat ggcttccagc tccattcata ttgctgtaaa ggatatgatt catttttcat
                                                          2400
ggccatgcag tattccatat tgcgtataga tcacattttc tttctttttt tttttgaga
                                                          2460
cggagtcttg ctttgctgcc taggctggag tgcagtagca cgatctcggc tcactgcaag
                                                          2520
cttcacctcc ggggttcacg tcattcttct gtctcagctt cccaagtagc tgggactaca
                                                          2580
ggcgccgcc accacgtccg gctaattttt ttgtgtgttt tagtagaga tgggggtttc
                                                          2640
actgtgttag ccaggatggt cttgatctcc tgaccttgtg gtccacctgc ctcggtctcc
                                                          2700
caaagtgctg ggattacagg ggtgagccac tgcgcccggc ccatatatac cacattttct
                                                          2760
ttaaccaatc caccattgat gggcaactag gtagattcca tggattccac agttttgcta
                                                          2820
ttgtgtgcag tgtggcagta gacatatgaa tgaatgtgtc ttttttggtat aatgatttgc
                                                          2880
attcctttgg gtatacagtc attaatagga gtgctgggtt gaacggtggc tctgtttaaa
                                                          2940
attctttgag aattttccaa actgtttgcc atagagagca aactaattta catttccacg
                                                          3000
aacagtatat aagcattccc ttttctccac agctttgtca tcatggtttt ttttttttctt
                                                          3060
tattttaaaa aagaatatgt tgttgttttc ccagggtaca tgtgcaggat gtgcaggttt
                                                          3120
gttacatagg tagtaaacgt gagccatggt ggtttgctgc acctgtcaac ccattacctg
                                                          3180
ggtatgaagc cctgcctgca ttagctcttt tccctaatgc tctcactact gccccaccct
                                                          3240
caccctgaca gggcaaacag acaacctaca gaatgggagg aaatttttgc aatctattca
                                                          3300
```

-continued

```
tctgacaaag gtcaagaata tccagaatct acaaggaact taagcaaatt tttactttt
3360 aataatagcc actctgactg gcgtgaaatg gtatctcatt gtggttttca tttgaatttc
3420 tctgatgatc agtgacgatg agcatttttt catatttgtt ggctgcttgt acgtcttttg
3480 agaagtgtct cttcatgcct tttggccact ttaatgggat tattttttgc tttttagttt
3540 aagttcctta tagattctgg atattagact tcttattgga tgcatagttt gtgaatactc
3600 tcttccattc tgtaggttgt ctgtttactc tattgatggc ttcttttgct gtgccgaagc
3660 atcttagttt aattagaaac cacctgccaa tttttgtttt tgttgcaatt gcttttgggg
3720 acttagtcat aaactctttg ccaaggtctg ggtcaagaag agtatttcct aggttttctt
3780 ctagaatttt gaaagtctga atgtaaacat ttgcatttt aatgcatctt gagttagttt
3840 ttgtatatgt gaaaggtcta ctctcatttt cttcctct tctttctttt cttctttttc
3900 tttcttctt tctttctttc tttctttctt tcttctttc tttcttttg tccttctttc
3960 tttcttctt tctctttctt tctctctttc tttttttttt ttgatggagt attgctctgt
4020 tgcccaggct gcagtgcagc ggcacgatct cggctcactg caacctctgc ctcctgggtt
4080 caactgattc tcctgcatca gccttccaag tagctgggat tataggcgcc cgccaccacg
4140 cccgactaat ttttgtattt ttagtagaga cggggttgtg ccatgttggc caggctggtt
4200 tgaaactcct gacctcaaac gatctgcctg ccttggcctc ccaaagtgct gggattacag
4260 gtgtgagcca ctgtgcccag ccaagaatgt cattttctaa gaggtccaag aacctcaaga
4320 tattttggga ccttgagaag agaggaattc atacaggtat tacaagcaca gcctaatggc
4380 aaatctttgg catggcttgg cttcaagact ttaggctctt aaaagtcgaa tccaaaaatt
4440 tttataaaag ctccagctaa gctaccttaa aaggggcctg tatggctgat cactcttctt
4500 gctatacttt acacaaataa acaggccaaa tataatgagg ccaaaattta ttttgcaaat
4560 aaattggtcc tgctatgatt tactcttggt aagaacaggg aaaatagaga aaaatttaga
4620 ttgcatctga cctttttttc tgaatttta tatgtgccta caatttgagc taaatcctga
4680 attattttct ggttgcaaaa actctctaaa gaagaacttg gttttcattg tcttcgtgac
4740 acatttatct ggctctttac tagaacagct ttcttgtttt tggtgttcta gcttgtgtgc
4800 cttacagttc tactcttcaa attattgtta tgtgtatctc atagttttcc ttcttttgag
4860
```

```
aaaactgaag ccatggtatt ctgaggacta gagatgactc aacagagctg gtgaatctcc    4920
tcatatgcaa tccactgggc tcgatctgct tcaaattgct gatgcactgc tgctaaagct    4980
atacatttaa aaccctcact aaaggatcag ggaccatcat ggaagaggag gaaacatgaa    5040
attgtaagag ccagattcgg ggggtagagt gtggaggtca gagcaactcc accttgaata    5100
agaaggtaaa gcaacctatc ctgaaagcta acctgccatg gtggcttctg attaacctct    5160
gttctaggaa gactgacagt ttgggtctgt gtcattgccc aaatctcatg ttaaattgta    5220
atccccagtg ttcggaggtg ggacttggtg gtaggtgatt cggtcatggg agtagatttt    5280
cttctttgtg gtgttacagt gatagtgagt gagttctcgt gagatctggt catttaaaag    5340
tgtgtggccc ctcccctccc tctcttggtc ctcctactgc catgtaagat acctgctcct    5400
gctttgcctt ctaccataag taaaagcccc ctgaggcctc cccagaagca gatgccacca    5460
tgcttcctgt acagcctgca gaaccatcag ccaattaaac ctcttttctg tataaattac    5520
cagtcttgag tatctcttta cagcagtgtg agaacggact aatacaaggg tctccaaaat    5580
tccaagttta tgtattcttt cttgccaaat agcaggtatt taccataaat cctgtcctta    5640
ggtcaaacaa ccttgatggc atcgtacttc aattgtctta cacattcctt ctgaatgact    5700
cctcccctat ggcatataag ccctgggtct tgggggataa tggcagaggg gtccaccatc    5760
ttgtctggct gccacctgag acacggacat ggcttctgtt ggtaagtctc tattaaatgt    5820
ttctttctaa gaaactggat ttgtcagctt gtttctttgg cctctcagct tcctcagact    5880
ttggggtagg ttgcacaacc ctgcccacca cgaaacaaat gtttaatatg ataaatatgg    5940
atagatataa tccacataaa taaaagctct tggagggccc tcaataattg ttaagagtgt    6000
aaatgtgtcc aaagatggaa aatgtttgag aactactgtc ccagagattt tcctgagttc    6060
tagagtgtgg gaatatagaa cctggagctt ggcttcttca gcctagaatc aggagtatgg    6120
ggctgaagtc tgaagcttgg cttcagcagt ttggggttgg cttccggagc acatatttga    6180
catgttgcga ctgtgatttg gggtttggta tttgctctga atcctaatgt ctgtccttga    6240
ggcatctaga atctgaaatc tgtggtcaga attctattat cttgagtagg acatctccag    6300
tcctggttct gccttctagg gctggagtct gtagtcagtg acccggtctg gcatttcaac    6360
ttcatataca gtgggctatc ttttggtcca tgtttcaacc aaacaaccga ataaaccatt    6420
agaacctttc cccacttccc tagctgcaat gttaaaccta ggatttctgt ttaataggtt
```

```
                                                                6480 catatgaata atttcagcct gatccaactt tacattcctt ctaccgttat tctacaccca
                                                                6540 ccttaaaaat gcattcccaa tatattccct ggattctacc tatatatggt aatcctggct
                                                                6600 ttgccagttt ctagtgcatt aacatacctg atttacattc ttttacttta aagtggaaat
                                                                6660 aagagtccct ctgcagagtt caggagttct caagatggcc cttacttctg acatcaattg
                                                                6720 agatttcaag ggagtcgcca agatcatcct caggttcagt gattgctggt agccctcata
                                                                6780 taactcaatg aaagctgtta tgctcatggc tatggtttat tacagcaaaa gaatagagat
                                                                6840 gaaaatctag caagggaaga gttgcatggg gcaaagacaa ggagagctcc aagtgcagag
                                                                6900 attcctgttg ttttctccca gtggtgtcat ggaaagcagt atcttctcca tacaatgatg
                                                                6960 tgtgataata ttcagtgtat tgccaatcag ggaactcaac tgagccttga ttatattgga
                                                                7020 gcttggttgc acagacatgt cgaccacctt catggctgaa ctttagtact tagcccctcc
                                                                7080 agacgtctac agctgatagg ctgtaaccca acattgtcac cataaatcac attgttagac
                                                                7140 tatccagtgt ggcccaagct cccgtgtaaa cacaggcact ctaaacaggc aggatatttc
                                                                7200 aaaagcttag agatgacctc ccaggagctg aatgcaaaga cctggcctct ttgggcaagg
                                                                7260 agaatccttt accgcacact ctccttcaca gggttattgt gaggatcaaa tgtggtcatg
                                                                7320 tgtgtgagac accagcacat gtctggctgt ggagagtgac ttctatgtgt gctaacattg
                                                                7380 ctgagtgcta agaaagtatt aggcatggct ttcagcactc acagatgctc atctaatcct
                                                                7440 cacaacatgg ctacagggtg ggcactacta gcctcatttg acagaggaaa ggactgtgga
                                                                7500 taagaagggg gtgaccaata ggtcagagtc attctggatg caaggggctc cagaggacca
                                                                7560 tgattagaca ttgtctgcag agaaattatg gctggatgtc tctgccccgg aaaggggat
                                                                7620 gcactttcct tgacccccta tctcagatct tgactttgag gttatctcag acttcctcta
                                                                7680 tgataccagg agcccatcat aatctctctg tgtcctctcc ccttcctcag tcttactgcc
                                                                7740 cactcttccc agctccatct ccagctggcc aggtgtagcc acagtaccta actctttgca
                                                                7800 gagaactata aatgtgtatc ctacagggga gaaaaaaaa aagaactctg aaagagctga
                                                                7860 cattttaccg acttgcaaac acataagcta acctgccagt tttgtgctgg tagaactcat
                                                                7920 gagactcctg ggtcagaggc aaaagatttt attacccaca gctaaggagg cagcatgaac
                                                                7980 tttgtgttca catttgttca ctttgccccc caattcatat gggatgatca gagcagttca
                                                                8040
```

-continued ggtggatgga cacagggtt tgtggcaaag gtgagcaacc taggcttaga aatcctcaat    8100
cttataagaa ggtactagca aacttgtcca gtctttgtat ctgacggaga tattatcttt    8160
ataattgggt tgaaagcaga cctactctgg aggaacatat tgtatttatt gtcctgaaca    8220
gtaaacaaat ctgctgtaaa atagacgtta actttattat ctaaggcagt aagcaaacct    8280
agatctgaag gcgataccat cttgcaaggc tatctgctgt acaaatatgc ttgaaaagat    8340
ggtccagaaa agaaaacggt attattgcct ttgctcagaa gacacacaga aacataagag    8400
aaccatggaa aattgtctcc caacactgtt cacccagagc cttccactct tgtctgcagg    8460
acagtcttaa catcccatca ttagtgtgtc taccacatct ggcttcaccg tgcctaacca    8520
agatttctag gtccagttcc ccaccatgtt tggcagtgcc ccactgccaa ccccagaata    8580
agggagtgct cagaattccg agggacatg ggtggggatc agaacttctg ggcttgagtg    8640 cagaggggc ccatactcct tggttccgaa ggaggaagag gctggaggtg aatgtccttg    8700
gaggggagga atgtgggttc tgaactctta aatccccaag ggaggagact ggtaaggtcc    8760
cagcttccga ggtactgacg tgggaatggc ctgagaggtc taagaatccc gtatcctcgg    8820
gaaggagggg ctgaaattgt gaggggttga gttgcagggg tttgttagct tgagactcct    8880
tggtgggtcc ctgggaagca aggactggaa ccattggctc cagggtttgg tgtgaaggta    8940
atgggatctc ctgattctca aagggtcaga ggactgagag ttgcccatgc tttgatcttt    9000
ccatctactc cttactccac ttgagggtaa tcacctactc ttctagttcc acaagagtgc    9060
gcctgcgcga gtataatctg cacatgtgcc atgtcccgag gcctggggca tcatccactc    9120
atcattcagc atctgcgcta tgcgggcgag gccggcgcca tgacgtcatg tagctgcgac    9180
tatccctgca gcgcgcctct cccgtcacgt cccaaccatg gagctgtgga cgtgcgtccc    9240
ctggtggatg tggcctgcgt ggtgccaggc cggggcctgg tgtccgataa agatcctaga    9300
accacaggaa accaggactg aaaggtgcta gagaatggcc atatgtcgct gtccatgaaa    9360
tctcaaggac ttctgggtgg agggcacagg agcctgaact tacgggtttg ccccagtcca    9420
ctgtcctccc aagtgagtct cccagatacg aggcactgtg ccagcatcag cttcatctgt    9480
accacatctt gtaacaggga ctacccagga ccctgatgaa caccatggtg tgtgcaggaa    9540 gaggggtga aggcatggac tcctgtgtgg tcagagccca gaggggcca tgacgggtgg    9600

-continued

```
ggaggaggct gtggactggc tcgagaagtg ggatgtggtt gtgtttgatt tcctttggcc
9660 agataaagtg ctggatatag cattgaaaac ggagtatgaa gaccagttag aatggagggt
9720 caggttggag ttgagttaca gatggggtaa aattctgctt cggatgagtt tggggattgg
9780 caatctaaag gtggtttggg atggcatggc tttgggatgg aaataggttt gtttttatgt
9840 tggctgggaa gggtgtgggg attgaattgg ggatgaagta ggtttagttt tggagataga
9900 atacatggag ctggctattg catgcgagga tgtgcattag tttggtttga tctttaaata
9960 aaggaggcta ttagggttgt cttgaattag attaagttgt gttgggttga tgggttgggc
10020 ttgtgggtga tgtggttgga ttgggctgtg ttaaattggt ttgggtcagg ttttggttga
10080 ggttatcatg gggatgagga tatgcttggg acatggattc aggtggttct cattcaagct
10140 gaggcaaatt tcctttcaga cggtcattcc agggaacgag tggttgtgtg ggggaaatca
10200 ggccactggc tgtgaatatc cctctatcct ggtcttgaat tgtgattatc tatgtccatt
10260 ctgtctcctt cactgtactt ggaattgatc tggtcattca gctggaaatg ggggaagatt
10320 ttgtcaaatt cttgagacac agctgggtct ggatcagcgt aagccttcct tctggtttta
10380 ttgaacagat gaaatcacat ttttttttc aaaatcacag aaatcttata gagttaacag
10440 tggactctta taataagagt taacaccagg actcttattc ttgattcttt tctgagacac
10500 caaaatgaga tttctcaatg ccaccctaat tcttttttt ttttttttt ttttgagac
10560 acagtctggg tcttttgctc tgtcactcag gctggagcgc agtggtgtga tcatagctca
10620 ctgaacccctt gacctcctgg acttaaggga tcctcctgct tcagcctcct gagtagatgg
10680 ggctacaggt gcttgccacc acacctggct aattaaattt ttttttttt tttgtagaga
10740 aagggtctca ctttgttgcc ctggctgatc ttgaacttct gacttcaagt gattcttcag
10800 ccttggactc ccaaagcact gggattgctg gcatgagcca ctcaccgtgc ctggcttgca
10860 gcttaatctt ggagtgtata aacctggctc ctgatagcta gacatttcag tgagaaggag
10920 gcattggatt ttgcatgagg acaattctga cctaggaggg caggtcaaca ggaatccccg
10980 ctgtacctgt acgttgtaca ggcatggaga atgaggagtg aggaggccgt accggaaccc
11040 catattgttt agtggacatt ggattttgaa ataatggga acttggtctg ggagagtcat
11100 atttctggat tggacaatat gtggtatcac aaggttttat gatgagggag aaatgtatgt
11160 ggggaaccat tttctgagtg tggaagtgca agaatcagag agtagctgaa tgccaacgct
```

-continued

```
                                                                  11220
tctatttcag gaacatggta agttggaggt ccagctctcg ggctcagacg ggtatagggg a
11280 ccaggaagtc tcacaatccg atcattctga tatttcaggg catattaggt ttggggtgca
11340 aaggaagtac ttgggactta ggcacatgag actttgtatt gaaatcaat gattggggct
11400 ggccgtggtg ctcacgcctg taatctcatc actttgggag accgaagtgg gaggatggct
11460 tgatctcaag agttggacac cagcctaggc aacatggcca gaccctctct ctacaaaaaa
11520 attaaaaatt agctggatgt ggtggtgcat gcttgtggtc tcagctatcc tggaggctga
11580 gacaggagaa tcggttgagt ctgggagttc aaggctacag ggagctgcga tcacgccgct
11640 gcactccagc ctgggaaaca gagtgagact gtctcagaat ttttttaaaa aagaatcagt
11700 gatcatccca acccctgttg ctgttcatcc tgagcctgcc ttctctggct ttgttcccta
11760 gatcacatct ccatgatcca taggccctgc ccaatctgac ctcacaccgt gggaatgcct
11820 ccagactgat ctagtatgtg tggaacagca agtgctggct ctccctcccc ttccacagct
11880 ctgggtgtgg gagggggttg tccagcctcc agcagcatgg ggagggcctt ggtcagcatc
11940 taggtgccaa cagggcaagg gcggggtcct ggagaatgaa ggctttatag ggctcctcag
12000 ggaggcccc cagccccaaa ctgcaccacc tggccgtgga caccggt
12047
```

HRE-TRE

```
ccccgagg cagtgcat gaggctcagg gcgtgcgt gagtcgcagcgagacccg gggtgcag      SEQ ID NO:12
gccgga
```

PSA-TRE

```
aagcttctag ttttcttttc ccggtgacat cgtggaaagc actagcatct ctaagcaatg 60    SEQ ID NO:13 atctgtgaca atattcacag tgtaatgcca tccagggaac tcaactgagc cttgatgtcc
120 agagatttt gtgttttttt ctgagactga gtctcgctct gtgccaggct ggagtgcagt
180 ggtgcaacct tggctcactg caagctccgc ctcctgggtt cacgccattc tcctgcctca
240 gcctcctgag tagctgggac tacaggcacc cgccaccacg cctggctaat ttttttgtat
300 ttttagtaga gatggggttt cactgtgtta gccaggatgg tctcagtctc ctgacctcgt
360 gatctgccca ccttggcctc ccaaagtgct gggatgacag gcgtgagcca ccgcgcctgg
420 ccgatatcca gagattttt ggggggctcc atcacacaga catgttgact gtcttcatgg
480 ttgacttta gtatccagcc cctctagaaa tctagctgat atagtgtggc tcaaaacctt
540 cagcacaaat cacaccgtta gactatctgg tgtggcccaa accttcaggt gaacaaaggg
600
```

-continued

```
actctaatct ggcaggatac tccaaagcat tagagatgac ctcttgcaaa gaaaagaaa
660 tggaaaagaa aaagaaagaa aggaaaaaaa aaaaaaaaaa gagatgacct ctcaggctct
720 gaggggaaac gcctgaggtc tttgagcaag gtcagtcctc tgttgcacag tctccctcac
780 agggtcattg tgacgatcaa atgtggtcac gtgtatgagg caccagcaca tgcctggctc
840 tggggagtgc cgtgtaagtg tatgcttgca ctgctgaatg gctgggatgt gtcagggatt
900 atcttcagca cttacagatg ctcatctcat cctcacagca tcactatggg atgggtatta
960 ctggcctcat ttgatggaga aagtggctgt ggctcagaaa ggggggacca ctagaccagg
1020 gacactctgg atgctgggga ctccagagac catgaccact caccaactgc agagaaatta
1080 attgtggcct gatgtccctg tcctggagag ggtggaggtg gaccttcact aacctcctac
1140 cttgaccctc tcttttaggg ctctttctga cctccaccat ggtactagga ccccattgta
1200 ttctgtaccc tcttgactct atgacccccca ccgcccactg catccagctg ggtcccctcc
1260 tatctctatt cccagctggc cagtgcagtc tcagtgccca cctgtttgtc agtaactctg
1320 aaggggctga cattttactg acttgcaaac aaataagcta actttccaga gttttgtgaa
1380 tgctggcaga gtccatgaga ctcctgagtc agaggcaaag gcttttactg ctcacagctt
1440 agcagacagc atgaggttca tgttcacatt agtacacctt gccccccca aatcttgtag
1500 ggtgaccaga gcagtctagg tggatgctgt gcagaagggg tttgtgccac tggtgagaaa
1560 cctgagatta ggaatcctca atcttatact gggacaactt gcaaacctgc tcagcctttg
1620 tctctgatga agatattatc ttcatgatct tggattgaaa acagacctac tctggaggaa
1680 catattgtat cgattgtcct tgacagtaaa caaatctgtt gtaagagaca ttatctttat
1740 tatctaggac agtaagcaag cctggatctg agagagatat catcttgcaa ggatgcctgc
1800 tttacaaaca tccttgaaac aacaatccag aaaaaaaaag gtgttactgt cttttgctcag
1860 aagacacaca gatacgtgac agaaccatgg agaattgcct cccaacgctg ttcagccaga
1920 gccttccacc ctttctgcag gacagtctca acgttccacc attaaatact tcttctatca
1980 catcccgctt ctttatgcct aaccaaggtt ctaggtcccg atcgactgtg tctggcagca
2040 ctccactgcc aaacccagaa taaggcagcg ctcaggatcc cgaagggggca tggctgggga
2100 tcagaacttc tgggtttgag tgaggagtgg gtccaccctc ttgaatttca aaggaggaag
2160 aggctggatg tgaaggtact gggggaggga aagtgtcagt tccgaactct taggtcaatg
```

-continued

```
                                                            2220
agggaggaga ctggtaaggt cccagctccc gaggtactga tgtgggaatg gcctaagaat
                                                            2280
ctcatatcct caggaagaag gtgctggaat cctgagggt agagttctgg gtatatttgt
                                                            2340
ggcttaaggc tctttggccc ctgaaggcag aggctggaac cattaggtcc agggtttggg
                                                            2400
gtgatagtaa tgggatctct tgattcctca agagtctgag gatcgagggt tgcccattct
                                                            2460
tccatcttgc cacctaatcc ttactccact tgagggtatc accagcccct ctagctccat
                                                            2520
gaaggtcccc tgggcaagca caatctgagc atgaaagatg ccccagaggc cttgggtgtc
                                                            2580
atccactcat catccagcat cacactctga gggtgtggcc agcaccatga cgtcatgttg
                                                            2640
ctgtgactat ccctgcagcg tgcctctcca gccacctgcc aaccgtagag ctgcccatcc
                                                            2700
tcctctggtg ggagtggcct gcatggtgcc aggctgaggc ctagtgtcag acagggagcc
                                                            2760
tggaatcata gggatccagg actcaaaagt gctagagaat ggccatatgt caccatccat
                                                            2820
gaaatctcaa gggcttctgg gtggagggca cagggacctg aacttatggt ttcccaagtc
                                                            2880
tattgctctc ccaagtgagt ctcccagata cgaggcactg tgccagcatc agccttatct
                                                            2940
ccaccacatc ttgtaaaagg actacccagg gccctgatga acaccatggt gtgtacagga
                                                            3000
gtaggggtg gaggcacgga ctcctgtgag gtcacagcca agggagcatc atcatgggtg
                                                            3060
gggaggaggc aatggacagg cttgagaacg gggatgtggt tgtatttggt tttctttggt
                                                            3120
tagataaagt gctgggtata ggattgagag tggagtatga agaccagtta ggatggagga
                                                            3180
tcagattgga gttgggttag ataaagtgct gggtatagga ttgagagtgg agtatgaaga
                                                            3240
ccagttagga tggaggatca gattggagtt gggttagaga tggggtaaaa ttgtgctccg
                                                            3300
gatgagtttg ggattgacac tgtggaggtg gtttgggatg gcatggcttt gggatggaaa
                                                            3360
tagatttgtt ttgatgttgg ctcagacatc cttggggatt gaactgggga tgaagctggg
                                                            3420
tttgatttg gaggtagaag acgtggaagt agctgtcaga tttgacagtg gccatgagtt
                                                            3480
ttgtttgatg gggaatcaaa caatgggga agacataagg gttggcttgt taggttaagt
                                                            3540
tgcgttgggt tgatggggtc ggggctgtgt ataatgcagt tggattggtt tgtattaaat
                                                            3600
tgggttgggt caggttttgg ttgaggatga gttgaggata tgcttgggga caccggatcc
                                                            3660
atgaggttct cactggagtg gagacaaact tcctttccag gatgaatcca gggaagcctt
                                                            3720
aattcacgtg taggggaggt caggccactg gctaagtata tccttccact ccagctctaa
                                                            3780
```

-continued

```
gatggtctta aattgtgatt atctatatcc acttctgtct ccctcactgt gcttggagtt    3840
tacctgatca ctcaactaga aacagggaa gattttatca aattctttt tttttttttt    3900 ttttttgag acagagtctc actctgttgc ccaggctgga gtgcagtggc gcagtctcgg    3960
ctcactgcaa cctctgcctc ccaggttcaa gtgattctcc tgcctcagcc tcctgagttg    4020
ctgggattac aggcatgcag caccatgccc agctaatttt tgtatttta gtagagatgg    4080 ggtttcacca atgtttgcca ggctggcctc gaactcctga cctggtgatc cacctgcctc    4140
agcctcccaa agtgctggga ttacaggcgt cagccaccgc gcccagccac ttttgtcaaa    4200
ttcttgagac acagctcggg ctggatcaag tgagctactc tggttttatt gaacagctga    4260
aataaccaac ttttttggaaa ttgatgaaat cttacggagt taacagtgga ggtaccaggg    4320
ctcttaagag ttcccgattc tcttctgaga ctacaaattg tgattttgca tgccaccta    4380 atcttttttt tttttttttt aaatcgaggt ttcagtctca ttctatttcc caggctggag    4440
ttcaatagcg tgatcacagc tcactgtagc cttgaactcc tggccttaag agattctcct    4500
gcttcggtct cccaatagct aagactacag tagtccacca ccatatccag ataattttta    4560 aatttttttgg ggggccgggc acagtggctc acgcctgtaa tcccaacacc atgggaggct    4620
gagatgggtg gatcacgagg tcaggagttt gagaccagcc tgaccaacat ggtgaaactc    4680
tgtctctact aaaaaaaaaa aaaatagaaa aattagccgg gcgtggtggc acacggcacc    4740
tgtaatccca gctactgagg aggctgaggc aggagaatca cttgaaccca gaaggcagag    4800
gttgcaatga gccgagattg cgccactgca ctccagcctg ggtgacagag tgagactctg    4860
tctcaaaaaa aaaaaattt tttttttttt ttgtagagat ggatcttgct ttgtttctct    4920
ggttggcctt gaactcctgg cttcaagtga tcctcctacc ttggcctcgg aaagtgttgg    4980
gattacaggc gtgagccacc atgactgacc tgtcgttaat cttgaggtac ataaacctgg    5040
ctcctaaagg ctaaaggcta aatatttgtt ggagaagggg cattggattt tgcatgagga    5100
tgattctgac ctgggagggc aggtcagcag gcatctctgt tgcacagata gagtgtacag    5160
gtctggagaa caaggagtgg ggggttattg gaattccaca ttgtttgctg cacgttggat    5220
tttgaaatgc tagggaactt tgggagactc atatttctgg gctagaggat ctgtggacca    5280
caagatcttt ttatgatgac agtagcaatg tatctgtgga gctggattct gggttgggag    5340
```

```
tgcaaggaaa agaatgtact aaatgccaag acatctattt caggagcatg aggaataaaa
5400 gttctagttt ctggtctcag agtggtgcat ggatcaggga gtctcacaat ctcctgagtg
5460 ctggtgtctt agggcacact gggtcttgga gtgcaaagga tctaggcacg tgaggctttg
5520 tatgaagaat cggggatcgt acccaccccc tgtttctgtt tcatcctggg catgtctcct
5580 ctgcctttgt ccctagatg aagtctccat gagctacaag ggcctggtgc atccagggtg
5640 atctagtaat tgcagaacag caagtgctag ctctccctcc ccttccacag ctctgggtgt
5700 gggagggggt tgtccagcct ccagcagcat ggggagggcc ttggtcagcc tctgggtgcc
5760 agcagggcag gggcggagtc ctgggaatg aaggttttat agggctcctg ggaggctc
5820 cccagcccca agctt
5835
```

CEA TRE
```
aagctttta gtgctttaga cagtgagctg gtctgtctaa cccaagtgac ctgggctcca   60    SEQ ID NO:14
tactcagccc cagaagtgaa gggtgaagct ggtggagcc aaaccaggca agcctaccct  120
cagggctccc agtggcctga gaaccattgg acccaggacc cattacttct agggtaagga  180
aggtacaaac accagatcca accatggtct gggggggaaag ctgtcaaatg cctaaaaata  240
tacctgggag aggagcaggc aaactatcac tgccccaggt tctctgaaca gaaacagagg  300
ggcaacccaa agtccaaatc caggtgagca ggtgcaccaa atgcccagag atatgacgag  360
gcaagaagtg aaggaaccac ccctgcatca aatgttttgc atgggaagga aaggggggtt  420
gctcatgttc ccaatccagg agaatgcatt tgggatctgc cttcttctca ctccttggtt  480
agcaagacta agcaaccagg actctggatt tggggaaaga cgtttatttg tggaggccag  540
tgatgacaat cccacgaggg cctaggtgaa gaggcagga aggctcgaga cactgggggac  600
tgagtgaaaa ccacacccat gatctgcacc accctaggat gctccttcat tgctcacctt  660
tctgttgata tcagatggcc ccattttctg taccttcaca gaaggacaca ggctagggtc  720
tgtgcatggc cttcatcccc ggggccatgt gaggacagca ggtgggaaag atcatgggtc  780
ctcctgggtc ctgcagggcc agaacattca tcacccatac tgacctccta gatgggaatg  840
gcttccctgg ggctgggcca acggggcctg gcaggggag aaaggacgtc agggggacagg  900
gaggaagggt catcgagacc cagcctggaa ggttcttgtc tctgaccatc caggatttac  960
ttccctgcat ctacctttgg tcattttccc tcagcaatga ccagctctgc ttcctgatct 1020
cagcctccca ccctggacac agcaccccag tccctggccc ggctgcatcc acccaatacc 1080
ctgataaccc aggacccatt acttctaggg taaggagggt ccaggagaca gaagctgagg 1140
aaaggtctga agaagtcaca tctgtcctgg ccagaggggga aaaccatca gatgctgaac 1200
caggagaatg ttgacccagg aaagggaccg aggacccaag aaaggagtca gaccaccagg 1260
gtttgcctga gaggaaggat caaggccccg agggaaagca gggctggctg catgtgcagg 1320
acactggtgg ggcatatgtg tcttagattc tccctgaatt cagtgtccct gccatggcca 1380
gactctctac tcaggcctgg acatgctgaa ataggacaat ggccttgtcc tctctcccca 1440
ccattttggca agagacataa aggacattcc aggacatgcc ttcctgggag gtccaggttc 1500
tctgtctcac acctcaggga ctgtagttac tgcatcagcc atggtaggtg ctgatctcac 1560
```

-continued

```
ccagcctgtc caggcccttc cactctccac tttgtgacca tgtccaggac cacccctcag   1620
atcctgagcc tgcaaatacc cccttgctgg gtgggtggat tcagtaaaca gtgagctcct   1680
atccagcccc cagagccacc tctgtcacct tcctgctggg catcatccca ccttcacaag   1740
cactaaagag catggggaga cctggctagc tgggtttctg catcacaaag aaaataatcc   1800
cccaggttcg gattcccagg gctctgtatg tggagctgac agacctgagg ccaggagata   1860
gcagaggtca gccctaggga gggtgggtca tccacccagg gacagggt gcaccagcct    1920 tgctactgaa agggcctccc caggacagcg ccatcagccc tgcctgagag ctttgctaaa   1980
cagcagtcag aggaggccat ggcagtggct gagctcctgc tccaggcccc aacagaccag   2040
accaacagca caatgcagtc cttccccaac gtcacaggtc accaagggaa aactgaggtg   2100
ctacctaacc ttagagccat caggggagat aacagcccaa tttcccaaac aggccagttt   2160
caatcccatg acaatgacct ctctgctctc attcttccca aaataggacg ctgattctcc   2220
cccaccatgg atttctccct tgtcccggga gccttttctg cccctatga tctgggcact    2280 cctgacacac acctcctctc tggtgacata tcagggtccc tcactgtcaa gcagtccaga   2340
aaggacagaa ccttggacag cgcccatctc agcttcaccc ttcctccttc acagggttca   2400
gggcaaagaa taaatggcag aggccagtga gcccagagat ggtgacaggc agtgacccag   2460
gggcagatgc ctggagcagg agctggcggg gccacaggga gaaggtgatg caggaaggga   2520
aacccagaaa tgggcaggaa aggaggacac aggctctgtg gggctgcagc ccagggttgg   2580
actatgagtg tgaagccatc tcagcaagta aggccaggtc ccatgaacaa gagtgggagc   2640
acgtggcttc ctgctctgta tatggggtgg gggattccat gccccataga accagatggc   2700
cggggttcag atggagaagg agcaggacag gggatcccca ggataggagg accccagtgt   2760
ccccacccag gcaggtgact gatgaatggg catgcaggt cctcctgggc tgggctctcc     2820 cttttgtccct caggattcct tgaaggaaca tccggaagcc gaccacatct acctggtggg   2880
ttctggggag tccatgtaaa gccaggagct tgtgttgcta ggaggggtca tggcatgtgc   2940
tgggggcacc aaagagagaa acctgagggc aggcaggacc tggtctgagg aggcatggga   3000
gcccagatgg ggagatggat gtcaggaaag gctgccccat cagggagggt gatagcaatg   3060
gggggtctgt gggagtgggc acgtgggatt ccctgggctc tgccaagttc cctcccatag   3120
tcacaacctg gggacactgc ccatgaaggg gcgcctttgc ccagccagat gctgctggtt   3180
ctgcccatcc actaccctct ctgctccagc cactctgggt cttctccag atgccctgga    3240 cagccctggc ctgggcctgt ccctgagag gtgttgggag aagctgagtc tctggggaca   3300
ctctcatcag agtctgaaag gcacatcagg aaacatccct ggtctccagg actaggcaat   3360
gaggaaaggg ccccagctcc tcctttccc actgagaggg tcgaccctgg gtggccacag    3420
tgacttctgc gtcgtcccca gtcaccctga aaccacaaca aaaccccagc ccagaccct    3480 gcaggtacaa tacatgtggg gacagtctgt acccagggga agccagttct ctcttcctag   3540
gagaccgggc ctcagggctg tgcccgggc aggcggggc agcacgtgcc tgtccttgag     3600
aactcgggac cttaagggtc tctgctctgt gaggcacagc aaggatcctt ctgtccagag   3660
atgaaagcag ctcctgcccc tcctctgacc tcttcctcct tcccaaatct caaccaacaa   3720
ataggtgttt caaatctcat catcaaatct tcatccatcc acatgagaaa gcttaaaacc   3780
caatggattg acaacatcaa gagttggaac aagtggacat ggatgtgtta cttgtggaaa   3840
tttagatgtg ttcagctatc gggcaggaga atctgtgtca aattccagca tggttcagaa   3900
```

-continued

```
gaatcaaaaa gtgtcacagt ccaaatgtgc aacagtgcag gggataaaac tgtggtgcat   3960
tcaaactgag ggatattttg gaacatgaga aaggaaggga ttgctgctgc acagaacatg   4020
catgatctca cacatagagt tgaaagaaag gagtcaatcg cagaatagaa aatgatcact   4080
aattccacct ctataaagtt tccaagagga aaacccaatt ctgctgctag agatcagaat   4140
ggaggtgacc tgtgccttgc aatggctgtg agggtcacgg gagtgtcact tagtgcaggc   4200
aatgtgccgt atcttaatct gggcagggct ttcatgagca cataggaatg cagacattac   4260
tgctgtgttc attttacttc accggaaaag aagaataaaa tcagccgggc gcggtggctc   4320
acgcctgtaa tcccagcact ttagaagcct gaggtgggca gattacttga ggtcaggagt   4380
tcaagaccac cctggccaat atggtgaaac cccggctcta ctaaaaatac aaaaattagc   4440
tgggcatggt ggtgcgcgcc tgtaatccca gctactcggg aggctgaggc tggacaattg   4500
cttggaccca ggaagcagag gttgcagtga gccaagattg tgccactgca ctccagcttg   4560
ggcaacagag ccagactctg taaaaaaaaa aaaaaaaaa aaaaaagaa agaaagaaaa     4620 agaaaagaaa gtataaaatc tctttgggtt aacaaaaaaa gatccacaaa acaaacacca   4680
gctcttatca aacttacaca actctgccag agaacaggaa acacaaatac tcattaactc   4740
acttttgtgg caataaaacc ttcatgtcaa aaggagacca ggacacaatg aggaagtaaa   4800
actgcaggcc ctacttgggt gcagagaggg aaaatccaca aataaaacat taccagaagg   4860
agctaagatt tactgcattg agttcattcc ccaggtatgc aaggtgattt taacacctga   4920
aaatcaatca ttgcctttac tacatagaca gattagctag aaaaaaatta caactagcag   4980
aacagaagca atttggcctt cctaaaattc cacatcatat catcatgatg gagacagtgc   5040
agacgccaat gacaataaaa agagggacct ccgtcacccg gtaaacatgt ccacacagct   5100
ccagcaagca cccgtcttcc cagtgaatca ctctaacctc ccctttaatc agccccaggc   5160
aaggctgcct gcgatggcca cacaggctcc aacccgtggg cctcaacctc ccgcagaggc   5220
tctcctttgg ccaccccatg gggagagcat gaggacaggg cagagccctc tgatgcccac   5280
acatggcagg agctgacgcc agagccatgg gggctggaga gcagagctgc tggggtcaga   5340
gcttcctgag gacacccagg cctaagggaa ggcagctccc tggatggggg caaccaggct   5400
ccgggctcca acctcagagc ccgcatggga ggagccagca ctctaggcct ttcctagggt   5460
gactctgagg ggaccctgac acgacaggat cgctgaatgc acccgagatg aagggggccac   5520 cacgggaccc tgctctcgtg gcagatcagg agagagtggg acaccatgcc aggcccccat   5580
ggcatggctg cgactgaccc aggccactcc cctgcatgca tcagcctcgg taagtcacat   5640
gaccaagccc aggaccaatg tggaaggaag gaaacagcat ccccttagt gatgaaccc     5700 aaggtcagtg caaagagagg ccatgagcag ttaggaaggg tggtccaacc tacagcacaa   5760
accatcatct atcataagta gaagcccctgc tccatgaccc ctgcatttaa ataaacgttt   5820
gttaaatgag tcaaattccc tcaccatgag agctcacctg tgtgtaggcc catcacacac   5880
acaaacacac acacacacac acacacacac acacacacac acaggaaag tgcaggatcc    5940 tggacagcac caggcaggct tcacaggcag agcaaacagc gtgaatgacc catgcagtgc   6000
cctgggcccc atcagctcag agaccctgtg agggctgaga tggggctagg caggggagag   6060
acttagagag ggtgggggct ccaggagggg ggctgcaggg agctgggtac tgccctccag   6120
ggagggggct gcagggagct gggtactgcc ctcagggag ggggctgcag ggagctgggt     6180
actgccctcc aggaggggg ctgcagggag ctgggtactg ccctcagggg aggggctgc     6240 agggagctgg gtactgccct ccagggaggc aggagcactg ttcccaacag agagcacatc   6300
```

```
ttcctgcagc agctgcacag acacaggagc ccccatgact gccctgggcc agggtgtgga   6360
ttccaaattt cgtgccccat tgggtgggac ggaggttgac cgtgacatcc aagggcatc    6420 tgtgattcca aacttaaact actgtgccta caaaatagga aataaccta cttttttctac   6480 tatctcaaat tccctaagca caagctagca cccttaaat caggaagttc agtcactcct    6540
ggggtcctcc catgccccca gtctgacttg caggtgcaca gggtggctga catctgtcct   6600
tgctcctcct cttggctcaa ctgccgcccc tcctgggggt gactgatggt caggacaagg   6660
gatcctagag ctggccccat gattgacagg aaggcaggac ttggcctcca ttctgaagac   6720 tagggggtgtc aagagagctg ggcatcccac agagctgcac aagatgacgc ggacagaggg  6780
tgacacaggg ctcagggctt cagacgggtc gggaggctca gctgagagtt caggacaga   6840 cctgaggagc ctcagtggga aagaagcac tgaagtggga agttctggaa tgttctggac    6900
aagcctgagt gctctaagga aatgctccca ccccgatgta gcctgcagca ctggacggtc   6960
tgtgtacctc cccgctgccc atcctctcac agccccgcc tctagggaca caactcctgc    7020
cctaacatgc atctttcctg tctcattcca cacaaaaggg cctctggggt ccctgttctg   7080
cattgcaagg agtggaggtc acgttcccac agaccaccca gcaacagggt cctatggagg   7140
tgcggtcagg aggatcacac gtccccccat gccagggga ctgactctgg gggtgatgga    7200
ttggcctgga ggccactggt cccctctgtc cctgaggga atctgcaccc tggaggctgc    7260
cacatccctc ctgattcttt cagctgaggg ccccttctga aatcccaggg aggactcaac   7320
ccccactggg aaaggcccag tgtggacggt tccacagcag cccagctaag gcccttggac   7380
acagatcctg agtgagagaa ccttaggga cacaggtgca cggccatgtc cccagtgccc    7440
acacagagca ggggcatctg gaccctgagt gtgtagctcc cgcgactgaa cccagcctt    7500 ccccaatgac gtgaccctg gggtggctcc aggtctccag tccatgccac caaaatctcc    7560
agattgaggg tcctcccttg agtccctgat gcctgtccag gagctgcccc ctgagcaaat   7620
ctagagtgca gaggactggg attgtggcag taaaagcagc cacatttgtc tcaggaagga   7680
aagggaggac atgagctcca ggaagggcga tggcgtcctc tagtgggcgc ctcctgttaa   7740
tgagcaaaaa ggggccagga gagttgagag atcagggctg gccttggact aaggctcaga   7800
tggagaggac tgaggtgcaa agaggggct gaagtagggg agtggtcggg agagatggga   7860
ggagcaggta agggaagcc ccagggaggc cggggaggg tacagcagag ctctccactc     7920
ctcagcattg acatttgggg tggtcgtgct agtggggttc tgtaagttgt agggtgttca   7980
gcaccatctg gggactctac ccactaaatg ccagcaggac tccctcccca agctctaaca   8040
accaacaatg tctccagact ttccaaatgt cccctggaga gcaaaattgc ttctggcaga   8100
atcactgatc tacgtcagtc tctaaaagtg actcatcagc gaaatccttc acctcttggg   8160
agaagaatca caagtgtgag aggggtagaa actgcagact tcaaaatctt tccaaaagag   8220
ttttacttaa tcagcagttt gatgtcccag gagaagatac atttagagtg tttagagttg   8280
atgccacatg gctgcctgta cctcacagca ggagcagagt gggttttcca agggcctgta   8340
accacaactg gaatgacact cactgggtta cattacaaag tggaatgtgg ggaattctgt    8400
agactttggg aagggaaatg tatgacgtga gcccacagcc taaggcagtg gacagtccac   8460
tttgaggctc tcaccatcta ggagacatct cagccatgaa catagccaca tctgtcatta   8520
gaaaacatgt tttattaaga ggaaaaatct aggctagaag tgctttatgc tcttttttct   8580
ctttatgttc aaattcatat acttttgatt cattccttaa agaagaatct atcccctaa    8640
```

-continued

```
gtaaatgtta tcactgactg gatagtgttg gtgtctcact cccaacccct gtgtggtgac    8700
agtgccctgc ttccccagcc ctgggccctc tctgattcct gagagctttg ggtgctcctt    8760
cattaggagg aagagaggaa gggtgttttt aatattctca ccattcaccc atccacctct    8820
tagacactgg gaagaatcag ttgcccactc ttggatttga tcctcgaatt aatgacctct    8880
atttctgtcc cttgtccatt tcaacaatgt gacaggccta agaggtgcct tctccatgtg    8940 attttgagg agaaggttct caagataagt tttctcacac ctctttgaat tacctccacc    9000
tgtgtcccca tcaccattac cagcagcatt tggaccettt ttctgttagt cagatgcttt    9060
ccacctcttg agggtgtata ctgtatgctc tctacacagg aatatgcaga ggaaatagaa    9120
aaagggaaat cgcattacta ttcagagaga agaagacctt tatgtgaatg aatgagagtc    9180
taaaatccta agagagccca tataaaatta ttaccagtgc taaaactaca aaagttacac    9240
taacagtaaa ctagaataat aaaacatgca tcacagttgc tggtaaagct aaatcagata    9300
ttttttcctt agaaaaagca ttccatgtgt gttgcagtga tgacaggagt gcccttcagt    9360
caatatgctg cctgtaattt ttgttccctg gcagaatgta ttgtcttttc tcccttttaaa   9420 tcttaaatgc aaaactaaag gcagctcctg ggccccctcc ccaaagtcag ctgcctgcaa    9480
ccagccccac gaagagcaga ggcctgagct tccctggtca aaataggggg ctagggagct    9540
taaccttgct cgataaagct gtgttcccag aatgtcgctc ctgttcccag gggcaccagc    9600
ctggagggtg gtgagcctca ctggtggcct gatgcttacc ttgtgccctc acaccagtgg    9660
tcactggaac cttgaacact tggctgtcgc ccggatctgc agatgtcaag aacttctgga    9720
agtcaaatta ctgcccactt ctccagggca gataccggtg aacatccaaa accatgccac    9780
agaaccctgc ctgggtcta caacacatat ggactgtgag caccaagtcc agccctgaat    9840
ctgtgaccac ctgccaagat gcccctaact gggatccacc aatcactgca catggcaggc    9900
agcgaggctt ggaggtgctt cgccacaagg cagcccaat ttgctgggag tttcttggca    9960
cctggtagtg gtgaggagcc ttgggaccct caggattact ccccttaagc atagtgggga   10020
cccttctgca tccccagcag gtgccccgct cttcagagcc tctctctctg aggtttaccc   10080
agacccctgc accaatgaga ccatgctgaa gcctcagaga gagagatgga gctttgacca   10140
ggagccgctc ttccttgagg gccagggcag ggaaagcagg aggcagcacc aggagtggga   10200
acaccagtgt ctaagcccct gatgagaaca gggtggtctc tcccatatgc ccataccagg   10260
cctgtgaaca gaatcctcct tctgcagtga caatgtctga gaggacgaca tgtttcccag   10320
cctaacgtgc agccatgccc atctacccac tgcctactgc aggacagcac caacccagga   10380
gctgggaagc tgggagaaga catggaatac ccatggcttc tcaccttcct ccagtccagt   10440
gggcaccatt tatgcctagg acacccacct gccggcccca ggctcttaag agttaggtca   10500
cctaggtgcc tctgggaggc cgaggcagga gaattgcttg aacccgggag gcagaggtta   10560
cagtgagccg agatcacacc actgcactcc agcctgggtg acagaatgag actctgtctc   10620
aaaaaaaaag agaaagatag catcagtggc taccaagggc taggggcagg ggaaggtgga   10680
gagttaatga ttaatagtat gaagtttcta tgtgagatga tgaaaatgtt ctggaaaaaa   10740
aaatatagtg gtgaggatgt agaatattgt gaatataatt aacggcattt aattgtacac   10800
ttaacatgat taatgtggca tattttatct tatgtatttg actacatcca agaaacactg   10860
ggagagggaa agcccaccat gtaaaataca cccacccttaa tcagatagtc ctcattgtac   10920
ccaggtacag gcccctcatg acctgcacag gaataactaa ggatttaagg acatgaggct   10980
tcccagccaa ctgcaggtgc acaacataaa tgtatctgca aacagactga gagtaaagct   11040
```

-continued

```
gggggcacaa acctcagcac tgccaggaca cacaccttc tcgtggattc tgactttatc    11100
tgacccggcc cactgtccag atcttgttgt gggattggga caaggaggt cataaagcct    11160 gtccccaggg cactctgtgt gagcacacga gacctcccca ccccccacc gttaggtctc    11220 cacacataga tctgaccatt aggcattgtg aggaggactc tagcgcgggc tcagggatca    11280
caccagagaa tcaggtacag agaggaagac ggggctcgag gagctgatgg atgacacaga    11340
gcagggttcc tgcagtccac aggtccagct caccctggtg taggtgcccc atcccctga    11400 tccaggcatc cctgacacag ctccctcccg gagcctcctc ccaggtgaca catcagggtc    11460
cctcactcaa gctgtccaga gagggcagca ccttggacag cgcccacccc acttcactct    11520
tcctccctca cagggctcag ggctcagggc tcaagtctca gaacaaatgg cagaggccag    11580
tgagcccaga gatggtgaca gggcaatgat ccaggggcag ctgcctgaaa cgggagcagg    11640
tgaagccaca gatgggagaa gatggttcag gaagaaaaat ccaggaatgg gcaggagagg    11700
agaggaggac acaggctctg tggggctgca gcccaggatg ggactaagtg tgaagacatc    11760
tcagcaggtg aggccaggtc ccatgaacag agaagcagct cccacctccc ctgatgcacg    11820
gacacacaga gtgtgtggtg ctgtgccccc agagtcgggc tctcctgttc tggtccccag    11880
ggagtgagaa gtgaggttga cttgtccctg ctcctctctg ctaccccaac attccacttc    11940
tcctcatgcc cctctctctc aaatatgatt tggatctatg tccccgccca aatctcatgt    12000
caaattgtaa accccaatgt tggaggtggg gccttgtgag aagtgattgg ataatgcggg    12060
tggattttct gctttgatgc tgtttctgtg atagagatct cacatgatct ggttgtttaa    12120
aagtgtgtag cacctctccc ctctctctct ctctctctta ctcatgctct gccatgtaag    12180
acgttcctgt ttccccttca ccgtccagaa tgattgtaag ttttctgagg cctccccagg    12240
agcagaagcc actatgcttc ctgtacaact gcagaatgat gagcgaatta aacctctttt    12300
ctttataaat tacccagtct caggtatttc tttatagcaa tgcgaggaca gactaataca    12360
atcttctact cccagatccc cgcacacgct tagccccaga catcactgcc cctgggagca    12420
tgcacagcgc agcctcctgc cgacaaaagc aaagtcacaa aaggtgacaa aaatctgcat    12480
ttggggacat ctgattgtga aagagggagg acagtacact tgtagccaca gagactgggg    12540
ctcaccgagc tgaaacctgg tagcactttg gcataacatg tgcatgaccc gtgttcaatg    12600
tctagagatc agtgttgagt aaaacagcct ggtctggggc cgctgctgtc cccacttccc    12660
tcctgtccac cagagggcgg cagagttcct cccaccctgg agcctcccca ggggctgctg    12720
acctccctca gccgggccca cagcccagca gggtccaccc tcacccgggt cacctcggcc    12780
cacgtcctcc tcgccctccg agctcctcac acggactctg tcagctcctc cctgcagcct    12840
atcggccgcc cacctgaggc ttgtcggccg cccacttgag gcctgtcggc tgccctctgc    12900
aggcagctcc tgtcccctac accccctcct tccccgggct cagctgaaag ggcgtctccc    12960
agggcagctc cctgtgatct ccaggacagc tcagtctctc acaggctccg acgcccccta    13020
tgctgtcacc tcacagccct gtcattacca ttaactcctc agtccatga agttcactga    13080 gcgcctgtct cccggttaca ggaaaactct gtgacaggga ccacgtctgt cctgctctct    13140
gtggaatccc agggcccagc ccagtgcctg acacggaaca gatgctccat aaatactggt    13200
taaatgtgtg ggagatctct aaaaagaagc atatccactc cgtgtggccc ccagcagtca    13260
gagtctgttc catgtggaca caggggcact ggcaccagca tggaggagg ccagcaagtg    13320 cccgcggctg ccccaggaat gaggcctcaa cccccagagc ttcagaaggg aggacagagg    13380
```

-continued

```
cctgcaggga atagatcctc cggcctgacc ctgcagccta atccagagtt cagggtcagc    13440
tcacaccacg tcgaccctgg tcagcatccc tagggcagtt ccagacaagg ccggaggtct    13500
cctcttgccc tccaggggt gacattgcac acagacatca ctcaggaaac ggattccccct   13560 ggacaggaac ctggctttgc taaggaagtg gaggtggagc ctggtttcca tcccttgctc    13620
caacagaccc ttctgatctc tcccacatac ctgctctgtt cctttctggg tcctatgagg    13680
accctgttct gccagggtc cctgtgcaac tccagactcc ctcctggtac caccatgggg     13740
aaggtggggt gatcacagga cagtcagcct cgcagagaca gagaccaccc aggactgtca    13800
gggagaacat ggacaggccc tgagccgcag ctcagccaac agacacggag agggagggtc    13860
cccctggagc cttccccaag gacagcagag cccagagtca cccacctccc tccaccacag    13920
tcctctcttt ccaggacaca aagacacct cccctccac atgcaggatc tggggactcc     13980
tgagacctct gggcctgggt ctccatccct gggtcagtgg cggggttggt ggtactggag    14040
acagagggct ggtccctccc cagccaccac ccagtgagcc tttttctagc ccccagagcc    14100
acctctgtca ccttcctgtt gggcatcatc ccaccttccc agagccctgg agagcatggg    14160
gagacccggg accctgctgg gtttctctgt cacaaaggaa aataatcccc ctggtgtgac    14220
agacccaagg acagaacaca gcagaggtca gcactgggga agacaggttg tcctcccagg    14280 ggatggggt ccatccacct tgccgaaaag atttgtctga ggaactgaaa atagaaggga    14340 aaaagagga gggacaaaag aggcagaaat gagaggggag gggacagagg acacctgaat    14400
aaagaccaca cccatgaccc acgtgatgct gagaagtact cctgccctag gaagagactc    14460
```
transcription start site
```
agggcagagg gaggaaggac agcagaccag acagtcacag cagccttgac aaaacgttcc    14520
tggaactcaa gctcttctcc acagaggagg acagagcaga cagcagagac catggagtct    14580
ccctcggccc ctccccacag atggtgcatc ccctggcaga ggctcctgct cacaggtgaa    14640
gggaggacaa cctgggagag ggtgggagga gggagctggg gtctcctggg taggacaggg    14700
ctgtgagacg gacagagggc tcctgttgga gcctgaatag ggaagaggac atcagagagg    14760
gacaggagtc acaccagaaa aatcaaattg aactggaatt ggaaggggc aggaaaacct    14820 caagagttct attttcctag ttaattgtca ctggccacta cgttttttaaa aatcataata    14880 actgcatcag atgacacttt aaataaaaac ataaccaggg catgaaacac tgtcctcatc    14940
cgcctaccgc ggacattgga aaataagccc caggctgtgg agggccctgg gaaccctcat    15000
gaactcatcc acaggaatct gcagcctgtc ccaggcactg ggtgcaacc aagatc         15056
```
Mucin-TRE
```
cgagcggccc ctcagcttcg gcgcccagcc ccgcaaggct cccggtgacc actagagggc    60    SEQ ID NO:15 gggaggagct cctggccagt ggtggagagt ggcaaggaag gacccctaggg ttcatcggag
120 cccaggttta ctcccttaag tggaaatttc ttcccccact cctccttggc tttctccaag
180 gagggaaccc aggctgctgg aaagtccggc tgggcgggg actgtgggtt caggggagaa
240 cggggtgtgg aacgggacag ggagcggtta aagggtggg gctattccgg gaagtggtgg
300 ggggagggag cccaaaacta gcacctagtc cactcattat ccagccctct tatttctcgg
360 ccgctctgct tcagtggacc cggggagggc ggggaagtgg agtggagac ctaggggtgg
420 gcttcccgac cttgctgtac aggacctcga cctagctggc tttgttcccc atccccacgt
```

-continued

```
                                                                        480
tagttgttgc ctgaggcta aaactagagc ccaggggccc caagttccag actgcccctc
                                                                        540 cccctcccc cggagccagg gagtggttgg tgaaaggggg aggccagctg gagaacaaac
                                                                        600 gggtagtcag ggggttgagc gattagagcc cttgtaccct acccaggaat ggttggggag
                                                                        660 gaggaggaag aggtaggagg taggggaggg ggcggggttt tgtcacctgt cacctgctcg
                                                                        720 ctgtgcctag ggcgggcggg cggggagtgg ggggaccggt ataaagcggt aggcgcctgt
                                                                        780 gcccgctcca cctctcaagc agccagcgcc tgcctgaatc tgttctgccc cctccccacc
                                                                        840 catttcacca ccaccatg
                                                                        858
```

αFP-TRE
```
gaattcttag aaatatgggg gtaggggtgg tggtggtaat tctgttttca ccccataggt   60   SEQ ID NO:16 gagataagca ttgggttaaa tgtgctttca cacacacatc acatttcata agaattaagg
                                                                        120 aacagactat gggctggagg actttgagga tgtctgtctc ataacacttg ggttgtatct
                                                                        180 gttctatggg gcttgtttta agcttggcaa cttgcaacag ggttcactga ctttctcccc
                                                                        240 aagcccaagg tactgtcctc ttttcatatc tgttttgggg cctctggggc ttgaatatct
                                                                        300 gagaaaatat aaacatttca ataatgttct gtggtgagat gagtatgaga gatgtgtcat
                                                                        360 tcatttgtat caatgaatga atgaggacaa ttagtgtata atccttagt acaacaatct
                                                                        420 gagggtaggg gtggtactat tcaatttcta tttataaga tacttatttc tatttattta
                                                                        480 tgcttgtgac aaatgttttg ttcgggacca caggaatcac aaagatgagt ctttgaattt
                                                                        540 aagaagttaa tggtccagga ataattacat agcttacaaa tgactatgat ataccatcaa
                                                                        600 acaagaggtt ccatgagaaa ataatctgaa aggtttaata agttgtcaaa ggtgagaggg
                                                                        660 ctcttctcta gctagagact aatcagaaat acattcaggg ataattattt gaatagacct
                                                                        720 taagggttgg gtacattttg ttcaagcatt gatggagaag gagagtgaat atttgaaaac
                                                                        780 attttcaact aaccaaccac ccaatccaac aaacaaaaaa tgaaaagaat ctcagaaaca
                                                                        840 gtgagataag agaaggaatt ttctcacaac ccacacgtat agctcaactg ctctgaagaa
                                                                        900 gtatatatct aatatttaac actaacatca tgctaataat gataataatt actgtcattt
                                                                        960 tttaatgtct ataagtacca ggcatttaga agatattatt ccatttatat atcaaaataa
                                                                        1020 acttgagggg atagatcatt ttcatgatat atgagaaaaa ttaaaaacag attgaattat
                                                                        1080 ttgcctgtca tacagctaat aattgaccat aagacaatta gatttaaatt agttttgaat
                                                                        1140
```

-continued

```
ctttctaata ccaaagttca gtttactgtt ccatgttgct tctgagtggc ttcacagact
1200 tatgaaaaag taaacggaat cagaattaca tcaatgcaaa agcattgctg tgaactctgt
1260 acttaggact aaactttgag caataacaca catagattga ggattgtttg ctgttagcat
1320 acaaactctg gttcaaagct cctctttatt gcttgtcttg gaaaatttgc tgttcttcat
1380 ggtttctctt ttcactgcta tctattttc tcaaccactc acatggctac aataactgtc
1440 tgcaagctta tgattcccaa atatctatct ctagcctcaa tcttgttcca gaagataaaa
1500 agtagtattc aaatgcacat caacgtctcc acttggaggg cttaaagacg tttcaacata
1560 caaaccgggg agttttgcct ggaatgtttc ctaaaatgtg tcctgtagca cataggttcc
1620 tcttgttcct taaaatctaa ttacttttag cccagtgctc atcccaccta tggggagatg
1680 agagtgaaaa gggagcctga ttaataatta cactaagtca ataggcatag agccaggact
1740 gtttgggtaa actggtcact ttatcttaaa ctaaatatat ccaaaactga acatgtactt
1800 agttactaag tctttgactt tatctcattc ataccactca gctttatcca ggccacttat
1860 ttgacagtat tattgcgaaa acttcctaac tggtctcctt atcatagtct tatccccttt
1920 tgaaacaaaa gagacagttt caaaatacaa atatgatttt tattagctcc cttttgttgt
1980 ctataatagt cccagaagga gttataaact ccatttaaaa agtctttgag atgtggccct
2040 tgccaacttt gccaggaatt cccaatatct agtattttct actattaaac tttgtgcctc
2100 ttcaaaactg cattttctct cattccctaa gtgtgcattg ttttcccta ccggttggtt
2160 tttccaccac cttttacatt ttcctggaac actataccct ccctcttcat ttggcccacc
2220 tctaattttc tttcagatct ccatgaagat gttacttcct ccaggaagcc ttatctgacc
2280 cctccaaaga tgtcatgagt tcctcttttc attctactaa tcacagcatc catcacacca
2340 tgttgtgatt actgatacta ttgtctgttt ctctgattag gcagtaagct caacaagagc
2400 tacatggtgc ctgtctcttg ttgctgatta ttcccatcca aaaacagtgc ctggaatgca
2460 gacttaacat tttattgaat gaataaataa aaccccatct atcgagtgct actttgtgca
2520 agacccggtt ctgaggcatt tatatttatt gatttattta attctcattt aaccatgaag
2580 gaggtactat cactatcctt attttatagt tgataaagat aaagcccaga gaaatgaatt
2640 aactcaccca aagtcatgta gctaagtgac agggcaaaaa ttcaaaccag ttccccaact
2700
```

```
ttacgtgatt aatactgtgc tatactgcct ctctgatcat atggcatgga atgcagacat
2760 ctgctccgta aggcagaata tggaaggaga ttggaggatg acacaaaacc agcataatat
2820 cagaggaaaa gtccaaacag gacctgaact gatagaaaag ttgttactcc tggtgtagtc
2880 gcatcgacat cttgatgaac tggtggctga cacaacatac attggcttga tgtgtacata
2940 ttatttgtag ttgtgtgtgt attttatat atatatttgt aatattgaaa tagtcataat
3000 ttactaaagg cctaccattt gccaggcatt tttacatttg tccctctaa tcttttgatg
3060 agatgatcag attggattac ttggccttga agatgatata tctacatcta tatctatatc
3120 tatatctata tctatatcta tatctatatc tatatctata tatgtatatc agaaaagctg
3180 aaatatgttt tgtaaagtta taaagatttc agactttata gaatctggga tttgccaaat
3240 gtaacccctt tctctacatt aaacccatgt tggaacaaat acatttatta ttcattcatc
3300 aaatgttgct gagtcctggc tatgaaccag acactgtgaa agcctttggg atattttgcc
3360 catgcttggg caagcttata tagtttgctt cataaaactc tatttcagtt cttcataact
3420 aatacttcat gactattgct tttcaggtat tccttcataa caaatacttt ggctttcata
3480 tatttgagta aagtccccct tgaggaagag tagaagaact gcactttgta aatactatcc
3540 tggaatccaa acggatagac aaggatggtg ctacctcttt ctggagagta cgtgagcaag
3600 gcctgttttg ttaacatgtt ccttaggaga caaaacttag gagagacacg catagcagaa
3660 aatggacaaa aactaacaaa tgaatgggaa ttgtacttga ttagcattga agaccttgtt
3720 tatactatga taaatgtttg tatttgctgg aagtgctact gacggtaaac ccttttttgtt
3780 taaatgtgtg ccctagtagc ttgcagtatg atctattttt taagtactgt acttagctta
3840 tttaaaaatt ttatgtttaa aattgcatag tgctctttca ttgaagaagt tttgagagag
3900 agatagaatt aaattcactt atcttaccat ctagagaaac ccaatgttaa aactttgttg
3960 tccattattt ctgtcttta ttcaacattt tttttagagg gtgggaggaa tacagaggag
4020 gtacaatgat acacaaatga gagcactctc catgtattgt tttgtcctgt tttcagtta
4080 acaatatatt atgagcatat ttccatttca ttaaatattc ttccacaaag ttatttttgat
4140 ggctgtatat caccctactt tatgaatgta ccatattaat ttatttcctg gtgtgggtta
4200 tttgatttta taatcttacc tttagaataa tgaaacacct gtgaagcttt agaaaatact
4260 ggtgcctggg tctcaactcc acagattctg atttaactgg tctgggttac agactaggca
```

-continued

```
                                                                    4320
ttgggaattc aaaaagttcc cccagtgatt ctaatgtgta gccaagatcg ggaacccttg
                                                                    4380
tagacaggga tgataggagg tgagccactc ttagcatcca tcatttagta ttaacatcat
                                                                    4440
catcttgagt tgctaagtga atgatgcacc tgacccactt tataaagaca catgtgcaaa
                                                                    4500
taaaattatt ataggacttg gtttattagg gcttgtgctc taagttttct atgttaagcc
                                                                    4560
atacatcgca tactaaatac tttaaaatgt accttattga catacatatt aagtgaaaag
                                                                    4620
tgtttctgag ctaaacaatg acagcataat tatcaagcaa tgataatttg aaatgaattt
                                                                    4680
attattctgc aacttaggga caagtcatct ctctgaattt tttgtacttt gagagtattt
                                                                    4740
gttatatttg caagatgaag agtctgaatt ggtcagacaa tgtcttgtgt gcctggcata
                                                                    4800
tgataggcat ttaatagttt taaagaatta atgtatttag atgaattgca taccaaatct
                                                                    4860
gctgtctttt ctttatggct tcattaactt aatttgagag aaattaatta ttctgcaact
                                                                    4920
tagggacaag tcatgtcttt gaatattctg tagtttgagg agaatatttg ttatatttgc
                                                                    4980
aaaataaaat aagtttgcaa gttttttttt tctgccccaa agagctctgt gtccttgaac
                                                                    5040
ataaaataca ataaccgct atgctgttaa ttattggcaa atgtcccatt ttcaacctaa
                                                                    5100
ggaaatacca taaagtaaca gatataccaa caaaaggtta ctagttaaca ggcattgcct
                                                                    5160
gaaaagagta taaagaatt tcagcatgat tttccatatt gtgcttccac cactgccaat
                                                                    5220
aaca
5224
```

---

What is claimed is:

1. A replication-competent adenovirus vector comprising first and second genes co-transcribed as a single mRNA wherein the first and the second genes are under transcriptional control of a heterologous, target cell-specific transcriptional regulatory element (TRE), wherein the second gene has a mutation in or deletion of its endogenous promoter and is under translational control of an internal ribosome entry site (IRES) and wherein said vector exhibits greater specificity for the target cell than an adenovirus vector comprising a target cell-specific TRE operably linked to a gene and lacking an IRES, wherein at least one of said first and second genes is an adenovirus gene.

2. The vector of claim 1, wherein both of said first and said second genes are adenovirus genes.

3. The vector of claim 1, wherein at least one of said first and said second adenovirus gene is essential for viral replication.

4. The vector of claim 1 wherein said TRE has an endogenous silencer element deleted.

5. The vector of claim 1 wherein said adenovirus vector comprises an E3 region.

6. The vector of claim 1 wherein said first adenovirus gene is essential for viral replication and said second adenovirus gene is the adenovirus death protein gene (ADP).

7. The vector of claim 2 wherein said first gene is essential for viral replication and said second gene is E3.

8. A composition comprising the vector according to claim 1, and a pharmaceutically acceptable excipient.

9. The vector of claim 2, wherein both said first and said second adenovirus genes are essential for viral replication.

10. The vector of claim 3, wherein the adenovirus gene essential for viral-replication is an adenovirus early gene.

11. The vector of claim 3, wherein the adenovirus gene essential for viral replication is an adenovirus late gene.

12. The vector of claim 10, wherein the adenovirus early gene includes E1A, E1B, E2, or E4.

13. The vector of claim 9, wherein at least one of said first and said second adenovirus genes is an adenovirus early gene.

14. The vector of claim 9, wherein at least one of said first and said second adenovirus genes is an adenovirus late gene.

15. The vector of claim 9, wherein said first adenovirus gene is E1A and said second adenovirus gene is E1B.

16. The vector of claim 13 wherein said first adenovirus gene has a deletion of its endogenous promoter.

17. The vector of claim 13 wherein said first and/or said second adenovirus gene has a deletion of an enhancer region.

18. The vector of claim 15 wherein E1A has its endogenous promoter deleted.

19. The vector of claim 15 wherein E1A has an inactivation of E1A enhancer I.

20. The vector of claim 15 wherein E1B has an inactivation of its endogenous promoter.

21. The vector of claim 15 wherein E1B has a deletion of the 19-kDa region.

22. The vector of claim 15 wherein E1A has an inactivation of its endogenous promoter and E1B has an inactivation of its endogenous promoter.

23. The adenovirus vector of claim 15 wherein said adenovirus comprises an E3 region.

24. The adenovirus vector of claim 15 further comprising a transgene.

25. The vector of claim 22 wherein E1B has a deletion of the 19-kDa region.

26. The vector of claim 22 wherein E1A has an inactivation of E1A enhancer I.

27. The vector of claim 16 wherein said first adenovirus gene is E1A.

28. The vector of claim 17 wherein said first gene is E1A and said enhancer is E1A enhancer I.

29. The vector of claim 5 further comprising an adenovirus death protein gene (ADP).

30. A composition comprising a vector according to claim 5.

31. The vector of claim 24 wherein said transgene is co-transcribed with said first and said second gene and said transgene is under the translation control of a separate internal ribosome entry site (IRES).

32. The vector of claim 24 wherein said transgene is a cytotoxic gene.

33. The vector of claim 31 wherein said IRES is from EMCV.

34. The vector of claim 31 wherein said IRES is from VEGF.

35. The vector of claim 6 wherein said first adenovirus gene is E1A.

36. The vector of claim 35 wherein E1A has a deletion of its endogenous promoter.

37. The vector of claim 35 wherein said E1A has a deletion of E1A enhancer I.

38. The vector of claim 7 wherein said first gene is E1A.

39. The composition of claim 30 further comprising a pharmaceutically acceptable excipient.

40. An adenovirus vector comprising E1B under transcriptional control of a heterologous, target cell specific TRE, wherein E1B has a deletion of part or all of the 19-kDa region.

41. An isolated host cell comprising the adenovirus vector of claim 40.

* * * * *

SEQUENCE LISTING

<160> NUMBER OF SEQ ID NOS: 35

<210> SEQ ID NO 1
<211> LENGTH: 519
<212> TYPE: DNA
<213> ORGANISM: Artificial Sequence
<220> FEATURE:
<223> OTHER INFORMATION: IRES from encephelomycarditis virus (EMCV)

<400> SEQUENCE: 1

```
gacgtcgact aattccggtt attttccacc atattgccgt cttttggcaa tgtgagggcc    60
cggaaacctg gccctgtctt cttgacgagc attcctaggg gtctttcccc tctcgccaaa   120
ggaatgcaag gtctgttgaa tgtcgtgaag gaagcagttc ctctggaagc ttcttgaaga   180
caaacaacgt ctgtagcgac cctttgcagg cagcggaacc ccccacctgg cgacaggtgc   240
ctctgcggcc aaaagccacg tgtataagat acacctgcaa aggcggcaca acccagtgc    300
```

-continued

| cacgttgtga gttggatagt tgtggaaaga gtcaaatggc tctcctcaag cgtattcaac | 360 |
| aagggctga aggatgccca gaaggtaccc cattgtatgg gatctgatct ggggcctcgg | 420 |
| tgcacatgct ttacatgtgt ttagtcgagg ttaaaaaacg tctaggcccc ccgaaccacg | 480 |
| gggacgtggt tttcctttga aaaacacgat gtcgacgtc | 519 |

<210> SEQ ID NO 2
<211> LENGTH: 188
<212> TYPE: DNA
<213> ORGANISM: Artificial Sequence
<220> FEATURE:
<223> OTHER INFORMATION: IRES from vascular endothelial growth factor (VEGF)

<400> SEQUENCE: 2

| acgtagtcga cagcgcagag gcttggggca gccgagcggc agccaggccc cggcccgggc | 60 |
| ctcggttcca gaagggagag gagcccgcca aggcgcgcaa gagagcgggc tgcctcgcag | 120 |
| tccgagccgg agagggagcg cgagccgcgc cggccccgga cggcctccga aaccatggtc | 180 |
| gacacgta | 188 |

<210> SEQ ID NO 3
<211> LENGTH: 341
<212> TYPE: DNA
<213> ORGANISM: Artificial Sequence
<220> FEATURE:
<223> OTHER INFORMATION: 5' UTR region of HCV

<400> SEQUENCE: 3

| gccagccccc tgatgggggc gacactccgc catgaatcac tcccctgtga ggaactactg | 60 |
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tcctttcttg gattaacccg ctcaatgcct ggagatttgg gcgtgccccc | 240 |
| gcaagactgc tagccgagta gtgttgggtc gcgaaaggcc ttgtggtact gcctgatagg | 300 |
| gtgcttgcga gtgccccggg aggtctcgta gaccgtgcac c | 341 |

<210> SEQ ID NO 4
<211> LENGTH: 595
<212> TYPE: DNA
<213> ORGANISM: Artificial Sequence
<220> FEATURE:
<223> OTHER INFORMATION: 5' UTR region of BiP

<400> SEQUENCE: 4

| cccggggtca ctcctgctgg acctactccg acccccctagg ccgggagtga aggcgggact | 60 |
| tgtgcggtta ccagcggaaa tgcctcgggg tcagaagtcg caggagagat agacagctgc | 120 |
| tgaaccaatg ggaccagcgg atggggcgga tgttatctac cattggtgaa cgttagaaac | 180 |
| gaatagcagc caatgaatca gctggggggg cggagcagtg acgtttattg cggagggggc | 240 |
| cgcttcgaat cggcggcggc cagcttggtg gcctgggcca atgaacgcc tccaacgagc | 300 |
| agggccttca ccaatcggcg gcctccacga cggggctggg ggagggtata agccgagt | 360 |
| aggcgacggt gaggtcgacg ccggccaaga cagcacagac agattgacct attgggtgt | 420 |
| ttcgcgagtg tgagagggaa gcgccgcggc ctgtatttct agacctgccc ttcgcctggt | 480 |
| tcgtggcgcc ttgtgacccc gggcccctgc cgcctgcaag tcgaaattgc gctgtgctcc | 540 |
| tgtgctacgg cctgtggctg gactgcctgc tgctgcccaa ctggctggca agatg | 595 |

<210> SEQ ID NO 5
<211> LENGTH: 575
<212> TYPE: DNA
<213> ORGANISM: Artificial Sequence
<220> FEATURE:
<223> OTHER INFORMATION: 5' UTR of PDGF

<400> SEQUENCE: 5

```
gtttgcacct ctccctgccc gggtgctcga gctgccgttg caaagccaac tttggaaaaa      60
gttttttggg ggagacttgg gccttgaggt gcccagctcc gcgctttccg attttggggg     120
ctttccagaa aatgttgcaa aaaagctaag ccggcgggca gaggaaaacg cctgtagccg     180
gcgagtgaag acgaaccatc gactgccgtg ttccttttcc tcttggaggt tggagtcccc     240
tgggcgcccc cacacccta gacgcctcgg ctggttcgcg acgcagcccc ccggccgtgg      300
atgctgcact cgggctcggg atccgccag gtagccggcc tcggacccag gtcctgcgcc      360
caggtcctcc cctgccccc agcgacggag ccggggccgg gggcggcggc gccggggggca     420
tgcgggtgag ccgcggctgc agaggcctga gcgcctgatc gccgcggacc tgagccgagc     480
ccacccccct ccccagcccc ccaccctggc cgcggggcg cgcgctcga tctacgcgtc       540
cggggccccg cggggccggg cccggagtcg gcatg                                 575
```

<210> SEQ ID NO 6
<211> LENGTH: 2240
<212> TYPE: DNA
<213> ORGANISM: Artificial Sequence
<220> FEATURE:
<223> OTHER INFORMATION: Human uroplakin II 5' flanking region

<400> SEQUENCE: 6

```
tcgataggta cccactatag ggcacgcgtg gtcgacggcc cgggctggtc tggcaacttc      60
aagtgtgggc ctttcagacc ggcatcatca gtgttacggg gaagtcacta ggaatgcaga    120
attgattgag cacggtggct cacacctgta atcccaacac tctgggaggc caaggcaggt    180
ggatcacttg tggtcaggag tttgagacca gcctggccaa catggtgaaa cctcatctct    240
actaaaaata caaaaattag ctgggaatgg tggcacatgc ctataatccc agttactcag    300
gaggctgagg caggagaatc atttgaacct gggaggcaga ggttgcagtg agccgagatc    360
acgccactgc actccagcct gggtgacaca gcgagactct gtctcaaaaa aaaaaaaatg    420
cagaatttca ggcttcaccc cagacccact gcatgactgc atgagaagct gcatcttaac    480
aagatccctg gtaattcata cgcatattaa atttggagat gcactggcgt aagaccctcc    540
tactctctgc ttaggcccat gagttcttcc tttactgtca ttctccactc accccaaact    600
ttgagcctac ccttcccacc ttggcggtaa ggacacaacc tccctcacat tcctaccagg    660
accctaagct tccctgggac tgaggaagat agaatagttc gtggagcaaa cagatataca    720
gcaacagtct ctgtacagct ctcaggcttc tggaagttct acagcctctc ccgacaaagt    780
attccacttt ccacaagtaa ctctatgtgt ctgagtctca gtttccactt ttctctctct    840
ctctctctct caactttctg agacagagtt tcacttagtc gcccaggctg gagtgcaggg    900
gcacaatctc ggctcactgc aacctccacc tcctgggttc aagtgttttct cctgtctcag   960
cctcccgagt agctgggatt acaggcacac accaccgcgt tagttttttgt atttttggta  1020
gagatggtgt ttcgccatat tggccaggct gatctcgaac tcctgacctc aggtgatccg   1080
cccacctcgg cctcccaaag tgctgggatt acaggcatga gccaccacgc ccggctgatc   1140
tctttttctat tttaatagag atcaaactct ctgtgttgcc taggctggtc ttgaactcct  1200
```

```
ggcctcgagt gatcctccca ccttggcctc ccaaagtgtt gagattacag gcatgagcca    1260
ctgtgcctgg cctcagttct actacaaaag gaagccagta ccagctacca cccagggtgg    1320
ctgtagggct acaatggagc acacagaacc cctacccagg gcccggaaga agccccgact    1380
cctctcccct ccctctgccc agaactcctc cgcttctttc tgatgtagcc cagggccgga    1440
ggaggcagtc agggaagttc tgtctctttt tcatgttatc ttacgaggtc tcttttctcc    1500
attctcagtc caacaaatgg ttgctgccca aggctgactg tgcccacccc caaccctgc    1560 tggccagggt caatgtctgt ctctctggtc tctccagaag tcttccatgg ccaccttcgt    1620
ccccaccctc cagaggaatc tgaaaccgca tgtgctccct ggcccccaca gcccctgcct    1680
ctcccagagc agcagtacct aagcctcagt gcactccaag aattgaaacc ctcagtctgc    1740
tgcccctccc caccagaatg tttctctccc attcttaccc actcaaggcc ctttcagtag    1800 cccccttggag tattctcttc ctacatatca gggcaacttc caaactcatc accccttctga    1860 ggggtggggg aaagaccccc accacatcgg gggagcagtc ctccaaggac tggccagtct    1920
ccagatgccc gtgcacacag gaacactgcc ttatgcacgg gagtcccaga agaaggggtg    1980
atttctttcc ccaccttagt tacaccatca agacccagcc agggcatccc ccctcctggc    2040
ctgagggcca gctccccatc ctgaaaaacc tgtctgctct ccccacccct ttgaggctat    2100
agggcccaag gggcaggttg gactggattc ccctccagcc cctcccgccc ccaggacaaa    2160
atcagccacc ccaggggcag ggcctcactt gcctcaggaa cccagcctg ccagcaccta    2220 ttccacctcc cagcccagca                                                2240

<210> SEQ ID NO 7
<211> LENGTH: 3592
<212> TYPE: DNA
<213> ORGANISM: Artificial Sequence
<220> FEATURE:
<223> OTHER INFORMATION: Mouse uroplakin II 5' flanking region

<400> SEQUENCE: 7
ctcgaggatc tcggccctct ttctgcatcc ttgtcctaaa tcattttcat atcttgctag      60
acctcagttt gagagaaacg aaccttctca ttttcaagtt gaaaaaaaaa agaggttcaa     120
agtggctcac tcaaagttac aagccaacac tcaccactac gagtacaatg gccaccatta    180
gtgctggcat gccccaggag acaggcatgc atattattct agatgactgg gaggcagagg    240
ggtggcctag tgaggtcaga ctgtggacag atcaggcaga tgtgggttct gatcccaatt    300
cctcaggccg cagaactact gtggttcaag aagggacaa aaggactgca gtccggaaca    360
ggaggtccat ttgagagctg actgagcaga agaggaaagt gaagaacttc tggggcaaga    420
gcttacccta ctttacagct ttgttgtctt ctttactcca gggcgtccc tggtactcag     480 taaatgtctg ttggcttgag gaacatatgt gtaaggagga aggagaggga acttgaggga    540
gttaagactc aagaatcaat caaggagagg acagcagaga agacagggtt tgggagagag    600
actccagaca ttggccctgg ttccttcctt ggccactgtg aaaccctcca gaggaactga    660
gtgctgtggc tttaaatgat ctcagcactg tcagtgaagc gctctgctca aagagttatc    720
ctcttgctcc tgtgccgggg cctcccctc ctctcagctc ccaaacccctt ctcagccact    780 gtgatggcat aattagatgc gagagctcag accgtcaggt ctgctccagg aaccacccat    840
tttccccaac cccagagaaa ggtcctagtg gaaaagtggg ggccactgaa gggctgatgg    900
ggttctgtcc tttcccccat gctgggtgga cttaaagtct gcgatgtgtg taggggtag     960
```

```
aagacaacag aacctggggg ctccggctgg gagcaggagg aactctcacc agacgatctc   1020
caaatttact gtgcaatgga cgatcaggaa actggttcag atgtagcttc tgatacagtg   1080
ggtctgaggt aaaacccgaa acttaatttc tttcaaaaat ttaaagttgc atttattatt   1140
ttatatgtgt gcccatatgt gtgccacagt gtctatgtgg aggtcagagg gcaagttgtg   1200
ggcattggct ctctcctttc ataatgtggc ttctggggac caaaatgtca ggcatggtgg   1260
caagagcttt tacctgttga gccatctcat ggtttcgtaa aacttcctat gacgcttaca   1320
ggtaacgcag agacacagac tcacatttgg agttagcaga tgctgtattg gtgtaaacac   1380
tcatacacag acacacacac atactcatac acacacacac acacttatca catgcacaca   1440
catactcgta tacacacaga cacacacaca tgcactctca cattcacata ttcatacaca   1500
tccacacaca cactcatcca cacacacaga cacacatact catccacaca cacacacaca   1560
catactcata cacacacaca gacacacata ctcatacaca cacacagaca cacacatata   1620
atcatacata cacagacaca ctcatacatg tgcacacaca cactcatcca cacacacaca   1680
ctcatacaca cacacactca tacacacaca cactcataca cacacacacg aggtttttct   1740
caggctgcct ttgggtggag actggaactg atttctgttt ttcagctcct tggcttttttg  1800 tcccttaga tgagatctcc tcctcactttt acacacagaa agatcacaca cgagggagaa   1860
ctggcggtgc ggaagagggc tacacggtag ggtgtcaggg tcaggagatc ttcctggcaa   1920
gtctcaaacc tccacatagc acagtgttta cgtgaggatt taggaggaat caggaagagg   1980
attggtttac tgcagagcag accatatagg tccactccta agcccatttt gaaattagaa   2040
gtgagacagt gtgggataaa aagagcagat ctctggtcac attttttaaag ggatatgagg   2100 gtcctgtgcc tttaagcctt cccatctccc tccaatcccc cctcaccttc cccaccctaa   2160
ccctccccag gtttctggag gagcagagtt gcgtcttctc cctgccctgc cgagctgctc   2220
actggctgct ctagaggctg tgctttgcgg tctccatgga aaccattagt tgctaagcaa   2280
ctggagcatc atctgtgctg agctcaggtc ctatcgagtt cacctagctg agacacccac   2340
gcccctgcag ccactttgca gtgacaagcc tgagtctcag gttctgcatc tataaaaacg   2400
agtagccttt caggagggca tgcagagccc cctggccagc gtctagagga gaggtgactg   2460
agtggggcca tgtcactcgt ccatggctgg agaacctcca tcagtctccc agttagcctg   2520
gggcaggaga gaaccagagg agctgtggct gctgattgga tgatttacgt acccaatctg   2580
ttgtcccagc catcgaaccc cagagcgacc tgcacacatg ccaccgctgc cccgccctcc   2640
acctcctctg ctcctggtta caggattgtt ttgtcttgaa gggttttgtt gttgctactt   2700
tttgctttgt tttttctttt ttaacataag gtttctctgt gtagccctag ctgtcctgga   2760
actcactctg tagaccaggc tggcctcaaa ctcagaaatc caccttcctc ccaagtgctg   2820
ggattaaagg cattcgcacc atcgcccagc ccccggtctt gtttcctaag gtttttcctgc  2880 tttactcgct acccgttgca caaccgcttg ctgtccaagt ctgtttgtat ctactccacc   2940
gcccactagc cttgctggac tggacctacg tttacctgga agccttcact aacttccctt   3000
gtctccacct tctggagaaa tctgaaggct cacactgata ccctccgctt ctcccagagt   3060
cgcagtttct taggcctcag ttaaatacca gaattggatc tcaggctctg ctatccccac   3120
cctacctaac caacccctc ctctcccatc cttactagcc aaagcccttt caacccttgg    3180
ggcttttcct acacctacac accagggcaa ttttagaact catggctctc ctagaaaacg   3240
cctacctcct tggagactga ccctctacag tccaggaggc agacactcag acagaggaac   3300
tctgtccttc agtcgcggga gttccagaaa gagccatact cccctgcaga gctaactaag   3360
```

```
ctgccaggac ccagccagag catcccccctt tagccgaggg ccagctcccc agaatgaaaa      3420
acctgtctgg ggcccctccc tgaggctaca gtcgccaagg ggcaagttgg actggattcc      3480
cagcagcccc tcccactccg agacaaaatc agctaccctg gggcaggcct cattggcccc      3540
aggaaacccc agcctgtcag cacctgttcc aggatccagt cccagcgcag ta              3592
```

<210> SEQ ID NO 8
<211> LENGTH: 822
<212> TYPE: DNA
<213> ORGANISM: Artificial Sequence
<220> FEATURE:
<223> OTHER INFORMATION: APF-TRE

<400> SEQUENCE: 8

```
gcattgctgt gaactctgta cttaggacta aactttgagc aataacacac atagattgag       60
gattgtttgc tgttagcata caaactctgg ttcaaagctc ctctttattg cttgtcttgg      120
aaaatttgct gttcttcatg gtttctcttt tcactgctat ctattttttct caaccactca     180 catggctaca ataactgtct gcaagcttat gattcccaaa tatctatctc tagcctcaat      240
cttgttccag aagataaaaa gtagtattca aatgcacatc aacgtctcca cttggagggc      300
ttaaagacgt ttcaacatac aaaccgggga gttttgcctg gaatgtttcc taaaatgtgt      360
cctgtagcac atagggtcct cttgttcctt aaaatctaat tacttttagc ccagtgctca      420
tcccacctat ggggagatga gagtgaaaag ggagcctgat taataattac actaagtcaa      480
taggcataga gccaggactg tttgggtaaa ctggtcactt tatcttaaac taaatatatc      540
caaaactgaa catgtactta gttactaagt ctttgacttt atctcattca taccactcag      600
ctttatccag gccacttatg agctctgtgt ccttgaacat aaaatacaaa taaccgctat      660
gctgttaatt attggcaaat gtcccatttt caacctaagg aaataccata agtaacaga      720 tataccaaca aaaggttact agttaacagg cattgcctga aaagagtata aagaatttc       780 agcatgattt tccatattgt gcttccacca ctgccaataa ca                         822
```

<210> SEQ ID NO 9
<211> LENGTH: 451
<212> TYPE: DNA
<213> ORGANISM: Artificial Sequence
<220> FEATURE:
<223> OTHER INFORMATION: Probasin-TRE

<400> SEQUENCE: 9

```
aag ctt cca caa gtg cat tta gcc tct cca gta ttg ctg atg aat cca         48 cag ttc agg ttc aat ggc gtt caa aac ttg atc aaa aat gac cag act         96 tta tat tta cac caa cat cta tct gat tgg agg aat gga taa tag tca       144 tca tgt tta aac atc tac cat tcc agt taa gaa aat atg ata gca tct       192 tgt tct tag tct ttt tct taa tag gga cat aaa gcc cac aaa taa aaa       240 tat gcc tga aga atg gga cag gca ttg ggc att gtc cat gcc tag taa       288 agt act cca aga acc tat ttg tat act aga tga cac aat gtc aat gtc       336 tgt gta caa ctg cca act ggg atg caa gac act gcc cat gcc aat cat       384 cct gaa aag cag cta taa aaa gca gga agc tac tct gca cct tgt cag       432 tag gtc cag ata cct aca g                                             451
```

<210> SEQ ID NO 10

```
<211> LENGTH: 546
<212> TYPE: DNA
<213> ORGANISM: Artificial Sequence
<220> FEATURE:
<223> OTHER INFORMATION: Tyrosinase-TRE

<400> SEQUENCE: 10
ccggttgaaa atgataagtt gaattctgtc ttcgagaaca tagaaaagaa ttatgaaatg      60
ccaacatgtg gttacaagta atgcagaccc aaggctcccc agggacaaga agtcttgtgt     120
taactctttg tggctctgaa agaaagagag agagaaaaga ttaagcctcc ttgtggagat     180
catgtgatga cttcctgatt ccagccagag cgagcatttc catggaaact tctcttcctc     240
ttcactcgag attactaacc ttattgttaa tattctaacc ataagaatta aactattaat     300
ggtgaataga gttttttcact ttaacatagg cctatcccac tggtgggata cgagccaatt    360
cgaaagaaaa agtcagtcat gtgcttttca gaggatgaaa gcttaagata aagactaaaa     420
gtgtttgatg ctggaggtgg gagtggtatt atataggtct cagccaagac atgtgataat     480
cactgtagta gtagctggaa agagaaatct gtgactccaa ttagccagtt cctgcagacc     540
ttgtga                                                                546

<210> SEQ ID NO 11
<211> LENGTH: 12047
<212> TYPE: DNA
<213> ORGANISM: Artificial Sequence
<220> FEATURE:
<223> OTHER INFORMATION: Human glandular kallikrein-TRE

<400> SEQUENCE: 11
gaattcagaa ataggggaag gttgaggaag gacactgaac tcaaagggga tacagtgatt      60
ggtttatttg tcttctcttc acaacattgg tgctggagga attcccaccc tgaggttatg     120
aagatgtctg aacacccaac acatagcact ggagatatga gctcgacaag agtttctcag     180
ccacagagat tcacagccta gggcaggagg acactgtacg ccaggcagaa tgacatggga     240
attgcgctca cgattggctt gaagaagcaa ggactgtggg aggtgggctt tgtagtaaca     300
agagggcagg gtgaactctg attcccatgg gggaatgtga tggtcctgtt acaaattttt      360
caagctggca gggaataaaa cccattacgg tgaggacctg tggagggcgg ctgccccaac     420
tgataaagga aatagccagg tgggggcctt tcccattgta gggggacat atctggcaat      480
agaagccttt gagacccttt aggtacaag tactgaggca gcaaataaaa tgaaatctta      540
tttttcaact ttatactgca tgggtgtgaa gatatatttg tttctgtaca gggggtgagg     600
gaaaggaggg gaggaggaaa gttcctgcag gtctggttg gtcttgtgat ccaggggtc       660
ttggaactat ttaaattaaa ttaaattaaa acaagcgact gttttaaatt aaattaaatt     720
aaattaaatt ttactttatt ttatcttaag ttctgggcta catgtgcagg acgtgcagct     780
ttgttacata ggtaaacgtg tgccatggtg gtttgctgta cctatcaacc catcacctag     840
gtattaagcc cagcatgcat tagctgtttt tcctgacgct ctccctctcc ctgactccca     900
caacaggccc cagtgtgtgt tgttccctc cctgtgtcca tgtgttctca ttgttcagct      960
cccacttata agtgagaaca tgtggtgttt ggttttctgt ttctgtgtta gtttgctgag    1020
gataatggct tccacctcca tccatgttcc tgcaaaggac gtgatcttat tctttttat    1080
ggttgcatag aaattgtttt tacaaatcca attgatattg tatttaatta caagttaatc    1140
taattagcat actagaagag attacagaag atattaggta cattgaatga ggaaatatat    1200
aaaataggac gaaggtgaaa tattaggtag gaaaagtata atagttgaaa gaagtaaaaa    1260
```

-continued

```
aaaatatgca tgagtagcag aatgtaaaag aggtgaagaa cgtaatagtg acttttTaga    1320
ccagattgaa ggacagagac agaaaaattt taaggaattg ctaaaccatg tgagtgttag    1380
aagtacagtc aataacatta aagcctcagg aggagaaaag aataggaaag gaggaaatat    1440
gtgaataaat agtagagaca tgtttgatgg attttaaaat atttgaaaga cctcacatca    1500
aaggattcat accgtgccat tgaagaggaa gatgaaaaag ccaagaagcc agatgaaagt    1560
tagaaatatt attggcaaag cttaaatgtt aaaagtccta gagagaaagg atggcagaaa    1620
tattggcggg aaagaatgca gaacctagaa tataaattca tcccaacagt ttggtagtgt    1680
gcagctgtag ccttttctag ataatacact attgtcatac atcgcttaag cgagtgtaaa    1740
atggtctcct cactttattt atttatatat ttatttagtt ttgagatgga gcctcgctct    1800
gtctcctagg ctggagtgca atagtgcgat accactcact gcaacctctg cctcctctgt    1860
tcaagtgatt ttcttacctc agcctcccga gtagctggga ttacaggtgc gtgccaccac    1920
acccggctaa ttttttgtatt ttttgtagag acggggtttt gccatgttgg ccaggctggt    1980
cttgaactcc tgacatcagg tgatccacct gccttggcct cctaaagtgc tgggattaca    2040
ggcatgagcc accgtgccca accactttat ttatttttta ttttttattt taaatttcag    2100
cttctatttg aaatacaggg ggcacatata taggattgtt acatgggtat attgaactca    2160
ggtagtgatc atactaccca acaggtaggt tttcaaccca ctcccccctct tttcctcccc    2220 attctagtag tgtgcagtgt ctattgttct catgtttatg tctatgtgtg ctccaggttt    2280
agctcccacc tgtaagtgag aacgtgtggt atttgatttt ctgtccctgt gttaattcac    2340
ttaggattat ggcttccagc tccattcata ttgctgtaaa ggatatgatt cattttTcat    2400
ggccatgcag tattccatat tgcgtataga tcacattttc ttctttttt tttttTgaga    2460 cggagtcttg ctttgctgcc taggctggag tgcagtagca cgatctcggc tcactgcaag    2520
cttcacctcc ggggttcacg tcattcttct gtctcagctt cccaagtagc tgggactaca    2580
ggcgcccgcc accacgtccg gctaattttt ttgtgtgttt ttagtagaga tggggtttc    2640 actgtgttag ccaggatggt cttgatctcc tgaccttgtg gtccacctgc ctcggtctcc    2700
caaagtgctg ggattacagg ggtgagccac tgcgcccggc ccatatatac cacattttct    2760
ttaaccaatc caccattgat gggcaactag gtagattcca tggattccac agttttgcta    2820
ttgtgtgcag tgtggcagta gacatatgaa tgaatgtgtc tttttggtat aatgatttgc    2880
attcctttgg gtatacagtc attaatagga gtgctgggtt gaacggtggc tctgtttaaa    2940
attcttTgag aattttccaa actgtttgcc atagagagca aactaattta catttccacg    3000
aacagtatat aagcattccc ttttctccac agctttgtca tcatgttttt tttttTtctt    3060
tattttaaaa aagaatatgt tgttgttttc ccagggtaca tgtgcaggat gtgcaggttt    3120
gttacatagg tagtaaacgt gagccatggt ggtttgctgc acctgtcaac ccattacctg    3180
ggtatgaagc cctgcctgca ttagctcttt tccctaatgc tctcactact gccccaccct    3240
caccctgaca gggcaaacag acaacctaca gaatgggagg aaattttTgc aatctattca    3300
tctgacaaag gtcaagaata tccagaatct acaaggaact taagcaaatt tttacttttt    3360
aataatagcc actctgactg gcgtgaaatg gtatctcatt gtggttttca tttgaatttc    3420
tctgatgatc agtgacgatg agcatttttt catatttgtt ggctgcttgt acgtcttttg    3480
agaagtgtct cttcatgcct tttggccact ttaatgggat tattttttgc ttTttagttt    3540
aagttcctta tagattctgg atattagact tcttattgga tgcatagttt gtgaatactc    3600
```

```
tcttccattc tgtaggttgt ctgtttactc tattgatggc ttcttttgct gtgccgaagc   3660
atcttagttt aattagaaac cacctgccaa ttttttgttt tgttgcaatt gcttttgggg   3720
acttagtcat aaactcttg ccaaggtctg ggtcaagaag agtatttcct aggttttctt   3780
ctagaatttt gaaagtctga atgtaaacat ttgcatttt aatgcatctt gagttagttt   3840
ttgtatatgt gaaaggtcta ctctcatttt cttccctct ttctttcttt ctttcttttc   3900
tttctttctt tctttctttc tttctttctt tctttcttttc tttcttttg tccttctttc   3960 tttctttctt tctctttctt tctctctttc tttttttttt ttgatggagt attgctctgt   4020
tgcccaggct gcagtgcagc ggcacgatct cggctcactg caacctctgc ctcctgggtt   4080
caactgattc tcctgcatca gccttccaag tagctgggat tataggcgcc cgccaccacg   4140
cccgactaat tttgtattt tagtagaga cggggttgtg ccatgttggc caggctggtt   4200
tgaaactcct gacctcaaac gatctgcctg ccttggcctc ccaaagtgct gggattacag   4260
gtgtgagcca ctgtgcccag ccaagaatgt catttctaa gaggtccaag aacctcaaga   4320
tattttggga ccttgagaag agaggaattc atacaggtat tacaagcaca gcctaatggc   4380
aaatctttgg catggcttgg cttcaagact ttaggctctt aaaagtcgaa tccaaaaatt   4440
tttataaaag ctccagctaa gctaccttaa aaggggcctg tatggctgat cactcttctt   4500
gctatacttt acacaaataa acaggccaaa tataatgagg ccaaaattta ttttgcaaat   4560
aaattggtcc tgctatgatt tactcttggt aagaacaggg aaaatagaga aaatttaga   4620 ttgcatctga ccttttttc tgaatttta tatgtgccta caatttgagc taaatcctga   4680 attatttct ggttgcaaaa actctctaaa gaagaacttg gttttcattg tcttcgtgac   4740
acatttatct ggctctttac tagaacagct ttcttgtttt tggtgttcta gcttgtgtgc   4800
cttacagttc tactcttcaa attattgtta tgtgtatctc atagttttcc ttcttttgag   4860
aaaactgaag ccatggtatt ctgaggacta gagatgactc aacagagctg gtgaatctcc   4920
tcatatgcaa tccactgggc tcgatctgct tcaaattgct gatgcactgc tgctaaagct   4980
atacatttaa aaccctcact aaaggatcag ggaccatcat ggaagaggag gaaacatgaa   5040
attgtaagag ccagattcgg ggggtagagt gtggaggtca gagcaactcc accttgaata   5100
agaaggtaaa gcaacctatc ctgaaagcta acctgccatg gtggcttctg attaaccctct   5160 gttctaggaa gactgacagt ttgggtctgt gtcattgccc aaatctcatg ttaaattgta   5220
atccccagtg ttcggaggtg ggacttggtg gtaggtgatt cggtcatggg agtagatttt   5280
cttctttgtg gtgttacagt gatagtgagt gagttctcgt gagatctggt catttaaaag   5340
tgtgtggccc ctcccctccc tctcttggtc ctcctactgc catgtaagat acctgctcct   5400
gctttgcctt ctaccataag taaaagcccc ctgaggcctc cccagaagca gatgccacca   5460
tgcttcctgt acagcctgca gaaccatcag ccaattaaac ctcttttctg tataaattac   5520
cagtcttgag tatctcttta cagcagtgtg agaacggact aatacaaggg tctccaaaat   5580
tccaagttta tgtattcttt cttgccaaat agcaggtatt taccataaat cctgtcctta   5640
ggtcaaacaa ccttgatggc atcgtacttc aattgtctta cacattcctt ctgaatgact   5700
cctcccctat ggcatataag ccctgggtct tggggataa tggcagaggg gtccaccatc   5760
ttgtctggct gccacctgag acacggacat ggcttctgtt ggtaagtctc tattaaatgt   5820
ttctttctaa gaaactggat ttgtcagctt gtttctttgg cctctcagct tcctcagact   5880
ttggggtagg ttgcacaacc ctgcccacca cgaaacaaat gtttaatatg ataaatatgg   5940
atagatataa tccacataaa taaaagctct tggagggccc tcaataattg ttaagagtgt   6000
```

```
aaatgtgtcc aaagatggaa aatgtttgag aactactgtc ccagagattt tcctgagttc    6060
tagagtgtgg gaatatagaa cctggagctt ggcttcttca gcctagaatc aggagtatgg    6120
ggctgaagtc tgaagcttgg cttcagcagt ttggggttgg cttccggagc acatatttga    6180
catgttgcga ctgtgatttg gggtttggta tttgctctga atcctaatgt ctgtccttga    6240
ggcatctaga atctgaaatc tgtggtcaga attctattat cttgagtagg acatctccag    6300
tcctggttct gccttctagg gctggagtct gtagtcagtg acccggtctg gcatttcaac    6360
ttcatataca gtgggctatc ttttggtcca tgtttcaacc aaacaaccga ataaaccatt    6420
agaacctttc cccacttccc tagctgcaat gttaaaccta ggatttctgt ttaataggtt    6480
catatgaata atttcagcct gatccaactt tacattcctt ctaccgttat tctacaccca    6540
ccttaaaaat gcattcccaa tatattccct ggattctacc tatatatggt aatcctggct    6600
ttgccagttt ctagtgcatt aacatacctg atttacattc ttttactttg aagtggaaat    6660
aagagtccct ctgcagagtt caggagttct caagatggcc cttacttctg acatcaattg    6720
agatttcaag ggagtcgcca agatcatcct caggttcagt gattgctggt agccctcata    6780
taactcaatg aaagctgtta tgctcatggc tatggtttat tacagcaaaa gaatagagat    6840
gaaaatctag caagggaaga gttgcatggg gcaaagacaa ggagagctcc aagtgcagag    6900
attcctgttg ttttctccca gtggtgtcat ggaaagcagt atcttctcca tacaatgatg    6960
tgtgataata ttcagtgtat tgccaatcag ggaactcaac tgagccttga ttatattgga    7020
gcttggttgc acagacatgt cgaccacctt catggctgaa ctttagtact tagcccctcc    7080
agacgtctac agctgatagg ctgtaaccca acattgtcac cataaatcac attgttagac    7140
tatccagtgt ggcccaagct cccgtgtaaa cacaggcact ctaaacaggc aggatatttc    7200
aaaagcttag agatgacctc ccaggagctg aatgcaaaga cctggcctct ttgggcaagg    7260
agaatccttt accgcacact ctccttcaca gggttattgt gaggatcaaa tgtggtcatg    7320
tgtgtgagac accagcacat gtctggctgt ggagagtgac ttctatgtgt gctaacattg    7380
ctgagtgcta agaaagtatt aggcatggct ttcagcactc acagatgctc atctaatcct    7440
cacaacatgg ctacagggtg ggcactacta gcctcatttg acagaggaaa ggactgtgga    7500
taagaagggg gtgaccaata ggtcagagtc attctggatg caagggctc cagaggacca    7560 tgattagaca ttgtctgcag agaaattatg gctggatgtc tctgcccgg aaagggggat    7620 gcactttcct tgaccccta tctcagatct tgactttgag gttatctcag acttcctcta    7680
tgataccagg agcccatcat aatctctctg tgtcctctcc ccttcctcag tcttactgcc    7740
cactcttccc agctccatct ccagctggcc aggtgtagcc acagtaccta actctttgca    7800
gagaactata aatgtgtatc ctacagggga gaaaaaaaa aagaactctg aaagagctga    7860
cattttaccg acttgcaaac acataagcta acctgccagt tttgtgctgg tagaactcat    7920
gagactcctg ggtcagaggc aaaagatttt attacccaca gctaaggagg cagcatgaac    7980
tttgtgttca catttgttca ctttgccccc caattcatat gggatgatca gagcagttca    8040
ggtggatgga cacagggggtt tgtggcaaag gtgagcaacc taggcttaga aatcctcaat    8100
cttataagaa ggtactagca aacttgtcca gtctttgtat ctgacggaga tattatcttt    8160
ataattgggt tgaaagcaga cctactctgg aggaacatat tgtatttatt gtcctgaaca    8220
gtaaacaaat ctgctgtaaa atagacgtta actttattat ctaaggcagt aagcaaacct    8280
agatctgaag gcgataccat cttgcaaggc tatctgctgt acaaatatgc ttgaaaagat    8340
```

```
ggtccagaaa agaaaacggt attattgcct ttgctcagaa gacacacaga aacataagag   8400
aaccatggaa aattgtctcc caacactgtt cacccagagc cttccactct tgtctgcagg   8460
acagtcttaa catcccatca ttagtgtgtc taccacatct ggcttcaccg tgcctaacca   8520
agatttctag gtccagttcc ccaccatgtt tggcagtgcc ccactgccaa ccccagaata   8580
agggagtgct cagaattccg agggacatg gtgtgggatc agaacttctg ggcttgagtg    8640
cagaggggc ccatactcct tggttccgaa ggaggaagag gctggaggtg aatgtccttg    8700
gagggagga atgtgggttc tgaactctta aatccccaag ggaggagact ggtaaggtcc    8760
cagcttccga ggtactgacg tgggaatggc ctgagaggtc taagaatccc gtatcctcgg   8820
gaaggagggg ctgaaattgt gaggggttga gttgcagggg tttgttagct tgagactcct   8880
tggtgggtcc ctgggaagca aggactggaa ccattggctc cagggtttgg tgtgaaggta   8940
atgggatctc ctgattctca aagggtcaga ggactgagag ttgcccatgc tttgatcttt   9000
ccatctactc cttactccac ttgagggtaa tcacctactc ttctagttcc acaagagtgc   9060
gcctgcgcga gtataatctg cacatgtgcc atgtcccgag gcctggggca tcatccactc   9120
atcattcagc atctgcgcta tgcgggcgag gccggcgcca tgacgtcatg tagctgcgac   9180
tatccctgca gcgcgcctct cccgtcacgt cccaaccatg gagctgtgga cgtgcgtccc   9240
ctggtggatg tggcctgcgt ggtgccaggc cggggcctgg tgtccgataa agatcctaga   9300
accacaggaa accaggactg aaaggtgcta gagaatggcc atatgtcgct gtccatgaaa   9360
tctcaaggac ttctgggtgg agggcacagg agcctgaact tacgggtttg ccccagtcca   9420
ctgtcctccc aagtgagtct cccagatacg aggcactgtg ccagcatcag cttcatctgt   9480
accacatctt gtaacaggga ctacccagga ccctgatgaa caccatggtg tgtgcaggaa   9540
gagggggtga aggcatggac tcctgtgtgg tcagagccca gaggggccca tgacgggtgg   9600
ggaggaggct gtgactggc tcgagaagtg ggatgtggtt gtgtttgatt cctttggcc    9660
agataaagtg ctggatatag cattgaaaac ggagtatgaa gaccagttag aatggagggt   9720
caggttggag ttgagttaca gatggggtaa aattctgctt cggatgagtt tggggattgg   9780
caatctaaag gtggtttggg atggcatggc tttgggatgg aaataggttt gttttatgt    9840
tggctgggaa gggtgtgggg attgaattgg ggatgaagta ggtttagttt tggagataga   9900
atacatggag ctggctattg catgcgagga tgtgcattag tttggtttga tctttaaata   9960
aaggaggcta ttagggttgt cttgaattag attaagttgt gttgggttga tgggttgggc   0020
ttgtgggtga tgtggttgga ttgggctgtg ttaaattggt ttgggtcagg ttttggttga   0080
ggttatcatg gggatgagga tatgcttggg acatggattc agtgggttct cattcaagct   0140
gaggcaaatt tcctttcaga cggtcattcc agggaacgag tggttgtgtg ggggaaatca   0200
ggccactggc tgtgaatatc cctctatcct ggtcttgaat tgtgattatc tatgtccatt   0260
ctgtctcctt cactgtactt ggaattgatc tggtcattca gctggaaatg ggggaagatt   0320
ttgtcaaatt cttgagacac agctgggtct ggatcagcgt aagccttcct tctggttta    0380
ttaacagat gaaatcacat ttttttttc aaaatcacag aaatcttata gagttaacag    0440
tggactctta taataagagt taacaccagg actcttattc ttgattcttt tctgagacac   0500
caaaatgaga tttctcaatg ccaccctaat tctttttttt tttttttttt ttttttgagac   0560
acagtctggg tcttttgctc tgtcactcag gctggagcgc agtggtgtga tcatagctca   0620
ctgaacccctt gacctcctgg acttaaggga tcctcctgct tcagcctcct gagtagatgg   0680
ggctacaggt gcttgccacc acacctggct aattaaattt tttttttttt tttgtagaga   0740
```

-continued

```
aagggtctca ctttgttgcc ctggctgatc ttgaacttct gacttcaagt gattcttcag    0800
ccttggactc ccaaagcact gggattgctg gcatgagcca ctcaccgtgc ctggcttgca    0860
gcttaatctt ggagtgtata aacctggctc ctgatagcta gacatttcag tgagaaggag    0920
gcattggatt ttgcatgagg acaattctga cctaggaggg caggtcaaca ggaatccccg    0980
ctgtacctgt acgttgtaca ggcatggaga atgaggagtg aggaggccgt accggaaccc    1040
catattgttt agtggacatt ggattttgaa ataatagggga acttggtctg ggagagtcat    1100
atttctggat tggacaatat gtggtatcac aaggttttat gatgagggag aaatgtatgt    1160
ggggaaccat tttctgagtg tggaagtgca agaatcagag agtagctgaa tgccaacgct    1220
tctatttcag gaacatggta agttggaggt ccagctctcg ggctcagacg ggtataggga    1280
ccaggaagtc tcacaatccg atcattctga tatttcaggg catattaggt ttggggtgca    1340
aaggaagtac ttgggactta ggcacatgag actttgtatt gaaaatcaat gattgggct     1400 ggccgtggtg ctcacgcctg taatctcatc actttgggag accgaagtgg gaggatggct    1460
tgatctcaag agttggacac cagcctaggc aacatggcca gaccctctct ctacaaaaaa    1520
attaaaaatt agctggatgt ggtggtgcat gcttgtggtc tcagctatcc tggaggctga    1580
gacaggagaa tcggttgagt ctgggagttc aaggctacag ggagctgcga tcacgccgct    1640
gcactccagc ctgggaaaca gagtgagact gtctcagaat ttttttaaaa aagaatcagt    1700
gatcatccca accctgttg ctgttcatcc tgagcctgcc ttctctggct ttgttcccta     1760
gatcacatct ccatgatcca taggccctgc ccaatctgac ctcacaccgt gggaatgcct    1820
ccagactgat ctagtatgtg tggaacagca agtgctggct ctccctcccc ttccacagct    1880
ctgggtgtgg gagggggttg tccagcctcc agcagcatgg ggagggcctt ggtcagcatc    1940
taggtgccaa cagggcaagg gcggggtcct ggagaatgaa ggctttatag ggctcctcag    2000
ggaggccccc cagccccaaa ctgcaccacc tggccgtgga caccggt                 2047
```

<210> SEQ ID NO 12
<211> LENGTH: 67
<212> TYPE: DNA
<213> ORGANISM: Artificial Sequence
<220> FEATURE:
<223> OTHER INFORMATION: HRE-TRE

<400> SEQUENCE: 12

```
ccccgaggca gtgcatgagg ctcagggcgt gcgtgagtcg cagcgagacc ccggggtgca    60
ggccgga                                                              67
```

<210> SEQ ID NO 13
<211> LENGTH: 5835
<212> TYPE: DNA
<213> ORGANISM: Artificial Sequence
<220> FEATURE:
<223> OTHER INFORMATION: PSA-TRE

<400> SEQUENCE: 13

```
aagcttctag ttttcttttc ccggtgacat cgtggaaagc actagcatct ctaagcaatg    60
atctgtgaca atattcacag tgtaatgcca tccaggaac tcaactgagc cttgatgtcc     120
agagattttt gtgttttttt ctgagactga gtctcgctct gtgccaggct ggagtgcagt    180
ggtgcaacct ggctcactg caagctccgc ctcctgggtt cacgccattc tcctgcctca    240
gcctcctgag tagctgggac tacaggcacc cgccaccacg cctggctaat ttttttgtat    300
```

-continued

```
ttttagtaga gatggggttt cactgtgtta gccaggatgg tctcagtctc ctgacctcgt    360
gatctgccca ccttggcctc ccaaagtgct gggatgacag gcgtgagcca ccgcgcctgg    420
ccgatatcca gagatttttt gggggctcc atcacacaga catgttgact gtcttcatgg     480
ttgactttta gtatccagcc cctctagaaa tctagctgat atagtgtggc tcaaaacctt    540
cagcacaaat cacaccgtta gactatctgg tgtgcccaa accttcaggt gaacaaaggg     600
actctaatct ggcaggatac tccaaagcat tagagatgac ctcttgcaaa gaaaaagaaa    660
tggaaaagaa aaagaaagaa aggaaaaaaa aaaaaaaaa gagatgacct ctcaggctct     720 gagggaaac gcctgaggtc tttgagcaag gtcagtcctc tgttgcacag tctccctcac     780 aggtcattg tgacgatcaa atgtggtcac gtgtatgagg caccagcaca tgcctggctc     840
tggggagtgc cgtgtaagtg tatgcttgca ctgctgaatg gctgggatgt gtcagggatt    900
atcttcagca cttacagatg ctcatctcat cctcacagca tcactatggg atgggtatta    960
ctggcctcat ttgatggaga aagtggctgt ggctcagaaa ggggggacca ctagaccagg   1020
gacactctgg atgctgggga ctccagagac catgaccact caccaactgc agagaaatta   1080
attgtggcct gatgtccctg tcctggagag ggtggaggtg gaccttcact aacctcctac   1140
cttgaccctc tcttttaggg ctctttctga cctccaccat ggtactagga ccccattgta   1200
ttctgtaccc tcttgactct atgacccca ccgcccactg catccagctg ggtcccctcc    1260
tatctctatt cccagctggc cagtgcagtc tcagtgccca cctgtttgtc agtaactctg   1320
aaggggctga cattttactg acttgcaaac aaataagcta actttccaga gttttgtgaa   1380
tgctggcaga gtccatgaga ctcctgagtc agaggcaaag gcttttactg ctcacagctt   1440
agcagacagc atgaggttca tgttcacatt agtacacctt gccccccca aatcttgtag    1500 ggtgaccaga gcagtctagg tggatgctgt gcagaagggg tttgtgccac tggtgagaaa   1560
cctgagatta ggaatcctca atcttatact gggacaactt gcaaacctgc tcagcctttg   1620
tctctgatga agatattatc ttcatgatct tggattgaaa acagacctac tctggaggaa   1680
catattgtat cgattgtcct tgacagtaaa caaatctgtt gtaagagaca ttatcttat   1740 tatctaggac agtaagcaag cctggatctg agagagatat catcttgcaa ggatgcctgc   1800
tttacaaaca tccttgaaac aacaatccag aaaaaaaag gtgttactgt ctttgctcag   1860
aagacacaca gatacgtgac agaaccatgg agaattgcct cccaacgctg ttcagccaga   1920
gccttccacc ctttctgcag gacagtctca acgttccacc attaaatact tcttctatca   1980
catcccgctt ctttatgcct aaccaaggtt ctaggtcccg atcgactgtg tctggcagca   2040
ctccactgcc aaacccagaa taaggcagcg ctcaggatcc cgaagggca tggctgggga   2100 tcagaacttc tgggtttgag tgaggagtgg gtccaccctc ttgaatttca aggaggaag   2160 aggctggatg tgaaggtact gggggaggga aagtgtcagt tccgaactct taggtcaatg   2220
agggaggaga ctggtaaggt cccagctccc gaggtactga tgtgggaatg gcctaagaat   2280
ctcatatcct caggaagaag gtgctggaat cctgagggt agagttctgg gtatatttgt    2340
ggcttaaggc tctttggccc ctgaaggcag aggctggaac cattaggtcc agggtttggg   2400
gtgatagtaa tgggatctct tgattcctca agagtctgag gatcgagggt tgcccattct   2460
tccatcttgc cacctaatcc ttactccact tgagggtatc accagccctt ctagctccat   2520
gaaggtcccc tggcaagca caatctgagc atgaaagatg cccagaggc cttgggtgtc    2580 atccactcat catccagcat cacactctga gggtgtggca agcaccatga cgtcatgttg   2640
ctgtgactat ccctgcagcg tgcctctcca gccacctgcc aaccgtagag ctgcccatcc   2700
```

-continued

```
tcctctggtg ggagtggcct gcatggtgcc aggctgaggc ctagtgtcag acagggagcc   2760
tggaatcata gggatccagg actcaaaagt gctagagaat ggccatatgt caccatccat   2820
gaaatctcaa gggcttctgg gtggaggggca cagggacctg aacttatggt ttcccaagtc   2880
tattgctctc ccaagtgagt ctcccagata cgaggcactg tgccagcatc agccttatct   2940
ccaccacatc ttgtaaaagg actacccagg gccctgatga acaccatggt gtgtacagga   3000
gtaggggggtg gaggcacgga ctcctgtgag gtcacagcca agggagcatc atcatgggtg   3060
gggaggaggc aatggacagg cttgagaacg gggatgtggt tgtatttggt tttctttggt   3120
tagataaagt gctgggtata ggattgagag tggagtatga agaccagtta ggatggagga   3180
tcagattgga gttgggttag ataaagtgct gggtatagga ttgagagtgg agtatgaaga   3240
ccagttagga tggaggatca gattggagtt gggttagaga tggggtaaaa ttgtgctccg   3300
gatgagtttg ggattgacac tgtggaggtg gtttgggatg gcatggcttt gggatggaaa   3360
tagatttgtt ttgatgttgg ctcagacatc cttggggatt gaactgggga tgaagctggg   3420
tttgattttg gaggtagaag acgtggaagt agctgtcaga tttgacagtg gccatgagtt   3480
ttgtttgatg gggaatcaaa caatggggga agacataagg gttggcttgt taggttaagt   3540
tgcgttgggt tgatgggggtc ggggctgtgt ataatgcagt tggattggtt tgtattaaat   3600
tgggttgggt caggttttgg ttgaggatga gttgaggata tgcttgggga caccggatcc   3660
atgaggttct cactggagtg gagacaaact tcctttccag gatgaatcca gggaagcctt   3720
aattcacgtg tagggggaggt caggccactg gctaagtata tccttccact ccagctctaa   3780
gatggtctta aattgtgatt atctatatcc acttctgtct ccctcactgt gcttggagtt   3840
tacctgatca ctcaactaga aacaggggaa gattttatca aattctttt ttttttttt    3900
ttttttttgag acagagtctc actctgttgc ccaggctgga gtgcagtggc gcagtctcgg   3960
ctcactgcaa cctctgcctc ccaggttcaa gtgattctcc tgcctcagcc tcctgagttg   4020
ctgggattac aggcatgcag caccatgccc agctaatttt tgtattttta gtagagatgg   4080
ggtttcacca atgtttgcca ggctggcctc gaactcctga cctggtgatc cacctgcctc   4140
agcctcccaa agtgctggga ttacaggcgt cagccaccgc gcccagccac ttttgtcaaa   4200
ttcttgagac acagctcggg ctggatcaag tgagctactc tggttttatt gaacagctga   4260
ataaccaac tttttggaaa ttgatgaaat cttacggagt taacagtgga ggtaccaggg    4320
ctcttaagag ttcccgattc tcttctgaga ctacaaattg tgattttgca tgccaccta    4380
atctttttt ttttttttt aaatcgaggt ttcagtctca ttctatttcc caggctggag    4440
ttcaatagcg tgatcacagc tcactgtagc cttgaactcc tggccttaag agattctcct   4500
gcttcggtct cccaatagct aagactacag tagtccacca ccatatccag ataatttta    4560
aattttttgg ggggccgggc acagtggctc acgcctgtaa tcccaacacc atgggaggct   4620
gagatgggtg gatcacgagg tcaggagttt gagaccagcc tgaccaacat ggtgaaactc   4680
tgtctctact aaaaaaaaaa aaatagaaa aattagccgg gcgtggtggc acacggcacc    4740
tgtaatccca gctactgagg aggctgaggc aggagaatca cttgaaccca gaaggcagag   4800
gttgcaatga gccgagattg cgccactgca ctccagcctg ggtgacagag tgagactctg   4860
tctcaaaaaa aaaaaatttt tttttttttt ttgtagagat ggatcttgct tgtttctct    4920
ggttggcctt gaactcctgg cttcaagtga tcctcctacc ttggcctcgg aaagtgttgg   4980
gattacaggc gtgagccacc atgactgacc tgtcgttaat cttgaggtac ataaacctgg   5040
```

-continued

| | |
|---|---|
| ctcctaaagg ctaaaggcta aatatttgtt ggagaagggg cattggatttt tgcatgagga | 5100 |
| tgattctgac ctgggagggc aggtcagcag gcatctctgt tgcacagata gagtgtacag | 5160 |
| gtctggagaa caaggagtgg ggggttattg gaattccaca ttgtttgctg cacgttggat | 5220 |
| tttgaaatgc tagggaactt tgggagactc atatttctgg gctagaggat ctgtggacca | 5280 |
| caagatcttt ttatgatgac agtagcaatg tatctgtgga gctggattct ggggttgggag | 5340 |
| tgcaaggaaa agaatgtact aaatgccaag acatctattt caggagcatg aggaataaaa | 5400 |
| gttctagttt ctggtctcag agtggtgcat ggatcaggga gtctcacaat ctcctgagtg | 5460 |
| ctggtgtctt agggcacact gggtcttgga gtgcaaagga tctaggcacg tgaggctttg | 5520 |
| tatgaagaat cggggatcgt acccaccccc tgtttctgtt tcatcctggg catgtctcct | 5580 |
| ctgcctttgt ccctagatg aagtctccat gagctacaag ggcctggtgc atccagggtg | 5640 |
| atctagtaat tgcagaacag caagtgctag ctctccctcc ccttccacag ctctgggtgt | 5700 |
| gggaggggt tgtccagcct ccagcagcat ggggagggcc ttggtcagcc tctgggtgcc | 5760 |
| agcagggcag gggcggagtc ctggggaatg aaggttttat agggctcctg ggggaggctc | 5820 |
| cccagcccca agctt | 5835 |

<210> SEQ ID NO 14
<211> LENGTH: 15056
<212> TYPE: DNA
<213> ORGANISM: Artificial Sequence
<220> FEATURE:
<223> OTHER INFORMATION: CEA TRE

<400> SEQUENCE: 14

| | |
|---|---|
| aagcttttta gtgctttaga cagtgagctg gtctgtctaa cccaagtgac ctgggctcca | 60 |
| tactcagccc cagaagtgaa gggtgaagct gggtggagcc aaaccaggca agcctaccct | 120 |
| cagggctccc agtggcctga gaaccattgg acccaggacc cattacttct agggtaagga | 180 |
| aggtacaaac accagatcca accatggtct gggggacag ctgtcaaatg cctaaaaata | 240 |
| tacctgggag aggagcaggc aaactatcac tgccccaggt tctctgaaca gaaacagagg | 300 |
| ggcaacccaa agtccaaatc caggtgagca ggtgcaccaa atgcccagag atatgacgag | 360 |
| gcaagaagtg aaggaaccac ccctgcatca aatgttttgc atgggaagga gaggggggtt | 420 |
| gctcatgttc ccaatccagg agaatgcatt tgggatctgc cttcttctca ctccttggtt | 480 |
| agcaagacta agcaaccagg actctggatt tggggaaaga cgtttatttg tggaggccag | 540 |
| tgatgacaat cccacgaggg cctaggtgaa gagggcagga aggctcgaga cactggggac | 600 |
| tgagtgaaaa ccacacccat gatctgcacc acccatggat gctccttcat tgctcacctt | 660 |
| tctgttgata tcagatggcc ccattttctg taccttcaca gaaggacaca ggctagggtc | 720 |
| tgtgcatggc cttcatcccc ggggccatgt gaggacagca ggtgggaaag atcatgggtc | 780 |
| ctcctgggtc ctgcagggcc agaacattca tcacccatac tgacctccta gatgggaatg | 840 |
| gcttccctgg ggctgggcca acggggcctg gcaggggag aaaggacgtc aggggacagg | 900 |
| gaggaagggt catcgagacc cagcctggaa ggttcttgtc tctgaccatc caggatttac | 960 |
| ttccctgcat ctacctttgg tcattttccc tcagcaatga ccagctctgc ttcctgatct | 1020 |
| cagcctccca ccctggacac agcaccccag tccctggccc ggctgcatcc acccaatacc | 1080 |
| ctgataaccc caggacccatt acttctaggg taaggagggt ccaggagaca gaagctgagg | 1140 |
| aaaggtctga agaagtcaca tctgtcctgg ccagagggga aaaccatca gatgctgaac | 1200 |
| caggagaatg ttgacccagg aaagggaccg aggacccaag aaaggagtca gaccaccagg | 1260 |

-continued

```
gtttgcctga gaggaaggat caaggccccg agggaaagca gggctggctg catgtgcagg    1320
acactggtgg ggcatatgtg tcttagattc tccctgaatt cagtgtccct gccatggcca    1380
gactctctac tcaggcctgg acatgctgaa ataggacaat ggccttgtcc tctctcccca    1440
ccatttggca agagacataa aggacattcc aggacatgcc ttcctgggag gtccaggttc    1500
tctgtctcac acctcaggga ctgtagttac tgcatcagcc atggtaggtg ctgatctcac    1560
ccagcctgtc caggcccttc cactctccac tttgtgacca tgtccaggac caccccctcag   1620 atcctgagcc tgcaaatacc cccttgctgg gtgggtggat tcagtaaaca gtgagctcct    1680
atccagcccc cagagccacc tctgtcacct tcctgctggg catcatccca ccttcacaag    1740
cactaaagag catggggaga cctggctagc tgggtttctg catcacaaag aaaataatcc    1800
cccaggttcg gattcccagg gctctgtatg tggagctgac agacctgagg ccaggagata    1860
gcagaggtca gccctaggga gggtgggtca tccacccagg ggacagggt gcaccagcct    1920 tgctactgaa agggcctccc caggacagcg ccatcagccc tgcctgagag ctttgctaaa    1980
cagcagtcag aggaggccat ggcagtggct gagctcctgc tccaggcccc aacagaccag    2040
accaacagca caatgcagtc cttccccaac gtcacaggtc accaaaggga aactgaggtg    2100
ctacctaacc ttagagccat caggggagat aacagcccaa tttcccaaac aggccagttt    2160
caatcccatg acaatgacct ctctgctctc attcttccca aaataggacg ctgattctcc    2220 ccaccatgg atttctccct tgtcccggga gccttttctg cccctatga tctgggcact     2280 cctgacacac acctcctctc tggtgacata tcagggtccc tcactgtcaa gcagtccaga    2340
aaggacagaa ccttggacag cgcccatctc agcttcaccc ttcctccttc acagggttca    2400 ggcaaagaa taaatggcag aggccagtga gcccagagat ggtgacaggc agtgacccag    2460
gggcagatgc ctggagcagg agctggcggg gccacaggga gaaggtgatg caggaaggga    2520
aacccagaaa tgggcaggaa aggaggacac aggctctgtg gggctgcagc ccagggttgg    2580
actatgagtg tgaagccatc tcagcaagta aggccaggtc ccatgaacaa gagtgggagc    2640
acgtggcttc ctgctctgta tatggggtgg gggattccat gccccataga accagatggc    2700
cggggttcag atggagaagg agcaggacag gggatcccca ggataggagg acccagtgt    2760 ccccacccag gcaggtgact gatgaatggg catgcagggt cctcctgggc tgggctctcc    2820
ctttgtccct caggattcct tgaaggaaca tccggaagcc gaccacatct acctggtggg    2880
ttctggggag tccatgtaaa gccaggagct tgtgttgcta ggaggggtca tggcatgtgc    2940
tgggggcacc aaagagagaa acctgagggc aggcaggacc tggtctgagg aggcatggga    3000
gcccagatgg ggagatggat gtcaggaaag gctgccccat cagggagggt gatagcaatg    3060 ggggtctgt gggagtgggc acgtgggatt ccctgggctc tgccaagttc cctcccatag    3120
tcacaacctg ggacactgc ccatgaaggg gcgccttgc ccagccagat gctgctggtt       3180
ctgcccatcc actaccctct ctgctccagc cactctgggt cttctccag atgccctgga    3240 cagccctggc ctgggcctgt ccctgagag tgttgggag aagctgagtc tctggggaca      3300
ctctcatcag agtctgaaag gcacatcagg aaacatccct ggtctccagg actaggcaat    3360
gaggaaaggg ccccagctcc tcccttgcc actgagaggg tcgaccctgg gtggccacag     3420
tgacttctgc gtctgtccca gtcaccctga aaccacaaca aaacccagc cccagaccct     3480 gcaggtacaa tacatgtggg gacagtctgt acccagggga agccagttct ctcttcctag    3540
gagaccgggc ctcagggctg tgcccggggc aggcggggc agcacgtgcc tgtccttgag     3600
```

-continued

```
aactcgggac cttaagggtc tctgctctgt gaggcacagc aaggatcctt ctgtccagag    3660
atgaaagcag ctcctgcccc tcctctgacc tcttcctcct tcccaaatct caaccaacaa    3720
ataggtgttt caaatctcat catcaaatct tcatccatcc acatgagaaa gcttaaaacc    3780
caatggattg acaacatcaa gagttggaac aagtggacat ggagatgtta cttgtggaaa    3840
tttagatgtg ttcagctatc gggcaggaga atctgtgtca aattccagca tggttcagaa    3900
gaatcaaaaa gtgtcacagt ccaaatgtgc aacagtgcag gggataaaac tgtggtgcat    3960
tcaaactgag ggatattttg gaacatgaga aggaaggga ttgctgctgc acagaacatg    4020
gatgatctca cacatagagt tgaaagaaag gagtcaatcg cagaatagaa aatgatcact    4080
aattccacct ctataaagtt tccaagagga aacccaatt ctgctgctag agatcagaat    4140
ggaggtgacc tgtgccttgc aatggctgtg agggtcacgg gagtgtcact tagtgcaggc    4200
aatgtgccgt atcttaatct gggcagggct ttcatgagca cataggaatg cagacattac    4260
tgctgtgttc attttacttc accggaaaag aagaataaaa tcagccgggc gcggtggctc    4320
acgcctgtaa tcccagcact ttagaaggct gaggtgggca gattacttga ggtcaggagt    4380
tcaagaccac cctggccaat atggtgaaac cccggctcta ctaaaaatac aaaaattagc    4440
tgggcatggt ggtgcgcgcc tgtaatccca gctactcggg aggctgaggc tggacaattg    4500
cttggaccca ggaagcagag gttgcagtga gccaagattg tgccactgca ctccagcttg    4560
ggcaacagag ccagactctg taaaaaaaaa aaaaaaaaaa aaaaaagaa agaaagaaaa    4620 agaaagaaaa gtataaaatc tctttgggtt aacaaaaaaa gatccacaaa acaaacacca    4680
gctcttatca aacttacaca actctgccag agaacaggaa acacaaatac tcattaactc    4740
acttttgtgg caataaaaacc ttcatgtcaa aaggagacca ggacacaatg aggaagtaaa    4800
actgcaggcc ctacttgggt gcagagaggg aaaatccaca aataaaacat taccagaagg    4860
agctaagatt tactgcattg agttcattcc ccaggtatgc aaggtgattt taacacctga    4920
aaatcaatca ttgcctttac tacatagaca gattagctag aaaaaaatta caactagcag    4980
aacagaagca atttggcctt cctaaaattc cacatcatat catcatgatg gagacagtgc    5040
agacgccaat gacaataaaa agagggacct ccgtcacccg gtaaacatgt ccacacagct    5100
ccagcaagca cccgtcttcc cagtgaatca ctgtaacctc ccctttaatc agccccaggc    5160
aaggctgcct gcgatggcca cacaggctcc aacccgtggg cctcaacctc ccgcagaggc    5220
tctcctttgg ccaccccatg gggagagcat gaggacaggg cagagccctc tgatgcccac    5280
acatggcagg agctgacgcc agagccatgg gggctggaga gcagagctgc tggggtcaga    5340
gcttcctgag gacacccagg cctaagggaa ggcagctccc tggatggggg caaccaggct    5400
ccgggctcca acctcagagc ccgcatggga ggagccagca ctctaggcct ttcctagggt    5460
gactctgagg ggaccctgac acgacaggat cgctgaatgc acccgagatg aaggggccac    5520
cacgggaccc tgctctcgtg gcagatcagg agagagtggg acaccatgcc aggcccccat    5580
ggcatggctg cgactgaccc aggccactcc cctgcatgca tcagcctcgg taagtcacat    5640
gaccaagccc aggaccaatg tggaaggaag gaaacagcat cccctttagt gatggaaccc    5700
aaggtcagtg caaagagagg ccatgagcag ttaggaaggg tggtccaacc tacagcacaa    5760
accatcatct atcataagta gaagccctgc tccatgaccc ctgcatttaa ataaacgttt    5820
gttaaatgag tcaaattccc tcaccatgag agctcacctg tgtgtaggcc catcacacac    5880
acaaacacac acacacacac acacacacac acacacacac acagggaaag tgcaggatcc    5940
tggacagcac caggcaggct tcacaggcag agcaaacagc gtgaatgacc catgcagtgc    6000
```

-continued

```
cctgggcccc atcagctcag agaccctgtg agggctgaga tggggctagg caggggagag    6060
acttagagag ggtggggcct ccagggaggg ggctgcaggg agctgggtac tgccctccag    6120 ggaggggggct gcagggagct gggtactgcc ctccaggag ggggctgcag ggagctgggt    6180
actgccctcc aggagggggg ctgcaggag ctgggtactg ccctccaggg aggggctgc     6240 agggagctgg gtactgccct ccaggaggc aggagcactg ttcccaacag agagcacatc    6300
ttcctgcagc agctgcacag acacaggagc ccccatgact gccctgggcc agggtgtgga    6360
ttccaaattt cgtgccccat tgggtgggac ggaggttgac cgtgacatcc aaggggcatc    6420
tgtgattcca aacttaaact actgtgccta caaaatagga ataaccccta ctttttctac    6480
tatctcaaat tccctaagca caagctagca ccctttaaat caggaagttc agtcactcct    6540
ggggtcctcc catgccccca gtctgacttg caggtgcaca gggtggctga catctgtcct    6600
tgctcctcct cttggctcaa ctgccgcccc tctgggggt gactgatggt caggacaagg    6660
gatcctagag ctgcccccat gattgacagg aaggcaggac ttggcctcca ttctgaagac    6720 tagggtgtc aagagagctg gcatcccac agagctgcac aagatgacgc ggacagaggg    6780
tgacacaggg ctcagggctt cagacgggtc gggaggctca gctgagagtt cagggacaga    6840
cctgaggagc ctcagtggga aaagaagcac tgaagtggga agttctggaa tgttctggac    6900
aagcctgagt gctctaagga aatgctccca ccccgatgta gcctgcagca ctggacggtc    6960
tgtgtacctc cccgctgccc atcctctcac agcccccgcc tctagggaca caactcctgc    7020
cctaacatgc atctttcctg tctcattcca cacaaaggg cctctggggt ccctgttctg    7080
cattgcaagg agtggaggtc acgttccac agaccaccca gcaacagggt cctatggagg    7140
tgcggtcagg aggatcacac gtcccccat gcccagggga ctgactctgg gggtgatgga    7200
ttggcctgga ggccactggt cccctctgtc cctgagggga atctgcaccc tggaggctgc    7260
cacatccctc ctgattcttt cagctgaggg cccttcttga aatcccaggg aggactcaac    7320
ccccactggg aaaggcccag tgtggacggt tccacagcag cccagctaag gcccttggac    7380
acagatcctg agtgagagaa cctttaggga cacaggtgca cggccatgtc cccagtgccc    7440
acacagagca gggcatctg gaccctgagt gtgtagctcc cgcgactgaa cccagccctt    7500
ccccaatgac gtgaccctg gggtggctcc aggtctccag tccatgccac caaaatctcc    7560
agattgaggg tcctcccttg agtccctgat gcctgtccag gagctgcccc ctgagcaaat    7620
ctagagtgca gagggctggg attgtggcag taaaagcagc cacatttgtc tcaggaagga    7680
aagggaggac atgagctcca ggaagggcga tggcgtcctc tagtgggcgc ctcctgttaa    7740
tgagcaaaaa ggggccagga gagttgagag atcagggctg gccttggact aaggctcaga    7800
tggagaggac tgaggtgcaa agaggggggct gaagtagggg agtggtcggg agagatggga    7860
ggagcaggta agggaagcc ccaggaggc cgggggaggg tacagcagag ctctccactc    7920
ctcagcattg acatttgggg tggtcgtgct agtgggggttc tgtaagttgt agggtgttca    7980
gcaccatctg gggactctac ccactaaatg ccagcaggac tccctcccca agctctaaca    8040
accaacaatg tctccagact ttccaaatgt cccctggaga gcaaaattgc ttctggcaga    8100
atcactgatc tacgtcagtc tctaaaagtg actcatcagc gaaatccttc acctcttggg    8160
agaagaatca caagtgtgag aggggtagaa actgcagact tcaaaatctt tccaaaagag    8220
ttttacttaa tcagcagttt gatgtcccag gagaagatac atttagagtg tttagagttg    8280
atgccacatg gctgcctgta cctcacagca ggagcagagt gggttttcca agggcctgta    8340
```

```
accacaactg gaatgacact cactgggtta cattacaaag tggaatgtgg ggaattctgt    8400
agactttggg aagggaaatg tatgacgtga gcccacagcc taaggcagtg acagtccac    8460
tttgaggctc tcaccatcta ggagacatct cagccatgaa catagccaca tctgtcatta   8520
gaaaacatgt tttattaaga ggaaaaatct aggctagaag tgctttatgc tcttttttct   8580
ctttatgttc aaattcatat acttttagat cattccttaa agaagaatct atcccctaa    8640
gtaaatgtta tcactgactg gatagtgttg gtgtctcact cccaaccct gtgtggtgac    8700
agtgccctgc ttccccagcc ctgggccctc tctgattcct gagagctttg ggtgctcctt   8760
cattaggagg aagagaggaa gggtgttttt aatattctca ccattcaccc atccacctct   8820
tagacactgg gaagaatcag ttgcccactc ttggatttga tcctcgaatt aatgacctct   8880
atttctgtcc cttgtccatt tcaacaatgt gacaggccta agaggtgcct tctccatgtg   8940
atttttgagg agaaggttct caagataagt tttctcacac ctctttgaat tacctccacc   9000
tgtgtcccca tcaccattac cagcagcatt tggaccctt ttctgttagt cagatgcttt    9060
ccacctcttg agggtgtata ctgtatgctc tctacacagg aatatgcaga ggaaatagaa   9120
aagggaaat cgcattacta ttcagagaga agaagacctt tatgtgaatg aatgagagtc    9180
taaaatccta agagagccca tataaaatta ttaccagtgc taaaactaca aaagttacac   9240
taacagtaaa ctagaataat aaaacatgca tcacagttgc tggtaaagct aaatcagata   9300
tttttttctt agaaaaagca ttccatgtgt gttgcagtga tgacaggagt gcccttcagt   9360
caatatgctg cctgtaattt ttgttccctg gcagaatgta ttgtcttttc tcccttaaa   9420
tcttaaatgc aaaactaaag gcagctcctg ggcccctcc ccaaagtcag ctgcctgcaa    9480
ccagccccac gaagagcaga ggcctgagct tccctggtca aaatagggg ctagggagct    9540
taaccttgct cgataaagct gtgttccag aatgtcgctc ctgttcccag gggcaccagc    9600
ctggaggtg gtgagcctca ctggtggcct gatgcttacc ttgtgccctc acaccagtgg    9660
tcactggaac cttgaacact tggctgtcgc ccggatctgc agatgtcaag aacttctgga   9720
agtcaaatta ctgcccactt ctccagggca gatacctgtg aacatccaaa accatgccac   9780
agaaccctgc ctggggtcta caacacatat ggactgtgag caccaagtcc agccctgaat   9840
ctgtgaccac ctgccaagat gcccctaact gggatccacc aatcactgca catggcaggc   9900
agcgaggctt ggaggtgctt cgccacaagg cagccccaat ttgctgggag tttcttggca   9960
cctggtagtg gtgaggagcc ttgggaccct caggattact ccccttaagc atagtgggga  10020
cccttctgca tccccagcag gtgccccgct cttcagagcc tctctctctg aggtttaccc  10080
agacccctgc accaatgaga ccatgctgaa gcctcagaga gagagatgga gctttgacca  10140
ggagccgctc ttccttgagg gccagggcag ggaaagcagg aggcagcacc aggagtggga  10200
acaccagtgt ctaagcccct gatgagaaca gggtggtctc tcccatatgc ccataccagg  10260
cctgtgaaca gaatcctcct tctgcagtga caatgtctga gaggacgaca tgtttcccag  10320
cctaacgtgc agccatgccc atctacccac tgcctactgc aggacagcac caacccagga  10380
gctgggaagc tgggagaaga catggaatac ccatggcttc tcaccttcct ccagtccagt  10440
gggcaccatt tatgcctagg acacccacct gccggcccca ggctcttaag agttaggtca  10500
cctaggtgcc tctgggaggc cgaggcagga gaattgcttg aacccgggag gcagaggttg  10560
cagtgagccg agatcacacc actgcactcc agcctgggtg acagaatgag actctgtctc  10620
aaaaaaaaag agaaagatag catcagtggc taccaagggc taggggcagg ggaaggtgga  10680
gagttaatga ttaatagtat gaagtttcta tgtgagatga tgaaaatgtt ctggaaaaaa  10740
```

```
aaatatagtg gtgaggatgt agaatattgt gaatataatt aacggcattt aattgtacac    10800
ttaacatgat taatgtggca tattttatct tatgtatttg actacatcca agaaacactg    10860
ggagagggaa agcccaccat gtaaaataca cccaccctaa tcagatagtc ctcattgtac    10920
ccaggtacag gcccctcatg acctgcacag gaataactaa ggatttaagg acatgaggct    10980
tcccagccaa ctgcaggtgc acaacataaa tgtatctgca aacagactga gagtaaagct    11040
gggggcacaa acctcagcac tgccaggaca cacaccttc tcgtggattc tgactttatc     11100
tgacccggcc cactgtccag atcttgttgt gggattggga caagggaggt cataaagcct    11160
gtccccaggg cactctgtgt gagcacacga gacctcccca cccccccacc gttaggtctc    11220
cacacataga tctgaccatt aggcattgtg aggaggactc tagcgcgggc tcagggatca    11280
caccagagaa tcaggtacag agaggaagac ggggctcgag gagctgatgg atgacacaga    11340
gcagggttcc tgcagtccac aggtccagct caccctggtg taggtgcccc atcccctga    11400 tccaggcatc cctgacacag ctccctcccg gagcctcctc ccaggtgaca catcagggtc    11460
cctcactcaa gctgtccaga gagggcagca ccttggacag cgcccacccc acttcactct    11520
tcctccctca cagggctcag ggctcagggc tcaagtctca gaacaaatgg cagaggccag    11580
tgagcccaga gatggtgaca gggcaatgat ccaggggcag ctgcctgaaa cgggagcagg    11640
tgaagccaca gatgggagaa gatggttcag gaagaaaaat ccaggaatgg gcaggagagg    11700
agaggaggac acaggctctg tggggctgca gcccaggatg ggactaagtg tgaagacatc    11760
tcagcaggtg aggccaggtc ccatgaacag agaagcagct cccacctccc ctgatgcacg    11820
gacacacaga gtgtgtggtg ctgtgccccc agagtcgggc tctcctgttc tggtccccag    11880
ggagtgagaa gtgaggttga cttgtccctg ctcctctctg ctaccccaac attcaccttc    11940
tcctcatgcc cctctctctc aaatatgatt tggatctatg tccccgccca aatctcatgt    12000
caaattgtaa accccaatgt tggaggtggg gccttgtgag aagtgattgg ataatgcggg    12060
tggattttct gctttgatgc tgtttctgtg atagagatct cacatgatct ggttgtttaa    12120
aagtgtgtag cacctctccc ctctctctct ctctctctta ctcatgctct gccatgtaag    12180
acgttcctgt ttccccttca ccgtccagaa tgattgtaag ttttctgagg cctccccagg    12240
agcagaagcc actatgcttc ctgtacaact gcagaatgat gagcgaatta aacctctttt    12300
ctttataaat tacccagtct caggtatttc tttatagcaa tgcgaggaca gactaataca    12360
atcttctact cccagatccc cgcacacgct tagccccaga catcactgcc cctgggagca    12420
tgcacagcgc agcctcctgc cgacaaaagc aaagtcacaa aagtgacaa aaatctgcat     12480 ttggggacat ctgattgtga aagagggagg acagtacact tgtagccaca gagactgggg    12540
ctcaccgagc tgaaacctgg tagcacttg gcataacatg tgcatgaccc gtgttcaatg     12600
tctagagatc agtgttgagt aaaacagcct ggtctgggc cgctgctgtc cccacttccc     12660
tcctgtccac cagagggcgg cagagttcct cccaccctgg agcctcccca ggggctgctg    12720
acctccctca gccgggccca cagcccagca gggtccaccc tcacccgggt cacctcggcc    12780
cacgtcctcc tcgccctccg agctcctcac acggactctg tcagctcctc cctgcagcct    12840
atcggccgcc cacctgaggc ttgtcggccg cccacttgag gcctgtcggc tgccctctgc    12900
aggcagctcc tgtcccctac accccctcct tccccgggct cagctgaaag ggcgtctccc    12960
agggcagctc cctgtgatct ccaggacagc tcagtctctc acaggctccg acgccccta    13020 tgctgtcacc tcacagccct gtcattacca ttaactcctc agtcccatga agttcactga    13080
```

-continued

```
gcgcctgtct cccggttaca ggaaaactct gtgacaggga ccacgtctgt cctgctctct      13140
gtggaatccc agggcccagc ccagtgcctg acacggaaca gatgctccat aaatactggt      13200
taaatgtgtg ggagatctct aaaaagaagc atatcacctc cgtgtggccc ccagcagtca      13260
gagtctgttc catgtggaca caggggcact ggcaccagca tgggaggagg ccagcaagtg      13320
cccgcggctg ccccaggaat gaggcctcaa cccccagagc ttcagaaggg aggacagagg      13380
cctgcaggga atagatcctc cggcctgacc ctgcagccta atccagagtt cagggtcagc      13440
tcacaccacg tcgaccctgg tcagcatccc tagggcagtt ccagacaagg ccggaggtct      13500
cctcttgccc tccagggggt gacattgcac acagacatca ctcaggaaac ggattcccct      13560
ggacaggaac ctggctttgc taaggaagtg gaggtggagc ctggtttcca tcccttgctc      13620
caacagaccc ttctgatctc tcccacatac ctgctctgtt cctttctggg tcctatgagg      13680
accctgttct gccaggggtc cctgtgcaac tccagactcc ctcctggtac caccatgggg      13740
aaggtggggt gatcacagga cagtcagcct cgcagagaca gagaccaccc aggactgtca      13800
gggagaacat ggacaggccc tgagccgcag ctcagccaac agacacgag agggagggtc       13860 cccctggagc cttccccaag gacagcagag cccagagtca cccacctccc tccaccacag      13920
tcctctcttt ccaggacaca caagacacct cccctccac atgcaggatc tggggactcc       13980
tgagacctct gggcctgggt ctccatccct gggtcagtgg cggggttggt ggtactggag      14040
acagagggct ggtccctccc cagccaccac ccagtgagcc tttttctagc ccccagagcc      14100
acctctgtca ccttcctgtt gggcatcatc ccaccttccc agagccctgg agagcatggg      14160
gagacccggg accctgctgg gtttctctgt cacaaaggaa aataatcccc ctggtgtgac      14220
agacccaagg acagaacaca gcagaggtca gcactgggga agacaggttg tcctcccagg      14280
ggatgggggt ccatccacct tgccgaaaag atttgtctga ggaactgaaa atagaaggga      14340 aaaagagga gggacaaaag aggcagaaat gagaggggag gggacagagg acacctgaat       14400
aaagaccaca cccatgaccc acgtgatgct gagaagtact cctgccctag aagagactc       14460 agggcagagg gaggaaggac agcagaccag acagtcacag cagccttgac aaaacgttcc      14520
tggaactcaa gctcttctcc acagaggagg acagagcaga cagcagagac catggagtct      14580
ccctcggccc ctccccacag atggtgcatc ccctggcaga ggctcctgct cacaggtgaa      14640
gggaggacaa cctgggagag ggtgggagga gggagctggg gtctcctggg taggacaggg      14700
ctgtgagacg gacagagggc tcctgttgga gcctgaatag ggaagaggac atcagagagg      14760
gacaggagtc acaccagaaa aatcaaattg aactggaatt ggaaaggggc aggaaaacct      14820
caagagttct attttcctag ttaattgtca ctggccacta cgttttttaaa aatcataata      14880 actgcatcag atgacacttt aaataaaaac ataaccaggg catgaaacac tgtcctcatc      14940
cgcctaccgc ggacattgga aaataagccc caggctgtgg agggccctgg gaaccctcat      15000
gaactcatcc acaggaatct gcagcctgtc ccaggcactg gggtgcaacc aagatc         15056
```

<210> SEQ ID NO 15
<211> LENGTH: 858
<212> TYPE: DNA
<213> ORGANISM: Artificial Sequence
<220> FEATURE:
<223> OTHER INFORMATION: Mucin-TRE

<400> SEQUENCE: 15

```
cgagcggccc ctcagcttcg gcgcccagcc ccgcaaggct cccggtgacc actagagggc         60
gggaggagct cctggccagt ggtggagagt ggcaaggaag gaccctaggg ttcatcggag        120
```

-continued

| | |
|---|---|
| cccaggttta ctcccttaag tggaaatttc ttccccact cctccttggc tttctccaag | 180 |
| gagggaaccc aggctgctgg aaagtccggc tggggcgggg actgtgggtt caggggagaa | 240 |
| cggggtgtgg aacgggacag ggagcggtta aaggtggg gctattccgg gaagtggtgg | 300 |
| ggggagggag cccaaaacta gcacctagtc cactcattat ccagccctct tatttctcgg | 360 |
| ccgctctgct tcagtggacc cggggagggc ggggaagtgg agtgggagac ctaggggtgg | 420 |
| gcttcccgac cttgctgtac aggacctcga cctagctggc tttgttcccc atccccacgt | 480 |
| tagttgttgc cctgaggcta aaactagagc ccaggggccc caagttccag actgcccctc | 540 |
| ccccctcccc cggagccagg gagtggttgg tgaaggggg aggccagctg agaacaaac | 600 |
| gggtagtcag ggggttgagc gattagagcc cttgtaccct acccaggaat ggttggggag | 660 |
| gaggaggaag aggtaggagg taggggaggg ggcggggttt tgtcacctgt cacctgctcg | 720 |
| ctgtgcctag ggcgggcggg cggggagtgg ggggaccggg ataaagcggt aggcgcctgt | 780 |
| gcccgctcca cctctcaagc agccagcgcc tgcctgaatc tgttctgccc cctccccacc | 840 |
| catttcacca ccaccatg | 858 |

<210> SEQ ID NO 16
<211> LENGTH: 5224
<212> TYPE: DNA
<213> ORGANISM: Artificial Sequence
<220> FEATURE:
<223> OTHER INFORMATION: AlphaFP-TRE

<400> SEQUENCE: 16

| | |
|---|---|
| gaattcttag aaatatgggg gtaggggtgg tggtggtaat tctgtttttca ccccataggt | 60 |
| gagataagca ttgggttaaa tgtgctttca cacacacatc acatttcata agaattaagg | 120 |
| aacagactat gggctggagg actttgagga tgtctgtctc ataacacttg ggttgtatct | 180 |
| gttctatggg gcttgtttta agcttggcaa cttgcaacag ggttcactga cttctccc | 240 |
| aagcccaagg tactgtcctc ttttcatatc tgttttgggg cctctgggc ttgaatatct | 300 |
| gagaaaatat aaacatttca ataatgttct gtggtgagat gagtatgaga gatgtgtcat | 360 |
| tcatttgtat caatgaatga atgaggacaa ttagtgtata aatccttagt acaacaatct | 420 |
| gagggtaggg gtggtactat tcaatttcta tttataaaga tacttatttc tatttatta | 480 |
| tgcttgtgac aaatgttttg ttcgggacca caggaatcac aaagatgagt ctttgaattt | 540 |
| aagaagttaa tggtccagga ataattacat agcttacaaa tgactatgat ataccatcaa | 600 |
| acaagaggtt ccatgagaaa ataatctgaa aggtttaata agttgtcaaa ggtgagaggg | 660 |
| ctcttctcta gctagagact aatcagaaat acattcaggg ataattattt gaatagacct | 720 |
| taagggttgg gtacattttg ttcaagcatt gatggagaag gagagtgaat atttgaaaac | 780 |
| attttcaact aaccaaccac ccaatccaac aaacaaaaaa tgaaaagaat ctcagaaaca | 840 |
| gtgagataag agaaggaatt ttctcacaac ccacacgtat agctcaactg ctctgaagaa | 900 |
| gtatatatct aatatttaac actaacatca tgctaataat gataataatt actgtcatttt | 960 |
| tttaatgtct ataagtacca ggcatttaga agatattatt ccatttatat atcaaaataa | 1020 |
| acttgagggg atagatcatt ttcatgatat atgagaaaaa ttaaaaacag attgaattat | 1080 |
| ttgcctgtca tacagctaat aattgaccat aagacaatta gatttaaatt agttttgaat | 1140 |
| cttttctaata ccaaagttca gtttactgtt ccatgttgct tctgagtggc ttcacagact | 1200 |
| tatgaaaaag taaacggaat cagaattaca tcaatgcaaa agcattgctg tgaactctgt | 1260 |

```
acttaggact aaactttgag caataacaca catagattga ggattgtttg ctgttagcat    1320
acaaactctg gttcaaagct cctctttatt gcttgtcttg gaaaatttgc tgttcttcat    1380
ggtttctctt ttcactgcta tctattttc tcaaccactc acatggctac aataactgtc    1440
tgcaagctta tgattcccaa atatctatct ctagcctcaa tcttgttcca gaagataaaa    1500
agtagtattc aaatgcacat caacgtctcc acttggaggg cttaaagacg tttcaacata    1560
caaaccgggg agttttgcct ggaatgtttc ctaaaatgtg tcctgtagca catagggtcc    1620
tcttgttcct aaaatctaa ttacttttag cccagtgctc atcccaccta tggggagatg    1680
agagtgaaaa gggagcctga ttaataatta cactaagtca ataggcatag agccaggact    1740
gtttgggtaa actggtcact ttatcttaaa ctaaatatat ccaaaactga acatgtactt    1800
agttactaag tctttgactt tatctcattc ataccactca gctttatcca ggccacttat    1860
ttgacagtat tattgcgaaa acttcctaac tggtctcctt atcatagtct tatccccttt    1920
tgaaacaaaa gagacagttt caaaatacaa atatgatttt tattagctcc cttttgttgt    1980
ctataatagt cccagaagga gttataaact ccatttaaaa agtctttgag atgtggccct    2040
tgccaacttt gccaggaatt cccaatatct agtattttct actattaaac tttgtgcctc    2100
ttcaaaactg catttctct cattccctaa gtgtgcattg ttttccctta ccggttggtt    2160
tttccaccac cttttacatt ttcctggaac actatacccc ccctcttcat ttgcccacc    2220 tctaattttc tttcagatct ccatgaagat gttacttcct ccaggaagcc ttatctgacc    2280
cctccaaaga tgtcatgagt tcctcttttc attctactaa tcacagcatc catcacacca    2340
tgttgtgatt actgatacta ttgtctgttt ctctgattag gcagtaagct caacaagagc    2400
tacatggtgc ctgtctcttg ttgctgatta ttcccatcca aaaacagtgc ctggaatgca    2460
gacttaacat tttattgaat gaataaaataa aaccccatct atcgagtgct actttgtgca    2520
agacccggtt ctgaggcatt tatatttatt gatttattta attctcattt aaccatgaag    2580
gaggtactat cactatcctt attttatagt tgataaagat aaagcccaga gaaatgaatt    2640
aactcaccca agtcatgta gctaagtgac agggcaaaaa ttcaaaccag ttccccaact    2700
ttacgtgatt aatactgtgc tatactgcct ctctgatcat atggcatgga atgcagacat    2760
ctgctccgta aggcagaata tggaaggaga ttggaggatg acacaaaacc agcataatat    2820
cagaggaaaa gtccaaacag gacctgaact gatagaaaag ttgttactcc tggtgtagtc    2880
gcatcgacat cttgatgaac tggtggctga cacaacatac attggcttga tgtgtacata    2940
ttatttgtag ttgtgtgtgt attttttatat atatatttgt aatattgaaa tagtcataat    3000
ttactaaagg cctaccattt gccaggcatt tttacatttg tccctctaa tcttttgatg    3060 agatgatcag attggattac ttggccttga agatgatata tctacatcta tatctatatc    3120
tatatctata tctatatcta tatctatatc tatatctata tatgtatatc agaaaagctg    3180
aaatatgttt tgtaaagtta taaagatttc agactttata gaatctggga tttgccaaat    3240 gtaaccccctt tctctacatt aaacccatgt tggaacaaat acatttatta ttcattcatc    3300
aaatgttgct gagtcctggc tatgaaccag acactgtgaa agcctttggg atattttgcc    3360
catgcttggg caagcttata tagtttgctt cataaaactc tatttcagtt cttcataact    3420
aatacttcat gactattgct tttcaggtat tccttcataa caaatacttt ggctttcata    3480
tatttgagta aagtcccccct tgaggaagag tagaagaact gcactttgta aatactatcc    3540
tggaatccaa acgatagac aaggatggtg ctacctcttt ctggagagta cgtgagcaag    3600
gcctgttttg ttaacatgtt ccttaggaga caaaacttag gagagacacg catagcagaa    3660
```

```
aatggacaaa aactaacaaa tgaatgggaa ttgtacttga ttagcattga agaccttgtt    3720
tatactatga taaatgtttg tatttgctgg aagtgctact gacggtaaac ccttttgtt     3780 taaatgtgtg ccctagtagc ttgcagtatg atctatttt taagtactgt acttagctta    3840
tttaaaaatt ttatgtttaa aattgcatag tgctctttca ttgaagaagt tttgagagag    3900
agatagaatt aaattcactt atcttaccat ctagagaaac ccaatgttaa aactttgttg    3960
tccattattt ctgtctttta ttcaacattt tttttagagg gtgggaggaa tacagaggag    4020
gtacaatgat acacaaatga gagcactctc catgtattgt tttgtcctgt ttttcagtta    4080
acaatatatt atgagcatat ttccatttca ttaaatattc ttccacaaag ttattttgat    4140
ggctgtatat caccctactt tatgaatgta ccatattaat ttatttcctg gtgtgggtta    4200
tttgatttta taatcttacc tttagaataa tgaaacacct gtgaagcttt agaaaatact    4260
ggtgcctggg tctcaactcc acagattctg atttaactgg tctgggttac agactaggca    4320
ttgggaattc aaaaagttcc cccagtgatt ctaatgtgta gccaagatcg ggaacccttg    4380
tagacaggga tgataggagg tgagccactc ttagcatcca tcatttagta ttaacatcat    4440
catcttgagt tgctaagtga atgatgcacc tgacccactt tataaagaca catgtgcaaa    4500
taaaattatt ataggacttg gtttattagg gcttgtgctc taagttttct atgttaagcc    4560
atacatcgca tactaaatac tttaaaatgt accttattga catacatatt aagtgaaaag    4620
tgtttctgag ctaaacaatg acagcataat tatcaagcaa tgataatttg aaatgaattt    4680
attattctgc aacttaggga caagtcatct ctctgaattt tttgtacttt gagagtattt    4740
gttatatttg caagatgaag agtctgaatt ggtcagacaa tgtcttgtgt gcctggcata    4800
tgataggcat ttaatagttt taaagaatta atgtatttag atgaattgca taccaaatct    4860
gctgtctttt ctttatggct tcattaactt aatttgagag aaattaatta ttctgcaact    4920
tagggacaag tcatgtcttt gaatattctg tagtttgagg agaatatttg ttatatttgc    4980
aaaataaaat aagtttgcaa gttttttttt tctgccccaa agagctctgt gtccttgaac    5040
ataaaataca aataaccgct atgctgttaa ttattggcaa atgtcccatt ttcaacctaa    5100
ggaaatacca taaagtaaca gatataccaa caaaaggtta ctagttaaca ggcattgcct    5160
gaaaagagta taaagaatt tcagcatgat tttccatatt gtgcttccac cactgccaat     5220
aaca                                                                 5224
```

<210> SEQ ID NO 17
<211> LENGTH: 307
<212> TYPE: DNA
<213> ORGANISM: Artificial Sequence
<220> FEATURE:
<223> OTHER INFORMATION: Nucleotide sequence for ADP

<400> SEQUENCE: 17

```
gatgaccggc tcaaccatcg cgcccacaac ggactatcgc aacaccactg ctaccggact     60
aacatctgcc ctaaatttac cccaagttca tgcctttgtc aatgactggg cgagcttgga   120
catgtggtgg ttttccatag cgcttatgtt tgtttgcctt attattatgt ggcttatttg   180
ttgcctaaag cgcagacgcg ccagaccccc catctatagg cctatcattg tgctcaaccc   240
acacaatgaa aaaattcata gattggacgg tctgaaacca tgttctcttc ttttacagta   300
tgattaa                                                             307
```

<210> SEQ ID NO 18

```
<211> LENGTH: 101
<212> TYPE: PRT
<213> ORGANISM: Artificial Sequence
<220> FEATURE:
<223> OTHER INFORMATION: Amino acid sequence for ADP

<400> SEQUENCE: 18
```

Met Thr Gly Ser Thr Ile Ala Pro Thr Thr Asp Tyr Arg Asn Thr Thr
1               5                   10                  15

Ala Thr Gly Leu Thr Ser Ala Leu Asn Leu Pro Gln Val His Ala Phe
            20                  25                  30

Val Asn Asp Trp Ala Ser Leu Asp Met Trp Trp Phe Ser Ile Ala Leu
        35                  40                  45

Met Phe Val Cys Leu Ile Ile Met Trp Leu Ile Cys Cys Leu Lys Arg
    50                  55                  60

Arg Arg Ala Arg Pro Pro Ile Tyr Arg Pro Ile Ile Val Leu Asn Pro
65              70                  75                  80

His Asn Glu Lys Ile His Arg Leu Asp Gly Leu Lys Pro Cys Ser Leu
                85                  90                  95

Leu Leu Gln Tyr Asp
            100

```
<210> SEQ ID NO 19
<211> LENGTH: 28
<212> TYPE: DNA
<213> ORGANISM: Artificial Sequence
<220> FEATURE:
<223> OTHER INFORMATION: PCR EMCV IRES (PCR primer 96.74.2)

<400> SEQUENCE: 19
gacgtcgact aattccggtt attttcca                                    28

<210> SEQ ID NO 20
<211> LENGTH: 28
<212> TYPE: DNA
<213> ORGANISM: Artificial Sequence
<220> FEATURE:
<223> OTHER INFORMATION: PCR EMCV IRES (PCR primer 96.74.1)

<400> SEQUENCE: 20
gacgtcgaca tcgtgttttt caaaggaa                                    28

<210> SEQ ID NO 21
<211> LENGTH: 25
<212> TYPE: DNA
<213> ORGANISM: Artificial Sequence
<220> FEATURE:
<223> OTHER INFORMATION: Ad5 sequence to 1314 to 1338
      (PCR primer 96.74.3)

<400> SEQUENCE: 21
cctgagacgc ccgacatcac ctgtg                                       25

<210> SEQ ID NO 22
<211> LENGTH: 30
<212> TYPE: DNA
<213> ORGANISM: Artificial Sequence
<220> FEATURE:
<223> OTHER INFORMATION: Antisense of Ad5 sequence 1572 to 1586
      (PCR primer 96.74.6)

<400> SEQUENCE: 22
gtcgaccatt cagcaaacaa aggcgttaac                                  30
```

<210> SEQ ID NO 23
<211> LENGTH: 30
<212> TYPE: DNA
<213> ORGANISM: Artificial Sequence
<220> FEATURE:
<223> OTHER INFORMATION: Ad5 sequence 1714 to 1728
    (PCR primer 96.74.4)

<400> SEQUENCE: 23
tgctgaatgg tcgacatgga ggcttgggag                               30

<210> SEQ ID NO 24
<211> LENGTH: 26
<212> TYPE: DNA
<213> ORGANISM: Artificial Sequence
<220> FEATURE:
<223> OTHER INFORMATION: Antisense of Ad5 sequence 2070 to 2094
    (PCR primer 96.74.5)

<400> SEQUENCE: 24
cacaaaccgc tctccacaga tgcatg                                   26

<210> SEQ ID NO 25
<211> LENGTH: 29
<212> TYPE: DNA
<213> ORGANISM: Artificial Sequence
<220> FEATURE:
<223> OTHER INFORMATION: Human UPII (PCR primer 127.2.1)

<400> SEQUENCE: 25
aggaccggtc actatagggc acgcgtggt                                29

<210> SEQ ID NO 26
<211> LENGTH: 31
<212> TYPE: DNA
<213> ORGANISM: Artificial Sequence
<220> FEATURE:
<223> OTHER INFORMATION: Human UPII (PCR primer 127.2.2)

<400> SEQUENCE: 26
aggaccggtg ggatgctggg ctgggaggtg g                             31

<210> SEQ ID NO 27
<211> LENGTH: 29
<212> TYPE: DNA
<213> ORGANISM: Artificial Sequence
<220> FEATURE:
<223> OTHER INFORMATION: PCR primer 100.113.1

<400> SEQUENCE: 27
aggggtaccc actatagggc acgcgtggt                                29

<210> SEQ ID NO 28
<211> LENGTH: 32
<212> TYPE: DNA
<213> ORGANISM: Artificial Sequence
<220> FEATURE:
<223> OTHER INFORMATION: PCR primer 100.113.2

<400> SEQUENCE: 28
acccaagctt gggatgctgg gctgggaggt gg                            32

<210> SEQ ID NO 29
<211> LENGTH: 30
<212> TYPE: DNA
<213> ORGANISM: Artificial Sequence

```
<220> FEATURE:
<223> OTHER INFORMATION: PCR primer 127.50.1

<400> SEQUENCE: 29
aggaccggtc aggcttcacc ccagacccac                              30

<210> SEQ ID NO 30
<211> LENGTH: 24
<212> TYPE: DNA
<213> ORGANISM: Artificial Sequence
<220> FEATURE:
<223> OTHER INFORMATION: PCR primer 31.166.1

<400> SEQUENCE: 30
tgcgccggtg tacacaggaa gtga                                    24

<210> SEQ ID NO 31
<211> LENGTH: 21
<212> TYPE: DNA
<213> ORGANISM: Artificial Sequence
<220> FEATURE:
<223> OTHER INFORMATION: PCR primer 32.32.1

<400> SEQUENCE: 31
gagtttgtgc catcggtcta c                                       21

<210> SEQ ID NO 32
<211> LENGTH: 21
<212> TYPE: DNA
<213> ORGANISM: Artificial Sequence
<220> FEATURE:
<223> OTHER INFORMATION: PCR primer 32.32.2

<400> SEQUENCE: 32
aatcaatcct tagtcctcct g                                       21

<210> SEQ ID NO 33
<211> LENGTH: 25
<212> TYPE: DNA
<213> ORGANISM: Artificial Sequence
<220> FEATURE:
<223> OTHER INFORMATION: PCR primer 51.176

<400> SEQUENCE: 33
gcagaaaaat cttccaaaca ctccc                                   25

<210> SEQ ID NO 34
<211> LENGTH: 27
<212> TYPE: DNA
<213> ORGANISM: Artificial Sequence
<220> FEATURE:
<223> OTHER INFORMATION: PCR primer 99.120.1

<400> SEQUENCE: 34
acgtacaccg gtcgttacat aacttac                                 27

<210> SEQ ID NO 35
<211> LENGTH: 26
<212> TYPE: DNA
<213> ORGANISM: Artificial Sequence
<220> FEATURE:
<223> OTHER INFORMATION: PCR primer 99.120.2

<400> SEQUENCE: 35
ctagcaaccg gtcggttcac taaacg                                  26
```